US006365401B1

(12) United States Patent
Mahan et al.

(10) Patent No.: US 6,365,401 B1
(45) Date of Patent: Apr. 2, 2002

(54) METHOD AND PROBES FOR THE IDENTIFICATION OF MICROBIAL GENES SPECIFICALLY INDUCED DURING HOST INFECTION

(75) Inventors: Michael J. Mahan; Christopher P. Conner, both of Santa Barbara; Douglas M. Heithoff, Goleta, all of CA (US)

(73) Assignee: The Regents of the University of California, Oalkand, CA (US)

( * ) Notice: Subject to any disclaimer, the term of this patent is extended or adjusted under 35 U.S.C. 154(b) by 0 days.

(21) Appl. No.: 08/651,155

(22) Filed: May 17, 1996

(51) Int. Cl.$^7$ .............................................. C12N 19/31

(52) U.S. Cl. .................... 435/320.1; 536/23.1; 536/23.7

(58) Field of Search .................. 435/6, 320.1; 536/23.1, 536/23.7

(56) References Cited

U.S. PATENT DOCUMENTS

| | | | |
|---|---|---|---|
| 4,358,535 A | 11/1982 | Falkow et al. .................. | 435/5 |
| 5,434,065 A | 7/1995 | Mahan et al. ............ | 435/172.3 |

OTHER PUBLICATIONS

"Relative Expression of the Products of Glyoxylate Bypass Operon: Contributions of Transcription and Translation," Chun, et al., *Journal of Bacteriology*, Jul. 1993, 175(14):4572–5. Abstract Only.
"Isocitrate Dehydrogenase Kinase/Phosphatase: Identification of Mutations Which Selectively Inhibit Phosphatase Activity," Ikeda, et al., *Journal of Bacteriology*, Feb. 1992, 174(4):1414–6. Abstract Only.
"Regulation of the Acetate Operon in *Escherichia coli*: Purification and Functional Characterization of the Ic1R Repressor," Cortay, et al., *Embo Journal*, Mar. 1991, 10(3):675–9. Abstract Only.
"The Absence of Glyoxylate Cycle Enzymes in Rodent and Embryonic Chick Liver," Holmes, *Biochimica et Biophysica Acta*, Aug. 20, 1993, 1158(1):47–51. Abstract Only.
"The Isocitrate Dehydrogenase Phosphorylation Cycle: Regulation and Enzymology," LaPorte, *Journal of Cellular Biochemistry*, Jan. 1993, 51(1):14–8. Abstract Only.
"Isolation and Properties of a Mutant of *Escherichia coli* with an Insertional Inactivation of the uspA Gene, Which Encodes a Universal Stress Protein," Nystrom, et al., *Journal of Bacteriology*, Jul. 1993, 175(13):3949–56. Abstract Only.
"Regulatory Circuits Involved with pH–Regulated Gene Expression in *Salmonella typhimurium*," Foster, et al., *Microbiology*, Feb. 1994, 140(Pt. 2):341–52. Abstract Only.
"Characterization of the Micro–Environment of *Salmonella typhimurium*–Containing Vacuoles Within MDCK Epithelial Cells," Garcia–del, et al., *Molecular Microbiology*, Nov. 1992, 6(22):3289–97. Abstract Only.

"Altered pH and Lysine Signalling Mutants of cadC, a Gene Encoding a Membrane–bound Transcriptional Activator of the *Escherichia coli* cadBA Operon," Dell, et al., *Molecular Microbiology*, Oct. 1994, 14(1):7–16. Abstract Only.
"Roles of LysP and CadC in Mediating the Lysine Requirement for Acid Induction of the *Escherichia coli* cad Operon," Neely, et al, *Journal of Bacteriology*, Jun. 1994, 176(11):3278–85. Abstract Only.
"Identification of Elements Involved in Transcriptional Regulation of the *Escherichia coli* Cad Operon by External pH," Watson, et al., *Journal of Bacteriology*, Jan. 1992, 174(2):530–40. Abstract Only.
"*Escherichia coli* Cad Operon Functions as a Supplier of Carbon Dioxide," Takayama, et al., *Molecular Microbiology*, Mar. 1994, 11(5):913–8. Abstract Only.
"PhoE Porin of *Escherichia coli* and Phosphate Reversal of Acid Damage and Killing and of Acid Induction of the CadA Gene Product," Rowbury, et al., *Journal of Applied Bacteriology*, Jun. 1993, 74(6):652–61. Abstract Only.
"Identification of a Gene Involved in the Biosynthesis of Cyclopropanated Mycolic Acids in Mycobacterium Tuberculosis," Yuan, et al., *Proceedings of the National Academy of Sciences of the United States of America*, Jul. 3, 1995, 92(14):6630–4. Abstract Only.
"Cyclopropane Fatty Acid Synthase of *Escherichia coli*: Deduced Amino Acid Sequence, Purification, and Studies of the Enzyme Active Site," Wang, et al., *Biochemistry*, Nov. 17, 1992, 31(45):11020–8. Abstract Only.
"Influence of Stringent and Relaxed Response on Excretion of Recombinant Proteins and Fatty Acid Composition in *Escherichia coli*," Gitter, et al., *Appl. Microbiol Biotechnol*, Apr. 1995, 43(1):89–92. Abstract Only.
"Synthesis of Methyl 3–(2–Octadecylcyclopropen–1–yl) Proponoate and Methyl 3–(2–Octadecylcyclopropen–1–yl) Pentanoate and Cyclopropane Fatty Acids as Possible Inhibitors of Mycolic Acid Biosynthesis," Hartmann, et al., *Chemistry and Physics of Lipids*, May 6, 1994, 71(1):99–108. Abstract Only.
"Studies on Phospholipids of Different Mutants of *Salmonella minnesota*," Saha, et al., *Indian Journal of Biochemistry and Biophysics*, Aug. 1992, 29(4):355–9. Abstract Only.
"Fatty Acid Profile and Acid Phosphatase Activity of Fresh Isolates of *Pseudomonas pseudomallei*," Kondo, et al., *Japanese Journal of Medical Science and Biology*, Oct.–Dec. 1991, 44(5–6):195–211. Abstract Only.

(List continued on next page.)

Primary Examiner—James Martinell
(74) Attorney, Agent, or Firm—Morrison & Foerster LLP

(57) ABSTRACT

The present invention relates to a class of microbial coding sequences the transcription or cotranscription of which is specifically induced during microbial infection of a host. These particular coding sequences or defined regions thereof may be used as probes to identify and isolate microbial virulence genes. The products of these virulence genes will provide potential targets for the development of vaccines or antimicrobial agents.

25 Claims, 1 Drawing Sheet

OTHER PUBLICATIONS

"Adaptational Changes of Fatty Acid Composition and the Physical State of Membrane Lipids Following the Change of Growth Temperature in *Yersinia enterocolitica*," Nagamachi, et al., *Microbiology and Immunology*, 1991, 35(12):1085–93. Abstract Only.

"A Novel Antifungal Antibiotic, FR–900848. I. Production, Isolation, Physico–Chemical and Biological Properties," Yoshida, et al., *Journal of Antibiotics*, Jul. 1990, 43(7):748–54. Abstract Only.

"Unusual Fatty Acid Substitution in Lipids and Lipopolysaccharides of *Helicobacter pylori*," Geis, et al., *Journal of Clinical Microbiology*, May 1990, 28(5):930–2. Abstract Only.

"Roles of Different Coli Surface Antigens of Colinization Factor Antigen II in Colonization by and Protective Immunogenicity of Enterotoxigenic *Escherichia coli* in Rabbits," Svennerholm, et al., *Infection and Immunology*, Feb. 1990, 58(2):341–6. Abstract Only.

"The Binding of Colonization Factor Antigens of Enterotoxigenic *Escherichia coli* to Intestinal Cell Membrane Proteins," Wenneras, et al., *Fems Microbiology Letters*, Jan. 1, 1990, 54(1–3):107–12. Abstract Only.

"Binding of the Fibrillar CS3 Adhesin of Enterotoxigenic *Escherichia coli* to Rabbit Intestinal Glycoproteins is Competitively Prevented by GalNAc Beta 1–4Gal–Containing Glycoconjugates," Wenneras, et al., *Injection and Immunology*, Feb. 1995, 63(2):640–6. Abstract Only.

"In Vivo Requirement of Integration Host Factor for nar (Nitrate Reductase) Operon Expression in *Escherichia coli* K–12," Rabin, et al., *Proceedings of the National Academy of Sciences of the United States of America*, Sep. 15, 1992, 89(18):8701–5. Abstract Only.

"Localization of Upstream Sequence Elements Required for Nitrate and Anaerobic Induction of FDN (Formate Dehydrogenase–N) Operon Expression in *Escherichia coli* K–12," Li, et al., *Journal of Bacteriology*, Aug. 1992, 174(15):4935–42. Abstract Only.

"Structural Genes for Nitrate–Inducible Formate Dehydrogenase in *Escherichia coli* K–12," Berg, et al., *Genetics*, Aug. 1990, 125(4):691–702. Abstract Only.

"Fur Regulon of *Salmonella typhimurium*: Identification of New Iron–Regulated Genes," Tsolis, et al, *Journal of Bacteriology*, Aug. 1995, 177(16):4628–37. Abstract Only.

"The TonB–Dependent Ferrichrome Receptor FcuA of *Yersinia enterocolitica*: Evidence Against a Strict Co–Evolution of Receptor Structure and Substrate Specificity," Koebnik, et al., *Molecular Microbiology*, Feb. 1993, 7(3):383–93. Abstract Only.

"Structure and Function of X–Pro Dipeptide Repeats in the TonB Proteins of *Salmonella typhimurium* and *Escherichia coli*," Brewer, et al., *Journal of Molecular Biology*, Dec. 20, 1990, 216(4):883–95. Abstract Only.

"TonB Protein of *Salmonella typhimurium*. A Model for Signal Transduction Between Membranes," Hannavy, et al., *Journal of Molecular Biology*, Dec. 20, 1990, 216(4):897–910. Abstract Only.

"The FhuA Protein is Involved in Microcin 25 Uptake," Salomon, et al., *Journal of Bacteriology*, Dec. 1993, 175(23):7741–2. Abstract Only.

"Conversion of the FhuA Transport Protein into a Diffusion Channel Throught the Outer Membrane of *Escherichia coli*," Killmann, et al., *Embo Journal*, Aug. 1993, 12(8):3007–16. Abstract Only.

"The TonB–Dependent Ferrichrome Receptor FcuA of *Yersinia enterocolitica*: Evidence Against a Strict Co–Evolution of Receptor Structure and Substrate Specificity," Koebnik, et al., *Molecular Microbiology*, Feb. 1993, 7(3):383–93. Abstract Only.

"Structure and Function of X–Pro Dipeptide Repeats in the TonB Proteins of *Salmonella typhimurium* and *Escherichia coli*," Brewer, et al., *Journal of Molecular Biology*, Dec. 20, 1990, 216(4):883–95. Abstract Only.

"Mutual Inhibition of Cobalamin and Siderophore Uptake Systems Suggests Their Competition for TonB Function," Kadner, et al., *Journal of Bacteriology*, Sep. 1995, 177(17):4829–35. Abstract Only.

"The Peptide Antibiotic Microcin 25 is Imported Through the TonB Pathway and the SbmA Protein," Salomon, et al., *Journal of Bacteriology*, Jun. 1995, 177(11):3323–5. Abstract Only.

"Ferrioxamine Uptake in *Yersinia enterocolitica*: Characterization of the Receptor Protein FoxA," Baumler, et al., *Molecular Microbiology*, May 1992, 6(10):1309–21. Abstract Only.

"Iron (III) Hydroxamate Transport Into *Escherichia coli*. Substrate Binding to the Periplasmic FhuD Protein," Koster, et al., *Journal of Biological Chemistry*, Dec. 15, 1990, 265(35):21407–10. Abstract Only.

"In Vivo Evidence for FhuA Outer Membrane Receptor Interaction With the TonB Inner Membrane Protein of *Escherichia coli*," Gunter et al., *Febs Letters*, Nov. 12, 1990, 274(1–2):85–8. Abstract Only.

"Colicin M is Only Bactericidal When Provided from Outside the Cell," Harkness, et al., *Molecular and General Genetics*, Jun. 1990, 222(1):37–40. Abstract Only.

"Insertion Mutagenesis of the Gene Encoding the Ferrichrome–Iron Receptor of *Escherichia coli* K–12," Carmel, et al., *Journal of Bacteriology*, Apr. 1990, 172(4):1861–9. Abstract Only.

"Sequence and Characterization of the *Escherichia coli* Genome Between the ndk and gcpE Genes," Baker, et al., *Fems Microbiology Letters*, Sep. 1, 1994, 121(3):293–6. Abstract Only.

"Sequence and Characterization of the gcpE Gene of Escherichia coli," Baker, et al., *Fems Microbiology Letters*, Jul. 1, 1992, 73(1–2):175–80. Abstract Only.

"Cloning and Nucleotide Sequence of the gcv Operon Encoding the *Escherichia coli* Glycine–Cleavage System," Okamura–Ikeda, et al., *European Journal of Biochemistry*, Sep. 1, 1993, 216(2):539–48. Abstract Only.

"Roles of the GcvA and PurA Proteins in Negative Regulation of the *Escherichia coli* Glycine Cleavage Enzyme System," Wilson, et al., *Journal of Bacteriology*, Aug. 1993, 175(16):5129–34. Abstract Only.

"Positive Regulation of the *Escherichia coli* Glycine Cleavage Enzyme System," Wilson, et al., *Journal of BacteriologyFeb*. 1993, 175(3):902–4. Abstract Only.

"The lpd Gene Product Functions as the L Protein in the *Escherichia coli* Glycine Cleavage Enzyme System," Steiert, et al., *Journal of Bacteriology*, Oct. 1990, 172(10):6142–4. Abstract Only.

"gltF, a Member of the gltBDF Operon of *Escherichia coli*, is Involved in Nitrogen–Regulated Gene Expression," Castano, et al., *Molecular Microbiology*, Sep. 1992, 6(18):2733–41. Abstract Only.

"Identification of Phosphate Starvation–Inducible Genes in *Escherichia coli* K–12 by DNA Sequence Analysis of psi:: lacZ(Mu d1) Transcriptional Fusions," Metcalf, et al., *Journal of Bacteriology*, Jun. 1990, 172(6):3191–200. Abstract Only.

"Mutants Defective in the Energy–Conserving NADH Dehydrogenase of *Salmonella typhimurium* Identified by a Decrease in Energy–Dependent Proteolysis After Carbon Starvation," Archer, et al., *Proceedings of the National Academy of Sciences of the United States of America*, Nov. 1, 1993, 90(21):9877–81. Abstract Only.

"Characterization of the hemA–prs Region of the *Escherichia coli* and *Salmonella tyhimurium* Chromosomes: Identification of Two Open Reading Frames and Implications for PRS Expresion," Post, et al., *Journal of General Microbiology*, Feb. 1993, 139 (Pt 2):259–66. Abstract Only.

"A hemA Mutation Renders *Salmonella typhimurium* Avirulent in Mice, Yet Capable of Eliciting Protection Against Intravenous Infection with *S. typhimurium*," Benjamin, et al., *Microbial Pathogenesis*, Oct. 1991, 11(4):289–95. Abstract Only.

"*Salmonella typhimurium* prfA Mutants Defective in Release Factor 1," Elliott, et al., *Journal of Bacteriology*, Jul. 1991, 173(13):4144–54. Abstract Only.

"Cloning and Sequence of the *Salmonella typhimurium* hemL Gene and Identification of the Missing Enzyme in hemL Mutants as Glutamate–1–semialdehyde Aminotransferase," Elliott, et al., *Journal of Bacteriology*, Dec. 1990, 172(12):7071–84. Abstract Only.

"Phenotypic Suppression of DNA Gyrase Deficiencies by a Deletion Lowering the Gene Dosage of a Major tRNA in *Salmonella typhimurium*," Blanc–Potard, et al., *Journal of Bacteriology*, Apr. 1994, 176(8):2216–26. Abstract Only.

"Role of tRNA Modification in Translational Fidelity," Hagervall, et al., *Biochimica et Biophysica Acta*, Aug. 27, 1990, 1050(1–3):263–6. Abstract Only.

"Altered Growth–Rate–Dependent Regulation of 6–Phosphogluconate Dehydrogenase Level in hisT Mutants of *Salmonella typhimurium* and *Escherichia coli*," Jones, et al., Journal of Bacteriology, Mar. 1990, 172(3):1197–205. Abstract Only.

"Sequence Analysis of Four New Heat–Shock Genes Constituting the hs1TS/ibpAB and hs1VU Operons in *Escherichia coli*," Chuang, et al., Gene, Nov. 30, 1993, 134(1):1–6. Abstract Only.

"Threonine Formation Via the Coupled Activity of 2–Amino–3–Ketobutyrate Coenzyme A Lyase and Threonine Dehydrogenase," Marcus, et al., *Journal of Bacteriology*, Oct. 1993, 175(20):6505–11. Abstract Only.

"Regulation of kdp Operon Expression in *Escherichia coli*: Evidence Against Turgor as Signal for Transcriptional Control," Asha, et al., Journal of Bacteriology, Jul. 1993, 175(14):4528–37. Abstract Only.

"The Products of the kdpDE Operon are Required for Expression of the Kdp ATPase of *Escherichia coli*," Polarek, et al., *Journal of Bacteriology*, Apr. 1992, 174(7):2145–51. Abstract Only.

"Thiogalactoside Transacetylase of the Lactose Operon as an Enzyme for Detoxification," Andrews, et al., *Journal of Bacteriology*, Oct. 1976, 128(1):510–3. Abstract Only.

"The nodL Gene from *Rhizobium leguminosarum* is Homologous to the Acetyl Transferases Encoded by lacA and cysE," Downie, *Molecular Microbiology*, Nov. 1989, 3(11):1649–51. Abstract Only.

"Genetic Rearrangements and Gene Amplification in *Escherichia coli*: DNA Sequences at the Junctures of Amplified Gene Fusions," Whoriskey, et al., *Genes and Development*, May 1987, 1(3):227–37. Abstract Only.

"Specific Endonucleolytic Cleavage Sites for Decay of *Escherichia coli* mRNA," Cannistraro, et al., *Journal of Molecular Biology*, Nov. 20, 1986, 192(2):257–74. Abstract Only.

"Coordinate Expression of a Small Polypeptide with the Lactose Carrier of *Escherichia coli*," Lagarias, et al., *Journal of Biological Chemistry*, Nov. 15, 1985, 260(26):14235–41. Abstract Only.

"DNA Sequence of the Lactose Operon: The lacA Gene and the Transcriptional Termination Region," Hediger, et al., *Proceedings of the National Academy of Sciences of the United States of America*, Oct. 1985, 82(19):6414–8. Abstract Only.

"An Extraintestinal, Pathogenic Isolate of *Escherichia coli* (04/K54/H5) Can Produce a Group 1 Capsule Which is Divergently Regulated from its Constitutively Produced Group 2, K54 Capsular Polysaccharide," Russo, et al., *Journal of Bacteriology*, Dec. 1993, 175(23):7617–23. Abstract Only.

"Nucleotide Sequence of rmpB, a *Klebsiella pneumoniae* Gene that Positively Controls, Colanic Biosynthesis in *Escherichia coli*," Vesselon, et al., *Research in Microbiology*, Jan. 1991, 142(1):47–54. Abstract Only.

"The Occurrence of Duplicate lysyl–tRNA Synthetase Gene Homologs in *Escherichia coli* and Other Procaryotes," Saluta, et al., *Journal of Bacteriology*, Apr. 1995, 177(7):1872–8. Abstract Only.

"Control and Function of lysyl–tRNA Synthetases: Diversity and Co–Ordination," Nakamura, et al., *Molecular Microbiology*, Oct. 1993, 10(2):225–31. Abstract Only.

"Multiple Control of *Escherichia coli* lysyl–tRNA Synthetase Expression Involves a Transcriptional Repressor and a Translational Enhancer Element," Ito, et al., *Proceedings of the National Adacemy of Sciences of the United State of America*, Jan. 1, 1993, 90(1):302–6. Abstract Only.

"Differential Regulation of Two Genes Encoding lysyl–tRNA Synthetases in *Escherichia coli*: lysU–Constitutive Mutations Compensate for a lysS Null Mutation," Kawakami, et al, *Molecular Microbiology*, Jul. 1992, 6(13):1739–45. Abstract Only.

"Overproduction and Purification of lysyl–tRNA Synthetase Encoded by the herC Gene of *E coli*," Nakamura, et al., *Biochimie*, Jun. 1992, 74(6):581–4. Abstract Only.

"Control of *Escherichia coli* lysyl–tRNA Synthetase Expression by Anaerobiosis," Leveque, et al., *Journal of Bacteriology*, Dec. 1991, 173(24):7903–10. Abstract Only.

"Roles of the Two lysyl–tRNA Synthetases of *Escherichia coli*: Analysis of Nucleotide Sequences and Mutant Behavior," *Journal of Bacteriology*, Clark et al, Jun. 1990, 172(6):3237–43. Abstract Only.

"Homology of lysS and lysU, the Two *Escherichia coli* Genes Encoding Distinct lysyl–tRNA Synthetase Species," Leveque, et al., *Nucleic Acids Research*, Jan. 25, 1990, 18(2):305–12. Abstract Only.

"Magnesium Transport in *Salmonella typhimurium*: mgtA Encodes a P–type ATPase and is Regulated by Mg2+ in a Manner Similar to That of the mgtB P–type ATPase," Tao, et al., Journal of Bacteriology, May 1995, 177(10):2654–62. Abstract Only.

"Magnesium Transport Systems: Genetics and Protein Structure (a review)," Roof, et al., *Journal of the Americal College of Nutrition*, Oct. 1994, 13(5):424–8. Abstract Only.

"Molecular Aspects of Mg2+ Transport Systems," Smith, et al., *Mineral and Electrolyte Metabolism*, 1993, 19(4–5):266–76. Abstract Only.

"MgtA and MgtB: Prokaryotic P–type ATPases that Mediate Mg2+ Influx," Maguire, *Journal of Bioenergetics and Biomembranes*, Jun. 1992, 24(3):319–28. Abstract Only.

"Magnesium Transport in *Salmonella typhimurium*. Regulation of mgtA and mgtB Expression," Snavely, et al., Journal of Biological Chemistry, Jan. 15, 1991, 266(2):824–9. Abstract Only.

"Membrane Topology of a P–type ATPase. The MgtB Magnesium Transport Protein of *Salmonella typhimurium*," Smith, et al., Journal of Biological Chemistry, Oct. 25, 1993, 268(30):22469–79. Abstract Only.

"Characterization of the Micro–Environment of *Salmonella typhimurium*–Containing Vacuoles Within MDCK Epithelial Cells," Garcia–del Portillo, et al., Molecular Microbiology, Nov. 1992, 6(22):3289–97. Abstract Only.

The mgtB Mg2+ Transport Locus of *Salmonella typhimurium* Encodes a P–type ATPase, Snavely, et al., Journal of Biological Chemistry, Jan. 15, 1991, 266(2):815–23. Abstract Only.

"Sequence and Characterization of the *Escherichia coli* Genome Between the ndk and gcpE Genes," Baker, et al., *Fems Microbiology Letters*, Sep. 1, 1994, 121(3):293–6. Abstract Only.

"Nucleoside Diphosphate Kinase from *Escherichia coli*; Its Overproduction and Sequence Comparison with Eukaryotic Enzymes," Hama, et al., *Gene*, Aug. 30, 1991, 105(1):31–6. Abstract Only.

"Oxygen Inhibition of Nitrogenase Activity of *Klebsiella pneumoniae*," Kavanagh, et al., *Journal of General Microbiology*, Jun. 1993, 139 (Pt 6):1307–14. Abstract Only.

"Isolation and Characterization of the Proton–translocating NADH: Ubiquinone Oxidoreductase From *Escherichia coli*," Leif, et al., *European Journal of Biochemistry*, Jun. 1, 1995, 230(2):538–48. Abstract Only.

"Transcriptional Control of the Nuo Operon Which Encodes the Energy–Conserving NADH Dehydrogenase of *Salmonella typhimurium*," Archer, et al., Journal of Bacteriology, May 1995, 177(9):2335–42. Abstract Only.

"Mutations in NADH: Ubiquinone Oxidoreductase of *Escherichia coli* Affect Growth on Mixed Amino Acids," Pruss, et al., *Journal of Bacteriology*, Apr. 1994, 176(8):2143–50. Abstract Only.

"The Gene Locus of the Proton–translocating NADH: Ubiqinone Oxidoreductase in *Escherichia coli*. Organization of the 14 Genes and Relationship Between the Derived Proteins and Subunits of Mitochondrial Complex I," Weidner, et al., *Journal of Molecular Biology*, Sep. 5, 1993, 233(1):109–22. Abstract Only.

"Demonstration of Separate Genetic Loci Encoding Distinct Membrane–bound Respiratory NADH Dehydrogenases in *Escherichia coli*," Calhoun, et al., *Journal of Bacteriology*, May 1993, 175(10):3013–9. Abstract Only.

"Molecular Genetic Analysis of a Locus Required for Resistance to Antimicrobial Peptides in *Salmonella typhimurium*," Parra–Lopez, et al., Embo Journal, Nov. 1993, 12(11):4053–62. Abstract Only.

"Membrane Topology of the Integral Membrane Components, OppB and OppC, of the Oligopeptide Permease of *Salmonella typhimurium*," Pearce, et al., Molecular Microbiology, Jan. 1992, 6(1):47–57. Abstract Only.

"The Leucine–responsive Regulatory Protein, a Global Regulator of Metabolism in *Escherichia coli*," Calvo, et al., *Microbiological Reviews*, Sep. 1994, 58(3):466–90. Abstract Only.

"Turnover and Recycling of the Murein Sacculus in Oligopeptide Permease–negative Strains of *Escherichia coli*: Indirect Evidence for an Alternative Permease System and for a Monolayered Sacculus," Park, *Journal of Bacteriology*, Jan. 1993, 175(1):7–11. Abstract Only.

"Expression of Periplastic Binding Proteins for Peptide Transport is Subject to Negative Regulation by Phosphate Limitation in *Escherichia coli*," Smith, et al., *Fems Microbology Letters*, Dec. 15, 1992, 79(1–3):183–90. Abstract Only.

"UDP–Glucose is a Potential Intracellular Signal Molecule in the Control of Expression of Sigma S and Sigma S–dependent Genes in *Escherichia coli*," Bohringer, et al., *Journal of Bacteriology*, Jan. 1995, 177(2):413–22. Abstract Only.

"Analysis of the otsBA Operon for Osmoregulatory Trehalose Systhesis in *Escherichia coli* and Homology of the OtsA and OtsB Proteins to the Yeast Trehalose–6–phosphate Synthase/Phosphatase Complex," Kaasen, et al., *Gene*, Jul. 1994 22, 145(1):9–15. Abstract Only.

"Molecular Cloning and Physical mapping of the otsBA Genes, Which Encode the Osmoregulatory Trehalose Pathway of *Escherichia coli*: Evidence that Transcirption is Activated by katF" (AppR) [published erratum appears in J Bacteriol May 1992:174(10):34422], Kaasen, et al., *Journal of Bacteriology*, Feb. 1992, 174(3):889–98. Abstract Only.

"Methylchloroisothiazolone–induced Growth Inhibition and Lethality in *Escherichia coli*," Chapman, et al., *Journal of Applied Bacteriology*, Feb. 1995, 78(2):134–41. Abstract Only.

"The Bcl–2 Oncoprotein Functions as a Pro–Oxidant," Steinman, *Journal of Biological Chemistry*, Feb. 24, 1995, 270(8):3487–90. Abstract Only.

"Mutational Analysis of the Redox–Sensitive Transcriptional Regulator OxyR: Regions Important for DNA Binding and Multimerization," Kullik, et al., *Journal of Bacteriology*, Mar. 1995, 177(5):1285–91. Abstract Only.

"Mutational Analysis of the Redox–sensitive Transcriptional Regulator OxyR: Regions Important for DNA Binding and Transcriptional Activation," Kulik, et al., *Journal of Bacteriology*, Mar. 1995, 177(5):1275–84 Abstract Only.

"Effects of Peroxides on Susceptibilities of *Escherichia coli* and *Myocobacterium smegmatis* to Isoniazid," Rosner, et al., *Antimicrobial Agents and Chemotherapy*, Aug. 1994, 38(8):1829–33. Abstract Only.

"The dps Promoter is Activated by OxyR During Growth and by IHF and Sigma S in Stationary Phase," Altuvia, et al., *Molecular Microbiology*, Jul. 1994, 13(2):265–72. Abstract Only.

"Redox–dependent Shift of OxyR–DNA Contacts Along an Extended DNA–binding Site: A Mechanism for Differential Promoter Selection," Toledano, et al., *Cell*, Sep. 9, 1994, 78(5):897–909. Abstract Only.

"Comparison of the Sensitivities of *Salmonella typhimurium* oxyR and kat G Mutants to Killing by Human Neutrophils," Papp–Szabo, et al., Infection and Immunity, Jul. 1994, 62(7):2662–8. Abstract Only.

"Role of rpoS (katF) in oxyR–independent Regulation of Hydroperoxidase I in *Escherichia coli*," Ivanova, et al., *Molecular Microbiology*, May 1994, 12(4):571–8. Abstract Only.

"Induction of *Escherichia coli* Hydroperoxidase I by Acetate and Other Weak Acids," Mukhopadhyay, et al., *Journal of Bacteriology*, Apr. 1994, 176(8):2300–7. Abstract Only.

"Protein–sulfenic Acid Stabilization and Function in Enzyme Catalysis and Gene Regulation," Claiborne, et al., *Faseb Journal*, Dec. 1993, 7(15):1483–90. Abstract Only.

"Susceptibilities of oxyR Regulon Mutants of *Escherichia coli* and *Salmonella typhimurium* to Isoniazid," Rosner, Antimicrobial Agents and Chemotheraphy, Oct. 1993, 37(10):2251–3. Abstract Only.

"PhoE Porin of *Escherichia coli* and Phosphate Reversal of Acid Damage and Killing and of Acid Induction of the CadA Gene Product," Rowbury, Goodson, *Journal of Applied Bacteriology*, Jun. 1993, 74(6):652–61. Abstract Only.

"Isolation and Characterization of *Escherichia coli* Strains Containing New Gene Fusions (soi::lacZ) Inducible by Superoxide Radicals," Mito, et al., *Journal of Bacteriology*, May 1993, 175(9):2645–51. Abstract Only.

"Involvement of the RNA Polymerase Alpha Subunit C–terminal Region in Co–operative Interaction and Transcriptional Activation with OxyR Protein," Tao, et al., *Molecular Microbiology*, Mar. 1993, 7(6):859–64. Abstract Only.

"Modulation of the $H_2O_2$–induced SOS Response in *Escherichia coli* PQ300 by Amino Acids, Metal Chelators, Antioxidants, and Scavengers of Reactive Oxygen Species," Muller, et al., *Environmental and Molecular Mutagenesis*, 1993, 22(3):157–63. Abstract Only.

"Physical Map of the OxyR–trmA Region (minute 89.3) of the *Escherichia coli* Chromosome," Gustafsson, et al., *Journal of Bacteriology*, Dec. 1992, 174(23):7878–9. Abstract Only.

"Structural and Biochemistry Characterization of the *Escherichia coli* argE Gene Product," Meinnel, et al., *Journal of Bacteriology*, Apr. 1992, 174(7):2323–31. Abstract Only.

"OxyR: A Regulator of Antioxidant Genes," Storz, et al., *Journal of Nutrition*, Mar. 1992, 122(3 Suppl):627–30. Abstract Only.

"Multidegenerate DNA Recognition by the OxyR Transcriptional Regulator," Tartaglia, et al., *Journal of Biological Chemistry*, Jan. 25, 1992, 267(3):2038–45. Abstract Only.

"Assessment of Oxidative DNA Damage in the OxyR–deficient SOS Chromotest Strain *Escherichia coli* PQ300," Muller, Janz, *Environmental and Molecular Mutagenesis*, 1992, 20(4):297–306. Abstract Only.

"Oxidative Stress Responses in *Escherichia coli* and *Salmonella typhimurium*," Farr, et al., Microbiological Reviews, Dec. 1991, 55(4):561–85. Abstract Only.

"Purification and Characterization of the *Escherichia coli* OxyR Protein, the Positive Regulator for a Hydrogen Peroxide–Inducible Regulon," Tao, et al., *Journal of Biochemistry*, Feb. 1991, 109(2):262–6. Abstract Only.

"The OxyR Regulon," Storz, et al., *Antonie Van Leeuwenhoek*, Oct. 1990, 58(3):157–61. Abstract Only.

"Transcriptional Regulator of Oxidative Stress–Inducible Genes: Direct Activation by Oxidation," Storz, et al., *Science*, Apr. 13, 1990, 248(4952):189–94. Abstract Only.

"Identification and Characterization of a Gene that Controls Colony Morphology and Auto–Aggregation in *Escherichia coli* K12," Warne, et al., *Journal of General Microbiology*, Mar. 1990, 136(Pt 3):455–62. Abstract Only.

"Interaction of Lead Nitrate and Cadmium Chloride with *Escherichia coli* K–12 and *Salmonella typhimurium* Global Regulatory Mutants," LaRossa, et al., J Ind Microbiol. Mar.–Apr. 1995, 14(3–4):252–8. Abstract Only.

"Increased Mutability by Oxidative Stress in OxyR–deficient *Escherichia coli* and *Salmonella typhimurium* Cells: Clonal Occurrence of the Mutants During Growth on Nonselective Media," Blanco, et al., Mutation Research, Apr. 1995, 346(4):215–20. Abstract Only.

"OxyR: A Regulator of Antioxidant Genes," Storz, et al., *Journal of Nutrition*, Mar. 1992, 122(3 Suppl):627–30. Abstract Only.

"Transcriptional Regulator of Oxidative Stress–inducible Genes: Direct Activation by Oxidation," Storz, et al., *Science*, Apr. 13, 1990, 248(4952):189–94. Abstract Only.

"Transcriptional Autoregulation of the *Salmonella typhimurium* phoPQ Operon," Soncini, et al., Journal of Bacteriology, Aug. 1995, 177(15):4364–71. Abstract Only.

"The Role of the PhoP/PhoQ Regulon in Salmonella Virulence," Garcia, et al., Research in Microbiology, Jun.–Aug. 1994, 145(5–6):473–80. Abstract Only.

"Spontaneous pmrA Mutants of *Salmonella typhimurium* LT2 Define a New Two–Component Regulatory System with a Possible Role in Virulence," Roland, et al., Journal of Bacteriology, Jul. 1993, 175(13):4154–64. Abstract Only.

"The Outer Membranes of Brucella Spp. are Resistant to Bactericidal Cationic Peptides," Marinez de Tejada, et al., *Infection and Immunity*, Aug. 1995, 63(8):3054–61. Abstract Only.

"Role of an *Escherichia coli* Stress–Response Operon in Stationary–phase Survival," Weiner, et al., *Proceedings of the National Academy of Sciences of the United States of America*, Mar. 15, 1994, 91(6):2191–5. Abstract Only.

"Expression of the pspA Gene Stimulates Efficient Protein Export in *Escherichia coli*", Kleerebezem, et al., *Molecular Microbiology*, Mar. 1993, 7(6):947–56. Abstract Only.

"Stress–induced Expression of the *Escherichia coli* Phage Shock Protein Operon in Dependent on Sigma 54 and Modulated by Positive and Negative Feedback Mechanisms," Weiner, et al., *Genes and Deelopment*, Oct. 1991, 5(10):1912–23. Abstract Only.

"The *Salmonella typhimurium* Virulence Plasmid Encodes a Positive Regulator of a Plasmid–encoded Virulence Gene," Caldwell, et al., Journal of Bacteriology, Nov. 1991, 173(22):7176–85. Abstract Only.

"Molecular Analysis of spv Virulence Genes of the Salmonella Virulence Plasmids," Gulig, et al., *Molecular Microbiology*, Mar. 1993, 7(6):825–30. Abstract Only.

"Stress Induction of the Virulence Proteins (SpvA, –B, and –C) from Native Plasmid pSDL2 of *Salmonella dublin*," Valone, et al., *Infection and Immunity*, Feb. 1993, 61(2):705–13. Abstract Only.

"A New Gene Involved in Stationary–phase Survival Located at 59 Minutes on the *Escherichia coli* Chromosome," Li, et al., *Journal of Bacteriology*, Oct. 1994, 176(19):6015–22. Abstract Only.

"Purification, Gene Cloning, and Sequence Analysis of an L–Isoaspartyl Protein Carboxyl Methytransferase from *Escherichia coli* [Published Erratum Appears in J Biol Chem Jun. 5, 1992 ;267;(16):11660]," Fu, et al., *Journal of Biological Chemistry*, Aug. 5, 1991, 266(22):14562–72. Abstract Only.

"Isolation and Characterization of a Tn–5 Induced tolQ Mutant of *Escherichia coli*," Madrid, et al., *Canadian Journal of Microbiology*, Jun. 1994, 40(6):503–7. Abstract Only.

"Colicin A and the Tol Proteins Involved in its Tranlocation are Preferentially Located in the Contact Sites Between the Inner and Outer Membranes of *Escherichia coli* Cells," Guihard, et al., *Journal of Biological Chemistry*, Feb. 1994 24, 269(8):5874–80. Abstract Only.

"Membrane Topology and Mutational Analysis of the TolQ Protein of *Escherichia coli* Required for the Uptake of Macromolecules and Cell Envelope Integrity," Vianney, et al., *Journal of Bacteriology*, Feb. 1994, 176(3):822–9. Abstract Only.

"Energy Transduction Between Membranes. TonB, a Cytoplasmic Membrane Protein, Can be Chemically Cross–Linked in vivo to the Outer Membrane Receptor FepA," Skare, et al., *Journal of Biological Chemmistry*, Aug. 5, 1993, 268(22):16302–8. Abstract Only.

"Membrane Topologies of the TolQ and TolR Proteins of *Escherichia coli*: Inactivation of TolQ by a Missense Mutation in the Proposed First Transmembrane Segment," Kampfenkel, et al., *Journal of Bacteriology*, Jul. 1993, 175(14):4485–91. Abstract Only.

"The Proton Motive Force Drives the Outer Membrane Transport of Cobalamin in *Escherichia coli*," Bradbeer, *Journal of Bacteriology*, May 1993, 175(10):3146–50. Abstract Only.

"Evolutionary Relationship of Uptake Systems for Biopolymers in *Escherichia coli*: Cross–complementation Between the TonB–ExbB–ExbD and the TolA–TolQ–TolR Proteins," Braun, et al., *Molecular Microbiology*, Apr. 1993, 8(2):261–8. Abstract Only.

"Role of tol Genes in Cloacin DF13 Susceptibility of *Escherichia coli* K–12 Strains Expressing the Cloacin DF13–Aerobactin Receptor IutA," Thomas, et al., *Journal of Bacteriology*, Jan. 1993, 175(2):548–52. Abstract Only.

"A New colicin that Absorbs to Outer–membrane Protein Tsx But is Dependent on the TonB Instead of the TolQ Membrane Transport System," Bradley, et al., *Journal of General Microbiology*, Dec. 1992, 138 (Pt 12):2721–4. Abstract Only.

"TolQ is Required for Cloacin DF13 Susceptibility in *Escherichia coli* Expressing the Aerobactin/Cloacin DF13 Receptor IutA," Thomas, et al., *Fems Microbiology Letters*, Mar. 1, 1992, 70(2):107–11. Abstract Only.

"The TonB Gene of *Serratia marcescens*: Sequence, Activity and Partial Complementation of *Escherichia coli* TonB Mutants," Gaisser, et al., *Molecular Microbiology*, Nov. 1991, 5(11):2777–87. Abstract Only.

"Phospholipase–A–Independent Damage Caused by the Colicin A Lysis Protein During Its Assembly Into the Inner and Outer Membranes of *Escherichia coli*," Howard, et al., *Journal of General Microbiology*, Jan. 1991, 137 (Pt 1):81–9. Abstract Only.

"vacB, a Novel Chromosomal Gene Required for Expression of Virulence Genes on the Large Plasmid of *Shigella flexneri*," Tobe, et al., *Journal of Bacteriology*, Oct. 1992, 174(20):6359–67. Abstract Only.

"vacC, a Virulence–associated Chromosomal Locus of *Shigell flexneri*, is Homologous to tgt, a Gene Encoding tRNA–Guanine Transglycosylase (Tgt) of *Escherichia coli* K–12," Durand, et al., *Journal of Bacteriology*, Aug. 1994, 176(15):4627–34. Abstract Only.

"The Promoter of the tgt/sec Operon in *Escherichia coli* is Preceded by an Upstream Activation Sequence that Contains a High Affinity FIS Binding Site," Slany, et al., *Nucleic Acids Research*, Aug. 25, 1992, 20(16):4193–8. Abstract Only.

"Exploring New Strategies to Fight Drug–Resistant Microbes," Gibbons, *Science*, Aug. 1992, 257:1036–38.

"The Crisis in Antibiotic Resistance," Neu, *Science*, Aug. 1992, 257:1064–72.

"Vancomycin Resistance: Decoding the Molecular Logic," Walsh, *Science*, Jul. 1993, 261:308–9.

"The Origin of Plagues: Old and New," Krause, *Science*, Aug. 1992, 257:1073–77.

"Structure–Based Strategies for Drug Design and Discovery," Kuntz, *Science*, Aug. 1992, 257:1078–82.

"Antibiotic–based Selection for Bacterial Genes That are Specifically Induced During Infection of a Host," Mahan, et al., *Proc. Natl. Acad. Sci. USA*, Jan. 1995, 92:669–673.

"Bacteriophage P22 Transduction of Integrated Plasmids: Single–Step Cloning of *Salmonella typhimurium* Gene Fusions," Mahan, et al., *Journal of Bacteriology*, Nov. 1993, 175(21):7086–91.

SEQUENCE LISTING (1) GENERAL INFORMATION:

(iii) NUMBER OF SEQUENCES: 255

(2) INFORMATION FOR SEQ ID NO:1:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:1:

CATTGGGTGC CCAGTACG                                            18

(2) INFORMATION FOR SEQ ID NO:2:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

TGTGCCTTCG TCGAGCAC                                            18

(2) INFORMATION FOR SEQ ID NO:3:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

CAACGGTGGT ATATCCAG                                            18

(2) INFORMATION FOR SEQ ID NO:4:

(i) SEQUENCE CHARACTERISTICS:
       (A) LENGTH: 390 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:4:

```
GATCCGGATG GAATGGCTCC AGCGCGTCGG TTTTCTCGCC GACACCGAGG AATTTAATCG      60
GCTTGCCGGT GATATGACGA ATAGAGAGCG CCGCACCGCC ACGCGCATCA CCATCAACTT     120
TGGTCAGCAC CACGCCGGTT AACGGCAGCG CTTCGTTAAA GGCTTTTGCG GTATTCGCCG     180
CATCCTGACC GGTCATCGCA TCGACGACAA ACAGCGTTTC TACTGGCTTG ATAGAAGCGT     240
GGACCTGTTT GATTTCGTCC ATCATCGCTT CGTCAACATG CAGACGACCG GCGGTATCCA     300
CCAGCAGCAC GTCGTAGAAT TTGAGCTGCT TCTTGGCGGT TGACAGTATC ACGTTCTGCG     360
AAATCAGACG GAGAATCACG CAATTGTACA                                     390
```

(2) INFORMATION FOR SEQ ID NO:5:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:5:

```
GATCATAGAG GTGGATACGG CTTTTCAACG CCTGTTGGAC GGCGTGCCAG TCGGCCTGTT      60
CAAAACGCTG CTGCGCGCCG GAAGTCACTT CCAGAAATCG ACCATACTGC GCGTCAAAGC     120
CTTGCAGGAT GGTTTGAGCA ATCAGTAATT CCAGGCCACG CGGCATTTTT TTACCTCATC     180
CGGCACCACG TCATGCCGGA TGCGCGTTCG CTTATCCGGC CTACGCTATC TGTAGGCC      238
```

(2) INFORMATION FOR SEQ ID NO:6:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:6:

```
GATCGAGAGG ATGCGGTGGT GGATGCGCAT ATTACCGGAT GACGGCGTGA ACGTGTTATG      60
CGGCCTACCA GCCCAATGCG CGATACCAAG CCGGATAAGC CGCCAACGCC CACCCCGGCC     120
CCGCCGCGTA TTTAATCAAG TTATTACCTT TGATCGCACC CTTGAGGTCA GGCGCGTGAT     180
AAGTTCGTAA GCACTTACTT TTGTCATTTC AGCGATACGT TCAACCGGCA GACTTACCCA     240
TAGACACGAT CGCGGTATCT CGGTTGCCAA TTCGAATCTA CCATGGACG CGACATCGAC     300
TACGACATT                                                            309
```

(2) INFORMATION FOR SEQ ID NO:7:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:7:

| | | | | | |
|---|---|---|---|---|---|
| GATCCGTTTT | GACCATCCCG | TGTTTGGTCG | AAACCGTGCA | GCCTTCTACC | AGCGGCAGTA | 60 |
| AGTCGGGCTG | TACGCCTTCG | CGTGAAACAT | CCGGGCCGGA | GGTTTCGGCA | CGCTTACAAA | 120 |
| TTTTGTCAAT | TTCATCGATA | AACACGATGC | CGTGCTGTTC | AACCGCGTCG | ATAGGTCCTG | 180 |
| TTTCAGCTCT | TCCGGGTTGA | CCAGTTTAGC | AGCCTCTTCT | TCAACCAACA | GTTTCATCGC | 240 |
| GTCTTTAATT | TTCAGCTTAC | GGGTTTCTGT | TTCTGACCGC | CCAGGTTCTG | GAACATAGAC | 300 |
| TGCACTGCTG | TCATCTCTCA | TGCCGAGCCA | TATCTCTAGC | CATCGGCGCA | GTATTGACTT | 360 |
| TA | | | | | | 362 |

(2) INFORMATION FOR SEQ ID NO:8:

(i) SEQUENCE CHARACTERISTICS:
          (A) LENGTH: 206 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:8:

GATCAAGAAT GTGTTCTCCC AGCGCATCCT TGATGGTTTC TCCCAGCACC TTGCCGAGCA    60
TACTGACATT ACTAGCAACG CGGAATATTG TTCGTTCATA TGCCCCCAGA CGCCCCATCT   120
TTAATGTAAT TGCCCTGTCT CTTTCATGCC ACAGCGCAGT GGCTGCGTGC GTATGCAGTT   180
ATGCGAATGC TCGTGCTGCG ACTAAT                                       206

(2) INFORMATION FOR SEQ ID NO:9:

(i) SEQUENCE CHARACTERISTICS:
          (A) LENGTH: 250 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:9:

GATCGTCGGT GCGAATGGTG ACGTCGGCAA TCTCTTCGTA CAGCGGATTG CGTTCGTTAG    60
CCAGCGCTTC CAGAACTTCG CGAGGCGGTG CTTCAACCTG CAACAGCGGG CGTTTTTTAT   120
CACGCTGCGT GCGGCAGTTG TTTTTCGATC GGTCGTTTCA AGGTAGACCA CGACGCACGG   180
CGAGAGACGG TTACGGTTTC ACAATTTTAC AGAGCCACAT CGGAACACAC ATACCTTTAT   240
ATCTATACTT                                                         250

(2) INFORMATION FOR SEQ ID NO:10:

(i) SEQUENCE CHARACTERISTICS:
          (A) LENGTH: 176 base pairs (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:10:

```
GATCCAGGCT TCGCGTTCTG ATAGCTGTCA TACGGTACGG TGGTGATTTC CGGATGCTTA        60

TCCATGATGA ATTTCTGGTG TCGTCGTACC GTTCTGTACG CCGACTTTCT TGCCTTTCAG       120

TTGATCAACG CTGGTGTATT GCCTGCTGAC CACGAACAGC GTGAGTAGGG TATATG          176
```

(2) INFORMATION FOR SEQ ID NO:11:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:11:

```
GATCTTCCGC CCAGCCTGCG ACTTCTACTT TCGAGGCCTG GATTTCGAAA CTTTGCCCCT        60

GTGCCGGCGA CGCGACAACC TTACCTGTTA CTACCACGGA GCAGCCTGTC GACAGGTGTA       120

ATACTTCTTC ATTATAATTG GGCAGAGAAT TATTAATGAC AGCCTGTACA GGATCAAAGC       180

AGGAGCCGTC ATAAACGGCG AGGAAGGAGA TGTCCAGCTT TTGAATCTCG GTCGGGTACG       240

ACCCATCCCG CGCAGTGACT TCTTGGTCAA CGGCTACTGG CCTGGAGTAC TGCGGCTACG       300

GCACACGTCA TA                                                          312
```

(2) INFORMATION FOR SEQ ID NO:12:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:12:

```
GATCCCAGAT AATCGCCAGG ATCACCATCA CCACCGTTGG CATCAACCAA GCCAGTCCCT        60

GTTCCGCCAG CGCAAACGCT GACTCCAGGC TGGCAGCATA TCGCCGAAGG ATGCTTTGAT       120

GCCGTCAAGG ATACCAAAAA GCAGACTGAT AAACATGGCC GGCGCCGATG ATACGGGTGG       180

AATTATGCCA CCATGAGCGG GTAAAACTTA ATACAACCAG TGCGATACAC GGCGGATAGA       240

TAGCGTCATG ACGGAATTGG AGATTATCAG ATCGCTCAGT CGAGGTTGA                  289
```

(2) INFORMATION FOR SEQ ID NO:13:

(i) SEQUENCE CHARACTERISTICS:
        (A) LENGTH: 240 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:13:

```
GATCAATAAT GTTATCCCGG CTTAACACTT CATCCGGGTG ATGCGCAAAA TACATCAGAA      60

GATCGATCAG CCGTGGTTCA AGAGTAATCT GGCGTCCCTG ACGACTGATC TGACCAACAG     120

AAGGTATAAC CAGCCACTCT CCAATGCGTA CAACAGGTTG CTGCATAAAA AGATGCCTAA     180

CGAGCTAAGT CATACGTATA TACACGATTG CACAGACTTT TATCCTTTGT AAGAAGCTAA     240
```

(2) INFORMATION FOR SEQ ID NO:14:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:14:

```
GATCAGAACC TTAAAACAGC GTAGACACTT TTTTGGCTTT GTGAGAAATC CACGGACAAT      60

TCCGCGAGCC AGTTATCGAC GTAGAACAGA GGAAGGGAGG AGCCCTTGCC GAAAAGGCCA     120

TCCCATGGTG AATCGGGAAC GCTCCGGTTC CCGTTAATGC CTAATAATTA TCGTAATATA     180

AACAACCGGA AATCAGTATA GGCCGCAATT TTGACGATTC ACCGAAATTG TTAGCGTGCT     240

AATTACAGAG TACAGTTAGT                                                 260
```

(2) INFORMATION FOR SEQ ID NO:15:

(i) SEQUENCE CHARACTERISTICS:
        (A) LENGTH: 314 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:15:

```
GATCGGCATA CAGCGCGTAC ACTTCATCCA GACGTTTGAG GGCGTTAACC ACTTCCGAAA      60

CGGCCTCTTC AATCGACTCG CGTACCGTGT GTTCCGGGTT TAGCTGAGGT TCCTGCGGCA     120

GGTAGCCAAT CTTAATGCCG GGCTGCGGGC GCGCTTCGCC CTCGATATCT TTATCGAGCC     180

CCGCCATGAT GCGCAGCAGG GTAGACTTAC CGGCGCCGTT AAGGCCCAGC ACATCCGATT     240

TGGGCCCAGG AGAGCTCAGG CAGATGTTTC AGATATGACG TTCAGACACT GCGAACCGAT     300

GCTGATAGAT GAGC                                                       314
```

(2) INFORMATION FOR SEQ ID NO:16:

(i) SEQUENCE CHARACTERISTICS:
    (A) LENGTH: 350 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:16:

```
GATCGCCATT CTGCTAACGA CTCTGACGCT GGCGCTGCTC TCCAGGCTGC ATCGGTTATA      60
ACATTCTGGC GACACGGGCA AAACGCGGCT GTCGCCAGTC TCTGTCAGAA ACGGTAATCC     120
ACCGCCATAA AGTAACGACG TCCGTCTTCG GTATAACCGT AGTCGTCGCG TTTGAGATCT     180
TTATCGCCCA CGTTCAGAAC GCCCGCACGC AGTTTAACGT TTTTCGTCGC CTGCCATGCC     240
GCGCCGGTAT CCCAGACCAC GTACCCGCCC GGCGTTTTTC GCTGTTTGCC TCTGTCGGCC     300
CGCTTACGCC GGTATAATTC CTGATACGTA GATGACAGTT GAGCTGACCG                350
```

(2) INFORMATION FOR SEQ ID NO:17:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:17:

```
GATCGTGCAA ATGCGCGCTA AAGGTGGCGG CGTCCATAAA GCCGGTGACT CGCGATTGCG      60
GCTGTTCCTG GCCTTGGGTA TTAAAGAACA GAATGGTGGG CAGCCCGAGG ACTTGCAGAT     120
GCTTTAACAG CGCGACATCC TGCGCATTGT TAGCGGTGAC GTTAGCCTGC AAGAGCACCG     180
TGTCGCCGAG CGCCTGCTGG ACCCGCGGAT CGCTGAAGGT ATACTTTTCA AACTCTTTTA     240
CAGGCCACGC ACCAGTCGGC GTAGAAATCA GCATAACGGT TTGCCTTTGG CCTGCGCCTG     300
ATTGAGTTCA TCCACGTAGA ATAGCCGTGA ATTGAG                              336
```

(2) INFORMATION FOR SEQ ID NO:18:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:18:

```
GATCCGCGAG GTGCGCCAGT TGCACCATCT CCAGCAATTG CGTCACTTTG TTTTAATCGC      60
CGCCGCCGCA GTTGGGCGTC GCTCGCGCAG ACCGTAGCCA AAAGCGATGT TGTCAAACAC     120
CGTCATATGG CGAAACAGCG CATAGTGCTG AAAACACAAA ACCGACTTTA CCTACTGGTG     180
AGGCGCTAAC GTCGTACGTG GAAACGATAT ACCGTGGACT GTGTCAGCCC GGCAATAATC     240
```

CCGGCTGTTT GCGGAACTAC GCACAGGACA TTGCGAGATA TTACGG        286

(2) INFORMATION FOR SEQ ID NO:19:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:19:

GATCGCGAAA GGCGTACATC TCACGGAATT CCAACCGGT ATCAACGTGC AATAGCGGGA        60

ACGGCAACGT ACCCGGATAA AACGCCTTAC GCGCCAGATG CAGCATGACG CTGGAGTCTT       120

TACCAATGGA GTACAGCATG ACCGGATTAG CGAATTCCGC TGCCACTTCA CGATAATGTG       180

ATACTTCGCA CAGTTGCGCA GTGGTGAGTC GTTTTGATCA TACGTCTTTG CATCGTTTTG       240

CTAACTGATA CGACTAGGCG GTATATCGAT GATGTGTCTA GATACGCACA TCACACCGAT       300

CCTGCAATTC ACGTACACGA TCTGC                                            325

(2) INFORMATION FOR SEQ ID NO:20:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:20:

GATCAGGTGC GGTCGGTAAT TGACAAAATA TGGGCAAATG GCCACGACAT TACCCCTTAA        60

TTGATTGGCA GCAGCTCGTG GCTGATTGAT TTTAGCCGGA GCCGGACGCT CCGATTTTGG       120

CGTCAGATAC CAATAACCCA ATCCATGAAT ACACACGACA AGTATACGGG TTACACACAG       180

TATACATCGC AGATCGCTGT                                                  200

(2) INFORMATION FOR SEQ ID NO:21:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:21:

GATCGGTTTT ACCCTTCGTC CCTTTGATAT AACGCGTGAC GCCGTTAACG TACCGCCAGT        60

GCCGACGCCG AGATAAACAC ATCCACCTGA CCATCGGTCT CCAGAGTTTC CGGGCCGGTG       120

GTTTTTCATG GATTCTCGGG TTGGCAGGGT TGCTGAACTG CTGGAGCAGG AGATATTTTT       180

| | |
|---|---|
| GCGGATCCGT GGCGACAATT TCTTCGGCTT TCTTGAATAG CGCCTTCATC CTGGCCTTGT | 240 |
| CAGCACCAGA TTGGCTATGC TTAG | 264 |

(2) INFORMATION FOR SEQ ID NO:22:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:22:

| | |
|---|---|
| GATCAGAATC TATGTTGTCA CAGATTAATA GTTTATTATA TATTTCATCA AAATAATCGA | 60 |
| CGTCAAGTTC TTTGTTTTTA TTTAGAGTGA ATACTTCCTG TCGTTTTTTA TCGTTTACAT | 120 |
| AATCGACTAC CGTAACTGCA ACATTCTTAT TTTTTTGTTT CTCTATACAT AGTAATATGG | 180 |
| TGTCAAGTTC AAATTTTATT TCTTCAAATC GCAAATCAAA GAAAAAATCT ATATTTTTAT | 240 |
| TTAAAATCGT TGTCAATTAT CTTTAAAACG ATGTTTTACG TAACATTGTC GTATATATCG | 300 |
| TCTGAGTCTA ATCAATATCA TAGT | 324 |

(2) INFORMATION FOR SEQ ID NO:23:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:23:

| | |
|---|---|
| GATCTTCGCC TACCGGCACC AGATTGGTTT GGTACAACAG AATGTCTGCC GCCATCAGCA | 60 |
| CCGGGTAATC AAACAGGCCG GCGTTAATGT TTTCCGCATA GNNNCAGATT TATCTTTAAA | 120 |
| CTGCGTCATA CGGCTCAGCT CGCCGAAATA GGTATAGCAG TTCAGCGCCC AGCCAAGCTG | 180 |
| CGCATGTTCC GGCACATGGG ACTGAACGAA AATAGTGCTC TTTTAGGATC ATACCACATG | 240 |
| CCAGGTACAG NNAGATTCCA GGCGTTTACG TAGTGT | 276 |

(2) INFORMATION FOR SEQ ID NO:24:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:24:

| | |
|---|---|
| GATCCGGCGC CGGAGCCACC ACGCCTTCAC GCGGGGCTCC GGGTTCGGCG CGGGCAGATT | 60 |

CATCAGCTTC GCCAGAATGC TCGCCAGCTT CAGGCGCATT TCCGGCGGC GGACTATCAT        120

ATCAATAGCG CCTTTTTCGA TCAGGAACTC ACTGCGCTGG AATCCTGGCG GCAGTTTTTC        180

GCGAACGGTC TGTTCGATAA CGCGCGGGCC GGCGAAGAAT CGAGACTTTT GGCTCGGCGA        240

TGTTGAGATC GCCAGCATCG CAAAACTGGC GGAAAAGGCC CATTGTCGAT CGTACTACGA        300

AATGTAGGGC AGACGCTCTG CATTTAGAC        329

(2) INFORMATION FOR SEQ ID NO:25:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:25:

GATCCCTAAC ACCCGGTCAG TTCCCGACAG GCCGGTCTTT TCTACTAGCT GACCTATCAC        60

AAAATTCACG ACAGCGCCGA TCGATAAGCG TCGCGATAAA CAGTACCGCG ATACGAATTC        120

CCATTACGAA CCAGTTCGTC TTCAAAGCCC GTAAACCAGA CAGACAGGTA AGTGTAGTAG        180

TGACTGGCGA CAAAGAAGCA CACCCACGTA CCAGCATACG TC        222

(2) INFORMATION FOR SEQ ID NO:26:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:26:

GATCAGTATA CAACTATCAG TAATTCGACG ATAGACCGAA GTGTGCTTGC TGGCGCTTTA        60

TCGTCAAGGA TAATTGCCGC TTTGACGGCC TTCGCGCTTC CTGCCAACTG GCTTCGTCTT        120

TGTGCATGAA TCACCGCCAG CGGCTCTGCC GCTCGATNTG TCGATC        166

(2) INFORMATION FOR SEQ ID NO:27:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:27:

GATCGCTTAA CAGATAATGA CTGGCGCTGC GGGGCTCCAG TACGATATAG CCGCCTAGCA        60

ACACGACAGG CGCGCTTTTA TGGTTCAGGT CGCGACGAAT GGTCATTTCA GAGACGCCCA        120

ACAGGGTCGC GGCTTCTTTA AGATGAAGTT TATCGCTGCG TTTTAAGGCC TGCAGCAATT        180

GACCAATAGC GTCGTCGCTC GGCTTTCCAT AGTTCCCCTG GAGAGTTAAA TAAGCGCTCC        240

GCACCATACA GAGCGCTTAA TATTACTCTT TTTTGCGCTA TTTAGTCACG TACCCAGCCT        300

TTTCGAATGG GCAATGCAAC AGAACGTACA CGT                                    333

(2) INFORMATION FOR SEQ ID NO:28:

(i) SEQUENCE CHARACTERISTICS:
        (A) LENGTH: 221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:28:

GATCGCGCTC AATCGCTTCC GCCGCCAGTT TAGCCGCCAG CTCCGGCGTT TTTTCATGCA         60

CCAGAGCTTT CTTAAGCGCT TTTGGCGTAG CACCACTTCT TTGGTTTGTA CTACCGGCGT        120

GGTGGCCTTC CAGCGATAAG CCTCTTTCTT TACTGGCGGT TTCCAGCGGG ACGGNGGGNT        180

GTACNNTCCG AAACCGAGGA GCGTCAGNAG AGTTATTACG G                           221

(2) INFORMATION FOR SEQ ID NO:29:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:29:

GATCGTCGTA CCGCCAACCG AGCCGCCGGG TATGTGTCGT TAAACTCTGT CGCCAGACCA         60

TAGTTAGAGG TAATAGAAGC CCCCCAGCCA AACTGGTCGT TAATCGGGGC GACAAAATGG        120

ACGTTCGGCA CCCAGGCCGT CAGCGCGATG TTATCCGCAT CTAACGTCCG ACGAGATGGC        180

GATGTCCCGC TAATATTAAC ATCAGGATCA ATATAAACGC GCCCGCTGAA AACGTCGGGC        240

GGTCAAACAT GTATTACGCG GGTGCGCTAC GTACGCATCA TCTGCGATGC GCTCACGATA        300

GCGCAGCAGA GAGAATCGTA CTGAGCTCGC GACAGTGTGA TGTCGATCGG ATCGCGCTTT        360

GCAGTTTG                                                                368

(2) INFORMATION FOR SEQ ID NO:30:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:30:

```
GATCTCCACA AACTGTTCCG GCTGAGCGAT AGCTTAAGTA GCGCATGTTT CCTCCAGGTA      60

TGGAAATGCT CTGTGAGGCG GTAAGTCGAG CCCACGTACG GCCCCTGCTC CTTCTTACCC     120

ATGCGCAGCA TCTTCTTCAT ACAGACGCGC CGCCGGGTTC GAGACCACAT TCGGGTGCAG     180

CGGGTTAGTG CCCAGCGGCG TTTCATCGCT CGTAGTGTCA GGAACGCCTT CGCATTATCA     240

TAGCAAACGA ACGTTCCAGC CCTTTCGCGT CATGAAAGAT GCGTCCGG                 288
```

(2) INFORMATION FOR SEQ ID NO:31:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:31:

```
GATCAATAAC CGCATCGTTG TAGAAGTTCC CCTGCAATTT CANNNNATCC AGATAGTTGT      60

TCTGGCTCAG GCCGACGGAA GAGAAGCCAC GGATAATCAC GAAGTCATAG GTATTGGAAG     120

CGCCGCGCTG CTTACCGTTA CACCCGCGTG TAACCCAACG CTTCTTTACT GACTGGAATT     180

GATGCATCTG CATCTCTTCG TTAGTGACCA CCGAAACCGA CTGTGCGTTT TTCGATAGTA     240

TCAGTTTGTG TGCG                                                      254
```

(2) INFORMATION FOR SEQ ID NO:32:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:32:

```
GATCTTGTTG GCTCGCCTCT CCCCTCGGAC AACACGGTAT AAAACGCGGT GATAGAGCCA      60

CCGCCGTGGA TGCCATTACC GGCACGCTCG ACCAGCGCCG GCAGCTTTGC GAACACCGAG     120

GGCGGATAAC CTTTGGTGGC TGGCGGTCGC GATTGCCAGC GCATTAGTGC ATTGAT         176
```

(2) INFORMATION FOR SEQ ID NO:33:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:33:

```
GATCGTGATA TTCAATGCAC GCCTGCAGCG TGTTTTCGAT AAGCGTGGCG ACCGTCATCG      60

GGCCGACGCC GCCCGGTACT GGCGTGATGT ATGACGCGCG CGCCCGGGCT TCGTCAAACA     120

CGACGACGCC AACGACCTTG CCATTTTCCA GACGGTTAAT ACCGACATCA ATCACAATTG     180

CGCCTTCTTT AATCCATTCG CCGGGAATAA AGCCCGGTTT ACCTACGGCG ACAATGAGCA     240

AATCAGCATG CTCGACATGG TGACGCAGAT CTTTGGTAAA GCGTGCGTAA CGGTAGTCGT     300

ACAGCCAGCC AGCAACAGTC ATGCTCATTG GGCTCAAC                             338
```

(2) INFORMATION FOR SEQ ID NO:34:

(i) SEQUENCE CHARACTERISTICS:
        (A) LENGTH: 319 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:34:

```
GATCTTGCAG CGCGCCGTGC CAGGCATAGC GCACCTGCTC ATTAAAGACG TTCGTTTTAC      60

GTGAGTTCGG TTTCGGCGTC GGCTTCTGGC GTGCTGGCGC GTTGCCGCCG CCTGTTCCGC     120

GCGAGACTTA CGCAGTCGAT CCAGCCGTGC GCGAACTGCC TGATTTGGTT AATCGCGTGG     180

GCCTATTCAT TGGCCAGGCC ACCATGCAGA TGTCCATCGT CAGGACGAGC TGCCTATAGG     240

AACGACGGGA CATAAGTCCA ATATGTGCGA GCGTCAGTAC CGTACCCTAA GTAAACTCTT     300

CAACAGAAGT AAATGCCTT                                                  319
```

(2) INFORMATION FOR SEQ ID NO:35:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:35:

```
GATCGATTTG CGCTGGCAGG TTGCTGCCGG TATTGACCTC TTTGTACATA TTCAGCGGCG      60

CGTTCTGCGA GTAGCGCAGG TTATCTTCGA TATAGGTATT AAACACGCCT TTGGAGAGCG     120

CGGCTTCATC ACCGCCGCCC GTCCAGACGC GTTGGCCTTT TTTACCCATG ATAATCGCCG     180

TGCCGGTATC CTGGCAGGTC GGCAGAATGC TTTGGGCGAT CTGCAGGTGG CACTTTTCGG     240

GGAAATGTGC GCGGAACCCC TATTTGTTTA TTTTTCTAAA TACATTCAAA TATGTATACG     300

CTCATGAGAC AATAACCCTG ATAAATGCTT CAATAATATT GAAAAGGAAG AGTATGAGTA     360

TCACATTCGG GCTATCTTTG GATTCTCGTT GACACAGAAC GAGGAAGAAG CGAGACAT      418
```

(2) INFORMATION FOR SEQ ID NO:36:

(i) SEQUENCE CHARACTERISTICS:
        (A) LENGTH: 350 base pairs
        (B) TYPE: nucleic acid (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:36:

```
GATCAAGAGT CAGGGGTAAT TTTACCTTTT GCATAGGGCG CGCATATTAA CTTCGTAACG        60

TCATATAGTC AAAGAAAAAG GCAGCCTGCG GTTGCCTTTT GCCAATAATT CGCACACATT       120

GCGGGTTACA GACTTATTTT CGCTCAAGAC GAGTCAGTAT GACAGGCTTG AAGACCGAAG       180

AGCTATGTTT AAGATGGCTC TCATCATTAC GCTATATCTG AGGGAAAAAA TATGCCCCGT       240

CTCATCCTTG CGTCTACCTC TCCCTGGGCG TCGCGCGCTG CTGGAAAAGC TGACGATGCC       300

TTCCGATGCG CGCGCGATGT GATGAACCCA TGCCGGGCAC GCGCTCAGTG                  350
```

(2) INFORMATION FOR SEQ ID NO:37:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:37:

```
TGCGACAACA CACCCGCCAA AGCCGCCGCC GGTCATGCGC ACGGCGCCTC GATCGCCGAT        60

GGTCGCTTTG ACGATGTCTA CCAGCGTGTC TATCTGCGGG ACGGTAATTT CGAAATCATC       120

GCGCATTGAG GCATGGGACT CCGCCATCAG TTGGCCCATA CTTCGAAATC ACCTTTCTCC       180

AGCAGGCTTG CCGCTTCAAC GGCGGGCATT TTCGGTCAAT ACATGGCGAA CCGTTTTCGG       240

ATACCGGGAC AGTTCCGTGG CAACGGCATT                                        270
```

(2) INFORMATION FOR SEQ ID NO:38:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:38:

```
GATCCAGTGC TTTCGCCGCG TCATCCACAA TGACGTCAAA GCCAAAGGTT TCGGCGCGAG        60

TACGCACGAC GTCCAGAGTT TGCGGATGGA CATCAGAGGC GACAAAGAAC CGGTTGGCAT       120

TTTTCAGTTT GCTGACGGCT TTGCCATCGC CATCGCTTCA GCGGCGGCGT CGCTTCATCC       180

AGCAGCGAGG CGAACGATGT CCAGCCCTGT AGTACAGCGT ACTGTTGAGT TACAGACTCA       240

AACTAAATCG TATAGATTTA GCCTACACTG ATTTACATTA                             280
```

(2) INFORMATION FOR SEQ ID NO:39:

(i) SEQUENCE CHARACTERISTICS:
    (A) LENGTH: 275 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:39:

```
GATCATCGCC TTCAAATTGA CCTGCTTGAG ATCGAAAATG AGCTGCGCTA AGTCCTCGAT      60
AGAGTAGATA GCGTGGTGCG GTGGCGGGGA GATCAGCGTC ACGCCCGGCA CTGAATACGC     120
GAGTTTAGCG ATATACGGAG TGACTTTATC CCCCGGCAAC TGACCGCCTT CGCCGTTCGC     180
CTCACTTTAA TCTGAATCAC ATCGGCATGA CAGTAGGTCG GTCACAAGCG CGACGACTCT     240
ATCGCAATAT GTCAATCCGG TCCTACATAT CATTT                                275
```

(2) INFORMATION FOR SEQ ID NO:40:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:40:

```
GATCTTTCGA CTCGATGTTG GCGACGAAGA TAAAGTTCGG CAGCAGCTTG CCCGCGTTGT      60
CATAAACCGG GAAATACTTC TGGTCGCCCT TCATGGTGTA CACCAGCGCT TCGGCAGGCA     120
CGGCGAGGAA TTTCTCTTCG AATTTCGCCG TCAATACCAC CGGCCATTCC ACCAGCGAAG     180
CTACTTCTTC CAGCAGGCTT TCGCTCAGGT CGGCATTACC GCCAATATTA CGTGCTGCTC     240
TCAGCGTCCG TTTGATTTGG CTTAGGCTCG TAGTCGCATG ACTTACGGAC TCAGAGAATT     300
GCGGTACTGT CAGATGTGAG GACCGTACAT AAG                                  333
```

(2) INFORMATION FOR SEQ ID NO:41:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:41:

```
GATCGGGCAT CGGCACGACA CCGGTATTCG GTTCGATAGT GCAGAACGGA AAGTTTGCCG      60
CTTCAATACC GGCTTTTGTC AGCGCGTTGA ACAGGGTGGA TTTCCCGACG TTGGGCAGAC     120
CGACGATACC GCATTTGAAT CCCATGATTT AACTCACCTT AATATCTTAA TAATCAACCT     180
GTTATAGAAA ACAGATTGCA GAATGGAATA CTCGCTATTA TCACGCGCGC AAA            233
```

(2) INFORMATION FOR SEQ ID NO:42:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:42:

```
GATCAAGCGT GTCCGGCGAA AACGTTACGC GTTCTCGCAG CGATACAGGT GCCGTTTTAT      60

GGTTAATACC GAGCGCTAAA AGGGTCATGT CTGCGGGAGT AGTACCAGCG TTGATATGGT     120

TAGTCTGCTT GCATCATACA GGATGCGCGT GGTCAATAAA AGAGAGAGCC CCCTTTTGGA     180

GTAATTGGCA GCGCTCGCTA ATTTGATGAT TTAAGACACT TGAAAGTAGA CGATGTCACC     240

AGGCGCCTAC ATTAAAGGCT ATACTGTACG ATAGCAAAAT TTCCGATCCG CCACTTTCAC     300

TC                                                                    302
```

(2) INFORMATION FOR SEQ ID NO:43:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:43:

```
GATCTACTTT CGGGATGGCA GCGTATCTGC CGCAATACAC CCTGATGGAT GTTATGCCTG      60

GATCTGATTA CTCTTCTTTG GGCGAAGTTT TCGACCCGGC TCTTTAACTT CTGCCCGGGT     120

CTGAAGGTCA CCACGCGCCG TGCTGTAATA GGAATATCTT CACCCGTTTT CGGTTACGCC     180

CCGGACGTTG ATTTTTATCA CGCAGATCGA AGTTACCAAA ACCAGAGAGT TCACCTGCTC     240

ACGTTTCAGA GCACGACGAT CT                                              262
```

(2) INFORMATION FOR SEQ ID NO:44:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:44:

```
GATCAGGTCC ATATTTGTCT TTGCCTTTCT ACCCGACACG TTTCGGGTGT GCGATTCGGA      60

TTAGTCCGCC AGAAATAGCG GGCCCATTGG CGGTTTTGGA AGGTCAAAAA GGTCAGGGTA     120

ATCCACCGCA ACCAAATATA GCCCTTCCGC CTT                                  153
```

(2) INFORMATION FOR SEQ ID NO:45:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:45:

```
GGCGCGTTGG CAGATTTTGC CAGACGACGG GCGATTTCGG TTTTACCGAC GCCGGTCGGC        60

CAATCATCAG AATATTTTTC GGCGTTACTT CGTGGCGCNN CTTCATCAAG CTGCATACAC       120

GCACGTTACN ATCNNGACGG AACCTTTGTA TCTGCGATAA TNNTTGTAG                   169
```

(2) INFORMATION FOR SEQ ID NO:46:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:46:

```
GATCGCTGTA GATTTTACAA GTCTTCTTCA GCGATACACG TCTGCACAGC AGGCCGAAAC        60

CGGTGTTGAT GCCGTAGGAG TACGCCTTCA GGCAACGATA TCATTGACAA CGCGACGTGG       120

CGTTAATACG TCAATGGCAT GGCCTTCCAG CGAAAGCTGT ACGATGAGAT ATGACATGAG       180

AGAGACTTAA CTGCCCCAGA GTATATATTG TGTTCATATC AGCCTTTCCT CAACAACCAT       240

CGTAAATTCA GACTTACTCA CACACATTCA CGTAGATCAT TC                         282
```

(2) INFORMATION FOR SEQ ID NO:47:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:47:

```
GATCGCGGGT CAGTGTACGC ACCGCTTCCG GCGTATTTTT CCCGCTATTA AAATAGAGCT        60

TGTCGCCAAC AATCAGGTTA TCGAGATTAA TGACCAGCAG CGTATTTTTC TTCTCAGCGT       120

CACTCATCGT TTGAGTAAAT TTGGGGGCCT AGCTTTCCCT CTTCTTCCCC GCTGGTGGCG       180

ATAAAACGAA TCCCGTAATG GGTCGGTATA TCTTTCAGAC GGCGCAGTTC CAGCATAAGC       240

CCTAATCCCG CGGCATTA                                                     258
```

(2) INFORMATION FOR SEQ ID NO:48:

(i) SEQUENCE CHARACTERISTICS:
    (A) LENGTH: 315 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:48:

```
GATCGCGACA TGCGCAACAT CTACCAGTTT ACTTAACTGA CTAAACAGTA AGTCGACCGA      60
CCGGGGACTG GCAACGGTCA ATTCAATATT TATATTCTGC GCATCGGTCG CGGCTTCCAT     120
ATTCAATGGA GCACACCTGA AAACCACGAT GGCGCACCAC GCGTAAAACA CGTTCTAAGG     180
TTTCTGGATT ATAGCGTGCC GATACATTGA CCTGATGTTG CATCATGATA TTTCACGATT     240
TCAGAGTCAT GGCGCAGGCG CACACGCAGA CATTTGAAGT CTCGATGAGA CGAGAGACGC     300
CTCAGTCACT GTCGA                                                     315
```

(2) INFORMATION FOR SEQ ID NO:49:

(i) SEQUENCE CHARACTERISTICS:
    (A) LENGTH: 268 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:49:

```
GATCCAACGT CTGGCGTAAT GCCAGCATGT CGTACTGGGT GTTGTTGCCC AGCTCCGCAC      60
GTGGGTCGCC TTTCGCCACC ACGTTGAACG CCAGACCATC TTTAATTTGC GGCGTCGGCC     120
AGCATGGTAA AGCGGTTGCT GAGTACACGC GCTTCACGGA ATACCGTGGT GGCTTGAGCA     180
CCGCTCACCT GCTTGAGTCG GCTGTTCAAC TCGGCGTAGT CCCCACATTA AGGCTGGTTG     240
TACACGTCGT TGTTGGTGTA ACCGCGGT                                       268
```

(2) INFORMATION FOR SEQ ID NO:50:

(i) SEQUENCE CHARACTERISTICS:
    (A) LENGTH: 296 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:50:

```
GATCTAAAAT TCAAATACAG GAACAGGGAG TTCTGGTGCA GAGGGTACTA TGTCGATACG      60
GTGGGTAAGA ACACGGCGAA GATGCAGGAC TACATAAAGC ACCAGCTTGA AGAGGATAAA     120
ATGGGTGAGC AATTATCGAT CCCGTATCCG GGCAGCCCGT TTACGGCGTA AGTAACGAAG     180
TTTGATCGAA ATGTCAGATC GTATGCGCTG TTAGGCGGCT GGTAGAGAGC CTTATACCAT     240
```

```
CTGAAAACTC CGTATCCGAG ATATTATAGA CTATTGGCAA CCTGAATCTC TCGATT        296
```

(2) INFORMATION FOR SEQ ID NO:51:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:51:

```
GTACACAGAC GCCTTTCAGA TTGGCGATGA CGCATCCATT GAGAACACCC CATCGGTGGC     60

GATCAGGACA TGACGCGCGC CGGCCTCACG CGCCTCTTTC AGCCGCGCTT CCAGCTCTGC    120

CATATCGTTG TTGGCATACG CTTCGCTTTA CACAAACGCA CGCGTCAATG ATAGACTGGT    180

TCAGCGCGTC GGAATATAGC GTTCGCGCAG CAA                                 213
```

(2) INFORMATION FOR SEQ ID NO:52:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:52:

```
GATCGAAACT CGCCACGTTA ATCACCGTCG CCACCACCGG CGGCCAGCGT CCGTAAAGCA     60

GCGCAATCAC CACTACGGCC CAGGCAAATC GATGCATTAC CAGATTGGCG GCG           113
```

(2) INFORMATION FOR SEQ ID NO:53:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:53:

```
GATCTTCCGG GTTAAATTGC AACAATGCTT CGCTAACGCG CAGCCAGCTC CATTTGCGGT     60

TCCTCCATCA GCGAGGATTT CAGCGTATCC AGTAGCTTAC GAATCACTTC GGCGTTATCC    120

GCTTCGTCCA AATCTTCATT AAACAACTCG GCGACCGGAC TAATATTGCC TTTTAACCAG    180

ACTTCCGAG TATGTTCATC AAGCGTTTTC ACCGTTCGAA CGGTTAATCA GCCACATTTC    240

CCCTTTCCAG CGATTCAATA CGCAAATCAA CTGCGTTGGG AAGATAACCT AGGCACAACG    300

GCAAATCAAG ACGTTGCATA CATATAAATA GCGCCAC                             337
```

(2) INFORMATION FOR SEQ ID NO:54:

(i) SEQUENCE CHARACTERISTICS:
           (A) LENGTH: 313 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:54:

GATCATAAAA CTTCCGCGTG TATATGTTGG TTGGAACCGT AGAGATATAG ACAGGTGGTT     60

CTACACAGGC GTTTACCCCT ACCGTCGCAA ACATTTCTTT AATCAGGCTT TCTCTTTTTT    120

CTTCTGATGG ATGCGAGTGA TTAAACTCAT ACATTAACGT TTTCCCACGA AGTCTTTTTT    180

CCGGTAAGCC TTCGCATATA TCGGTAAATA GCTTGCCTGC TCTTATCTTT CGGTCATGGC    240

ATGTTCATCG CGATCACTCC GTTATGATAT GTCTCGATAG CCTCGATCCA ATGATGCTAC    300

GCATCATCAC TCA                                                      313

(2) INFORMATION FOR SEQ ID NO:55:

(i) SEQUENCE CHARACTERISTICS:
           (A) LENGTH: 300 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:55:

GATCGAATTC AGATTCCATT ATCGCCATCA GATATTCCAG ACGTTCAGAT TAACGTCGGA     60

CATCTCCAGT ACGGACTGTT TATCCGCCAG TTTCAGCGGC ATATGCGCGG CGATGGTGTC    120

AGCCAGACGT GCAGGGTCGT CAATGCTATT GAGTGACGTC AGCACTTCCG GCGGAATTTT    180

TTTGTTCAGC TTGATGTAGC CTTCGAACTG GCTGATAGCG GTACGACCAG CACTTCTTGT    240

TCACGCTCAT CAATGGCTGG CGAATAAGGT ACTCGCTTCG CGAGAAATGT CGCGTGCAGA    300

(2) INFORMATION FOR SEQ ID NO:56:

(i) SEQUENCE CHARACTERISTICS:
           (A) LENGTH: 423 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:56:

GATCCCACTT CTTGAACTGC TCGAAGCAAA CGCCTTCCGG CAGATCATCG CGCGCCACAT     60

ACAGCTGAAT GCGGCCGCCT ACGTCTTGCA GGGTAACAAA AGAGGCTTTA CCCATAATAC    120

GGCGCGTCAT CATACCGGCCC GCGACGGACA CTTCAATATT CAGCGCTTCC AGTTCTTCAG   180

CTTCTTTCGC GTCAAACTCT GCGTGCAGTT GGTCTGAGGT ACGGTCAGAC GGAAATCGTT    240

```
GGAACGGATA CCTGCTCACG CAGTCAGCCA GCTTTGCACG TGCCTTATTT ATTGTTAAGA    300

TCGACTACTG TACGCCTGTC TTTGTCAGAC ATGTGATCTC ATAGCCTGGC TTTCAAACTT    360

GCTCGATATG ATCAGACTAC GTCAGTACGC TGGATGCGTC ACAGTACAGC TTAATCGATC    420

AGA                                                                 423
```

(2) INFORMATION FOR SEQ ID NO:57:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:57:

```
ACAGAATCTT TTTCACGACG TTCTCGTTAA TAACCGATAA GACGTGAGGA GTTTAGCAGA     60

TTTAGTGCTT GATTTCGTGG CTTGTTTACA GTCAAAGAAG CCGGAGCAAA AGCCCCGGCA    120

TCGGCAGGAA CNCTTATTTA TTAATAAAAT CTTCCCCAAC TAATATCTTT TTT           173
```

(2) INFORMATION FOR SEQ ID NO:58:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:58:

```
GATCCTCCGT GGCATAAGAA ATGCCGCCAA GAATCGTGAG TAAGATGTTG AAAGGATTGC     60

GATAACATAC CCACAGATGC ACCCACCACG GCGAGGGTTT CTGTGCCGGA ACGGTTTTCG    120

CCATGCTTTT CACGCGCNNT CACCTCGGCA GCGTTTAATC CTCGGTGCGT ATCAAAACCT    180

GCAGAGAGTC TCTGCTCATG CGCGACTTCA GACAGTAG                            218
```

(2) INFORMATION FOR SEQ ID NO:59:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:59:

```
GATCGAGAAA AGTGAGCATC CCTTCGATGG TAAGTTCGGT CTCATCCTCC ACACTTAATG     60

TCGGATTGTT CCCGGAACCA TCCAGCTTAC GTGTCGCTAT CAGCAATACT CGGAATCCCT    120

GCGCATTGTA ATCTTCGGTT TTCGCCAGCA GTAGCTCGCG GCGTGTTTCC GTCAAGCGCC    180
```

```
ACCACACGAT CGCCTTCGCG AAGATGGGTG GCTACCATCA TCATCTCTTC AACGGCGCTT    240

TGCAGATCAG GCATCTGTCT CATGCTGCGC ATCTCACAGA CGATACCGCG ACGTACAAGT    300

CGATGCAGTC ATCGTTATGA GCCCTTGCGA TGTGCATGAC TGCAAC                  346
```

(2) INFORMATION FOR SEQ ID NO:60:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:60:

```
GATCCTGACG AATGGCCACA ACGGAAGGCT CATTCAATAC GATGCCTTGT CCTTTTACAT     60

AAATGAGGGT ATTCGCGGTA CCCAGGTCAA TGGACAGGTC ATTGGAAAAC ATGCCACGAA    120

ATTTTTTCGA ACATACTAAG GGATTAATTC CTTGAAAGCT GGGGCGAAAA CAAAATGCGT    180

TTACTTTACC AACCACACGC AGCAGCGACA AGCGCGAAAA TCATCTGCTA CGTGAATTAG    240

TGCGTCGTTC TTTGTACAAT CTCGCTGAGT CAGCTGAAAA TCACGCGATC TGCTCGTGAC    300

TTGAAGATCT CGATTCTCGA CAT                                           323
```

(2) INFORMATION FOR SEQ ID NO:61:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:61:

```
GATCGCGCGT GGTTTGCAGC GTCGGTTCCA CCACCAGTTG GTTAATGCGG TTCGTTTCCA     60

GACCACCAAT CTCTTTCATA AAATCTGGCG CTTTGATACC CGCCGCCCAC ACCATCCAGA    120

TCGGCCTGAA TATATTCACC TTCTTTCGTA TGCAGACCGC CTTCGGCGGC GCTGGTGACC    180

ATAGTTTGCG TCAGCGCGAA CGCCAGTTTG GTCAGTTCAT TATGCGCGGC GTGGAGATAC    240

GCGCGCACGA GGCAGATACG CGCAGTCACA CGAGTC                             276
```

(2) INFORMATION FOR SEQ ID NO:62:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:62:

```
GGGCCAGAGG TATGACTCCA CCAGACCGTC AAAGACGGCG TTGCGTCGTG CTCAGCATAG        60

AAGCCGCGCG CCTGCTCAAC GGTCAGGTGC AGCATTATTA GTGCCCAACA ATTTTGAACC       120

CTGCAGCTTC AAACGCGCGA AAGATCGTCC AATACGTTCT CCGACC                     166

(2) INFORMATION FOR SEQ ID NO:63:

(i) SEQUENCE CHARACTERISTICS:
        (A) LENGTH: 425 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:63:

GATCTTTAGC CGGGCAGACC TCTACGCATA AATTACAGCC AGTACAGTCT TCCGGCGCGA        60

CCTGCAGCAC ATATTTCTGG CCGCGCATAT CGCGGACTTC ACGTCCAGCG AATGCAGACT       120

GGCTGGCGCG TTCTCCATCG CCTGCGGGGA AACGACTTTC GCACGAATTG CCGAGTGAGG       180

GCAGGCAGCG ACGCAGTGAT TACATTGTGT ACACAGTTCC TCTTTCCAGA CAGGAATCTC       240

TTCGGCGATA TTGCGTTTTT CCCAGCGGTG GTGCCCATTG GCCATGTTCC GTCGGCGGCA       300

GGGCGGAAAC AGGCAGTGCG TGCCGAGGCC CGCCAACATG GGCCGTAACG TTTCAGAAAT       360

CGCAGTGAGA CGGCGGCATC CCATAGGATT ACGCTGAGAT CCAGATCTCC AACATCTCAT       420

CTAAA                                                                  425

(2) INFORMATION FOR SEQ ID NO:64:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:64:

GATCTACCGG GTGAGCGTAT AACCNATCTT AATCCCTCCC GGTTAGGTTG ACATTAGGAT        60

CCTGTTCCTT TCGGGTTATA CTGCGCTGAA CGCGGGTCCA GTCCAACGTG AATACGGCAG       120

ATAAACCAGA CCAGCCAGTA ACACAAAAAT AAAAATTCGC AGCTTCCACA AAGCCAACCC       180

AGCCGCTTTC GCGATAGAAG TCGACCATGC GAACAGATAC AGCGCTTCAA CGTCGAAGAT       240

AACGAAGAAC ATGGCTACCA GGTAAAATTC GGAGACAGGC GTAAGGCGCG CCGGTGCGAC       300

CATTCATCTC CATCCTTTGA ATTACGGACA GCA                                   333

(2) INFORMATION FOR SEQ ID NO:65:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (ii) MOLECULE TYPE: DNA (genomic)
```

(iii) HYPOTHETICAL: NO (iv) ANTI-SENSE: YES (xi) SEQUENCE DESCRIPTION: SEQ ID NO:65:

TTATCAATAC CCGCATTTTT ACTGAAACCG GGCGTGATGT TTTTGGCTTT GACATTGCGA      60

ATGACGAAAT GTTTGCCATT TTCTACGTGC ACAAGCTGTC GGCAATCAGA TCCGGTAATA     120

TTGGCCACCA CAAAGTTTTT TACTGCCTGG TCTTCAGGAT AACTGTTGTC ATAGGTGCTA     180

CCCGCCAGCC CGATCCCCCA GTTGATTTTG CCATTGGTAC AATTAATGCG TTCGATGACA     240

TGATCGGAAA TCAGGATGTC GCGGTCGTGA TCGCGACATT CCACTCATGG CGTCCCCTGT     300

AATCGCTAAG CGCTATCGTA ATCGCGCGCA TCCATTGTTA TGAATCCTGC GAGATGGCGA     360

GTGCGTGGTA CGGA                                                      374

(2) INFORMATION FOR SEQ ID NO:66:

(i) SEQUENCE CHARACTERISTICS:
            (A) LENGTH: 296 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:66:

GATCCTGAAA TGCCCATCCA CGCCAGCTTG GGTATAGAGC AATCTGGCAG TATAAGATTT      60

GGGATGTATT TTGGCCGCAG CCGCAAAAAA CGCGTCTGGG CGATTCGGAC AACCAGAAAG     120

AGGCGCTCTG TAATGCGGTC TGGGCTATGG GACGAATTTC CAGATAATAG TAAACGATTA     180

ACCCTACACG AAAGCGTAAC AGAAGCGCAT AACGCCTTTA AAAACCACAG TAACACGCCT     240

GCATTATAGT TTTTCTTACT CAACATCTAT CGTTCGCATA CCGGATGTAA TAGGCT         296

(2) INFORMATION FOR SEQ ID NO:67:

(i) SEQUENCE CHARACTERISTICS:
            (A) LENGTH: 178 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:67:

GATCGGCAAA GGTACCGGTG GTGCCGTCGT AGTTTTCTCC GCGCCGGGCG TTAACGTTCT      60

GGCCCAGCAG GTTGACCTCA CGCGCGCCCT GGCCGCTAAC TGGGCGATTT CGAACCGGAT     120

CATCGTCTCA GGGCCGGCTG ACTTCTTCGC CGCGGGTATA CGGCGCACAC GTAAGTAC       178

(2) INFORMATION FOR SEQ ID NO:68:

(i) SEQUENCE CHARACTERISTICS:
            (A) LENGTH: 327 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:68:

```
GATCAAAAGT TTTCTGCGCC GCCTCGTTCA TCAGTTTATA AGGATTGCTC TGATCCGCTG     60

CCGTTGCTGC GCTTAATGGC GCAATGACCA GCAGGGCCAC CATCATCAGT CGTTTAAACA    120

TGCCTCAATT CTCCTGAGAT TATTTCGTTT CGCCCGCGGG CTTGTGGCTT CAGTATGACC    180

TTCCGTTGCG GGCTGGCGCA TCGCAGAATT CTTATTGTCG TCGCCTTCGT GTTATAAGGA    240

ACTGCCAATC ATATCTCCAG CACATGCAGA CGGTCTGATC GTACTGCACG CTAGATAGAC    300

GTCAGACTCA ACACAACGAG CTAGCGA                                        327
```

(2) INFORMATION FOR SEQ ID NO:69:

(i) SEQUENCE CHARACTERISTICS:
            (A) LENGTH: 375 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:69:

```
GATCCAGCAG GTTGATTTTT GTTTCTTTGT TAGGAACTAC CGGGGTACTG CTTTCAGGTG     60

TGACAATTTG TTCAGACATA TGCTATTCCG GCCACGTTAT TACACGTTAT GGCCCCTGGA    120

GGTTGAAAAA AGAAACGCCC CGGTAAGCTT ACTGCTCGTC CGGGGGCGCT GCATTGTACA    180

AATTCTGGCG TAAGGAGTCC ACGTCTGCAC GCGCATTAGC AAAAATAATA TTTGAACCGA    240

TAATTTATCG CCAACGCATT TACAGCGTGA AAGACGAAGG AGATTAACGG GTGGGGCCA    300

CTCGCTTCAC GAGAAAAGCG ATTCGGCTGG CGATTCAGCG AATCGACGTG TGCGTTCAGT    360

ACTATCACGT AGTCG                                                    375
```

(2) INFORMATION FOR SEQ ID NO:70:

(i) SEQUENCE CHARACTERISTICS:
            (A) LENGTH: 298 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:70:

```
GATCGGACGG CGCCTTATCT TCTTCAATAT CGCGCGTACC GTAGAAACCT TCAGGCAAGG     60

TCGCTCAGCG ACAGCCTGCT GGCTGAGTCC GAGTTGTTCA CGGGCATTGC GCAGACGAAC    120

GCCGGTGGTT TGTGCTTCAT TTTGGTCGTG CGTTGCTTCA GTATTCATTC GCTACAGCTA    180

ACGGTACGTG TAAATTAGGA TTCAGGCGCC GACGAGCGTA ATGCCGCCAC GCGCAAACAT    240

CGTAGTACTT AGTCAGACAG TATACGTTAG CGCGCGATAC AGCTAGAACG CTAACTGT     298
```

(2) INFORMATION FOR SEQ ID NO:71:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:71:

```
GATCTCACCT TTTTTTAGCT GCGGCATCGC TTCCAGAGTG GCGACCGCCG GGTACGGGCA      60

AGGTTCGCCA ACCATATCCA GACGGTAATC AGGGACGATA TTTTTCATAC AGATTCCTTA     120

GCAGGCGTCA GCCCGCACGG CGAAAAAACG TTTTTTTCCC AGCCGATGAT TAACATTCAG     180

TGGTAAATAA CAACAAAGTA GGTGACACGC AGACCGTAGG ACCAAGTATT CAGC           234
```

(2) INFORMATION FOR SEQ ID NO:72:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:72:

```
AGCTCTGATT TCGGTAGCGA TACGTCATCC ATCAGATTCG CCAGCGGATG GACAAACGGC      60

AGGATGACCA GGCTGCCGAT CAATTTGAAC AATAGGCTGC CGAGCGCTAC CGGACGCGCG     120

GCAGCATTGG CGGCGCTGTT ATTGAGCATC GCCAGCAGCC CCGATCCCCA GATTGGCGCC     180

GATGACCAGG CACAACGCCA CCGGGAACGA TATAATCCCG CCGCCGTCAG GTCGCCGTCA     240

GCAACACCGC CGCCCACTGG GAATAACTGAT AATAGCGAAC ATCCGGCCAA TAGCGCATCA    300

GCATATGTGC CTGAGAG                                                    317
```

(2) INFORMATION FOR SEQ ID NO:73:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:73:

```
GATCGAGGGC ACAGGAGAAA CGGGCATTTT CGCCGCAATT AGTTGACCTG ATCTCCCAAG      60

ACCAAATTTT CCTCAGCCGG AATATACCAG AACTGGTCGC GATATCCGCA AGATCGCGCT     120

TCACGGCGTC GCTT                                                       134
```

(2) INFORMATION FOR SEQ ID NO:74:

(i) SEQUENCE CHARACTERISTICS:
    (A) LENGTH: 387 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:74:

```
GATCGTAATG TGCGGCCAGT TCAAAACCGA AGCGGCTATA TAACGCCGGA TCGCCCAGCG    60
TCACGACCGC CGCGTAGCGA ACTCGTTGAG CGAATCCAGC CCTTCATACA CTAACTGGCG   120
CGCCAGCCCT TGCCCGCGAT ACTTTTCATC GACCGCCAGC GCCATGCCGA CCCACTGTAA   180
ATCTTCGCCT GCACATCAAC CGGGCTAAAG GCGACATAGC CACACTGACC TTCATCATCG   240
TGCACAGTCG AGGTAGAAAA CATCTCACGA AATCGTGAAC AGCTTGCTTC GCATGTTTCG   300
ATGACGGCGT ACACGCGATC AATACAGCGC ATCATAGATT TATGATAGAT GTATAGAGTG   360
TGTCTAGAGT TTATCGCTAC ATCGAGT                                       387
```

(2) INFORMATION FOR SEQ ID NO:75:

(i) SEQUENCE CHARACTERISTICS:
    (A) LENGTH: 189 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:75:

```
GATCGTAAGG ATTGACGATT AACGCCGACG TCAGTTCATT CGCCGCTCCG CAAACTGTGA    60
CAGTACCAGT ACTCCAGGGT TAGCGGGGTC CTGCGCGGCG ACAAACTGTT TGTGGACCAG   120
GTTCATCCCG TCACTCAACG GGTTACTAGC CCGACGTCTG AATAACGGAA TATACTTCAT   180
TAACAGTTT                                                           189
```

(2) INFORMATION FOR SEQ ID NO:76:

(i) SEQUENCE CHARACTERISTICS:
    (A) LENGTH: 217 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:76:

```
GATCACGAAT ATTCATTATT CATCCTCCGT CGCCACGATA GTTCATGGCG ATAGGTAGCA    60
TAGCAATGAA CTGATTATCC CTATCAACCT TTCTGATTAA TAATACATCA CAGAAGCGGA   120
GCGGTTTCTC GTTTAACCCT TGAAGACACC GCCCGTTCAG AGGGTATCTC TCGAACCCGA   180
AATACTAAGC CAACCGTGAC TTTGCGACTT GGTTTTT                            217
```

(2) INFORMATION FOR SEQ ID NO:77:

(i) SEQUENCE CHARACTERISTICS:
        (A) LENGTH: 275 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:77:

```
GATCCCTTCT TTTGCTGATG CAGTAGCGGA CCAGGCTACC ACAAGGGGAA TGATGCAGAC      60
TGCGAAAAAG TTTTTCATTT CAGAACCTGC CTTAATATTG GGCTAAAAGA CAAGTTTCAC     120
GGTATAGGGT ATGATATAAC GATTCAATAA ACGAAGCCCA AAAAACGGTC TATTGTAACG     180
CTGGGTTTCT GTAAGCGGGT AAAATGAGAT GAGATTTAAT AACATCAGAT ATCTCGGATG     240
AATCACTCTC GAATCCGCAG CGTCCATCTA CGTAT                                275
```

(2) INFORMATION FOR SEQ ID NO:78:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:78:

```
GATCTTCATA CAGGCCCAGA TAGCCGTCAT AAATGCCCAT GACTTCCAGC CCTTACGTCA      60
ACGCTGCAAC ACAACACCGC GGATTTTTGA TTCATTCTCT T                        101
```

(2) INFORMATION FOR SEQ ID NO:79:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:79:

```
GATCCGCACG GATAAAAACT CGTTTCCCGG CCAGATCCAG ATCGGTCATC TTAATTACAG      60
ACATGGTGAA TCCTCTCAAT GATGCTTAAA GTTTTGTCGA CGCTGACGCG TGAGCCTGAA     120
ACCAACTGCG GCCATCGCTA ACGTGGTGTC GAGCATCCTG TTAGCAAAGC CCCATTCATT     180
ATCGCACCAG ACCTAGCGTC TTGATCAGTG GGCGCACTGA CCGGGTTGGG CATCACATGG     240
CGTGGCTGGT AATTTGGACG GTGCATGTAC TCATGATGGC TTGGTTGGCC GGATTGCTTG     300
CTT                                                                  303
```

(2) INFORMATION FOR SEQ ID NO:80:

(i) SEQUENCE CHARACTERISTICS:
    (A) LENGTH: 257 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:80:

```
GATCGTGACC CGGATAACGC TCATCATCTT TGGTCAGTTC CGGCGGCGTC ACGGCAAAAC    60

CGCGGCGCCA CTGTTTAACC TGCTCGTCAC CATATTTTTC TGCCGTTTGC GCTTTATTCA   120

GCCCCTGCAA CGGCCATAGT GACGTTCATT GAGTTTCCAG GATTTTTTCA CCGGCAGCCA   180

CGCTGATCCA GTTCATCCAG TACGTTCACA GGCTATGGAT AGCGCGTTTC AAGTACGGAA   240

GGTAGGCAAA TCAAGCG                                                  257
```

(2) INFORMATION FOR SEQ ID NO:81:

(i) SEQUENCE CHARACTERISTICS:
    (A) LENGTH: 290 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:81:

```
GATCGAGCAG GCATTGCAGC AGCAGACTTT TGCCCTCCCC GCTGCCGCCA ACCAATGCCA    60

CCATTTCGCC GGGCGCGATA TCAAAAGAGA CATTCTGTAA TAACGGCGAC CAGCGTCTCG   120

CGCCATACCA GCGATAACGG CGCTTTCCAG CGTAACCTGT TGTAAACTCA GATACGTCAC   180

TCCTTAGCAC AGCCGCTGAA TGGCGGAAAC TGTCGAAGAG CATCACAGCG TGAATAACAT   240

TAGGCCGGGA ATAGACAGCA CAGTTCATGG CTAATAACGT ACCGTCGAGA              290
```

(2) INFORMATION FOR SEQ ID NO:82:

(i) SEQUENCE CHARACTERISTICS:
    (A) LENGTH: 233 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:82:

```
TGCAGATCCA CCTGGAACGG CGGGATGTTG ATCACCTGGG AGGCCAGACC GCTATTACGG    60

CGCATTAACG CGCCATTACC TCTTCGATGT GGAATGGCTT CGTCACGTAG TCATCGGCCC   120

GGAGCTGAGA ACCTCGACTT TATCCTGCCA GCCTTCGCGC GCGTTAACAC CAGAACCGGC   180

AGTGAAACAT CACTCGTGCG CCCACGGGTA TTAAGGAAAG GCCGTCTTCA TCC          233
```

(2) INFORMATION FOR SEQ ID NO:83:

(i) SEQUENCE CHARACTERISTICS:
    (A) LENGTH: 284 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:83:

| | | | | | |
|---|---|---|---|---|---|
| GATCTCATCA | AAACGGTTGA | GTACCAGCGC | CAGGGTCATA | CCCGCCTGGT | TCAACGCCGT | 60 |
| CAGGTGCGCC | AGTTGTTGAC | GGGCGGTCAC | GTCAAGCCCG | TCGAACGGTT | CATCAAGGAT | 120 |
| CAATAACTCT | GGCTCAGACA | TCAGCACCTG | ACACAGCAGC | GCTTTTCGCG | TCTCGCCGGT | 180 |
| AGAAAGGTAT | TTAAAACGCC | TGTCGAGTAA | AGCGGAAATC | CGCGAACTGC | TGCGCCAGTA | 240 |
| TCGCACAGCG | CAGGATGGTG | ACATATCCTG | AATATTCGCG | TAGT | | 284 |

(2) INFORMATION FOR SEQ ID NO:84:

(i) SEQUENCE CHARACTERISTICS:
    (A) LENGTH: 367 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:84:

| | | | | | |
|---|---|---|---|---|---|
| GTTGCGATTA | TCCCGCAGCG | CCTGCTCGAA | CAATTGGATT | TGCTCAGTGC | TTTCATGCCA | 60 |
| TAACCAGAAG | GTACTGATTA | ACTGGAACAC | CAGCAGAATA | AGACCAATTG | TCAGCATTAA | 120 |
| ACGCTGGCGA | AGGGTCACTG | CTCTTCGCTG | AAAACGCATC | AGGCTCACTT | AGCTTTCCTC | 180 |
| AGTGGCAACC | AGCATGTAGC | CAAACCCGCG | AACCGTGCGA | ATGCGACTTG | CCGACTTTGT | 240 |
| CGCGCAAATT | ATGTATAGCA | CTTCCAGAGT | GTTGGTCGAG | GGTTCGTTAT | CCCAGTTGTG | 300 |
| ATATCGTTAT | AAAGAATTTC | CGGTGCACGA | CTGCCTGAGA | CTAACCGTGA | GAGCACGTAT | 360 |
| CTAGCTC | | | | | | 367 |

(2) INFORMATION FOR SEQ ID NO:85:

(i) SEQUENCE CHARACTERISTICS:
    (A) LENGTH: 320 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:85:

| | | | | | |
|---|---|---|---|---|---|
| GATCGTTGAT | CGCCTGGATA | ACAACCTGCT | GCTGCTCGTG | ACCGAATACC | ACCGCGCCCA | 60 |
| GCATAGTGTC | TTCGCTCAGC | AGTTCAGCTT | CGGATTCCAC | CATCAGCACA | GCCGCTTCGG | 120 |
| TACCGGCAAC | CACCAGGGTC | CAGCTTGCTT | CTTTCAGCTC | GTCTGGGTCG | GGTTCAGCAC | 180 |
| GTACTGGTCA | TTGATGTAAC | CTACGGCGCG | CGATTGGGCC | GTTGAACGGA | ATGCGGACAG | 240 |

CGACAGCACG ATGCGATCAT CGCACGATGA TCAGGTACTG CGTACGAACG ACGTCCGATA      300

ACTCGATGTA CAGCTCGGAA      320

(2) INFORMATION FOR SEQ ID NO:86:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:86:

GATCAATAAA TACTTTACGA ACTTCACTGG AGATTTCCCA TTTAGTGTCA TTTGGGCAGT      60

TTATAAACAA ACGCGCGGTA GTATAAAGGC AAGCCAGACG CATTGATATA CCCGTTAACG      120

CCGACGGGTG ATAAGGAGAT CGACCGTTAT GGCTTTTAAA CCTGGCAAAT AGGATTGCAT      180

TATTCCAGCC ATGAAGCGCT GGCCATCGCG TTATTCACGC GCATCGGCTG ACACGCACTG      240

TGCACTGCG      249

(2) INFORMATION FOR SEQ ID NO:87:

(i) SEQUENCE CHARACTERISTICS:
        (A) LENGTH: 275 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:87:

GATCGCCTTT TGCTGCCAAC GCTGCGGGAG AAAGAGCAGA AAGAGCGAAA ACAGCTGCGA      60

CAGCCGCCAG AGTCGATTTG AGCATGAGAT TTCCTTAAAG AGAGCAGAAA TAAAGCAAGT      120

GGAATGATTT TAAAGAGCCT TCTGGGCCAG GCAGCCTTTA CTATTTACGT ATATGAACAA      180

TGTACGTTAC GACGACGCGT ATCTGCATAT GATGTGACAA CATAATAATA AATGCATGAC      240

ATACTATACT ATATATTAGC TACAAGCTAT GCTCA      275

(2) INFORMATION FOR SEQ ID NO:88:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:88:

GATCGCCGCG AACCAGCAGA GCCACCAGCG GAGACTTGCT GTCTTTCACC GCTTTCACCA      60

GCAGCGTTTT TACCGTTTTT TCAATTGGCA GGTTGAATTG TTCCACCAGC TCCGCGATGG      120

```
TTTTGGCATT TGGCGTATCG ACCAGAGTCA TTTCCTGCGT CGCGCTGCGC GGCTTTGCGG      180

GATAGCTTCT GCAGTTCAAT GTTAGCCGCG TAATCAGAAA CATCAGAGAA AACGATATCG      240

TCTTGCGCTT TGGCAGCCTG GAATTCATGC TGGTTGGCGA TAGACGTATG CTGTACGGGA      300

ATCAGCCATA GTGAGATACG CTATA                                           325

(2) INFORMATION FOR SEQ ID NO:89:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:89:

GATCGATACG ACGTTCAAAG GATTCAAACC GCGCCATGGC TTCATCCAGT TGCCGCTGT       60

CAAGCTGACG ACGGACATCG CGGGAAGAAC TCGCCGCCTG ATGACGCAGC ATCAGCGCCT     120

GCGGGCGAGC GCGCGTGTTT CGCTGAGTTT GTTTTCCAGC GTCGCCAATC TCTTTCTTCA     180

TGCGCGCAGT GTCATCACAG CGTGACTTCT GTTCAGCTAG CATAATCGTC                230

(2) INFORMATION FOR SEQ ID NO:90:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:90:

GATCCCATCG CTTTTTCAGA TATCATGCAC TTTTTGCACT CAATCTGCGG CAAATCCGAC      60

CACTTTTTGC TCAGCCAGAA TGCAGTATTT CCGTCATACA TCGATTAGCT ACGACTCTAC     120

GAACTACCTC GACCACAAGA TCACCG                                          146

(2) INFORMATION FOR SEQ ID NO:91:

(i) SEQUENCE CHARACTERISTICS:
        (A) LENGTH: 184 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:91:

GATCTTTGTT AATAACAGTG AGAGAACCGT ACGAATGTAG AAGAACTCCC GCCAGGCGGC      60

AACATCTTTC ATAGTAGACC AAGCGTTAAC CCCTGCTGAT GTAAAAACGC TTCTATCTCT     120

TGCGCACCAC GGAACGGAAG GTTGCGCGCC TTTAGCGCTT ACGGCAATAG CCGCGGCGGA     180
```

TGGG                                                                                    184

(2) INFORMATION FOR SEQ ID NO:92:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:92:

GATCAAACAC ATGAATACCG AGGCCTTTGA GTTTTTCAGT CGAGGCGTCC GAGCTGGAGA      60

CCGCGCCTTC AATCTGGCCT TTCATTGTGC CCAGCGCATC AATAAAGTCT GCGGCCGTTG     120

AGCCTGTACC AACGCCCACA ATGGTGCCGG GCTGTACTAT CTGAAGTGCC GCCCATCCTA     180

CCGCTTTTTT CAGTTCATCT GCGTCATAGA TCGTTAGAAT GTGTGTGAAA TACGCCGCAT     240

TATAGAACAT GTCCGGGAAA ATCTCGGTCG TACACAGCTA CGATTCGATT GCGCGCAATT     300

TTGAGGGAAA A                                                         311

(2) INFORMATION FOR SEQ ID NO:93:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:93:

GATCCTCGAT TAGGGGAGGC GCTAATTGAA TGTGGCGAGG TGTAAGAAAG CAGAAAAGCA      60

AAGTGGGTTC TCGTTGCTCT GCATGTCGTC AAATTCAATT AAACGCATAA AAAAACCCCG    120

CCGGGCGTTT TCTTCAACT TCCAGGCGAT TACGGCGAAC GAAGTCGATG TGAGTCAGCT     180

TCGGTTTGTA AGCGTGACCG TGTACAGCCT GAGCTTTAAC TTTTACTTCT TTACCGTCAA    240

CAACGAGGGT CAGAACTTCG TGTAGAATTC AGCTTTAGCT TGCATGTTCA TCACCTGGTC    300

GTGGTCAGTT CGATAGCAAT CGGGCTTCAG AACCGCGTAG ATGATTGCCG GACTGTAGCG    360

CGCAGGCGGC AGCTCCTACA TGCTCTTACG TACTCTGCGT GATAGTAACA TTAATCTCTT    420

ATATCTGCAG ACTGCACGAG ACTCGTCG                                        448

(2) INFORMATION FOR SEQ ID NO:94:

(i) SEQUENCE CHARACTERISTICS:
        (A) LENGTH: 359 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:94:

```
GATCATATCG ACGGTATCGG CGTAATTATT TTGCAGATGG CGTAACACAT CCAGATTATC    60

TCCGGTCAGA AAAAGATTAT GGCTGTTTTT ATTTTCTGCC AGAGTATTGT GTTCCACGTC   120

AGGAACGATA ACGGTAACGG ATTTTTCACC CGCCTGTTTT TTTGCCGTAA TCTTTGCCAA   180

TAAAATCAAT CTGATAACCG CTAGTCAGCT CAATATTACG CGCTTTCAGG CGCTCAAATC   240

TGGCGAGATC AATCCGCCTT TCGCGATCAG TTCGCCCTCT CGTTATAGCG GATCGCGGTA   300

AAAATTCCGC GGTAATCGCA GTTGTAACTC AGACAGAAGC GCGTATTCGG CGCAGACGC    359
```

(2) INFORMATION FOR SEQ ID NO:95:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:95:

```
GATCCAGTTT AACCTCTGGC TGCCAAATCT TTCTGGAAAA CATGCGGTGC GTTTGGCGCT    60

TCGAAAGAAA CATCCTGGTA TAGATACGTT GGATCTGGAA AGCCATTTCA GTGTTATTTT   120

TGTTCTGACA TGTGTAAAAC CCTTTAGTGT TGTTCCTTAA ATACTTGAGT AACGCCTTAA   180

CGCAACAGCG GATCCAGTCC ACCACGCGCA TCCAGCGATA CAAGTCGTCA CAAGCGCAAT   240

GTGCTGTGCC TCAATCAAAT TTGCGACGTC GTCGCACTAC GTTGATATCT TTACGTCA     298
```

(2) INFORMATION FOR SEQ ID NO:96:

(i) SEQUENCE CHARACTERISTICS:
        (A) LENGTH: 217 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:96:

```
GATCGTAAGA GTCAGAAATA AGCAGGCGTA ATGTTGTCAT AGTGGTTTTC CTTACCTTTA    60

TTAAGCCGTC ATTTTACTCT TTTTCCTCAC GCTCTTCCTC TTCCGGAACA GGCTTGCTGG   120

CCGTTAGCAG GAAGGGCGAC TGCTGCCAGC GGGTGCGTTT ACCTTGTAGC AAGGTGNNNC   180

AGACACCACG CCTATCGCAG CGAGAGTAGC AGCATCA                            217
```

(2) INFORMATION FOR SEQ ID NO:97:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:97:

| | | | | | |
|---|---|---|---|---|---|
| GATCGAACTC | TTTAAGCAGC | ATCTTGGTAT | GGAAAATATT | TTCCTGATAC | ACGTTTACAT | 60 |
| CCACCATGTC | ATACAGCGAC | TTCATATCTT | CCGACATAAA | ATTCTGAATA | GAATTAATCT | 120 |
| CATGATCGAT | AAAGTGCTTC | ATACCGTTGA | CGTCGCGTGT | AAAGCCGCGC | ACGCGTAATC | 180 |
| GATGGTGACG | ATATCGGACT | CTAGCTGGTG | GATCAGGTAA | TTGAGCGCTT | TTAGCGTGAA | 240 |
| ATCACCCCGC | AGGTTGACAC | TTCGATCGTC | GGCGGAAAGG | TGCATAGCCC | GCCTTCCGAT | 300 |
| CGCTTCGATA | GGTATCGACG | CAGATATGCT | CTATG | | | 335 |

(2) INFORMATION FOR SEQ ID NO:98:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:98:

| | | | | | |
|---|---|---|---|---|---|
| GATCGTCGTA | GCTGCCGGCA | TTGTGGTTGG | GTAAATACTG | GCGGCAAAAC | GAGACTACGC | 60 |
| CAGCGTCTAT | CTCTACCATG | GTGATGGTTT | CGACGTTTTT | ATGCCGGGTA | ACTTCACGTA | 120 |
| GCATTGCGCC | GTCGCGCCGC | CGATAATCAG | AACGCTGTTT | CGCATGACCG | TCCGCCACAG | 180 |
| CGGGGACATG | GGTCATCATT | TCATGATAAA | TAAACTCGAC | GCGTTCGGTC | GGTCTGTACC | 240 |
| AGCCGTCCAG | CGCCATCACG | CGGCCAAAAG | CGGCTTTTCA | AAGATGATTA | AATCCTGGTG | 300 |
| ATCGTTTTCA | TGATACAGAA | CTTGTCTACG | GCAAGTCATG | ACCAAACTGG | TC | 352 |

(2) INFORMATION FOR SEQ ID NO:99:

(i) SEQUENCE CHARACTERISTICS:
        (A) LENGTH: 127 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:99:

| | | | | | |
|---|---|---|---|---|---|
| GATCTGTTTC | GGGAAGTGAA | CTTAAGGCCT | CCGCAATATC | ATTTATATAA | ACTGACATGG | 60 |
| CATTTTTAAA | CTGCTCAGTA | CTGCGTTTAC | ATTTGTGGAA | GATAGTCTCT | GAGAGCAGAG | 120 |
| TTTCTTT | | | | | | 127 |

(2) INFORMATION FOR SEQ ID NO:100:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:100:

| | |
|---|---|
| GATCGGCAAC CTGCATTGCC AGTTCGCGGG TTGGCGTCAG GATCAGAATG CGCGGCGGCC | 60 |
| CCGATTTTTT ACGCGGAAAG TCGAGCAGGT GCTGCAACGC CGGCAGCAGA TATGCCGCCG | 120 |
| TTTTACCGGT GCCTGTCGGC GCAGAACCGA GTACATCACG GCCATCGAGC GCAGGCGTAA | 180 |
| TGGCGGCGCT GAATGGCGTC GGGCGAGTGA AACCTTTATC CTGGAGGGCA TCCAGACAGG | 240 |
| CTTTCGTCAG ATTCAAGTTC GGAAAAAGTG TTACAGTCAT GTCTACCTCT GTGTGGGCGC | 300 |
| TGATTATAGA CTTACGCGCA TCTCATCTGT GATGATATCT CTCAG | 345 |

(2) INFORMATION FOR SEQ ID NO:101:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:101:

| | |
|---|---|
| GATCCGGGAC ATTCACGTTG AGAATACGCC CGGTACGCAA CGGCTCCCGG CTTAACCCTC | 60 |
| GCAAAAGCGC ACAAGTCACG GCCGCAGCGA TACATAATGC TGATAGCCGT TAAGGGAGAC | 120 |
| CGCTAATGCC GGAAAGCCGA GATGACGACC TTCATCGCGC GCACAGTACC GGAATAGATC | 180 |
| AACATCATCG CCAGATTCGG ACCGCGTTAT ACCGGAAACG ACATATCGGT GACGATTAGC | 240 |
| TTACGCAGAT | 250 |

(2) INFORMATION FOR SEQ ID NO:102:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:102:

| | |
|---|---|
| GATCCCGGCT TACGACGGTT GGCTGGATGA CGGTAAATAC TCATGGACTA AGCTGCCGAC | 60 |
| ATTCTACGGC AAAACCGTCG AAGTCGGGCC GCTGGCGAAC ATGCTGTGTA AACTGGCTGC | 120 |
| AGGTCGTGAA TCCACGCAGA CCAAGCTCAA TGAAATCATT GCGCTTTATC AGAAGCTGAC | 180 |
| CGGCAAAACG TCTTGGAAAT TGGCGCAACT TCACTCTACG TGGGTCGATA CATCGGGCGT | 240 |
| ACCGTTCACT GTTGTGAACT GCAAAACATA TTGCAGGATC ATACAGCTGA TTGTAATATC | 300 |
| GGCAAGGATT ACACCAGTTT GAGACGGCAA TCG | 333 |

(2) INFORMATION FOR SEQ ID NO:103:

(i) SEQUENCE CHARACTERISTICS:

(A) LENGTH: 284 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:103:

```
GATCCAGCCA GACGGAACCC CACGGCGGCG GAGACGGCAG AGCGTAAGGG CCGATAAACA      60

GACGCTGCCA GGCCTGTGCA ACGACTCTTC GCTGTGGGTC TTAAACATAG CCGCCACAGG     120

GCAAGGCTCG GCATCAAGCG GCCACTGCGC CTGCAGTCGT CGTTTAATAG TCGTCCTGGA     180

CCAGAGGAGC GGTTTCGTGG CTTTCCGCGA ATAATAAAAC AAGTGCCAAG AACAGTGTTA     240

CTGCAAATCA TCTCGTTGTA AAAGTGTAT TAAACATCCG TAAA                       284
```

(2) INFORMATION FOR SEQ ID NO:104:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:104:

```
GATCAACGCA AACAATCAGA ACCTCTGCTT CATTTAGCAG CGTGTTCTCT GCGTTGACAA      60

TGCGTTGCGT GAAAACCAAA GCGGTGCCAC GCATTGACGT AATTTCTGTT TGAGCTTCAA     120

GCATATCGTC GAGCCGCGCA GGCCATAGTA TTCCAGCTTC ATCTTGCGCA CCACAAAGGC     180

TACCCGCTCC GCAGCAGCAC CTGTTGCTGA AGTGATGGTG GACGTCAGCA TCTCGNNNTC     240

TTCATAAAA                                                              249
```

(2) INFORMATION FOR SEQ ID NO:105:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:105:

```
GATCCCTTTA CGACCAGGCG TCCCGGCGCC GTTATAGTGC CAGCCAAAAC CAAAGCCGCC      60

GCCCGGTAAA CCAATCTGTT CCAGCATTGC GGCCAGCACG ACGACCATCC ATGACCACTG     120

TTCGCATGCT GCATACGTTG TACGACCAGC CAGCGATGAT TTCGGTTCTG TCGTCGCATC     180

TGTGGCAACG CGACTGGGTG GTGTAATCAA GATCATTTCG CAGGACTTGG TGCATTGTAG     240

AATCGAGA                                                               248
```

(2) INFORMATION FOR SEQ ID NO:106:

(i) SEQUENCE CHARACTERISTICS:
    (A) LENGTH: 175 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:106:

GGCGGAGGAT TGCCACGTNG CAGCCTGCTA CGCCCGTCAG TTCTTTACGC AGGTTAGCCA      60

CCAGTTCGTT TACCATGTGG CGGCTCCNTG TCAGTTTCCA GTTACCCATC ACTAAAGGAT     120

GTGATTTATT TNTCCACGTT AGTAGCGAAT TAAGGAAGAT GGCCGCTCGT AGAGA          175

(2) INFORMATION FOR SEQ ID NO:107:

(i) SEQUENCE CHARACTERISTICS:
        (A) LENGTH: 307 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:107:

GATCATTATC TTAACCTAAA ACCGCTATAT TTATAAGTAT TATTACGAAT AATCTTAACC      60

TGGGATATGT TATACTAATC GGACCAGAAA GATATTATTA CGACTTTAGT AAATGCTTTT    120

TAAATATTAA ATAATAATTA ATTAAGATTT CTACCATTCA TTAATTATAC TTAACAATAG    180

TTTCACACCC CGCGCCGGAA AGGTCTAACC TTCTCATTTA CCTTTAATAC TCAGTATTCC    240

CGAATAGCCG ACCGACACTA ATGATGAATG CTTATCTCTC ATAAACCAGA TATTATGACA    300

CATAACC                                                             307

(2) INFORMATION FOR SEQ ID NO:108:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:108:

GATCAGGATA TGCCGCCGCC AGTAGCGATA GGGCGTCAAC CTCGTGCTTA TCGGTGATGA      60

GCGGCGCGTT GGCCGGGGCT TTTAAAAACG AAAGCATTAT CCTTCCTTAA ACGTAACGCT    120

GGGGCAACGA GACGCTCACC CGCGTACCGT GGGTACAAGA GATGGTTAGC GTCCGCCGAG    180

CGACGACACG CGCTTCGCAT TCGGTCAGGC CGAAGCCTCT TGGTGAGACC GCCG          234

(2) INFORMATION FOR SEQ ID NO:109:

(i) SEQUENCE CHARACTERISTICS:

(A) LENGTH: 352 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:109:

GATCGAGCGC GGAGAACGGT TCATCCAGCA GCAGTACCGG CTGTTCGCGT ACCAGGCAGC      60

GCGCCAGCTA CCCGCTGACG CTGGCCGCCG GACAGTTCGC CCGGTAAACG CGTCATCAGA     120

CTCTCAATGC CCATCTGATG TGCGATAGCT CCCGTTTTTC CCGCTGGCTG GCGTTGAGCG     180

TTAACCCAGG GTTTAGCCCC AGACCGATAT TTTGCCTGCA CATTCAGGTG GCTGAATAAA     240

TTATTCTCCT GAAACAGCAT TGAGACCGGA CGGCGTGAGG GCGGCGTAAG CTATGATCGT     300

CGGCAATAGT AGCGTACGCT GGCCAGGCGC AAGAAACCGC ATAATCTCTC TT            352

(2) INFORMATION FOR SEQ ID NO:110:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:110:

GATCAGGGTC AGACGCTTGT GCGCCCATAC AACGTTTTGT TCCAGTTGGC CTTTCTCGTT      60

AACGTTTTGG GAGCGCCAGA GCTGTTTAAC GCTCATGGGG CATTCCAGAA CGGGCAGTAT     120

CTCTTCAAAG GACGTTATCG TTTGTCAACG GCGGACAGCA TTTTCAAA                 168

(2) INFORMATION FOR SEQ ID NO:111:

(i) SEQUENCE CHARACTERISTICS:
        (A) LENGTH: 211 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:111:

GATCTTCGGG GCGCACCCAC GGGGTTTTTG CGCGGGGAC GCCTGTGTTA TCAGCATTGT       60

AGAAACTGCG ATAGATATTT CCGGTGAGGC AATTTTCGCT CGGCACGATG TGTCGCTTAT    120

CCGGTATGTG GTGAGCAGTG TGCGCCGGGG CGTGTGATAG AGCCATTGCG CGATGGATCG    180

TCTAGTGAGT TTCTCAGATA GGGGGTGACG A                                   211

(2) INFORMATION FOR SEQ ID NO:112:

(i) SEQUENCE CHARACTERISTICS:
        (A) LENGTH: 257 base pairs
        (B) TYPE: nucleic acid (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:112:

GATCCGCAGA TCCATCTAAT CGGATTAGGC GCATACTGGT AAAGATTCAG CCCCCCCGCC      60

AGCCCAATCG GATCCTGACT GACGAACCGT CCACACTCCG GTGCATAATA TCTGAACAGA     120

TTGTAATGCA GCCTGTCTCG TCGTCAAAAT ACTGCCCCGG CAGCCGCAGA CCGGCTGGTG     180

AAGTACGCCC GCTGTTGCTG ATGTCCGCCG CATTTCTCCA ACCCTGATAT ACCGCCACAC     240

AGCGTCGTCG CGCGTAC                                                    257

(2) INFORMATION FOR SEQ ID NO:113:

(i) SEQUENCE CHARACTERISTICS:
         (A) LENGTH: 359 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:113:

GATCCTGACT GGTACGACTT AACGTTTTAG GCTCGCCAAA ACTCAGCCCC GCCGCTTTCA      60

TCGCTTCCGC GCCTTTGCCC GCTTTCAGCT CGACCAGCAG TTTTTCCGCA TCCAGCTTCG     120

CCTGTTGTTC CGCTTTATTA TGCTTCACCA GGGCAGTGAC CTGTTCTTTC ACTTCTGCCA     180

ACGGCTTCAC GGCTTCAGGT TTATGTTCGC TCACGCGTAC GACAAAAGCC CGGTCAACCA     240

TCCACGGTGA TAATGTCTGA ATTCGGCCCG GCGTACCGTT TGCACAGACG CATAAGATAG     300

CATCGGCTAA CGTTGAAGTC AGCCTTCGGT AAGGTGTACG GCTAACAGCG GTTACGCTT     359

(2) INFORMATION FOR SEQ ID NO:114:

(i) SEQUENCE CHARACTERISTICS:
         (A) LENGTH: 427 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:114:

GATCGCGTAC CGCCAGTAAC GCCGCCGCTT TACCGTCAAT CGCCAGCAGG ACCGGAGTCG      60

AGCCTTGCGA GGCCTGCGCG GTGATTTCCG CCGTCATGTC ATCCGTGGCG ACGTGCTGTT     120

CGTTCAGCAA CGCCTGGTTC CCCAGAAGCA GTTGATGACC TTCCGCTTCA CCGCTGACGC     180

CCAGTCCGCG CAGCTTCTGA AACCGTTCAC CTGCGGCAGT TTATCATCGC CGGCTTTTTC     240

CAGAGAATCG CATGGGCCAG CGGGTGGCTG GAGCTTGTTC GAGCGCGGCA GCCAGACGTA     300

ATGCCTGAGC TTCTCAACGC GTTAAAGGTT TTATCGCACA CTTGCGGCTT GCTCGTCAGC     360

```
GTCCGGTTTA TCAAACTGAG GTATCAACGT ACTGGCGCGT GCAGGATGGC ATGTACAGAG      420

CGATGAG                                                                427
```

(2) INFORMATION FOR SEQ ID NO:115:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:115:

```
GATCTGGAGG TAGAGGTTAT CGAGGCCAGC GGTAAAACCT CACGTTTCAC CGTGCCTTAT       60

TCTTCCGAGC CGGATTCGGT TCGCCCCGGT AACTGGCACT ATTCGCTGGC CTTCGGCAGG      120

GTTCGTCAGT ACTACGATAT TGAAAATCGT TTCTTTGAGG AACGTTCCA GCACGGCGTT      180

AATAACACCA TTACCCTCAA CCTCGGTTCA CGAATTGCGC ACGGTTACCA GGCATGGCTG      240

GCGGGCGGCG TCTGGGCCAC CGGTATGGGC GCGTTCGGCC TTAACGTCAC CTGGTCGAA      299
```

(2) INFORMATION FOR SEQ ID NO:116:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:116:

```
GATCAGAGTA AAACCTGGCT GCTATGGTGC GAACGTGGCG TAATGAGTCG CCTGCAGGCC       60

TCTATCTGCG CGACGAGGGG TTTGCCAATG TGAAGGTGTA TCGTCCGTAA TTCCTTTGCC      120

GGGTGGCGGC TATGTCCTAC CCGGCCTATC GTTTTATTTC TGCCCCAACC GTTTTGCAAT      180

GCGCTCCAGC TTCATCATCA GCAGCAGCGT AATGGCCACC AGCACAATGG TCAGCGCGGC      240

GTCAGCATAT TTCACGTCGG TCAAGCTAAA GATAGCCACC GGCAGCGTCG TCAGCCGGCG      300

ATAATCATCA TCGTGGCCAA CTCCCATGAG AGCATAACT                             339
```

(2) INFORMATION FOR SEQ ID NO:117:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:117:

```
GATCGATATC AGGGAGGAAG TGGTTGCCCG CCACCAGCGT ATCGGTACTG ATCGCCAGGG       60
```

```
TCTGCTTTTC AGGAATATCA GGAGCGCGCA ATCGTCGCCA ATACCGGTTT CAACATCAAG      120

ACGAGAGCTT CTTACACGGT CAAAATAACG GGCAATCAGG GAAAACTCGC CACATGCCAT      180

ACGTTATGCC TCAGCAGAAA AAAGAAAAG GCCGGAGACG CGGGTATCGA GCGCCCGCTA       240

TCTTTCCGGC CTGTGAATCA CTTTTTGTTG GGACGAATCA CCGGAGCTGC TTTATCAGTA      300

CGCGTTGACG ATTTGTGGCT GTCTTCACGC GCCAAAGTTT GAGTTCATCG CTTCGTTGAT      360

GGCCATTATA AGCCAATC                                                    378

(2) INFORMATION FOR SEQ ID NO:118:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:118:

GATCTCTTAC GATAAAGAGC ACATTATCAA CCTTGGCGCG CCAGATTGGT ACGGAAGATT       60

TTGCCCGTGC GATGCCTGAA TACTGTGGCG TGATTTCAAA AAGTCCGACG GTGAAAGCCA      120

TTAAAGCGAA AATTGAAGCC GAAGAAGAAA ACTTCGACTT CAGTATTCTC GATAAGGTGG      180

TAGAAGAGGC GAACAACGTC GATATTCGTG AAATCGCCAG CAGACCCAGC AGGAGGTGGT      240

GGAGTAGAAC GTGATGATCG GTTTCT                                           266

(2) INFORMATION FOR SEQ ID NO:119:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:119:

GATCATCTTC CACTTCCAGA TGCACCGTCA CATCCGGGTT AGTGAGCTTC ACGCGCGCCG       60

ATTCAATATG CTGATTTAAT CCGCCGCCAA CATAGCGCTC CACTTCAATG GAGCTAAACT      120

CATGCTTACC GCGACGTTTT ACCCGCACGC AGAAGGTTTT GCCTTCAAGC TGTTCGCGAT      180

ACTGCGCCAA ACGCTTTCTC GAAAATGTCG TGCATATCGG TGAACGGCAC ATCTCGACTT      240

CAAGAATATG TGAATCCCGG GATCGTGGTC AGCGCTCGGA ATCACAGACG CTGGTTTCAC      300

TTGCGCGACT CATTTACAGT CAGACACGTG TAGTGCTTAA CTCAG                      345

(2) INFORMATION FOR SEQ ID NO:120:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: DNA (genomic)
```

(iii) HYPOTHETICAL: NO (iv) ANTI-SENSE: YES (xi) SEQUENCE DESCRIPTION: SEQ ID NO:120:

GATCATCCTG GAGGTCTTTA TGGCTGATTT CACTCTCTCA AAATCGCTGT TCAGCGGGAA      60

GCATCGAGAA ACCTCCTCTA CGCCCGGAAA TATTGCTTAC GCCATATTTG TACTGTTTTG     120

CTTCTGGGCC GGAGCGCAAC TCTTAAACCT GCTGGTTCAT GCGCCGGGCA TCTATGAGCA     180

TCTGATGCAG GTACAGGATA CAGGTCGACC GCGGGTAGAG ATTGGGCTGG GCGACGGACG     240

ATTTTGGCTG GTCCTTCTCA GGCGCTATTA GTACGCGGTT CATGCAGTAC ATACTACCTG     300

AAGTCACGAT GCACCGAATA G                                               321

(2) INFORMATION FOR SEQ ID NO:121:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:121:

GATCGGCGCG CGTATCTCAG GCATGTGCGC CGCCAGTTGG GAAACGCGCC CGCCGGGGCC      60

CTCAATTTCA TACGCAGAAT ATCCGCGCGC GCCGACCGCG CCGGCAACGG CGCGGCAGAC     120

ATTGACGCCG GCGGGCAGCT CGCGGGCTGT GGCAGAAGGG CGTCACGCTG CCAGGCCTCG     180

TCTGGATAGA TTGATATTCT CGACCACATC CCGAAA                               216

(2) INFORMATION FOR SEQ ID NO:122:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:122:

GATCGGCAAA CAGATAGTCC TGCGACGCAT TAAATCCAGG CATTGCCGAG GAGCACGCCG      60

AAGCGGATAC GCCAGGCGGG CAGGCCATAC CTACGGTATT TGTCAGACCA AACGCCTGCG     120

GGTTGGCAAG AATTTCCTTA AAGAGGCCGT TGATATCGGC ACGGGCTATA TTGCCGCCGT     180

GTTGCTCCAG CCCCTTCTCT TCCATCTGAT TATAATAATC GGTCAGAGCT GACGCTGCCC     240

TGCCGCCGTT CATAGTTGCA GAGTGTCACG AGCAGTGTGA TAATGATGGG TT             292

(2) INFORMATION FOR SEQ ID NO:123:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:123:

```
GATCAGCGCC GCGCTACGTT AATAGCCGGT TGCGACGACC GTGGACGCTA GCAGAGTCGC      60

GGATGACTTC CGTATCGGTT GGTCCACGCG TGAAATTAGT TGCGCGACA                 109
```

(2) INFORMATION FOR SEQ ID NO:124:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:124:

```
GATCGGTCGC ACGCCGGAAT ATCTGGGGAA AAAAATCGGC GTGCGTGAAA TGAAAATGAC      60

CGCGCTGGCG ATTCTGGTCA CGCCGATGCT GGTCTTGTTG GGTTCGGCCT GGCGATGATG     120

AACGGATGCC GGACGCAGCG CAATGCTGAA CCCTGGCCGC ACGGTTTTAG CGAAGTGCTA     180

TATGCCGTCT TCCTCTGCCG CCAACAACAA CGTAGATTTT TAGTCTACCT AACTACTTCT     240

GAACTACGGC ATCTCGAC                                                    258
```

(2) INFORMATION FOR SEQ ID NO:125:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:125:

```
GATCGTTGGT CTTTAAGGCC GCCGCCAAAT CGCTGTCGAC CTGCTTGTTG CTGTAAAAAG      60

CGGTATTAAA CTGCGTCGGC GGCCAGTTTT GTGATGCGAA GAGCGGCGAT AACGCCCAGT     120

CAGCTTCGCC CGTCAGACGC CGACCAGCCT GTATAGAACA TTCGCACGCG CTCTCTTTTT     180

GCCCTTTGCC CTCGACTTCC GCGGCGGCTG GCCGGCGTAC ATCGCGGTTA TCCGGGCTTT     240

AACGACCAAT CTGCGCCAGT TGCTGTTGGG TAAACTGCAA GAGTTTTTGG GTGCTATGGT     300

TGTGCATGAC ACAGCGTGTA CTGAACGTCT GATACCGCTT TCACGTCCCC TAGCGATCAT     360

GGCCAGTGAA GTTGCATAGC TAGA                                            384
```

(2) INFORMATION FOR SEQ ID NO:126:

(i) SEQUENCE CHARACTERISTICS:
        (A) LENGTH: 448 base pairs
        (B) TYPE: nucleic acid
        (C) STRANDEDNESS: single
        (D) TOPOLOGY: linear -continued (ii) MOLECULE TYPE: DNA (genomic)

(iii) HYPOTHETICAL: NO (iv) ANTI-SENSE: YES (xi) SEQUENCE DESCRIPTION: SEQ ID NO:126:

| | | | | |
|---|---|---|---|---|
| GATCATACCT | TGCTTGATGA | CTGCGCCACT | AAAAACCTGA | CGCCGGCGAA AACCCACTGG | 60 |
| GCGCGCCCGC | TTGATGCGCC | GCCCTACTAC | GGTTATGCGC | TGCGACCCGG CATCACGTTT | 120 |
| ACCTACCTGG | GTCTGAAAGT | CAATGAACGT | GCCGCGGTGC | ATTTGCCGGT CATCAAGCCG | 180 |
| CAACCTGTTT | GTTGCCGGCG | AGATGATGGC | AGGAAATGTT | CTGGGCAAGG GGTATACCGC | 240 |
| AGCGTAGGCA | TGTCTATCGG | CACAACCTTT | GGCCGCATTG | CAATAGAAGC CGCCCGCGCA | 300 |
| CAAGGAGGCG | CACGATGAAA | CAGCTTGAAA | ATTATCATTG | AGGCACGTGC TTACGAACGA | 360 |
| AGCGAGGTGA | ACTGTCATGC | AGTGTGTACG | TGTGTGCTAC | TCGAAGGTTT GCGGATTCGC | 420 |
| ATGACAGGTG | ATGTAGCGAT | ATATCGAT | | | 448 |

(2) INFORMATION FOR SEQ ID NO:127:

(i) SEQUENCE CHARACTERISTICS:
(A) LENGTH: 392 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:127:

| | | | | |
|---|---|---|---|---|
| GATCCCCAGG | AGGTCTGGTT | TGTCAAATCG | CCGAAATCCT | TTTTAGGCGC CACGGGCCTG | 60 |
| AAACCGCAGC | AGGTCGCGCT | GTTTGAAGAT | TTAGTCTGCG | CCATGATGGT ACATATTCGT | 120 |
| CATACGGCGC | ACAGCCAATT | GCCGGACCGA | TTACCCAGGC | AGTGATCTGC AGGTGGCACT | 180 |
| TTTCGGGGAA | ATGTGCGCGA | ACCCTATTTG | TTTATTTTTC | TAAATACATT CAAATATGTA | 240 |
| TCGCTCATGA | GACAATAACC | TGACAAATGC | TTCAATAATA | TTGAAAAGGA AGAGTATGAG | 300 |
| TATTCAACAT | TTCGTGTCGC | TTATCCTTTT | TCGCATTTGC | TTCCTGTTTG CTCACCAGAA | 360 |
| CGCTGGTGAA | GTAAAGATGC | CTGAAGATCA | GT | | 392 |

(2) INFORMATION FOR SEQ ID NO:128:

(i) SEQUENCE CHARACTERISTICS:
(A) LENGTH: 327 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:128:

| | | | | |
|---|---|---|---|---|
| GATCTTGTCA | AGCTGGTCAG | CATATCCCGG | ATATCCTCCG | CCTCCCCCCC CGCCACTCCG | 60 |
| CGCGGCTTAT | GAATCATCAT | CATGGCGTTT | TCCGGCATAA | TGACGGGATT ACCTACCATC | 120 |
| GCAATAGCGG | ATGCCATTGA | GCAGGCCATT | CCATCGATAT | ACACCGTTTT TTTCGCCGGA | 180 |
| TGATTTTTCA | GGAGGTTATA | AATGGCTATT | CCGTCCAGTA | CTGCTCCGCC AGTGAATGAA | 240 |

TATGCAGATT TATACGGTTA ATCTGTCCAG TGCAGCCAGT TCTCTGCAAA CCAGCGAGCC    300

GAAATTCCCA TCTCAATCTG TCATAAT                                        327

(2) INFORMATION FOR SEQ ID NO:129:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:129:

GATCCGCAGG AGAAAACACG ATTGTACAAA GAGGCGCAGG ATATTATCTG GAAAGAGTCG    60

CCCTGGATAC CGTTGGTGGT GGAGAAATTG GTTTCTGCTC ACAGTAAAAA TTTGACCGGT    120

TTCTGGATTA TGCCGGATAC CGGTTTCAGC TTTGACGATG CGGATTTAAG TAAGTAATGC    180

GATGGGGCTG GATGGCGCGC GGTTGTCGCC ATCCGTAAAA GGTTCGTGTA TGCTAACTAT    240

GTTCTCAGCG CTGCTGGATT ATTCTACGTG TTGATTGTGC AGTGCTGGTG TTTATTGTCA    300

TTGTCC                                                               306

(2) INFORMATION FOR SEQ ID NO:130:

(i) SEQUENCE CHARACTERISTICS:
        (A) LENGTH: 301 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:130:

GATCTCAGCG ATGTTCAGTT AAACGCTGTG CCGGATGCGG CGTAAACGTC TTACCCTGCC    60

AACGGGTTGG GTAAGCCGAA TAAGCGCCGC TCCATCCGGC AGCATTCACA TAAAGTCCGG    120

CACCAGACGC TGTAACGCGC CTTGCGCAGC AGCGCCGTCG CACACTCAAT ATCGGGCGCG    180

AAAAAACGAT CCTGCGTATA GTGCGCCTCC TGCTCGCGCA GTGTCTGCCG CGCCTGTTCC    240

AGTAACGGGC TGGAGGTTAA CCTTCCGTAA TTATCCTGAC AGCAGCAGCA TCACGCATAT    300

G                                                                    301

(2) INFORMATION FOR SEQ ID NO:131:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:131:

GATCGCCGGT CAGTTCCTCC ATTAAGAGCG GCGCGCGCGC CAGCATCTCC ATGCAGAAGA    60

GCCGCGACGC CTGCGGATAA TCACGCGAAA CTTCCAGCTT GAGACGGATA TACTCTTTGA   120

TGGCCTCCAT AGGGGAAAAT TCTGCGCGAA ACGCTTGAGC GGCGCACGAG ACATCCAGAA   180

TCTCGTCGCA TTACCGCGAC ATACAGCGCC TCTTTCGAGG GATAATAATA AAGCAGATTG   240

GTTTGGAGAC GCTGCCGTAG CGGCGACTGC TCAAGACGCG CGATGATGCA TACTGGAAAC   300

ACGAGCGCGT AGATAGCTGC GTTGCACGG                                    329

(2) INFORMATION FOR SEQ ID NO:132:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:132:

GATCCGCCCA CGCGTTAAGG GCCGTAAACA GAGCGTCATT CATCATTACC GCTGGATTCA    60

CCGCCCTTCG TTCTTCTTCT GTTAACACCA CGCGTAATCG CAGACAGGCC GGGCCGCCGC   120

CGTTGGCCAT ACTTTCTCGC AAATCAAACA CCTGCATCGC GCTGATGGGG TTATCCTCCG   180

CCACCAGCTT ATTCAGATAG CGTCCAGACG CGACATGGTC TGACTTCCGC GCACCTACGC   240

TTGAGCCGTG TTCGCTTGCA CTGCTT                                       266

(2) INFORMATION FOR SEQ ID NO:133:

(i) SEQUENCE CHARACTERISTICS:
        (A) LENGTH: 319 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:133:

GATCAAATGC AGGCAGTAAA AGGGCGTCAT CAAGATTATC GGTACACTGT GTAGCGGCGG    60

TTTGCAGAGT ACCATGTAGC GCCGGATAAT TATGCCGGGT CAGGTTGACA CCGTGCGTAC   120

CGTTAATAGC TTCAAAGGCG TCGCAAAACG CGCGGTGTTT TTCTGCGGTG ACGGGGTCTC   180

CCGGCGCTTC AAAAGTTCGC ATCAAATGCG GGCGATGCTC TGATTCTGGT ACTTATCGTA   240

CAAAACGACG ATCGCTCTCT CATGATATAC GCATATAGCA TCATGCCTGT CCGTGCATAG   300

TCGTAACTAG AGACATCAC                                               319

(2) INFORMATION FOR SEQ ID NO:134:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:134:

```
GATCAACCTG AACTCAACGG ACCCTGTACC GTCTAAAACG CCCTTAGCGT GAGTGATGCG      60
GATTCGTATA ACAAAAAAGG CACCGTCACC GTTTATGACA GCCAGGGTAA TGCCCATGAC     120
ATGAACGTCT ATTTTGTGAA AACCAAAGAT AATGAATGGG CCGTGTACAC CCATGACAGC     180
AGCGATCCTG CAGCCACTGC GCCAACAACG GCGTCCACTA CGCTGAAATT CAATGAAAAC     240
GGGATTCTGG AGTCTGGCGG TACGGTGAAC ATCACCACCG GTACGATTAA TGGCGGAGCC     300
ACCTTCTCCT CAGCTTCTTA CTCATGCAGC AGACACGGGC TATACATGGA CATCAAACGG     360
CTATAGGGGA CTGTGAGCTA CAGATTACAC TGATGGCACG TGTTGGCACT ACACGCGCGT     420
TCGGCGATGT GTATGAAC                                                   438
```

(2) INFORMATION FOR SEQ ID NO:135:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:135:

```
GATCTTATCC TTCCGCTACA AAATCAACTG CGCCATCTGA CGCATATTGT CGGCGTGGAT      60
AAACTGGCGG CTGCCACCAC AGCGCTTGCG TTAGTCAAAT CATCGACCGC AGCGAACCGT     120
TGCAGTCAGA CATTAACATT CACGGTGATG AACTGGCGGC AGTGCTGTTT ACCTCCGGCA     180
CAGAAGGAAT GCCGAAAGGG TGATGTTGAC CCACAATAAT ATTCTTGCCA GCGAACGGGC     240
GTATTGGGGG TTGAATTTAA CCTGGCAAGA TGTGTTCCTG ATGCTGGCGC ACTGGGAGAC     300
CGGATTTTAA GGAGGCTTTT ATGGGGTAGT ATTGCTGGAC ATCTTACCAG AGCTCTACTA     360
TAG                                                                   363
```

(2) INFORMATION FOR SEQ ID NO:136:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:136:

```
GATCGATTTT CCCCTCCATG TTTTCATAGG GGAACAGGTT CGGGTTAAAA ACCACCTGAC      60
GGATATCGCA CAAAAAGCCA ATCCGCTCCG CCCAGTAACC GCCCAGCCCC ACGCCACAGA     120
TTAAAGGGCG CTCGTCCACA TTCAACTGCA ACATTTTGTC CACTTCTTTC AGCAGATGCT     180
GCATATCGTG CTTAGGATGC CGCGTACTGT AGCTTACCAG CCGAACATCG GGTCGATAAA     240
```

```
CTGGTAATTG CGAACACTTT TTCATGGTGC GCGGACTATA TGAGTCAAAA CGTGTGATAT    300

ATATCATCTG GCACCTCACG AGACTGAGTG ATGCGTGCGT TTCTGCA                  347
```

(2) INFORMATION FOR SEQ ID NO:137:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:137:

```
GATCCCAGAC AATACCGTTA CTGTTATCCA ACGATACCCC TGCCAGTGAG GTACGCAGGA     60

ATCCATATTG GGTGTGATGC GCGTAAGAAA CGCCCGCCAT CATAGTACTT TTACGCCTGT    120

CCAGACGACG CAACTGATGG TCATCGCTGT CGCCCGGTTT GAAGTACATC GGGGACCAGT    180

ATGCCATGAT TGACAACTTA TCGGCATTGT CATTCACAAG TAGTACCGCG CCAGACACGA    240

CAGAGTTNTT CATAGGCATG ACGATCGATA ACAGCTAT                            278
```

(2) INFORMATION FOR SEQ ID NO:138:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:138:

```
GATCGTTATG AATCGCTTGC GTGATTTCCA GCGTCACCGG GTCGAGACGA TAAACTACGC     60

CGCCTTTATC CAGTTTACGG CTTTGCGATG TAGCCAGCCA GAGCGCGTTT TCTTGCTGAC    120

TCCAGGCCAT CTCATAACGC CTTTGCCTAC CGCTTTACGC AGCATGTCTT CCGCGCCAGC    180

GTGCTAAATG AGGATGCGAC GAGGAGCGAA CCTAACAATA AAGAACCACG CAGGCTGGCG    240

AAAAAAGATG ACGTAAGTGC ATGACGACTC CTTTGATAAA ACGTGTATAG CTGCTTCACA    300

CTACTTCGCT GCGTGGATCT GCAGGTGGCA CTTTTCGGGA AGTGCGCGAC CCTATTGTAT    360

TTCTAATACT CAATATGATC GTTAT                                         385
```

(2) INFORMATION FOR SEQ ID NO:139:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:139:

```
GATCAGCGGC TATGGCGGTC CGGAAGGCGC GAAGATGGCA CGCCGGCGGG CACAGTTTGG      60

TTTGCCTGGA ATATTAACAA TACAACTTTT ACAAGCCGAC AACATTTCAA CGGAGATTGT     120

CAGGAAGTAT TGGAAAAATG CGTACGCTTC GCCCTCGCTG AATTGCTTTT CTGTTAACGA     180

AGAAAGCATA ACATAATTTC ACTGACGTCA GATACTCCGG CTAGATAAAT CGAGCTTACC     240

GCGTGTTCGG AATTCGATGA TTCGGATATC GGTCGCCATC GT                        282
```

(2) INFORMATION FOR SEQ ID NO:140:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:140:

```
GATCGGCGAC TACAAAACCA ATCACCGCGG CTTTACCATC GAGTTCCATA TGCGTACGTT      60

TTATCGCTGG GAGTATGGCG AGAATATGTC CCCGGCCGGA TAGAACCGGT TAAAGAGACC     120

ATGCGTTACT TTTTCATGGC GGTATACATG CACAGTTGCT TGGTGGCATG ACATTGGAA      179
```

(2) INFORMATION FOR SEQ ID NO:141:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:141:

```
GATCAGTAAC AGGACGGTAG CAAAATTCGC ACTGAGCCCG GCGACATTCT GAACGAACGG      60

TTCAATATAG CTATAACTGT GTAATGCGCA GTCACCACAA CGACGGTCAG TACATAGAGG     120

CTCATCAGCG CCGGGCGTCT GAATAGCAAA AGGTAAACTT TTTAGTGAGC CGGAATGCTC     180

GTCTGGCAAT TCGGTAGAG CTTATCAGAA TAGCAGCGTA TATCTCCATG CGATGCAAAG      240

TGGCCCAGCA AATCTGACAC T                                               261
```

(2) INFORMATION FOR SEQ ID NO:142:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:142:

```
GATCATTTTG GTGCCGGTGT CAGCCTGCTG ATGTCCACTG GTCAGCGCAA CGGAATAGAA      60
```

```
CTCGCCGATA TAATTATCAC CGCGCAGAAT GCAGCTCGGG TATTTCCAGG TAATCGCCGA        120

ACCGGTTTCC GACTGGGTCA ACGACATCTT GCTGTTTTCC CTTCGCACAA GCCCGCTTGG        180

TCACAAAGTT CAGATCGCCG TGTGTGTGCC GGACAGTTGA CGTGA                       225

(2) INFORMATION FOR SEQ ID NO:143:

(i) SEQUENCE CHARACTERISTICS:
        (A) LENGTH: 301 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:143:

GATCATCCTC GGCGCGGGAG TGAATCACTG GTATCACATG GATATGAATT ACCGTGGGAT        60

GATTAACATG CTGGTGTTCT GCGGCTGTGT TGGACAAACC GGCGGCGGCT GGCCGCACTA       120

TGTCGGCCAG GAGAAGCTGC GGCCGCAAAC CGGCTGGCTG CCGCTGGCTT CGCGCTGGAC       180

TGGAATCGCC GCCGCTCAGA TGAACAGTAC TCGTTTTCTA CACCATGCCA GCCAGTGGCC       240

TATGAAACTG ACTGCGCAAG AGTTGCTGTG CGCTGCGATC GCTAATTCGA CTATCGATTA       300

C                                                                      301

(2) INFORMATION FOR SEQ ID NO:144:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:144:

GATCATGTGG GTTTAACCCG TTGATTAAAC ATTGGATTAC GGAATAGCAA TTGCTTATTT        60

TATTTGTCAT ACAAATAAGT ATAATACCCG CTTCCGATGT AGACCCGTCC TCCTTCGCCT       120

GCGTCACGGG TCCTGGTTAT ACGCAGGCGT TTCTGTATGG AATACGCCAT CCCCTCTGAT       180

AGATGCCTTG TTGCCTTAAG CAGTTAACCC GCCTGAAGCA AACGACAAGA CGGCAGACGC       240

TTACCGGCAT ACGACACGGA TGCTTCAGAA GA                                    272

(2) INFORMATION FOR SEQ ID NO:145:

(i) SEQUENCE CHARACTERISTICS:
        (A) LENGTH: 358 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:145:
```

```
GATCTGCGCA CATCATTCGG GTCATCGCTA AATTTTTCAC TTTTAATTCG CCGTCCGACA        60

GTTTTCCTTC GCCGGTGAAT TGATTGCACA TTTTGCCGGA TACCGTCATG TCCTCGCCAA       120

GGCTAGAGCT CCGGGCCGGT GACCGTTTTA CCGTTTACGC TTTCCAGAAC AAAGCGGTGG       180

TGCTCCAGTT CGTCGCGTTT GACGGACACT TTTCACTGCT CACACACCTG TCATTATGAT       240

GCTCAGGGCG ACCAGCGTGA TTTCTTCATT GATATTCTCT GTAATCTGAT AGGTTAACAC       300

TGACTATAGT AATGATATGA CCGGATAGAT CTTCAGGGTA TCCGAAAATC GTCCCTGA        358
```

(2) INFORMATION FOR SEQ ID NO:146:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:146:

```
GATCTGTTGT TACAGCATGG AATGCGCCGT CCTCCTCACC GGCCAGGCAA ACGGCGCGAT        60

CGTATCGAAC TGTGCGCCGC GCCGAAAGAA GGGGGGCTTA GCCCTTCTTT CGGCGTCTTA       120

CGCAGCGTAG CCAGCATATT AGCATTGCCT AACTGCATTA TTGTCTGCGG CGGGGATTTT       180

ACTACGTAGC GCAATTTGGC ACGTCTAGAA ATTCGTAAAG GTTC                       224
```

(2) INFORMATION FOR SEQ ID NO:147:

(i) SEQUENCE CHARACTERISTICS:
        (A) LENGTH: 268 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:147:

```
GATCCTGAAT CGCCACGACA CGGGCGCCAG GCCTGCAAAC AGACGCGCGG CTTCGCTGCC        60

GACGTTACCA AAACCCTGAA CCGCAACGCG AGCGCCTTCA ACAGCAATAT TCGCCCGACG       120

TGCGGCTTCC AGCCCGCTGA CGAAAACGCC GCGCCCCGTC GCTTTTTCAC GGCCCAGCGA       180

ACCGCCAAGA TGGATAGGCT TACCGGTGAC GTAAGATAGT GACCGTGTGC ATGATTCATG       240

GAATACGTAT CATATCATCA ATATTACT                                         268
```

(2) INFORMATION FOR SEQ ID NO:148:

(i) SEQUENCE CHARACTERISTICS:
        (A) LENGTH: 314 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:148:

| | |
|---|---|
| GATCCTGAAA AATACCAATT TTCAGCGGGC GAGCTTCGCC TTCCGCACTA AAACAGTGAG | 60 |
| GAAAACGCTC GGCCAGAAAC GCGATAACTT CTTTACTGCT ATTCAACTTA GGTTGATTTT | 120 |
| CCATGAAATT TCCTGATTAC AACGGACGTA GCCAACAAGC AGCAGGCATG AACAGGCGTC | 180 |
| ATTATAATGA CGCCATCAGT AATTGCTACG TTATCCGTTG ATTATCCTGC GACGTCGCAA | 240 |
| AGATTTTTTG TATCCGTCGT GCAGCACGTT CAGCTGTCAC CAGCGTACCA GGCGTGTCAT | 300 |
| CTCTCGTAAC GCAA | 314 |

(2) INFORMATION FOR SEQ ID NO:149:

(i) SEQUENCE CHARACTERISTICS:
        (A) LENGTH: 379 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:149:

| | |
|---|---|
| GATCCAGAAT ATATAAAACC CCATTAACNC CAGCGCGCTT AATAACCATG TGGTCATCTG | 60 |
| CGCTCCGTGG CTGGTTACGT TGTTATAAAT AAGGATGGCG ACCAGCCCAA CGAAGATAAC | 120 |
| GCTGTCTACG CGACCGCGGC GGAGAGGGCT ATAGAAAGCA GAGTGGGGCC ATTGCGACGG | 180 |
| GGCATGATGA ACTGATCGTA GAGAGCGTAA GCCAATAATT CGGCAATAAA GAGAATCAGC | 240 |
| ACCAGGTCCG TGATAGTCAT TTATCTCAGA GAAATAAAAA ACGGGCGTTT GCGTAGTGTA | 300 |
| CAACAGCCTT ACTGGCCAGC AGTCTACGAG TAGCCGGCGA TACCAATGAC GAGAGCCACG | 360 |
| ATATCACAGC GTACTTCTA | 379 |

(2) INFORMATION FOR SEQ ID NO:150:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:150:

| | |
|---|---|
| GATCCAACAA GCGGCTGGCG CCATAGCCGC CGCGAACCGG CATGACGATT GTATCCGGCG | 60 |
| ACGTTAGCGA GGCCAGCGAA TTAACATCGG CCAGCCGTTC CGCGTCCGTA CCGGCAAAAC | 120 |
| GCTGAAAGGG CGACGAATCA CCTCGTCATT CTCCACCTGA TGACCCGCGT CAGTCAGGCG | 180 |
| CTGAACGCCG CGTAACGGCT GTTGGTTAAT ACAGTAGCCC GACTGGGCGA TTAATGAAAC | 240 |
| AGAGACATGG TAATTCCTTG CTGACAATAG AATCGAATGT ATATCATGCG CATATATAGG | 300 |
| CGATGTCTCG TGTCGCAGTT CTGATCGGAC AGGAGGCACT AGCTCGGGGT ACTTT | 355 |

(2) INFORMATION FOR SEQ ID NO:151:

(i) SEQUENCE CHARACTERISTICS:
        (A) LENGTH: 278 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:151:

| | |
|---|---|
| GATCCTTATT CCCGATGTGT TCACCTTTAA TATTCTCCAC TCGCGCGTGG AGGAGATGAG | 60 |
| CGGCGTTCCG GTCGTTCCGC TATATGACAC GCCGCTATCA GGGATTAACC GTCTGCTTAA | 120 |
| ACGGGCAGAA GATATCGTGC TGGCGTCGCT GATTCTGCTG CTCATCTCAC CGGTACTGTG | 180 |
| CTGCATTGCG CTGGCGGTCA ATTGAGCTCG CCGGGCCGTG ATTTGCCGCA GACGCTACGG | 240 |
| ATGGCAGGCA AGCGATCAAG CTGAAGTCGT CATAGGAG | 278 |

(2) INFORMATION FOR SEQ ID NO:152:

(i) SEQUENCE CHARACTERISTICS:
        (A) LENGTH: 394 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:152:

| | |
|---|---|
| GATCAAAATA AAACTTTAAT CCCACTGGGG CAAGAGAGTG ATGTGGTGAC GCTCAGTCCG | 60 |
| GGTCAGGCGT CGGCGCATCT GCAATTTTAC GCGCGTTATC TTGCCGATGG CGGCGCGGTA | 120 |
| ACGCCGGGGA CGCCAATGCC TCCGCAACCT TCATTCTTGC CTATGAATAA GTTCTTTTTA | 180 |
| CGCTGCGCGC ATATATTGGT GCTTGCTTCC CATATCATGG GCGCAGGCTG GCGTGGTAAT | 240 |
| TGGCGGTACT CGCTTTATCT ATCATGCGGG CGCCCGGCAT TAAGCGTACC GGTAAGTAAC | 300 |
| CGTTCAGAAG TCGTTCTGTT AATTGATACG CATATTTACT GGTGGGTCGG TTACGGAACA | 360 |
| AAACGATGGA TATAGTCCTG TGTAGTGATA TGCT | 394 |

(2) INFORMATION FOR SEQ ID NO:153:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:153:

| | |
|---|---|
| GATCGTTAGC AAGGTTTGCT GCGTCATCTG CTGGGTTTCA CGCAATGTGT GCGCGTTAAG | 60 |
| CATCACAAAA TGGCTGGCGC GCGTCGCCCA GTGGGCATTG ATTTGTAATT CAAGCATACA | 120 |
| AACCAGGTTG CGGTTGATGG TCTGAATGGC CTCGAAAATA GATTTTTGTA TCCGGGTTTC | 180 |
| TTTACTGGCA GGCGTTATCA GCCCGCGCAT TTTGACGACA TCGTTCAGCA ACCGTTGCAA | 240 |
| ATGTTATCCA ACCGGGGAGT CAGCAATCGC GACAGCTGCC TTGATACCCA GTTACCTGAC | 300 |

CGATCCGGAT GATCCGATCG GAAA 324

(2) INFORMATION FOR SEQ ID NO:154:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:154:

GATGGCTGGG AAGACGGGTG CCGTTCTGGT TAAGCGTATT CAGCTCTTCG CGCGGGAAAT 60

AGCCTTTAAT CGCCAGGGTA CTGTACAACG CGGGGCCCGC ATGGCCTTTC GACAGTACGA 120

AGTAATCGCG TTCCGGCCAG TCCGGGTCGG AGGGTCGATT TTCATCACCG CGCCGTACAG 180

AACCGCCAGA GTCTCCACTA CCGACATGCT GCCGCCATAG TGACCAAAAG CCAAAGATGG 240

TTTAAGGATT TGACGGTGGA CCGAATATCG ACAGTTGGGT GATTTCGGTT ACGTTCATTC 300

TTCCTGAA 308

(2) INFORMATION FOR SEQ ID NO:155:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:155:

GATCGTGGTC CAGCTTATGA ACGGTATAAC TGAGGGCGGA CGGCGTTTTA AATAATTTTG 60

CCGACGCCGC CGCGAACGTG CCTTCTTTTT CTAACGCATC AAGAATAATC AGAACGTCCA 120

GCAGTGGTTT CATACTCGTC CCCTTGCCGC TATATGGCGA CCACCTGCTG GACAGCGACT 180

CACTCCATCG GCATCACCAA CGGATCGGGA TATTGATATT CAAATCCCAG CTCATTACAA 240

ATCGGCTACC GTCGATAATC TTCCCTTTTG CCGTTGTCGG TGGTACGAAA ATCGCGGCGG 300

CGATTCCCAG CAAGCGTATT GCGATAAACA CTG 333

(2) INFORMATION FOR SEQ ID NO:156:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:156:

GATCCACCCA CGTCATCAGT TGTTCAAAAC CCTGCTTCAC GGTGTGTTCC CATGGACCGA 60

```
CCATGTGGAA AGCGGCTATC TTGCGTTTTT GTGGCTGCCT GATTTCGTAA TCCATGCTGC      120

CTCCGTCACT TCACAATGCT GTATGAATGT ACAGTATAAT TACAGCCTTT TACGGTCACA      180

AGGACAGCGT GATCATTTTG TGAGCAACCT CGCAATCCCG CCCTTTTGAC ACCTCAGATG      240

ACGGTGAACG GTGTGTGTGA CAACGGCTTA CGCTTTATGT GAAAATAGTC GTCAGACGAG      300

AGAACATACC GCCTTTACCA CGATTCAGAG TGAC                                  334
```

(2) INFORMATION FOR SEQ ID NO:157:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:157:

```
CGTTTGCTAT CGACCTGCAG ATCGGAACGG ATTGGCGTCA CGTGATGGAT AAGACCGTGT       60

TCTTCAATGT TATCTCGGCG ACACGAGCGC ATCCGGCGAA ATATCGACCG CATCAACCTC      120

TGCGTCGGGA AGCATAACA CAGGCATGGC AT                                     152
```

(2) INFORMATION FOR SEQ ID NO:158:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:158:

```
GATCGAACGC GCGTTGCAGC AGCGCCCGGC TATTTTCTAC CCGTGTCGTA TCGCCGAAGT       60

TGTGCCATAA CCCCAGCGAA ATAGCGGGAA GTTTGACGCC GCTGCGTCCG CAGCACGATA      120

CTCCATTGTG TGATAACGAT TCTCATCGGG CTGATAAATC ATGACCTTTC CCCTGTGGCG      180

AGAATAATAT GTGTACGGTT ACTC                                             204
```

(2) INFORMATION FOR SEQ ID NO:159:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:159:

```
GATCTTACCG AGTGGGAAAC TAATCCGCAA TCGACCCGCT ATCTGACGTT TCTCAAAGGT       60

CGGGTAGGGC GCAAGGTCCG CTGACTTCTT TATGGATTTC CTCGGCGCCA CGGAAGGGTT     120
```

GAACGCCAAA GCGCAGAATC GCGGCCTGTT GCAGGCAGTG GATGATTTCA CCGCAGAAGC        180

GCAGTTGGAT AAAGCGGAAC GTCAGAACGT GCGCCACGAG GTGTACAGCT ACTGCAATGA        240

GCAATTACAG AGGGAGAATG AGCTGGATCG CTGTCTAAGA GCT                          283

(2) INFORMATION FOR SEQ ID NO:160:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:160:

GATCGCGTTC GCCAGGCAAA ATATTACCGT GCTCAAGAAT ACCGCTGCGC ACGGCATCCT         60

TTACCGTCTG GGCGAATTTC ATGTATAGCG GCGTATTATC CGCCGCTGAA ATTCGTTCAT        120

TCAGTTGCGC GATGAGCCGG GTATGCGCTT GTTCCATTTA TCTTTCCTGA CGACGGGTCT        180

GTAGGCAGTA TACTACCACC ACGCGTGGAA ATGATGTACC GGACCAATGC CCTTCCCCAC        240

TTCCAGCCGT GTACGCTGGC AGCGCCGAAG CATGCCTTGC TCGTTTACCG TCTCTCCCAA        300

CT                                                                      302

(2) INFORMATION FOR SEQ ID NO:161:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:161:

GATCCTGAAT GAAAATCTCA CTGCTCGGCT TGTTGGTCAG TTCGGCCATG GTCTGGCGCA         60

CGTGCTCCAG CATGCCGCCG ATATTGGTCC CGGCCTCGCC GTGACGTTGT CGAGCTTGCC        120

GCAACCGTCC ACCGCTTTGC TGATGGCTTC GGACGCCGGC GGCAACATCC ACACAGCGCA        180

CCGAGACCCT GAGCCTGACG CTACCGGATC CGGCGGTATG AGCGGTTAGC GAG              233

(2) INFORMATION FOR SEQ ID NO:162:

(i) SEQUENCE CHARACTERISTICS:
        (A) LENGTH: 236 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:162:

GATCTGTTCC GTCTGACGGC GGGTAAACTG ACCGGCCTGG ACCGAATGGG GCCAAAGTCC         60

```
GCGCAAAATG TTGTTAACGC GCTGGAAAAA TCCAAAACGA CGACCTTTGC GCGTTTTCTC      120

TATGCGCTGG GCATCCGTGA AGTGGGTGAA GTGACGGCGG CGGGGCTGGC GGCTTATTTC      180

GGTACGCTGG AGGCGCTGCA GGCCTCCGAC CATTGACGAG TTCGAGAAGT ACTACT         236
```

(2) INFORMATION FOR SEQ ID NO:163:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:163:

```
GATCGCGTGT CGGTGCGTGA TTTAAGCCGT GGCTTAATCG TGGATTCCGG TAACGATGCC       60

TGTGTGGCGC TGGCGGATTA TATCGCGGGC GGGCAGCCGC AGTTTGTGGC GATGATGAAC      120

AGCTATGTGA AAAAACTCAA TTTACAGGAT ACCCATTTTG AAACCGTCCA CGGTCTTGGA      180

TGCGCCGGGA CAACATAGCT CCGCGTATGA CCTGGCGTAC TCTACGGCGA TTATTCACCG      240

GCCGAAGCCT TGAATTTATC ACATGTACAC GAGAAAAGCC TTGACCTTGA ACCGATTAGA      300

GCAGAACCGA ACGCTTGATG GATAGACACG AATG                                 334
```

(2) INFORMATION FOR SEQ ID NO:164:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:164:

```
GATCGTAGTG GAGAGTGTCG CCGAACGTCT GGTGCAGCAA ATGCAAACCT TCGGCGCGCT       60

GCTGTTAAGC CCTGCCGATA CCGACAAACT CCGCGCCGTC TGCCTGCCTG AAGGCCAGGC      120

GAATAAAAAA CTGGTCGGCA AGAGCCCATC GGCCATGCTG GAAGCCGCCG GGATCGTCTG      180

TCCCTGCAAA AGCGCCGCGT CTGCTGATTG CGCTGGTTAA CGTCTGACGA TCCGTGGGTA      240

CCAGCGAACA GTTGATTGCC GATGCTGCCA GTGTAAAGTC AGCGATTCGA TAGTGTGTGG      300

CGCCTGAG                                                              308
```

(2) INFORMATION FOR SEQ ID NO:165:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:165:

```
GATCCCATCG CGAATATCGG TAAAACAGCG CTTCTGCTGA CCGCCGTCGA TAAGCTTGAT      60
CGGCGTTCCT TCTACCAGGT TCAGAATCAA CTGCGTTATC GCGCGTGAAC TGCCGATACG     120
CGCCGCGTTC AGGCTATCCA GCCGCGGCCC CATCCAGTTA AAGGGACGGA AAAGCGTGAA     180
GCCAATCCCT CTTTTTGCCA TAAGCCCAAA TCACCCGTCG AGAAGCTGTT TGGAAACGGA     240
GTAAATCAGG GCTTATTCAC CGGCCCGACG ATCAGATTGA TTGTGTTGTA AAGAGGCTCT     300
AATCGGTCAC ATTAGAGAGA GGAAACATTT AGTATTAGAT AAGATACCGA GTTTAATAGT     360
AA                                                                   362
```

(2) INFORMATION FOR SEQ ID NO:166:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:166:

```
ATCGCGTTGT GTTGCCGAGC ATTTATTACA AGGCGCTTCT GTGTGNCNCT CGAATGGTGC      60
NGCAAGACTG C                                                          71
```

(2) INFORMATION FOR SEQ ID NO:167:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:167:

```
GATCGTGTCG CAATTCTTAA TGCCATAGAG GGTAATCATA TTGAATCCTT TAACGCGAAA      60
TTCGAATAAA TAATCAATAG TATCGTCTGC GGGATAATAA GTGTGGCCGT TTATGGTTAT     120
TTATCCAGCG CTGATCGGCA ATCAATATAA CATTGTTGAG TGAATGTGAA TAATGATTCC     180
TTTTCGTTCC AGATGTGGCT TGTTTATACT TCGCCGGTAT AATCCTATTT GGGCAAATGC     240
AATTGTGTTT ACCATTGATA AGGTAGGTAG GAAAGGTATA TGTGCTAATA TGGCGTAGTC     300
ACATAATTAG TCTACGGCCA TGATCAGACG CAACAGGATC GACTCGTATG ACTTTACGAC     360
CGC                                                                  363
```

(2) INFORMATION FOR SEQ ID NO:168:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:168:

```
GATCCGGCGC TGATTTTCAC CATCACGTTT TTCATCGGCT GACCTGCGGC GTCTTTCACG      60

TCGATGGTGG CGGCCATCTG CTCGCCCTTC TTCGCCTTTG CGCTTCCGGT GGTTTCATCC     120

TGGCCTGCCA GCGTCAGCTC AGGCTGGCGG CGGCGCTGCG GGCGAGGCAA GACAGGTCTG     180

CATGTAGTAC ATCGAGGTGC TGGTCGTCGT TTGACATCAT TGCCGTCGTT AAACAGGTTG     240

ACCGCCGCAT AGAGCGACTT GTGCCGTCTG ACGATATCAC GTAATCCCGC CACAGTAGCG     300

CTGAGCTGTG TGCTGACTGT ATGCACTAG                                      329
```

(2) INFORMATION FOR SEQ ID NO:169:

(i) SEQUENCE CHARACTERISTICS:
            (A) LENGTH: 198 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:169:

```
GATCTGGCGG GCGCGTGAAA ATATGTTGCT GGCCTCCTGT ATGGCGGGAA TGGCCTTTTC      60

CAGCGCCGGT CTGGGGCTGT GTCATGCGAT GGCACACCAG CCTGGGGGGC GCTGCATATT     120

CCGACGGCCA GGCCAACCGA TCGTCGTCGC AACAGTCATG GGCTTTAACG GATCAGTTTA     180

CGGAAAGTTC AGTAATAT                                                  198
```

(2) INFORMATION FOR SEQ ID NO:170:

(i) SEQUENCE CHARACTERISTICS:
            (A) LENGTH: 273 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:170:

```
GATCAACATC AATAACTAAA ACTCTTTTAC CAAGATAGTT AGCCATGAAC TCAGCAATGC      60

CAACACATAG AGTTGTTTTT CCTACCCCGC CTTTCATATT AATAAAGCTA ATTACCGATG     120

CTGGCATAAT TATTCCTTGC TATGTTGAGA ATGAGTCATT TTGATAATTA CTCGAGCTTT     180

TATCTTAATC TTCGCGCGTT CGAATCCTTC CCTTCATGTA CTTCTCGTAC ATGGCATCCA     240

GTTCCTTGAG ACGAGATAAT ACCCGAAGAA AAT                                 273
```

(2) INFORMATION FOR SEQ ID NO:171:

(i) SEQUENCE CHARACTERISTICS:
            (A) LENGTH: 244 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:171:

| | | | | | |
|---|---|---|---|---|---|
| GATCGCTGGT | TCTGGCGGCA | CCCTGGCGCC | AACCCAAGCA | ACGTCGCGCG | CGCGGCATGG | 60 |
| CAGGATCTTA | CCGCCGGGCG | CGTTATTATT | TCCGGCGGCA | GTACGCTGAC | TATGCAGGTG | 120 |
| GCGAGACTGC | TGGACCCCGC | ATTCGCGCAC | GTTCGGCGGT | AAAATCCGCC | AGCTTTGGAG | 180 |
| CCCTCCAGCT | TGAATGGCAT | TTGTCCAAGC | GCGATATCCT | GACGCGTGTA | CTGAACCGAG | 240 |
| AGTG | | | | | | 244 |

(2) INFORMATION FOR SEQ ID NO:172:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:172:

| | | | | | |
|---|---|---|---|---|---|
| GATCGCGCAG | CGCTCTCATA | GCACAAAACG | AGGTTTTCCA | TTCTGTTATG | TTCCCTGGCG | 60 |
| ACGATAAACG | TTCGATTGTC | TCATGGCGCT | GGTGAACCTT | ATTTTTTAAC | GGAGATGTTG | 120 |
| AATGGCGGTA | GAGGTTGTAC | GTAATGGCCA | AACCCGGCGG | CGGATCTCGA | ATATTGATTC | 180 |
| GGCAATATTC | GTTCTATCTT | GGAAAAGGAG | CGCTGTACCG | GAACGGAATA | AAACTGCGAT | 240 |
| GTGCAGA | | | | | | 247 |

(2) INFORMATION FOR SEQ ID NO:173:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:173:

| | | | | | |
|---|---|---|---|---|---|
| GATCAGCTTG | CCGCACTGTA | TGCCTCCAGC | GACGGCAATA | AAATCCACAC | CGTATCCGGC | 60 |
| TGGCCGACTG | AGTATGACTA | CTGGTCATCC | ACCTTCGCCA | GCGCCGCTAC | ATGGCAGGCG | 120 |
| GTATCACTGG | CTGCGGGCGG | CTATACCGCT | TCCGGCGATG | CGGTCGGACT | ACGTGAGCTG | 180 |
| TCTGGTCAGC | AAAAATCGAC | GCGCGTCTAT | CACCATTGAG | CCGGTGGATG | CGCATTGTGT | 240 |
| ATACGCAACA | GCGAACACGC | GTGAAGGTGA | AAGGCATACG | TCAGCTTAAG | TGACGTAAGA | 300 |

(2) INFORMATION FOR SEQ ID NO:174:

(i) SEQUENCE CHARACTERISTICS:
        (A) LENGTH: 337 base pairs
        (B) TYPE: nucleic acid (C) STRANDEDNESS: single
(D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:174:

```
GATCCGGACC GTGCCTTATA CCCTGAAAAA GGGGGAGACG GTGGCGCAGG CGCACGGCCT      60

GACCGTCCCA CAGCTGAAAA AACTGAACGG GCTCCGCACT TTCGCCCGCG GCTTTGACCA     120

CCTGCAGGCC GGCGACGAGC TTGACGTTGC CGGCGGTCCC GCTGACCGGC GGGAAAGGTG     180

ACAATAACCG CCATGACGTC CGCGGTCCGT TTGCTGCTGA CCGGGAAAAT GAGGACGATC     240

GCAGGCAGCA GATGGCCGGC ATGGCTCACA GGCGGCAGCT TCTGCCAGCC ATCGGACGTT     300

AGGCCGCCGC GGATGGTTCG TATTCGCGTT GACATGT                              337
```

(2) INFORMATION FOR SEQ ID NO:175:

(i) SEQUENCE CHARACTERISTICS:
(A) LENGTH: 424 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:175:

```
GATCAATGAA GCTTTGTGGG AAGTCTTGAC TTTCGTCGAT AAATACGTAA TCAAGTGCCT      60

TTTTATCAGC TCTCCCACTA TTATTTATAT CTGCAATGGC TTTCTTACAT AGGGCATCAA     120

AATCGCCATT ACCAAATCCC CCAAATGGAA TTTCGCTAAT AATGGCATAT ATATCTGGTA     180

CATTCCAGAA AAAGGTTCTT TACGTCAAAC CCCAAGAGTT GAAGCAAAAA AGTTTTTGTA     240

CCCCATTCTA TCTGTTTTTC GACTCGCATA AATCGAAAAA CTCAGGGATT CTGGTTCTCA     300

TTGTGGAGCA GATTATAAGC AGTAATGCAT CTAGATACGG TTTGATACTC TCTAGTGTAG     360

TATCAGTTAC TGACAGCTAC TGCATAACCC TTTCAGCACT GAGACACGTG CGCAAATGTG     420

TAAA                                                                  424
```

(2) INFORMATION FOR SEQ ID NO:176:

(i) SEQUENCE CHARACTERISTICS:
(A) LENGTH: 190 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:176:

```
GATCATTTGA TTAAAACCTC ACACCGCAAG ATGCGACTTT TTGTAAACCT GCTTTACCGC      60

TGACACATTT CTCCGCATTA CTGCGGAACA AGGCTTAAAA AGCGTATCCG AACGTATAAC     120

CCTCCAACGT TCGCTACGGG AAAAATGGGG ATGAGTACTG GAAGGTCGCA TATATGACCA     180
```

AGCCAGACAT                                                                    190

(2) INFORMATION FOR SEQ ID NO:177:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:177:

GATCCATGCC TGTGATGCCT GGATGTCCCG AATACTTGAA GGTTTGATCG AACGGCAGGC      60

CAGTAATGGC AACGCCACTA TTCTGTTATC TGCGACGCTA TCGCAGCAGC AGCGAGATAA     120

GCTGGTGGCG GCATTTTCCC GTGGGGTGAG GCGTAGTGTG CAGGCGCGTT GCTAGGCATG     180

ACGATTATCC CTGGCTGACT CAGGTCACAC AAACAGAGCT GATTTCTCAG CGGGTTGATA     240

CACGCAAAGA GGTTGAGCGT TCGGTAGATA TTGGCTGGCT ACATAGTGAA GAGGCGTGTC     300

TGAACGTATA GTGAGCAGTG AAAGAACTGT ATCGCTGATA CGTACTCGTG ATGATCGATC     360

GATCTACCGA GCTACTCACT GGTAGGGCAG AACTTACTCA AGGCTCTCAG GCGTCTAACA     420

GGCGTCTAAC ACGTGGAAGT T                                               441

(2) INFORMATION FOR SEQ ID NO:178:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:178:

GATCGTCGTT ACCGGCGACG GTTAAAGCAA ACTGGGCATC AATGGGCCGT AAGAGTTTTT      60

GTTCAACGGC CTCCAGCAAC CGCTCCTGGA TTGTCATTGC GCCTCCTCAC TCATTTCACC     120

TGCAAACATA TCATCCAGTT GGTTAATTAA CGCCGCCGCA GGACGAGTGG TAAAAATACC     180

CTGCTGCGGA CTGTCGCCAT CCACCCCGCG TAAAAAGAGA TAGATGACTG CCGCCGAAAT     240

GGCGTTCATA GTCGTAATTC GTCATTCGAT GACGAAGGTA ACGGTGCAAT GCCAGCGTAT     300

AAAGCTGGTA CTGCAAATAT AGCGATCGCG TGCTCCGCGC AGCCATGCGT CTGGATAGCG     360

CTATCTGCCG                                                            370

(2) INFORMATION FOR SEQ ID NO:179:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:179:

| | | | | | |
|---|---|---|---|---|---|
| GATCCGGGTA | CTATGAGCCC | AATCCAACAC | GGGGAAGTGT | TCGTTACTGA | AGACGGCGCT | 60 |
| GAAACCGACC | TGGACCTGGG | GCACTACGAG | CGTTTCATCC | GACCAAGATG | TCTCGCCGCA | 120 |
| ACAACTTCAC | GACTGGCCGC | ATCTACTCGA | CGTTTCTGCG | TAAAGAACGG | TGACTATCTG | 180 |
| GGACGACAGT | ATCTAATATA | CGGATTAAGA | GG | | | 212 |

(2) INFORMATION FOR SEQ ID NO:180:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:180:

| | | | | | |
|---|---|---|---|---|---|
| GATCTTCTTC | ACGTCTGGCT | TCATCACTCT | GATGAACGAT | ATGCTCGGTC | AGATGACCTT | 60 |
| TAATCACCTC | GCGCATTAAG | CCATTTACCG | CGCCGCGAAT | CGCCGCGATC | TGTTGTAACA | 120 |
| CGGCCGCGCA | TTCATGCGGT | TCATCCAGCA | TTTTTTTTAG | CCGCTATCAC | CTGTCCCTGA | 180 |
| ATCTTGCTGG | TTCTGGCTTT | AAGCTTTTGT | TTGTCCCGGA | TGGTATGTGA | CATTACAACA | 240 |
| CCTCACTAAA | CATTAACGAA | TACAAATTAT | AGCATTACCA | GATGCTACTG | GGGGTAGTA | 300 |
| TCTATACTGG | GGGGAGTAGA | ATCGACGCCC | ACATAAAACA | ACTAAGAATC | ACTCATGGGT | 360 |
| GAATTTC | | | | | | 367 |

(2) INFORMATION FOR SEQ ID NO:181:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:181:

| | | | | | |
|---|---|---|---|---|---|
| GTATCACGTT | TGATGCGGCT | GTTATCGTCC | AGATAGCCGG | TGCGATAGGC | AAAATAATGC | 60 |
| GGCAATGAAA | GCGCCAATCG | CCAGGGGGA | TCCCCACAAT | ATATGCCAGC | ACGACCCCGG | 120 |
| GGAATACCGC | ATGACTCATT | GCATCGCATT | CGCGCTTTTA | CACTAAAACC | CGCGTAGGAG | 180 |
| ATCGCAATCG | GACTAG | | | | | 196 |

(2) INFORMATION FOR SEQ ID NO:182:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:182:

| | | | | |
|---|---|---|---|---|
| GATCTGTCGC | GTTTTCGCCA | GAATAGCGCG | CGGAATAGAT | ACCCGGCGCG | CCGCCTAAAA | 60 |
| CGTCAACGGC | CAGACCGGAG | TCATCGGCAA | TGGCGGGCAG | GCCGGTCATT | TTGGCGGCAT | 120 |
| GGCGCGCTTT | GAGAATCGCG | TTTTCAATAA | ACGTCAGGCC | GGTTTCTTCC | GCGGAATCGA | 180 |
| CGCCCAGTTC | CGTTTGCGCT | ACCACATCAA | GCCAAAATCG | CTTAACAGCG | AGCNNCACTT | 240 |
| ACGCGTNTGC | GAGACACTTT | NCTGAG | | | | 266 |

(2) INFORMATION FOR SEQ ID NO:183:

(i) SEQUENCE CHARACTERISTICS:
      (A) LENGTH: 351 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:183:

| | | | | | | |
|---|---|---|---|---|---|---|
| GATCATCATC | ATTCCGCAGC | CAAACGCGCG | GCTTTTACCG | AACCCCTGCG | CCAGACGTTG | 60 |
| CAGGAAAAGC | GCGGGTTCGT | TAATCACCAG | CACGCCGGTA | TAGTCCACGC | TGCTAAACTG | 120 |
| AATCATCTGG | CCGATCTTTT | CCCGCGACGT | ATCTGCCTGC | CTGCCGATAA | GCATCAACGC | 180 |
| TCGGCTCGGC | AGAGTAAAGC | CATTTTGCCT | CCCCCTGCGC | GCCAACCACG | CAGGCGCTGC | 240 |
| TGCTGATAAG | ACCAAATATG | CTGGCTATCA | CCTGCGTTTA | GTGGCGATTT | AGACTCATCA | 300 |
| GCAAATCGTG | AGTTGCGTTT | TGCAACGAGA | TTGGGAGGTT | AACGAGATGA | A | 351 |

(2) INFORMATION FOR SEQ ID NO:184:

(i) SEQUENCE CHARACTERISTICS:
      (A) LENGTH: 398 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:184:

| | | | | | | |
|---|---|---|---|---|---|---|
| GATCATGTGG | TGATCTGCGC | CGGACAGGAA | CCTCGCCGCG | AGCTGGCGGA | CCCGTTACGC | 60 |
| GCCGCAGGTA | AAACGGTACA | TCTTATCGGC | GGATGCGATG | TCGCGATGGA | GCTGGATGCC | 120 |
| CGACGGCGAT | TGCCAGGGCA | CCCGACTGGC | ACTGGAGATT | TAACGACTTT | GCCTGATGGC | 180 |
| GCTACGCTTA | TCGGGCTTAC | GCCGTCATAC | CGGTTTTATA | GGCCGGTATG | ACGCTTGAGC | 240 |
| GCTTATCGAC | GGCGTCCTGC | TTCACCGCTT | TCAAAATGAC | AAATTTATTG | TTGGTGCTAT | 300 |
| CGTCGCGCAA | TTACCGAAAT | CTTCTTCAGC | TGTGGAAATA | GTCAGATGGC | GTTCGCACAT | 360 |
| ATACAGTTGC | CGTGATTAGC | ACACGCTATG | CAATTCAG | | | 398 |

(2) INFORMATION FOR SEQ ID NO:185:

```
    (i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:185:

GATCGCTATT GGTATGGCCC CACTTGCCGT ATTTCACCGG AAGCGCCGGT GCCCGTGGTT      60

AAGGTAAATA CCGTTGAGGA ACGCCCGGGC GGCGCGGCGA ACGTGGCGAT GAACATTGCG     120

TGCTCTGGGA GCGAACGCCG TCTGGTCGGC CTGACGGGTT ATTGATGACG CCGCGGCGCC    180

TGAGCAAAAC GCTGGCGGAG GTCAATGTGA AGTGCCGACT TCGTTTCTGT GCCGACGCAT    240

CCGACGATTA CCAAACTGCG AGTACTATCT ACGTAATCAG CAGCTCATTC GTTTGATTTG    300

AAGAAGGCTT TGAGGATGAC CGCAAGCCGT TGCATGAGCT ATAACCA                  347

(2) INFORMATION FOR SEQ ID NO:186:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:186:

GATCGGCGTG CTGGCGGCGA CCTGGCCGCG GGAAATACCC TGGAAGAGGC GTGTTATTTC      60

GCCAATGCGG CGGCGGGCGT AGTGGTAGGT AAACTCGGGA CGTCAACGGT TTCCCCTATT    120

GAGCTGGAAA ACGCAGTGCG CGGACGGATA CCGGCTTCGG CGTTATGACC GAAGAGGAGT    180

TGAGACAGGC CGTCGCCAGC GCGTAAGTCG CGAGAAGTGT CATGACCAAC GCGTTCGATA    240

TCTGACGGCA TTATGACGCA ACTGGACCTA TCGGATACTT ACTAGACTAC ATAC          294

(2) INFORMATION FOR SEQ ID NO:187:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:187:

GATCCGCATT GTCAGGGATA TCGCCCTGAA CGCGAGCTAC GCCGGCATCT GCTGCTGATT      60

ATTGCCATTG ATCACCGCCA GCTTAACGGC CCGTCGCCCT GGAGCTGTAC CGTAATGTCA    120

CCAGCAAACT TCAGCGTCGC GTCAGTAGGC TAGTGGCGAC CAGCAGTTCG GCAGTACGTT    180

TTCACCGGCT GCGGATAGTT ATGATTGTCG AGGATCTGTT GCAAGGTTTC CGAAACAGTT    240

ACCAGCTCGC CGCGAACACA AAGTTTTCAA ACAGATAACG ATGTAATTGG TCATGTTGCG    300
```

CATAATCATC TCTCTTCAGT ACATTATTCA CTATACGTGT TTAAATCGTA CA         352

(2) INFORMATION FOR SEQ ID NO:188:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:188:

GATCCTTACC GTTTTGGTCC ATTAATACAG GAAATGGATG CCTGGCTATT GACGGAAGGC     60

ACCCACCTGC GTCCTTATGA AACGCTGGGC GCGCACGCCG ATACGATGGA TGGCGTCACC    120

GGCACCCGTT TCTCCGTCTG GGCGCCTAAT GCTCGTCGCG TTTCGGTTGT CGGGCAATTC    180

AACTATTGGG ATGCGCCGTC GCACCCGTAT GCGTCTGCGC AAAGAGAGCG TATTTGGGAG    240

CTGTTATCCC GGCATAATGG ACACTGATAA TCGAGCTCGT ATCGCAAGAA               290

(2) INFORMATION FOR SEQ ID NO:189:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:189:

GATCTTCAGC AACCACGACA GGAATGCCCG TCTCTTCCAT TAACAGACGG TCAAGGTTAC     60

GCAGCAGGCG CCGCCCCGGT GAGCACCATA CCGCGCTCGG AGATGTCTGA CGCAGCTCCG    120

GCGGACACTG TTCCGGCGCA CCATTACCGC GCTGACGATA CCGGTCAACG GTTCCTTGCA    180

ACGTTCCAGA ATCTCGTTTG CGTTCAGGGT AAA                                 213

(2) INFORMATION FOR SEQ ID NO:190:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:190:

GATCGCTTTG GTTAAATCCC CGCCGCCAGT GTCGGCGCGA CCAGAGCGGA ACGTGACGAT     60

TCTGTCGGGA AGCTGCAAGC CAGTGCTGCG GCGGCCATGA GGACTTCCTG CAACAGTAGA    120

CGCGCCAGTG CGGCGGCAAT TTCGCTGCGG CGGGTAAATT TAAGCTGATG CACCAGTAAA    180

CTCAAGGCGG TGTATAGTCA CTGACGCTCA CCAGACTTGC AGGGTGGCGG TTTTTTCAGG    240

CAGCGACCGC ATGGGG                                                            256

(2) INFORMATION FOR SEQ ID NO:191:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:191:

GATCGTGGCT GCCGGTGCTG TCGGTGTAGC CACCACATTG ACGGCGGTCT TGGGATACTC    60

TTTCAGCACC ATCGCCACGG CGGTCAGCGT CTTAGCGCCT GCCGGCTTTC AGCGTCGGCT   120

GCTGCTGTCG AAGGTGACAT TATTCGGCAT ATTAGAATGA CTACTTACTC GCCCGCCTTC   180

GGCTCACGCT AACGCCTGTG CCCCGATTTG TAGAGTTTGC TTCTGTACGT AGAGTAACCA   240

GCGCGCA                                                              247

(2) INFORMATION FOR SEQ ID NO:192:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:192:

GATCCATTTT AACTTTAGCG GCCCTTTTGG CGAGGAGATG ACTCAGCAAC TGGTCGGGCT    60

GGCGGAGTCT ATCAATGAGG AGCCGGGCTT CATCTGGAAA ATCTGGACAG AAAGCGAGAA   120

AAACCAGCAA GCTGGCGGTA TTTACTTGTT TGAATCCGAA GAAACGGCGC AGGCTTATAT   180

TAAAAAACAC ACTGCGCGTC TTCGAAAAAT CTTGGCGTTG ATGAGGTGAC GTTTACATTA   240

TTTGGCGTGA ACGACGCGCT GACGAAAATA AATCACGGCA ACCTTTGCCG CTAAATCACA   300

TAACGCAGGT TCTGTTCCGG TGCTGCTGAC CGCAACGGTA ATCTTTATAC CGGGCGAGTA   360

CCTAAGAGGC TTTATGGACG ACAGCGACAC GACGTTTCAG CG                      402

(2) INFORMATION FOR SEQ ID NO:193:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:193:

GATCGCGAAG CCGCACAACG TAAGCAGGGG TTATGTAGTG TGTTCTTCAA CACCACGCTA    60

TTCATGCCGT ACCGCAGGTA GATGTCCCCC TTAGGAGCAT CGCTTACGCT GGGAACAGCG    120

TTTAAGCAGC TTTTTGACAA GGGAGCTTTG ATGTATTGTT TGCAGTTCTA GACCTGACAC    180

GGGCGATGAA TAGGAGCAAA GCGTGGTTTA CACATCCATA TTGCTATGTT ACACTATTAC    240

(2) INFORMATION FOR SEQ ID NO:194:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:194:

GATCCCCTCT ATACCGCAGA CAACACAAGG CGCGCTTGCT AACGCGGTGT TACAGGGCGA    60

AATCTTTCTA CAGCGCGAGG GACATATCCA GCAACGGATG GGCGGGATGA ATGCGCGCTC    120

GAAAGTCGCA GGAATGTTAA TGCGCCAGGA TAACGCCCTC CGCTAAATTC TTGGTATTTT    180

ATTTGGCTGG CCGACGTCGC AAATTAGCCA AGTTAGCCA ACTTCTAGCT GATTCATCTA    240

CGATAATT    248

(2) INFORMATION FOR SEQ ID NO:195:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:195:

GATCGGGGTT CAGCTCAAAT TTTTCAATCG CCCAGGCAAC ACCATCTTCA AGGTTCGATT    60

TAGTCACAAA GTTAGCCACC TCTTTGACCG ACGGAATGGC GTTGTCCATT GCCACGCCCA    120

TACCGGCGTA TTCGATCATC GCAATGTCGT TTTCCTTGAT CGCCATCACC TCCTCTGCTT    180

AATACCCAGC GCCTCGACCA GTGATTTACG CCAGTGCCTT TATTAACCGT TATCGAGGAT    240

TCAAGGAAAT ACGACACTTA CGCACGGTAC TTCTCATTGC GAACGCATGC GCGAACGCAG    300

TCAT    304

(2) INFORMATION FOR SEQ ID NO:196:

(i) SEQUENCE CHARACTERISTICS:
        (A) LENGTH: 301 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:196:

GATCTGCGCC CCAGCGTTTG CAGCAGAAAA TAAAAGCCGA AAATCACCAC TAAACAGGCG    60

ATCAACACGT AGAGAAGCAA CCTCCCAATC AATTTCATGG TCTTCCATCC CGTGAAATGC   120

ACATAGGGGA TTTATGCACG ATTTGCGTGC AATCCTCAAG ACAGGAATGG TGAAAGAGCG   180

TTACAGCAGC GGCGAATCGT GTCGCGCGCA GGGTTTTTAC GGTTTTTCGG CGGAGAATCA   240

GTCAGCACGA TAGCGTGATG CGCAGCGATC GATGAGAGCG ATTTACCATC GGACTGAGAT   300

T                                                                 301

(2) INFORMATION FOR SEQ ID NO:197:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:197:

GATCCAATCC TGAACGCCGA ATTTTCACCA CAGGGCGTTG CGCTACGCCA GTTCACTACC    60

CGCTGGGAAG GCGGTATGGT CAGAACTTCC GGCGCCTGGT TACGCGAAGG CAAAGCGCTT   120

ATTCTGGACG ATACCGCTAT CGCCGGGCTG GAGTATACGC TGCCGGAAAA CTGGAAGCAG   180

TTATGGATGA AGCCGCTGCC CGACTGGTTG AACAGCTGAC GCTGAAAAAT TCAGGCAGCG   240

CAATCTGGTG ATTGATATCG ACCCGGCCTT CCGTGCAAAT CACCGCTCTG ACGCTACGCG   300

CAAACTGAGC TGTACAACCA TCATCAATGG GCTCTGAGCG CATCGACTAC GGCAGCGGAA   360

CTTTAC                                                            366

(2) INFORMATION FOR SEQ ID NO:198:

(i) SEQUENCE CHARACTERISTICS:
        (A) LENGTH: 310 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:198:

GATCGCTACC CAATTCCGCG CCCACACAGC CTGCTTTAAT CCATTGCGCT AGGTTTTCCG    60

GCGTCACGCG CCGACGCAAA TAGCGGAACA TCCGGCGGAA GTACCGCTTT CAGCGCGCTG   120

ATGTAGCCCG GACCAAACGC CGACGACGGG AAAATTTTTA ACTTCTGTGC TCTCTGCATC   180

CAGCGCAGAA AAGGCTTCCG TTGCCGTCGC GCAGCCGACA CACGTCATGC CATAGCTCAC   240

CGCCGCGAAT CACTCGGTTG ATATCGCGTA CATCACTTCG CCATCGCACG TGTTCTTCGT   300

TAGCTGTACA                                                        310

(2) INFORMATION FOR SEQ ID NO:199:

(i) SEQUENCE CHARACTERISTICS:
        (A) LENGTH: 348 base pairs
        (B) TYPE: nucleic acid (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:199:

| | | | | | |
|---|---|---|---|---|---|
| TCGAAAATAC | GTATACCCTG | ACAGTGAAAG | CAACCGATGT | TGCAGGCAAC ACGGCGACGG | 60 |
| AAACGCTCAA | TTTTATCATT | GATACCACAT | TGTGGACACC | GACCATCACG CTGGATAGCG | 120 |
| CAGATGATAG | CGGCACCGCC | AACGATAATA | AGACTAACGT | TAAAACGCCC GGGTTTTATT | 180 |
| ATCGGCGGTA | TTGATTGATT | CTGACGTGAC | TCAGGTCGTC | GTGCAGGTGA TGCGCGATGG | 240 |
| TCACAGCGAG | GAGGTGGAGC | TGACCGAGAC | TAACGGGCAG | TGGCGTTTGT ACCGGCACGC | 300 |
| GTGGACTGAT | AGGCGACTAT | CGCGTACGTA | GTGAAGATAG | CGTATATA | 348 |

(2) INFORMATION FOR SEQ ID NO:200:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:200:

| | | | | | |
|---|---|---|---|---|---|
| GATCGGATAA | CGACTCCGCG | GTGGATGCGC | AAATGTTGCT | TGGCCTGATT TACGCCAACG | 60 |
| GTGGGCATTG | CCGCCGATGA | TGAAAAAGCC | GCCTGGTATT | TCAAACGCAG TTCCGCCATT | 120 |
| TCCGTACCGG | CTATCAGAAT | ACTGCGGGAA | TGATGTTTTA | AACGGTGGAA CCGGGCTTTA | 180 |
| TTGAAAAGAA | TAAGCAGAAG | GTGTTGCACT | GGTTGGATCT | AGCTGTCTGG AGGTTTGATA | 240 |
| CCGATACCGT | TGCAAGATTC | GAACGCTACG | ATGCTATTT | | 279 |

(2) INFORMATION FOR SEQ ID NO:201:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:201:

| | | | | | |
|---|---|---|---|---|---|
| GATCGCCAGG | GACGATGGCG | AGCTGGGCCC | CTTGTAAATC | GTTTTTGGTG AGGCCGAGAT | 60 |
| GAAAAACATC | AGACTTGGAC | ATATAAAACT | CCTCTGTGAA | TCGGGTTTGT CAGAAGAAGA | 120 |
| AAGAGACACT | TTACCTAAGG | ATAAAGATAT | TTTGGTGCAT | CATCACTATG CGTAAAACAA | 180 |
| TTGCGTGTTC | CATTAAAAAG | AGATGCCCCA | TCACAATAAA | TAATCAATAT GCAGGCATTG | 240 |
| CACAAAGCAT | AGGCGTTTAG | GCATGTGTTG | TA | | 272 |

(2) INFORMATION FOR SEQ ID NO:202:

(i) SEQUENCE CHARACTERISTICS:
    (A) LENGTH: 401 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:202:

```
GATCCAATAA TGACTGCATT GCCTCATACC CCATACGTAA CGCGCTATAC AAAATATAGA      60
TGCCGATACC TAACGCAAAC AGGGCATCCG CACGATGCCA ACCGTACCAG GATAACCCCA     120
GCGCGATAAG AATCGCTCCG TTCATCATAA CATCAGACTG ATAATGAAGC ATATCGCCCG     180
TACCGCCTGA CTTTGGGTCT TGCGTACCAC CCAGCGCTGA AACGTGACCA GTATAATAGT     240
GCATATCAGA GCATGACGGT AACGCCAATC CCACGCGGGG TCGTTCATTG GCGTGGCTTT     300
AATCAGATTC TGAATACTGG TCAAAAACAG AAACACGCGA ACCGGAAATA ACTACTTTGC     360
GCGCGCAGGC ACTCGTTTAC GTGCCAAGGG TTAATGGTGG G                        401
```

(2) INFORMATION FOR SEQ ID NO:203:

(i) SEQUENCE CHARACTERISTICS:
    (A) LENGTH: 169 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:203:

```
GATCCAAAGT CGTTAAATAA CGGCGGGAAA AGCCTCCACG CCATGGAAGT GCCCCGGAAA      60
TCGCCCCGAC CATGGTGGCG ACAGTATCAG TATCATTGCC GATATTAACC GCCGGAGATA     120
ATAGCATCTA CGGCAGAATT CGGACAACAC GCGAACAGGC CAAAGCGGC                 169
```

(2) INFORMATION FOR SEQ ID NO:204:

(i) SEQUENCE CHARACTERISTICS:
    (A) LENGTH: 253 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:204:

```
GATCCAAAGT CGTTAAATAA TCGGCGGGAA AAGCCTCCAC GCCATGGAAT GCGCCGGAAA      60
TCACCCCGAC CATGGTGGCG ACAGTATCAG TATCATTGCC GATATTAACG CCGGAGATAA     120
TAGCATCTAC GGCAGAATTC GGACAACACG CGAACAGGCC AAAGGCCGG CACCGCTTCA     180
CTCACGTGCA GCCGGAGCAA TATATAGCAG TTCACACGCG TTCCATGGAT GAGCTTCGAT     240
ATAGCTCAGT ATG                                                       253
```

(2) INFORMATION FOR SEQ ID NO:205:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:205:

```
GATCGTACAG ACCCGCGTTG TCATAACCAC GGGTTTTTAG TTCCGCCACA CGCTCGCCCG      60

CCAGCGTTTT CATATCCTCT TTCGAGCCAA AATGAATGGC GCCGGTTGGA CAGGTCTTCA     120

CGTCAGGCCG GTTCTTGCCG ACGTGTCACG CGGTCAACGC ACAGCGTACA TTATGACGTC     180

GTTGTCTTCC GGTTGAGG                                                   198
```

(2) INFORMATION FOR SEQ ID NO:206:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:206:

```
GATCGGAATG CCTTTGAACA GCGGCAGGTC TTCCAGCGGC AGTCCGCCGG TCACGGTCAC      60

TTTAAAGCCC ATATCGGACA GCCGCTTAAT CGCGGTAATA TCCGCCTCGC CCCACGCCAC     120

GGCTGCCGCC TGGGGTCACG GCTGCGGTGA TAAACCACTT GCTGAATACC CGCATCACGC     180

CACTGCTGCG CCTGTTCCCA GGTCCAGTAA CCGGTCAGTT CGATCTGCAC GTCGCCGTTG     240

AACTCTTTCG CCACATCCAG GGCTTTTGCG GTGTTGATAT CGCACAGCAA ATCACGGTAC     300

CAGTACGGTT GGCTTCGAAA CACATACGGG AGAGGATTTA CGAATGCATT GGGAGAGATT     360

GGGTAGGTCA GTAGACGAGA ATGCAGAGAT GGCATGAAGA TTGAAGGGTA G              411
```

(2) INFORMATION FOR SEQ ID NO:207:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:207:

```
GATCCTGAGC CGGGTAGCCA GTATTTGCAG GCAGCAGAGG CAGGTGACAG ACGCGCACAA      60

TATTTTCTGG CCGACAGTTG GTTGAGCTAT GGCGATTTGA ACAAAGCTGA ATACTGGGCG     120

CAAAAAGCCG CCGACAGTGG CGACGCCGAC GCCCTGCGCG CTACTGGCCG AAATCAAAAT     180
```

```
CACTAATCCG GTAAGCCTGG ATTATCCCGA CGCGAAAAAG CTGGCTGAAA AGGCGGCTAA      240

CGCGGCAGTA AAGCGGGAGA AATTACGTGG CGCGGATCCT GGTCAACACC CAGGCCGGGC      300

CGGACTACCA AAGCCATCTC GCTGCTGCAA AAGGCCTCTG AAGATCTGGA TACGACTCGC      360

GTGATCGCAA TGTGCTTGCT ATTGACTGGG CATCTCGTTA AA                         402
```

(2) INFORMATION FOR SEQ ID NO:208:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:208:

```
GATCAAACGC GCTGGCGTAA TCGCTACTGG GTTGATAGCG AAGGCCAAAT TCGCCAGACG       60

GAACAGTATC TGGGCGCGAA TTACTTTCCG GTGAAAACCA CGATGATTAAGGCGGCAAAA      120

TCATGATGAA AAGGACGATA AGCGCGCTGG CGTGGCCTTT GTCGCGTCAT CCGCCTTTGC      180

CAGCGGCACT GTTACCGTTT TTACCCAGGG TAATAGCGAG CTAAAACGCT GACAGACGCT      240

GAGCGCTCGC TCGATTAGTG GACAGCGCGC TGCACGAGCT GGTGGCTG                   288
```

(2) INFORMATION FOR SEQ ID NO:209:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:209:

```
GATCAGGGAA CCTGTACCTC TTAAAGAGAA GTTCGATACC CCCAACGGTC TGGCGCAGTT       60

CTTCACCTGC GACTGGGTAG CGCCTATCGA TAAACTCACC GAAGAGTACC CGATGGTACT      120

GTCGACGGTC CGAGTCGCCA CTACTCTCCG TCAATGACCG GTAACTGTC                  169
```

(2) INFORMATION FOR SEQ ID NO:210:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:210:

```
GATCATCTTC GTCCTGCTCT TCCTGACTCA GCGCACTGTT TACGACAATA CTGTCCGCAT       60

CTCGTTGTGC GATTTTATCG GCGACGTCGC GGGAATAATC GCATATTCAC ATTCACCGCT      120
```

```
GTTATTGATA ACCAGACGGC AATCGCAGAC GCCCATTAAT CAGTTGCGTC TGAGTGAGCT      180

TATCCACGTC TATTTTTTTG ATGACGTTAT TATCGGTGAA GTTAAAACCA ATATCGCCTT      240

TAGATACATT GATTCTATTC ATTTCAATAA GTTGCTTAAC CTGAGCTTTA AACTCTTCGC      300

TAAAACCGCT G                                                          311
```

(2) INFORMATION FOR SEQ ID NO:211:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:211:

```
GATCAGTATC ATCAGTAATG GCCAGCGTTG CAGTATTCTG AATAGCCAGT GAGGTTTTCA       60

GCGGGAAAAT GGCGAGGGTA TACGGAACCG GTTCGGTGGT GCCTTTTGTA GCAACGGTAA      120

ACATTTCCAT ATTGCCGTTT TTGATAATCC GGTGGAAGAC TTCTGCCAGA CTGGGCTATC      180

AACGGTTCCT GAGATAGCGT CAGATTTTAC ACCATCAGCG GTAACGTCGC GTATCGGTAT      240

AAATAGAGAA CGCGCCGATT TTTACACCTT CGGTTGTTTG CCAACGCGAG ACATTGTGGA      300

TCAGATACTA TACTATAGTC ATATCGCATG GCTATGAGAT ACGAGTGCCT GGTGGTGTGC      360

ACGTATGA                                                              368
```

(2) INFORMATION FOR SEQ ID NO:212:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:212:

```
GATCATCCAC TCATCTTTGC CGGTTGAGCC CGATAGTTAC CCGTTCAATA CCGGCATCAA       60

TCGCCCCCGT TTTATTCACC ACCCCCAGAA AGCCGCCGAT AATCAAGACA ACAGCCGCG       120

ACGTCAATGG CGCCGGCGGT GTAGGTTTCT GGGTTATAGA GGCCGTCAAT CGGCGCCAGC      180

AAAACAGCGG TAATCCTTTC CGGATGCGCA CGGGGCATAC GCTCCGCACC GACTTTCAGA      240

GCTGCTATCG ATTGATTT                                                   258
```

(2) INFORMATION FOR SEQ ID NO:213:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:213:

| | | | | | |
|---|---|---|---|---|---|
| GATCATTGTC | ACGCCATTTT | TTTAAATTAT | TAGTATGGCG | TGTGGAGACG | CGTATCTGCT | 60 |
| CACCAATATA | CGTATTGTCC | ATAGGCGTAG | ACAAGCTCCA | TTGCTACAAA | GATAATTTTA | 120 |
| TTTAAGTGTC | AGGAAAATTC | CGGACAAATC | CCTTTTTTAA | TAAAAATACA | CACTCTCGGC | 180 |
| ATGGGATAAT | ACTTAATTAA | CTTTTGTTAG | CGTTTTGAAA | TTAAAAACAG | CGCAGAGGTA | 240 |
| ATAATAGAAA | ATAACGTTAA | CAGGCTGGGT | GAGTATATTT | GACTGACACA | ATTCCAGGTG | 300 |
| TATATGTATG | CGTTTATGCA | TG | | | | 322 |

(2) INFORMATION FOR SEQ ID NO:214:

(i) SEQUENCE CHARACTERISTICS:
        (A) LENGTH: 320 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:214:

| | | | | | |
|---|---|---|---|---|---|
| GATCATCCGC | AGAAGAAAAA | ATATGGCCGC | GTAGAGATGG | TGGGGCCGTT | CTCCGTTCGC | 60 |
| GACGGAGAGG | ATAATTACCA | GCTTTACTTG | ATTCGACCGG | CCAGCAGTTC | GCAATCCGAT | 120 |
| TTTATTAATC | TGCTGTTTGA | CCGCCCGCTT | CTGTTGCTCA | TTGTCACGAT | GCTGGTCAGT | 180 |
| TCGGCGCTCT | TGCCTATGGC | TGGCATGGAG | TCTGGCGAAA | CCGGCGCGTA | AGTTGAAAAA | 240 |
| CGGGCTGATG | AAGTGGCGCA | AGGCAACCTG | CGTCAGATCC | GGAGTGGAGG | GGAGAGTTCT | 300 |
| GGTGCAGTTT | AACAGATCTA | | | | | 320 |

(2) INFORMATION FOR SEQ ID NO:215:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:215:

| | | | | | |
|---|---|---|---|---|---|
| GATCAGATGG | ACCACAACGA | GCACCGAAAA | CAAAACGGCG | CTGACCATCA | GAATGACGGT | 60 |
| AGTGCCGAGT | TCATGGGGC | GTTTGCGTAA | CGCCGGCATG | GCAGGGAGTG | TTTCATAGTG | 120 |
| GACCTGAGCG | ACGAATCGTA | AGGTTATTAT | CCCTGATGAG | GCTCTAATTC | AAAGGCATAG | 180 |
| GCAGTCGTCC | AGTGTGAAAG | CCGCTGCTGC | AGGCCGCTAC | TGCATCGTAT | ATCGGACGAG | 240 |
| ATTTCAATCA | ATAACACGCA | ATTTCCGCAT | CCAACCG | | | 277 |

(2) INFORMATION FOR SEQ ID NO:216:

(i) SEQUENCE CHARACTERISTICS:
        (A) LENGTH: 330 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:216:

```
GATCCTGAAA CGCTGACCAG ACGCCGAGCG CGCCGTACCA CGAATCTCCG GTGGCACTCT      60

GCGCACAACC TCTACGCCCA GCGATGGGAA CATCAGCGAA CAGCCGCAGC CGGTAATCGC     120

CGCGCCAATC AGCGAGCCTG CTGACGGAGC GGCCCACATT ACCGCCAGTC CGGTCCCTCT     180

ACCAGTAGTG AAAAGGTTGC ACCGTGCGCG CGTAACGGTC GGGAAATTTG GCGCAGAAAA     240

GCGGACAGCG ATAAACGCAT CAACACTATG AAACGGTGAT ACAGTAGTGT GACAGAGTGT     300

ATCTAGTGAC ATCTGACAAC TTCTCTCAGC                                     330
```

(2) INFORMATION FOR SEQ ID NO:217:

(i) SEQUENCE CHARACTERISTICS:
          (A) LENGTH: 223 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:217:

```
GATCTGGGCG AAATCGCGCG GAGTCTGGCG GCGGGCGATA TCATTACCCA CTGTTACAAC      60

GGTAAGCCGA ACCGTATCTT CGGCCTGACG GCGAGCTGCG GCCTCGGTGA CACGAGCGCT     120

GGCCGGCGGC GAGGCTATGG AGTCGGCATG GTACCGCCAG TCCTGAGCTT TGCGTGGCTA     180

ACTCGCTATA GCTGGATTTA CCGCATACAT CAGTCGATAT CTC                     223
```

(2) INFORMATION FOR SEQ ID NO:218:

(i) SEQUENCE CHARACTERISTICS:
          (A) LENGTH: 316 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:218:

```
GATCGCCACC GTTTTGTGAT GCGCGCCAAT TTGGGCTGGA TAGAAACCGG TGATTTCGAC      60

AAAGTTCCGC CGGATTTACG TTTCTTCGCC GGGGGGACCG CAGTATTCGC GGCTATAAAT     120

ACAAATCTAT TTCGCCTAAA GATAGCGACG GCAATCTTAA AGGCGCCTCA AAACTGGCAA     180

CCGGATCGCT GGAGTACCAG TATAACGTCA CCGGTAAATG GTGGGGGCAG TGTTTGTCGA     240

TAGCGCGAGC GTGAGTGATA TCGCGTAGCA TTCAAACCGG ACGCCGACCG ACCGACCGTG     300

GCTTCAACCT ATTCAC                                                    316
```

(2) INFORMATION FOR SEQ ID NO:219:

(i) SEQUENCE CHARACTERISTICS:
    (A) LENGTH: 182 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:219:

```
GATCTGGGGT GGGGGATTGT TGATGGTGTG TGGAGCGCTG CTGAGCGGAT GGCGGGGGAG      60
GAAGCATCCT GAGTTATTGC CTGATGGCGC TGCGCTTATC AGGCCTACGA GTGAAAAGCA     120
TGGTAGGCCG GATAAGGCGT TCACCGCATC CCGAAAACGA TGTTACTTTT GGCTTTACTG     180
AT                                                                    182
```

(2) INFORMATION FOR SEQ ID NO:220:

(i) SEQUENCE CHARACTERISTICS:
      (A) LENGTH: 419 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:220:

```
TGCAGATCAA ACAGCGACG GCTGGCAAAA GCGGTAAAGG TTTACGACCG GTCAGCGCCC       60
CAGCCGCCGC CGTGCCAATC ACATTCGCCT CCATAATACC GCAGTTAATG ACATGCTGCG     120
GGTAGTCACG CGCCACGCTG TCATCGCCAT TGAGCTCATT AATCAGCCTC AGGATATGGC     180
TTCAGCCTCA AGCGCAATAA TTGGGCTTCC GGCCTCAATC TGCCCGGCGA TAAAACCGGC     240
GTAAACTTTG CGCATTTCGA TATCGTCTTT AAGCCCTGGG AAGCTTAATC ATGCATGACC     300
TCCAGTTGAT GAATGGCCTC ATTGAACGTT GCTTATCGCA TCGTCAGCGT AAGTGGTGAG     360
AATTCGTTAA CTGCTCAGGC ATGCACCCTG CCTTATGCTG TCAAGGATCA CACCGTGCT     419
```

(2) INFORMATION FOR SEQ ID NO:221:

(i) SEQUENCE CHARACTERISTICS:
      (A) LENGTH: 126 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:221:

```
GATCTTATGA CATTGTGAGT ATCCATCGCT TTTTGTACTG AGCTGTAGGC AACTCCGACA      60
GCTTTTGCTC AGCAGCTGTT GTTTCTCATA AGCTAGTGAC CAAGCTGCTG CTACCACAGG     120
TCTGGG                                                                126
```

(2) INFORMATION FOR SEQ ID NO:222:

(i) SEQUENCE CHARACTERISTICS:
    (A) LENGTH: 192 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:222:

```
GATCCTGCAC GCACGGGCGC ACAGCACCGA CAAGCTGTCC AGCTACTTGA CACAGCGCCA      60
GCGCGTGCTA GCGAGCGAAC CCGCAGGTGG CACATGGCGG GGACGGCGAG CAGGAGACAG     120
GCTAGAACGC TTTATGTGCG CACTATGCTA TCAAATAGGC CGTCCGGCTG CACGCCGACA     180
CTACCCTGAC AA                                                         192
```

(2) INFORMATION FOR SEQ ID NO:223:

(i) SEQUENCE CHARACTERISTICS:
        (A) LENGTH: 331 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:223:

```
GATCACCGCA TCGCGAACTG GTTACGGGCC TGTGGAGCGT ATTTTTTGAT GTTATTGGTA      60
TTCATAGAAA ATCCTGCAAA GGGCAGCAGA GCGCTGCCCT GAAATGGGGG TTACTGAAGA     120
CGAATCCGGT CACCTGCCTC AATAGCTGCC AGCAGCGAAG TACGAAGCGT ATCCAGCGCT     180
TTTTCCACCT GTTCGGCGGT TTCCAGCACT TCGCCACCGG TGGCTTTGCG CATCTCGCTG     240
GCGACATTCA CCAGATGCGT TTTTTCGGTA CCGGTTGGAT AACGGTTCTC TACCACAACA     300
TAAGCTCGTT GTGACTCGGC GCCTTAGCTT A                                    331
```

(2) INFORMATION FOR SEQ ID NO:224:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:224:

```
GATCTAACGT ATCACGACTA AACGTAAGGG TAAAGCGGCT GGCGTATCGT CCGGGCATAA      60
AGTCATATCG CCTGAACAGA TAACATCTCA CTGACTTTGA AACGCGATTT TATAATTTGC     120
TGCCCAAAAA TACGTGGCGC TGAAAGGCGC ATTTTTGATG CAAATCATTT ATTACTGTGA     180
TAACACTGCG CGCGATAAAA CATTAATATA TTCACATAGT AATATGTTCT ATTGGAATGG     240
TTGTTTCGAT ATGACAAAGT CTAAAAAACC ATTGATGTGA AAAGGAATAA GAATTGTCTA     300
TATTCCGATT CGGTGGAATT AAGTATTCTC GGATAAAATA GAATGATATT GATATTCTTT     360
```

```
TGATATGGTC TATAGCGCTA TGTATCAGAC GCGTGATCGT CGGAGATCAG              410
```

(2) INFORMATION FOR SEQ ID NO:225:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:225:

```
GATCTTCGAC TGCCGCGCTT CCGCGACAGC GACATACGGG TGTTCTTTGT CGGTGACGTT    60
TATCCGTTGT CGTGACCTTC ATCCGGTGGT GAAACCTGAG CCGAATAATA CTGTACACCA   120
CCACCAGGAC AGAATACTCA AACCACGTTC ATGTGATTGT TGCACCACAT ATTCATTGTT   180
GGAAC                                                              185
```

(2) INFORMATION FOR SEQ ID NO:226:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:226:

```
GATCCGCTGA CAGATGTCGT GTACAGCATT CTTTAGAGTG GAACGGTGAC CGTACCGCAA    60
AGCTGTGAAA TCAACGCCGG ACAAACGATT CTGGTAAATT TCGGCGCATT ATACAGCGGC   120
AATTTCAACC ATGCAGGCCA AAAGCCGGAG GGGGTACGAG CGAAAAAATT CAGTCGCTTC   180
CGGTAAAGTG CAGCGGTCTG GATTCGCAGG TCAATTTAAC AATGCGTCTT ATCGCTCCGC   240
GGATAGCACG TCCAGCTATC GCTCGATATG CGATGT                            276
```

(2) INFORMATION FOR SEQ ID NO:227:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:227:

```
GATCACCGAC CGGACGGTCC GTACCTGGAT TGGGGAGGCG GTTGAGTCCG CAGCGGCTGA    60
CGACGTGACG TTCTCAGACC CGGTGACACC CCATACTTCC GCCACTCCTA TGCGATGCAC   120
ATGCTGTACG CGGCATACCG CTGAAGGTGC TGCAGGCGCT GATGGGACAC AAATCGGTGA   180
GCCTGACGAG TGTACCGAAA GTGTTTGCGC TTGATGTTGC CGCACGACAC CGGGTGCAGT   240
```

```
TTCAGATGCC GGGTGCTGAT GCAGTGGCTA TGCTCAAAGG AGGTTCATAG AGACGTGTAT      300

GCATTTTCAG CTTCGCTGCA CAGCATCGAA CGGAGTTTAC GCGTTTATCA GCCATGTCTG      360

CGCACAGAGG AGTGTGCTCG AAA                                              383

(2) INFORMATION FOR SEQ ID NO:228:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:228:

ACTTGCCGGT AATTTCCATC CCTTCCAGCA CCGCCATCTC TTTACCCTCA ATGGCGATGG       60

ACAGTTTATC CAGCGTTAAC TTTTGGTCGC CCCACGTTCG CCAAAGCTTG CCAGTTTACT      120

GGTACCGTCG GTTTTCAAAT TATTAAAGGT GAGTTGGACC TTCTGATTAT ATTCGTTAAC      180

GGCATCGACC AGGCCGCTCT CGCGCTTCGC CTGACAGCGA AACCACATTA CCGTCTTTAT      240

CGGGCGTTAA CGGGAACTCG GCGCCGCTAA AGGCACCTTT ACCGGCATTC TCTGAGTTAA      300

CCGGCTTGAG AGAGATATCG GAGCGGTATC GCCGCCATAC ATGCGGTATT GATACAA        357

(2) INFORMATION FOR SEQ ID NO:229:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:229:

GATCTATTTC GGACAGCCAA AAGGCCGTGA AGGCAGCGGT CAGTACAAAA AGCCTTTGAT       60

ACCGAAGTTT ATCACCGGCT TTGAGATCGA GCGCAGTTGC CCGTATGCCT TTGAATCGGC      120

GCGTTAAACC GGCCGTAAAG TACCCTCTAT TGATAAAGCC AACTACTGCA AGCTCTATCT      180

GTGGCGTGAA TACGTCAATA GTGGAAAACG TATCCGATGT GAACT                      225

(2) INFORMATION FOR SEQ ID NO:230:

(i) SEQUENCE CHARACTERISTICS:
        (A) LENGTH: 275 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:230:

GATCGTTAAA CAGATTGACC AGTTCGCCAC ACTCTTCCAG ATTAAACCCC ACCTGCCTCG       60
```

```
CCTGTCGCAG CAACGTCAGC TCGTTTAAAT GCTTCTGCGT GTAGGTGCGA TAACCATTTT       120

CGCTACGTAA TGGCGGCGTC ACCAGCCCTT TCTCTTCATA AAACCGAATG GCTTTGTGGT       180

TAGCGTTTTG GCACATCGCT ATATCATATT GCCCTGCCTA CTGCTGAGTT ACTATACGGG       240

TACTACGTCT AGAGATCGCG AAAAGGTTAC AGTAC                                 275
```

(2) INFORMATION FOR SEQ ID NO:231:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:231:

```
GATCGACGTC GCCTGATTTA AGACCCGCAA GCAACATCGT ATTGTTCATG GTCGCGACCT        60

GTAACGAGGT CGATTTTTGC TGTTGATGGA ACCGCCCAAT AGCCGCCGGG AGTATACCCA       120

GCGCAGGTGG GGAGCGGCAA CACGCACCAT CGGCGCTAGC TCCTCTTTGG CGATTCGATC       180

GGATCCTGGC GGTGGTATTC ATGATCTAAT CCTTTTATCG ATGAGTAAAA TTG             233
```

(2) INFORMATION FOR SEQ ID NO:232:

(i) SEQUENCE CHARACTERISTICS:
        (A) LENGTH: 358 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:232:

```
GATCGGCGGA GAATCCCAGA CAGGCCAGGT CTTTCAGCTC GTCGCGGGTC ATCGGGCCGG        60

TAGTATCCTG AGAACCGACG GAGGTCATTT TCGGTTCGCA GTACGCGCCC GGACGGATAC       120

CTTTCACACC ACAGGCGCGA CCGACCATTT TCTGTGCCAG CGAGAAGCCA CGGCTGCTTT       180

CCGCCACGTC TTTTGCTGAC GGAAAACGTC TGAGTGCGCA GCCAGCGCTT CACGCTTTTG       240

TGCTAGCACG CGATATCACG ATACACACGC ACGACTCGTC ATCAGCACGT CGTTCAGTCG       300

AGTGCAGTAG CGCGTCATGA TGCGTACTGC TTGACGTAGA CTATCATGCC ATATCAGT        358
```

(2) INFORMATION FOR SEQ ID NO:233:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:233:

```
GATCCACAGG TAGCGTGATG CGTTTTAGTT CCCCCTGCTG CTCAAGTAGC GTCAGGCCGT      60

CGCGTAAATC GTGATATTTC ATGGCGTCCA TTGTAGCCTC TTGGTAAGCG CATCATTATA     120

CGGCGTTCAT CATCGGGATG CTGTATTTTT GTTAAATTAG CGTGAACTCT GGCAACCAAC     180

GCTAATCCAG ATACGGCTTA AAGGATGAAG TGTATATTAA CTTCGCGCAT GGCTTTTGCT     240

ATGCTTGCGC CCCGAACAGC GATAAGAGTC ATATGCATCT GGTATTTACT GTACTGCAAA     300

CG                                                                   302

(2) INFORMATION FOR SEQ ID NO:234:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:234:

GATCGTCACC TCCACCCTCG CGCGCGGGGC GGTGAAGCTC TCGAAACAGA AAGTTATCGT      60

GAAGCACCTT GATGCGATTC AGAACTTCGG CGCGATGGAT ATCTGTGCAC TGATAAAACC     120

GGCAACTCTG ACGCAGGATA AAATTGTGCT GGAGAAATCA CACGATATTT CTGGTAAGCC     180

CAGCGAGCAT GTCTGCATTG CGCCTTGCTG ACACATTATC AGACCGTCTA AAAAAATTTC     240

TGATACGCGT CTGAGAGTAG ACAACGCGGT CACCTCGACG TGCAGAAAAT CGATAGATCC     300

GTTATTTAGC GTGCGATGTC GTAGTGTGCG AGATCGACGT GCATCAGCTG GATCTGCAAG     360

CTAACGAGAC TCAC                                                      374

(2) INFORMATION FOR SEQ ID NO:235:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:235:

GATCGGACTT TATTCGCGCG ATAGTCACGG AAAAAATGGT TTAACTTTGC TAATTCATCC      60

TGAATGTAGG CTCTTCCATC GAAAAACTCC GCCTTGATTG ACTCTCCGGT ATGGAGATTG     120

TTTAACGTCA AAAATGCGCG CCGTGGGGTC GAGAGTGTGG CAAACGCTGA GCGCGGGCAG     180

GATGGCGGCG CGAGAGCGAC ACCACCAAGC GCCAGAGCTT GCGCGATTAG CGTCAAATTT     240

GTCATGATAA TCAGGTCTAC AGGTCAATGT TATCGTTAAT ACACTTCTAC CTTTAAGCAG     300

ACATGATACG CTGACACGAC TCTACGCGTG ATAGTGTGAT ACTTGGCACA GACTA          355

(2) INFORMATION FOR SEQ ID NO:236:

(i) SEQUENCE CHARACTERISTICS:
        (A) LENGTH: 363 base pairs
        (B) TYPE: nucleic acid
```

(C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:236:

```
GATCGTCACG TGATTTGCCC GTCACGCGAA TCTCTTCCCC CTGAATTTGC GCCTGCACCT      60
TCAGTTTGCT GTCTTTAATC AGCTTGACGA TTTTCTTCTG CACGGCGCTT TCAATGCCCT     120
GCTTCAGCTT CGCTTCCACA TACCAGGTTT TACCGCTATG CACGAACTCG TCCGGTACAT     180
CCAGCGAAGC GCTTCAATAC CGCGTTTAAG CAGCTTGGCG CGCAGAATAT CGAGCAACTG     240
ATTGACCTGG AAATCGGACT CGCTCAGCAC TTGATGGTTT ATTGGCATCG TTCAGTTCAT     300
AGTGCTCTAC GCACGGAGTC AAACAGACTC ACTGGAGCTA TCACACGTAC GCGCTCTCGA     360
GAT                                                                  363
```

(2) INFORMATION FOR SEQ ID NO:237:

(i) SEQUENCE CHARACTERISTICS:
        (A) LENGTH: 320 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:237:

```
GATCGTTAAT TAGGCGCTGG GCGTGCTGGA GCAGTAATTT ACCGCCTTCC GAGGGGCGTA      60
GTCCTTTACT GTGGCGCTCA AAAAGCGTGA TGCCTATCTC ATCTTCGAGT TGAGATAGCC     120
ACTTCGATAG CGCCGCCTGG GAGATATTCA TCATCCGGGC GACGTGTCCG TTCAAGGGTT     180
GGCCCTGTTC GGCCCAGCGC AACCAGCGTT TGCGGTGATG TAATTTCAAT TTCTCCCGTT     240
CCATTCGCTA TAACCTCAGG TTATGTCTCT CCTGAAACCA TTGTACTTTA TCCTCCTCTA     300
CACTCGTACT GCACTAACAC                                                320
```

(2) INFORMATION FOR SEQ ID NO:238:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:238:

```
GATCCTGCAA CGCTTTCGAC CCGGTCGAAA TAATGACTTT TTTCCCGGCG CGCAACGCCG      60
AGCGAGGTAA GCATAGGTCT TCCCGGTTCC GGTGCCGGCT TCAACAACCA GAGGCTGCGC     120
ATTTTCAATC GCTTGTGTTA CGGCAACCGC CATTTGTCGC TGTGGTTCGC GCGGTTTAAA     180
GCCGGTTATC GCTTTGGCCA GTTGGCATCT GCTGCAAAAT CGTCCGTCAC ACTGCCCCCT     240
```

```
GTTAATTTGC ACAGGGATTA TGTCAGGGTA GAAAGGCTTA CACAGTTACA GAGGTGACGG        300

CGGCACATTG TGCAGTCTTG AACCATTCAA ATGAAAAGCA AATGAGGAAT AAGTAATGTC        360

TATCGTGCGT ATGATGCGAG ATCGTGTCAG ACGTGTGACT CAATAT                      406

(2) INFORMATION FOR SEQ ID NO:239:

(i) SEQUENCE CHARACTERISTICS:
           (A) LENGTH: 263 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:239:

GATCCTACCG GCCCCCACGC TTTGATTTGA ATAATAGAGG CTACCGACGA CAGCGACATG         60

CTGATAATGT GCTGCGTATC CTGCGCCGGT AAACCCAACG CCTGGCAGAT TAACAGCGCT        120

GGCTGATTAC CGCGACAAAC ATGCCACGAG ATGCTGACAA GCGCAAAAGG TTGAGGAGCG        180

CGGCGATCTT CAAGACGGTA AATTAATCGC TGCACAATTG TACGCGACGA TGCATCTCGC        240

ATGCGTCTAC GACATAGACA TCT                                               263

(2) INFORMATION FOR SEQ ID NO:240:

(i) SEQUENCE CHARACTERISTICS:
           (A) LENGTH: 364 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:240:

GATCAACGCC TAATTTGGCC GCACAATCCA GAGAGACCTG CGGGTGCGGT TTGCTGTAGG         60

GCAATTTTTC TGCAGAAGCC AGCGCGTCAA AACTGTCGCG CAGTTCAAAC ATGGTGAGCA        120

CTTTTTCCAG CATATGCAGC GGCGATGCCA AGGCAAGCCC CACTAATAGC CCCTGCGCTT        180

TACACAGCGC CACAGCTTCG CGCACACCCG GCAAAAGAGG GCGCTCTCTT TCGATAAGCG        240

TAATCGCGCG GGCAATAACA CGGTTTGTCA CTTCTGGCGA TCGGGCGTTC ACGTTGCTGC        300

GCAACAGAGA TCGACAACCA TATCATGCGT AGCAAGCTGT TGCAGCTCAT GGCCGAGTAT        360

ATCT                                                                    364

(2) INFORMATION FOR SEQ ID NO:241:

(i) SEQUENCE CHARACTERISTICS:
           (A) LENGTH: 221 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: YES
```

(xi) SEQUENCE DESCRIPTION: SEQ ID NO:241:

```
GATCATTTTA ATGCTGTGTC TTGCCATTTT TTTCTCCATA AATTTCAAAA GGAAATCATG      60

CCTGATGCGC ATTGCGACGG CGTGAGTACC ATTCAAGGAT TTGGTGACGA TGCAAACTGA     120

TGGAACGACC AACGACAACA ACAATGAGAA GCGCACCGGA CAATGCGCTG GAATTGATTC     180

GGCACTCCGG CCATCTGTAG CCCTCGTGTA AATCCACCAG C                         221
```

(2) INFORMATION FOR SEQ ID NO:242:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:242:

```
GATCATCGAC GTATGTCCTT TCCAGATATT CCGCCCGCCG CCAGCCCACT CAAACAACGG      60

GGGGCGCCGG CAAAAAAGCG AAAGACATCC ACCGATTGCC GGAATTTATA TTAATTACGC     120

CAGTGCAAAG GCTTATTGCA GTTTTGCGAT TCAAGCCGGG CGAACTCAAG GGCGTTTTGC     180

TCGATGCTGT CCGCAGTTTT AACAGACATT CCGCCCGTGC TTTGGGTGTG GTCTGCCCAT     240

TCGGAAACGC GTTATCGGCG GCTGATCGCA GCGTAACCTG                           280
```

(2) INFORMATION FOR SEQ ID NO:243:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:243:

```
CACTATAACA ACGGCGCGGC GGTACCTGGG CGACGTCGCC AGCGTCACCG ACTCGGTGCA      60

GGATGTCCGT AACGCCGGGA TGACGAACGC TAAACCCGCT ATTTTGTTGA TGATCCGCAA     120

GCTGCCGGAG TGGAATTCCA CATGTGGAAT TCCCATGTCA GCCGTTAAGT GTTCCTGTGT     180

CACTCAAAAT TGCTTTGAGA GGCTCTAAGG GTTCTCAGTG CGTTACATCC CTAAGCTTGT     240

TGTCACAACC GTAACTAAAC TTAAACCTAT ATATCCT                              277
```

(2) INFORMATION FOR SEQ ID NO:244:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:244:

```
TGCAGATCAT TGCCTGATGT TCTACGGTCG CAAAATGCAC CAGNNNNCAG AACAACGACA        60

GCGACAACAA TACGGCTGAA GCGCTTTAAT CGCGCTAACT CCTTTTTCTC AAAGCCCCTT       120

TCCGTTCACC TGCTATAGCG TNGAGGGGCC CACTTACCAG GAACAAGACT ATGAACGTTA       180

TTGCTATCAT GAACCACATG GGCGTCTACT TTAAAGAAGA GCCTATTCGT GAACTGCATC       240

GTGCACTGGA AGGTTTAAAT TTCGTATCGT CTATCAAAAC GACCGAGAAG ACCTGCTGAA       300

GCTGATTGAA ATAACTCCGC CTTTNNGTCA TTTCGACTGG GATAATATAC CTTGAGCTTC       360

GAGAGAGATA GCAGTGAGCG                                                  380
```

(2) INFORMATION FOR SEQ ID NO:245:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:245:

```
GATCTGATTA TCGACGCGCT GCTTGGCACC GGCATAGCCC AGGCACCGCG CGACCCGGTA        60

GCCGGTCTGA TTGAACAGGC GAACGCATCC TGCGCCGGTT GTCGCCGTCG ATATCCCGTC       120

AGGTCTGCTG GCGCAAACGG GCGCACGCCT GGCGGGTGAT AAGCGCGCGC ATACGGTCAC       180

GTTTATCGCC CTGAAACCAG GCCTGCTGAC CGGCAAAGTG CGTGAGCTTA CCGGCATATT       240

GCATTATGAC GTTGGGACTG GAAGGCTGGC TGGCAGCAG ACGCGCGTCG GTTTTGAAGA       300

GAGTTGGGGC AATGGCTAAC GCGTGACGAC TGATAGGGAT ATGTGTAGAT ATG            353
```

(2) INFORMATION FOR SEQ ID NO:246:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:246:

```
CACCCGGCTG ACTGCCGTAT AATCCAGCTT TTTACGCGGG TCCGCGGAGG GTTTTGCCGT        60

CACAGAGAGC GTATTCTGCG AGTTTATGGT TGTCTTACCT AACGGATAGC CTTCGCTATC       120

ATAGCGGTAC TCGACCCTTC ATCTCTTTGC CCGTCGCCGA TACCACAAAA CCGTTGTCGT       180

CCGTTTCCCA GGTCACGCCC GCCGAACGAA CGCCGCCAGC TGGCACTTCC CCTGTAACTG       240

CACCTTTTTT TCCAGCGTCT GAGCATCCCG GTAATAATTG GCATCCAGCA CGAGTGCCAG       300

CCCCGTATTT ATCTCCAGAT CGTGTAACTC AAGCGTATCA AACAGCCTT CCTGTGAAAG       360

CGTACCGCGA CCTCTA                                                      376
```

(2) INFORMATION FOR SEQ ID NO:247:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:247:

```
GATCAAGACG CGAATCCCCG ACGCGCCGAT AACGCCGTAC AACAGCAGCG AGACGCCGCC      60

CATCACGGGT AACGGGATAA TCTGAATCGC CGCCGCCAGT TTGCCAACGC AGGAAAGCAT     120

GTAATAACGA AAATCGCGTC GCCGCCGATA ACCCAGGTAC TGTAAACGTC GGTGATCGCC     180

ATGACGCCAA TATTTTCCAT AGTGTATCGG CGTGAGTAGA ACCGAATATC GTCGACATCT     240

AGCACATC                                                             248
```

(2) INFORMATION FOR SEQ ID NO:248:

(i) SEQUENCE CHARACTERISTICS:
        (A) LENGTH: 253 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:248:

```
TTTCGACAAA GCGCGCCGCC GAGATATTCG CCATGATCAT GCACTCTTCG ATAAGCTTAT      60

GCGCGTCATT ACGCTGGGTC TGTTCGATAC GCTCAATGCG ACGTTCGGCG TTAAAGATAA     120

ACTTCGCCTC TTCGCACACA AACGAGATCC CCCCGCGCTC TTCACGCGCT TTATCCAGCA     180

CTTTGTAGAG GTTGTGCAGC TCTTCAATAT GCTTCACAGC GCGCATATGT CACGCAGATC     240

TGATCGCTGC AGC                                                       253
```

(2) INFORMATION FOR SEQ ID NO:249:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:249:

```
GATCAAACAC CAG ACGACCG CGACGCGCAC GACCATCGGT GGTATCTAAC TCAAATTTCA      60

TTATCACTCC TGCGTCAGAA AAACAGTCCG ACGTTTAACG ACTCGCTACG GAATGATTCC     120

ATAGCTAATA AATTCCCGAA GACGTCATCG GCGCAGAGTT TGGGGTCGAC CAGCGCACAG     180

CCACCGGAGC GTACACGCAG TACGTGAGGA TGGCAGCAC TGCCGCGTCA AATGCAGTGA      240

GATAGCTCTA CGACGTCAGA ATAGCTGCGA TGTACGTGAT AACTGCTCCG TAGCTAAAAG     300

CATTTGTCTA CGCAGTCTAT AGGCATCATG TGTGTGATAC GCATGCGAAC AGCATACACG     360
```

TGATCGCAGA TGAGTGTGAT CAGGCATATA CTGACGAACT GATATAGATT CGTG        414

(2) INFORMATION FOR SEQ ID NO:250:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:250:

GATCTTCCGG GTTCACGGCC ACGCGGTAAT TCTGCCGAGA ATAGTTTTCG GGCGGGTGGT        60

GGCGACAACC AGAAATCTTA CCGTCGCGGT TTTCGCGCCG TCGGCCAGCG GA        112

(2) INFORMATION FOR SEQ ID NO:251:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:251:

GATCGTTAAA TGTGCGGTAA TCCTGTGATG AATACCGATA CGCAGCCAGA CCAAACCGAG        60

TTAATGTTTG GGTCAGGTAT TTATTATAAG CAATCTGATA ACTCTGACCA TCAAATACGA        120

CGCCATTATC CTGTTTACTG TGCGCTCGCG TAGCTCAAGC GAAATGGCGC CAATCCGGGT        180

ATTCCACCCC GTGCCGAGGG TAAACGCATT ATAATGGTTC GATAGCATCG TACGCATAAG        240

CGTCAACAGG TTATTAGGCA TACTGATACT GATTGGTAAA TCGGCTGATA TCGGCGCTTC        300

AATTATGACT ACGCGCGAAA TCATACTGAG CCGTCCAGTC CATTC        345

(2) INFORMATION FOR SEQ ID NO:252:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:252:

GATCGGTCGC CGCCTTACCT TTTTCCAGTA CACTGAGCAG TTCGCTCAGC AGTTGTTCAA        60

CAGCTCCATC ACTAGAGCGG GAGAGTTCTG GCATAAATCA AAATCTGTTT GTTCATGAAA        120

CGGCAACACA TTAACCGCAG CAACAGTTTT TTTCTGCATT TTTCGGCCTA AATCATCGCC        180

TTACGATACT CTGAATACAG GGG        203

```
(2) INFORMATION FOR SEQ ID NO:253:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:253:

GATCGTAATC ATTCACTTCG GTCAGCAGCT CGAGCACTAA CGCGTCGAGC ACGCCTTCCA      60

TCGGCGCCAG TAAAACACGC ATATCGGTAT CCACAGCAAA AAAGAGGCG CTATCATAAC     120

GCCTCTCTGC GATGAGCAAA ACTTTTTTGC CGGGTGGCGG CGCAAACGCA CGCTACGTAC    180

GTAAGTGCTC ACGCGGCTTC AAGACCAGTT ATTTTTCCAG CCGACCAGCC ATTCGAACCG    240

CGATAAGCTC TGCGATCCTT TCCAAGTATG CTG                                 273

(2) INFORMATION FOR SEQ ID NO:254:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:254:

GATCTTCTCG CTTTCTTCAG GGCTTACTCC CGTCTCTTCT TCATCGACCG TGATCAAAAT     60

ACCGTCTTTA TCCACCAAGA AGCCGACTTC AATCTTCGTA TGAAAATAGC TCACCATTAC   120

GAACTATATT TTTCATCTCT CTTTCCAGCT TTTT                                 154

(2) INFORMATION FOR SEQ ID NO:255:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:255:

CGCTGTTCTG GTGTTAAGAC TTTGCTTAAA TCAAAATAAT ATTTAACCCG ATAATAGCGA     60

GCCTGTTGTT CTATGTTACT GAAGGCTGCA AGCTGCTGTT TTACGGCGGC GTCATCCCAT   120

TTACCGGATT TAATCACCTC TATCAGCGCA CCGTCTTTAA TTCCCTTCAT AGAAATCTGA   180

CTGACGTCGG TTTCCAGTTG TTGGTGAAGT TTTTTGATCC GGGTAATCTG ATCGTTTGTC   240

AGCTTCAGAT GCTGGACAAT AGGATCCTGG GCGGGCAGGG GGAGGATTGG GGACAGCGTG   300

CAAGCAAAAG AAACGCGCAG AGTCGCTGCA GTAAGTGGGC ATACGTTT                348
```

METHOD AND PROBES FOR THE IDENTIFICATION OF MICROBIAL GENES SPECIFICALLY INDUCED DURING HOST INFECTION

CONTRACTUAL ORIGIN OF THE INVENTION

This invention was made with Government support under Grant No. AI 36373 awarded by the National Institute of Health. The government has certain rights in this invention.

BACKGROUND OF THE INVENTION

1. Field of the Invention

The current invention relates to a class of microbial coding sequences that are specifically induced during infection of a host by a microbial pathogen and more particularly to a set of probes that may be used to identify and isolate microbial virulence genes. The products of these virulence genes will provide potential targets for the development of vaccines or antimicrobial agents.

2. Description of the State of the Art

Microbial pathogens, or disease-producing microorganisms, can infect a host by one of several mechanisms. For example, they may enter through a break in the skin, they may be introduced by vector transmission, or they may interact with a mucosal surface. Disease ensues following infection of a host, when the potential of the pathogen to disrupt normal bodily functions is fully expressed. Each disease-producing microorganism possesses a collection of virulence factors, that enhance their pathogenicity and allow them to invade host or human tissues and disrupt normal bodily functions. Infectious diseases have been major killers over the last several thousand years, and while vaccines and antimicrobial agents have played an important role in the dramatic decrease in the incidence of infectious diseases, infectious diseases are still the number one cause of death world-wide.

Vaccines

Attempts to vaccinate are almost as old as man's attempt to rid himself of disease. However, during the last 200 years, since the time Edward Jenner deliberately and systematically inoculated a population with cowpox to avoid a smallpox epidemic, vaccination, at least in parts of the world, has controlled the following nine major diseases: smallpox, diphtheria, tetanus, yellow fever, pertussis, poliomyelitis, measles, mumps and rubella. In the case of smallpox, the disease has been totally eradicated. The impact of vaccination on the health of the world's population is hard to exaggerate. With the exception of safer water, no other modality, not even antibiotics, has had such a major effect on mortality reduction and population growth.

Following the first exposure of a host to an antigen, the immune response is often slow to yield antibody and the amount of antibody produced is small, i.e., the primary response. Upon secondary challenge with the same antigen the response is more rapid and of greater magnitude, i.e., the secondary response. Achieving an immune state equal to the accelerated secondary response following reinfection with a pathogenic microorganism is the goal that is sought to be induced by vaccines. Vaccines are basically suspensions of viral, bacterial, or other pathogenic agents or their antigens which can be administered prophylactically to induce immunity.

In general, active vaccines can be divided into two general classes: subunit vaccines and whole organism vaccines. Subunit vaccines are prepared from components of the whole organism and are usually developed in order to avoid the use of live organisms that may cause disease, or to avoid the toxic components present in whole organism vaccines. The use of purified capsular polysaccharide material of H. influenza type b as a vaccine against the meningitis caused by this organism in humans is an example of a vaccine based upon an antigenic component. See Parks et al., *J. Inf. Dis.*, 136 (Suppl.):551 (1977), Anderson et al., *J. Inf. Dis.*, 136 (Suppl.):563 (1977); and Mäkela et al., *J. Inf Dis.*, 136 (Suppl.):543 (1977). Classically, subunit vaccines have been prepared by chemical inactivation of partially purified toxins, and hence have been called toxoids. Formaldehyde or glutaraldehyde have been the chemicals of choice to detoxify bacterial toxins. Both diphtheria and tetanus toxins have been successfully inactivated with formaldehyde resulting in a safe and effective toxoid vaccine which has been used for over 40 years to control diphtheria and tetanus. See, Pappenheimer, A. M., Diphtheria. In: *Bacterial Vaccines* (R. Germanier, ed.), Academic Press, Orlando, Fla., pp. 1–36 (1984); Bizzini, B., Tetanus. Id. at 37–68. In contrast to subunit vaccines, whole organism vaccines make use of the entire organism for vaccination. The organism may be used killed or alive (usually attenuated) depending upon the requirements necessary to elicit protective immunity. The following discussion will focus on live but attenuated microorganisms (live vaccines).

In the case of intracellular pathogens, it is generally agreed that live vaccines induce a highly effective type of immune response. Ideally, these attenuated microorganisms maintain the full integrity of cell-surface constituents necessary for specific antibody induction yet are unable to cause disease, because they fail to produce virulence factors, grow too slowly, or do not grow at all in the host. Additionally, these attenuated strains should have no probability of reverting to a virulent wild-type strain. Traditionally, live vaccines have been obtained by either isolating an antigenically related virus from another species, by selecting attenuation through passage and adaptation in a nontargeted species or in tissue cultures, or by selection of temperature-sensitive variants.

In contrast to these somewhat haphazard approaches of selecting for live vaccines, modern developmental approaches introduce specific mutations into the genome of the pathogen which affect the ability of that pathogen to induce disease, that is, specific mutations are introduced into genes involved in virulence. Defined genetic manipulation is the current approach being taken in an attempt to develop live vaccines for various diseases caused by pathogenic microorganisms.

U.S. Pat. No. 5,210,035, exemplifies this approach by describing the construction of vaccine strains from pathogenic microorganisms made non-virulent by the introduction of complete and non-reverting mutational blocks in the biosynthesis pathways, causing a requirement for metabolites not available in host tissues. Specifically, Stocker teaches that *S. typhi* may be attenuated by interrupting the pathway for biosynthesis of aromatic (aro) metabolites which renders Salmonella auxotrophic (i.e., nutritionally dependent) for p-aminobenzoic acid (PABA) and 2,3-dihydroxybenzoate, substances not available to bacteria in mammalian tissue. These aro⁻ mutants are unable to synthesize chorismic acid (a precursor of the aromatic compounds PABA and 2,3-dihydroxybenzoate), and no other pathways in Salmonella exist that can overcome this deficiency. As a consequence of this auxotrophy, the aro⁻ deleted bacteria are not capable of extensive proliferation within the host; however, they reside and grow intracellularly long enough to stimulate protective immune responses.

Unfortunately the development of vaccines based on chemical toxoids, discussed previously, is difficult since protective antigens and the genes encoding them must first be identified and then procedures must be developed to efficiently isolate the antigens. Similarly, modern approaches to the rational development of live vaccines has been hampered by the limited knowledge available concerning genes that are involved in virulence and thus the targets of mutagenesis.

Antimicrobial Agents

The medical literature up to about 1930 is full of vivid descriptions of gruesome infections by streptococci, staphylococci, and clostridia. The dawning of the age of antimicrobial therapy, with the introduction of the sulfonamides in the 1930s, allowed physicians finally to cure many of these fatal infections. From the outset, antibiotics were heralded as a panacea for everything from fungus-infected pear orchards to the common cold. Penicillin lozenges were popular as were nostrums such as antibiotic mouthwashes and throat sprays. By the 1950s, doctors jubilantly predicted an end to infectious diseases and, by the 1980s, half of all drug companies had stopped developing antibiotics, believing the battle won.

The stunning success of the pharmaceutical industry in the United Sates, Japan, the United Kingdom, France, and Germany in creating new antibiotics over the past three decades have caused society to become complacent about the potential of bacterial resistance, but what once was a situation where antibiotic controls prevailed has since deteriorated badly. C. T. Walsh, in a technical paper entitled "Vancomycin Resistance: Decoding the Molecular Logic," *Science*, 261:308–309 (1993) stated that "[t]he 1990s may come to be remembered as a decade in which infectious diseases made a dramatic worldwide resurgence, largely because of the appearance of antibiotic-resistant microbes."

In economic terms alone, such antibiotic resistance is costly. A recent estimate is that the extra expense of treating multiresistant infections is $100 to $200 million annually in the United States, see A. Gibbons, *Science*, 257:1036–1038 (1992). But economic impact reflects only part of the true costs of dealing with antibiotic resistant infections. More than 13,000 Americans are dying each year from drug resistant bacteria and doctors warn that the problem is steadily worsening. The FDA considers bacterial drug resistance threatening enough that it is planning incentives to encourage development of new antibiotics.

To date, the vast majority of antibiotics in the marketplace were derived from large-scale screens or from analog development programs. Classification of antibiotics by mechanisms of action appears below in Table 1.

TABLE 1

| Mechanisms of action | Agent |
| --- | --- |
| Inhibition of synthesis or damage to cell wall | Penicillins<br>Glycopeptides<br>Cephalosporins<br>Monobactams |
| Inhibition of synthesis or damage to cytoplasmic membrane | Polymyxins<br>Polyene antifungals |
| Inhibition of synthesis or metabolism of nucleic acids | Quinolones<br>Rifampin<br>Nitrofurantoins |

TABLE 1-continued

| Mechanisms of action | Agent |
| --- | --- |
| Protein biosynthesis | Tetracyclines<br>Chloramphenicol<br>Macrolides<br>Lincosamides<br>Aminoglycosides |
| Modification of energy metabolism | Sulfonamides<br>Trimethoprim<br>Dapsone |

As is shown in Table 1, there are very few mechanisms of action that are exploited by current antibiotics. Unfortunately, to date the majority of antimicrobial agents have been randomly discovered. Robotic systems can perform thousands of tests per day by means of radioactive labeling or spectroscopic detection making it feasible to scan 100,000 to 500,000 compounds in a year. While the efforts are still in their early stages, some companies are beginning to use "rational drug design" to design new drugs that can use selective mechanisms to destroy a specific microbe. Understanding the biological or biochemical mechanism of a disease often suggests the types of molecules needed for new drugs. Consequently, not knowing what makes infectious diseases virulent in the first place, is a fundamental fact which has severely limited the continued development of vaccines and antibiotics. A method of identifying genes that are expressed by microbial pathogens infecting a host has been developed: in vivo expression technology (IVET).

In Vivo Expression Technology

Essentially, the IVET selection strategy disclosed in U.S. Pat. No. 5,434,065, and herein incorporated by reference originates with a microbial strain carrying a mutation in a biosynthetic gene that highly attenuates its growth in a given host. Next, growth of the mutant strain in the host is complemented by transcriptional fusions to the same biosynthetic gene. Although, in theory, many different biosynthetic genes (e.g., aroA, thyA, asd) could be used in this selection scheme, initial efforts have focused on the purA gene of *Salmonella typhimurium*, purA mutants are highly attenuated in their ability to cause mouse typhoid and to persist in host tissues. This purA requirement provides a basis for the positive selection of microbial virulence genes that are specifically induced in a given host.

The first step in construction of purA operon fusions as per U.S. Pat. No. 5,434,065 was to build a pool of recombinant clones containing random fragments of Salmonella DNA. Partial Sau3A I restriction digests of total *S. typhimurium* DNA were used to obtain the random DNA fragments, which were then cloned 5' to an artificial operon having a promoterless purA gene fused to a promoterless lacZY gene on the vector, pIVET1. In the recombinant plasmids of interest, the fragment contained a Salmonella promoter in the proper orientation to drive the purA-lac fusion. This random pool was then introduced into a purA deletion strain of *S. typhimurium* that does not contain the Pi replication protein. Selection for ampicillin resistance requires the integration of the recombinant plasmids into the chromosome by homologous recombination, using the cloned Salmonella DNA as the source of homology. In the clones of interest, the product of the integration event generates a duplication of Salmonella material in which one promoter drives the purA-lac fusion, while the other promoter drives the expression of a wild-type copy of the putative virulence gene as shown in FIG. 1. The expression of both of these promoters is selected in the host. Expression of the purA-lac fusion is selected to overcome the parental purA auxotrophy. Expression of the virulence gene is selected because the gene product is required for infection. The expression levels of the operon fusions can be monitored both on laboratory media and in animal tissues by measuring the levels of β-galactosidase activity.

A large collection of recombinant plasmids that contained the purA-lac transcriptional fusions were integrated into the chromosome of a purA deletion strain of S. typhimurium, FIG. 1. The subsequent pool of integrated fusion strains was injected intraperitoneally (i.p.) into a BALB/c mouse. After a 3 day incubation, the mouse was sacrificed and the bacteria were recovered from an internal organ such as the spleen, intestine, or liver. Only those bacterial cells that contain fusions to chromosomal promoters that had sufficient transcription levels to provide enough of the purA gene product were selected (to overcome the parental purine deficiency) by demanding the survival and propagation of the fusion strain in the host. Note that all genes that have constitutively active promoters will answer the IVET selection because they would produce sufficient levels of purA gene product (and LacZ) all the time. Thus, when the mouse-selected pool was plated on MacConkey Lactose indicator medium, an increase in the percentage of Lac$^+$ clones is expected compared to the pre-selected pool. This expected shift has been termed the "RED SHIFT. " To test the prediction, the percentage of Lac$^+$ clones in the pre-selected and mouse-selected fusions was determined by plating on MacConkey Lactose indicator medium. In the pre-selected pool, 50% of the fusions were transcriptionally active or "ON" in vitro (red or pink in colonies), whereas in the mouse-selected pool 95% of the fusions were "ON" This observed shift in percentage in favor of Lac$^+$ clones (the RED SHIFT) suggests that the IVET system selected for promoters that are active in vivo. Since the underlying premise of IVET is that some virulence genes will be expressed only when they are in the proper environment and not on simple laboratory media, we focused our efforts on the rare 5% Lac$^-$ class of fusions that were recovered from the spleens of infected mice. Presumably, these Lac$^-$ strains contained fusions to genes that were "ON" in the mouse (to complement the purA deficiency) and "OFF" out of the mouse.

While the IVET approach provides an important new way to identify genes that are involved in virulence, some shortcomings were encountered using the IVET method discussed above. There is still a need, therefore, for a method and a means for identifying and isolating microbial virulence genes the products of which will provide a basis for rational vaccine and drug design.

SUMMARY OF THE INVENTION

Accordingly, it is an object of this invention to identify a class of microbial virulence genes involved in virulence.

It is an additional object of this invention to enhance the selectivity of methods currently available to identify virulence genes.

It is a further object of this invention to provide a set of coding sequences known to be involved in pathogenesis for use as probes to identify and isolate other microbial genes that are cotranscribed with said coding sequences during infection.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein, the method and compositions of this invention comprise using a class of coding sequences to identify genes, the transcription or cotranscription of which are induced during microbial infection of a host.

BRIEF DESCRIPTION OF THE DRAWINGS

The accompanying drawings, which are incorporated in and from a part of the specification, illustrate the preferred embodiments of the present invention, and together with the description serve to explain the principles of the invention. In the drawings.

DETAILED DESCRIPTION OF THE PREFERRED EMBODIMENT

Figure 1:
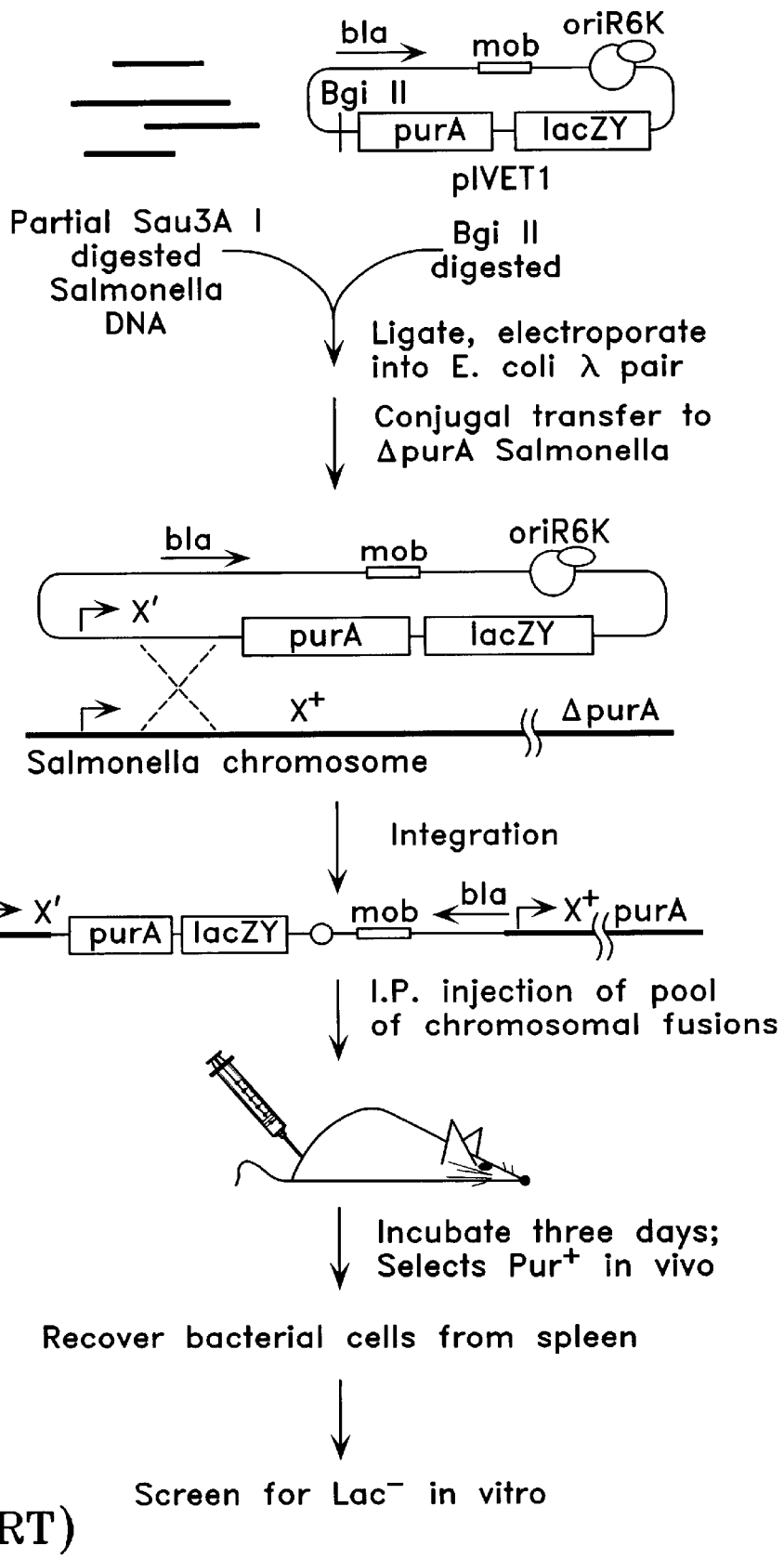
FIG. 1 is a flow sheet representing a method of selecting genes that are induced in a host according to the IVET methodology of U.S. Pat. No. 5,434,065.

In general and overall scope, the present invention provides a method and means for identifying and isolating a class of microbial virulence genes whose products will define metabolic, physiological, and genetic factors that contribute to the virulence of microbial pathogens, providing new targets for vaccine and antimicrobial drug development. By modifying the IVET methodology described previously, its selectivity was greatly enhanced, allowing for the identification of a number of genes which are induced during microbial infection of a host. In turn, these genes or portions thereof may be used as probes to identify other genes that are also induced during infection of a host. Consequently, the method of this invention further relies on a set of hybridization probes which comprise microbial coding sequences the transcription or cotranscription of which are induced during microbial infection of a host. These probes may be used to screen DNA libraries such as cosmid, lambda, or plasmid libraries thereby identifying and isolating genes that are transcribed or cotranscribed in connection with the coding sequences making up the hybridization probes of the present invention. The probes of the present invention may also be sequenced and the sequence compared to published sequences, thus (i) identifying genes that are known, but now known to be involved in virulence; or (ii) identifying genes that are unknown.

The method and probes of the present invention are based on the principals of a technology termed in vivo expression technology (IVET), disclosed in U.S. Pat. No. 5,434,065, and herein incorporated by reference. As alluded to previously, the IVET methodology suffers from a number of technical shortcomings which limit its selectivity as discussed below. The modifications also discussed below address these shortcomings and provide a number of coding sequences which are induced in vivo, and can be used as probes to identify other in vivo induced genes.

First, preliminary genetic and sequence analysis of in vivo induced (ivi) fusion join points revealed that some of the cloned fragments are comprised of small (e.g., 50 bp–100 bp), multiple inserts that have ligated at least two unrelated pieces of DNA together, making determination of the actual in vivo induced genes problematic. Second, the parental purA deletion, which is the basis of the IVET selection, was isolated as a Tn10-generated event, thus leaving a transposition competent IS10 element at the join point of the deletion, which extends from purA into an undetermined amount of adjacent chromosomal material, see Maloy S. R., et al., *J. Bacteriol.*, 145(2):1110–1112 (1981). This deletion-containing strain has a slight growth defect even in the presence of exogenous adenine, suggesting that the adjacent chromosomal material that was removed contributes to the slow growth phenotype. Also, the transposition competent IS10 element at the deletion join point contains an active promoter that reads outward into adjacent chromosomal material, see Ciampi, M. S., et al., *Proc. National Acad. Sci.*, 50:16–20 (1982). The transposition of this mobile promoter could unnecessarily complicate the IVET selection process. Finally, streptomycin resistance ($SM^r$) was used both as a counterselectable marker upon mating the initial pool of recombinant plasmids from *E. coli* into *S. typhimurium* and as a selection against normal flora present in host tissues (e.g., normal flora in the small intestine). The $SM^r$ mutation renders the parental strain somewhat attenuated in vivo. The parental $SM^r$ mutant used in all of the IVET selections to date are slightly attenuated when delivered intraperitoneally and even more so when delivered orally. Such parental attenuation can affect the classes of genes that answer the selection, particularly after an oral delivery of integrated fusion strains.

Taken together, the shortcomings uncovered with the current IVET methodology warrant consideration. Consequently, the method disclosed in U.S. Pat. 5,434,065 was modified as discussed below to produce in vivo induced fusions that circumvent the concerns addressed above. The first modification discussed below was implemented for the construction of all pIVET vectors, that is pIVET1, pIVET2 and pIVET8, while the second modification was only applicable to pIVET1 and pIVET8.

Construction of pIVET1, pIVET2 and pIVET8 Vectors

The pIVET1, pIVET2, and pIVET8 vectors were constructed as described in U.S. Pat. No. 5,434,065, incorporated herein by reference, using the following modifications.

First, for each vector the random fragments of chromosomal DNA were size fractionated. Random fragments of *S. typhimurium* DNA, obtained by partial Sau3A I restriction digestion, were size fractionated and removed from agarose gel after eletrophoresis. The cloning of large chromosomal fragments increases the probability that in vivo induced promoter regions will be contained in the initial pool of recombinant clones that will be integrated into the bacterial chromosome. This modification further decreases the probability of multiple inserts since the ends available for ligation will be limited to large fragments (1 to 4 kb).

The second modification was only necessary in the pIVET1 and pIVET8 selections. One way in which a purA mutation may be obtained by constructing a purA deletion in vitro that is associated with an antibiotic resistance marker. To perform the IVET selection in as native a parental background as possible, a purA deletion can be constructed in vitro. The wild-type *S. typhimurium* purA gene can be cloned by complementation of a purA deletion (on minimal medium) with a pool of recombinant clones representing the *S. typhimurium* chromosome. Once the wild-type purA gene is isolated, a purA mutation is constructed in vitro, by introduction of a DNA fragment encoding an antibiotic resistance marker (e.g., tetracycline) into the purA coding sequence. The tetracycline resistant mutation is then crossed into a chromosomal purA gene by introduction of the cloned insertion-bearing plasmid into wild-type *S. typhimurium*. The phenotype of the desired $purA'::Tc^r::'purA$ recombinant is $PurA^-Tc^r$. Additionally, the $Tc^r$ insertions in purA, thyA, or near $purA^+$, in the pIVET1, pIVET2, or pIVET8 selections, respectively, alleviate the need for the attenuating $Sm^r$ mutation as a counterselectable marker. In the alternative, insertions of a transposition defective transposon, e.g. Tn10d-Tc, in purA or thyA can be used as described here.

The implementation of these two changes to the current IVET selection protocol resulted in the construction of random individual pools of pIVET1, pIVET2 and pIVET8 fusions having 1 to 4 kb fragments of *S. typhimurium* DNA that contain very few multiple inserts. Each pool was then integrated into an otherwise wild-type *S. typhimurium* strain that contains a purA mutation, or thyA mutation in the case of pIVET1 and 2, respectively or a drug resistant mutation near the purA gene (e.g., $Tet^r$) in the case of pIVET8. Theoretically, using this revised protocol, there are no a priori limitations either to the mode of delivery of these integrated fusion pools (oral, intraperitoneal, intramuscular, etc.) or to the type of tissue from which the mouse-selected fusions are recovered.

A total of 100 BALB/c mice (Charles River Laboratories) were infected either orally or intraperitoneally with approximately $5 \times 10^8$ cells or $10^5$ cells, respectively, using either pools of purA-lac fusion strains i.e., pIVET1, thyA-lac fusion strains i.e. pIVET2, or cat-lac fusion strains i.e., pIVET8. Three days after infection, the mice were sacrificed and their internal organs removed and homogenized in 2 ml of sterile saline. The homogenate was grown overnight in LB containing ampicillin and $10^5$ cells were injected into a second set of mice, where the process was repeated. In addition to infecting mice, the cat-lac fusion strains were used to infect RAW 264.7 tissue culture macrophages for two or three hours. The bacterial cells recovered from the organs and macrophages were plated out on MacConkey Lactose indicator medium and approximately 2,894 white colonies were picked for further identification, date represented in Table 2.

TABLE 2

| Selection | Route of Administration | Tissue | Total Colonies Screened | White Colonies |
|---|---|---|---|---|
| purA-lac | Intraperitoneally | Spleen | 60,000 | 386 |
| | | Liver | 8,000 | 34 |
| | | Intestine | N/A | N/A |
| | Oral | Spleen | 16,000 | 97 |
| | | Liver | 8,000 | 26 |
| | | Intestine | 60,000 | 494 |
| thyA-lac | Intraperitoneally | Spleen | 16,000 | 34 |
| | | Liver | 8,000 | 14 |
| | | Intestine | N/A | N/A |
| | Oral | Spleen | 8,000 | 32 |
| | | Liver | 8,000 | 48 |
| | | Intestine | 16,000 | 119 |
| cat-lac | Intraperitoneally | Spleen | 30,000 | 764 |
| | Tissue Culture | Macrophage | 30,000 | 846 |

Identifying in vivo Induced Genes

In order to identify the in vivo induced genes, a genetic approach to clone the 2,894 selected in vivo induced fusions directly from the bacterial chromosome using phage P22 transduction was implemented, see Mahan M. J., et al., *J. of Bacteriol.*, 175:(21):7086–7091 (1993), incorporated herein by reference. Briefly a bacteriophage P22 lysate is made on the fusion strain of interest and used to transduce a recipient strain such as MT189, that contains the replication protein, Pi, which is required for autonomous replication of the pIVET1, 2, and 8 vectors. After introduction of the linear chromosomal fragments containing the integrated fusion construct into a Pi containing strain, the transduced fragment circularizes by homologous recombination at the region of duplication defined by the cloned S. typhimurium DNA. The circularized fragment can then replicate as a plasmid in the presence of the Pi replication protein, resulting in the cloned fusion of interest. In other organisms where cloning by transduction is not possible, the fusions can be cloned by more standard methods (S. Berger, et al., *Guide to Molecular Cloning Techniques*, Academic Press, Inc. (1987).

Plasmids from the recipient strain are isolated and used to transform E. coli cells following standard calcium chloride or electroporation procedures, see T. Maniatis, *Molecular Cloning: a Laboratory Manual*, Cold Spring Harbor, N.Y., (1989). DNA mini preps are performed followed by restriction digests. 1,037 clones containing the purA-lac fusions were digested using BamHI and EcoRI; 247 clones containing the thyA-lac fusions were digested using BamHI and EcoRI; and 1,610 clones containing the cat-lac fusions were digested using BamHI and Sal I. Restriction enzymes BamHI, EcoRI and Sal I were obtained from New England Biolabs, and the digests followed the Manufacturer's instructions. The DNA fragments resulting from the digests were separated on agarose gels and compared to one another for redundancy. 250 individual clones from the 2,894 clones digested were identified as having different digest patterns. Using primers homologous to the 5' end of the purA, thyA or cat gene approximately 70–400 base pairs of S. typhimurium DNA were sequenced immediately upstream or 5' to the purA, thyA or cat gene in each of the respective cloned fusions.

Sequence Analysis

The purA, thyA and cat primers used for sequencing were 5'-CATTGGGTGCCCAGTACG-3' (SEQ ID NO.: 1), 5'-TGTGCCTTCGTCGAGCAC-3' (SEQ ID NO.: 2), and 5'-CAACGGTGGTATATCCAG-3' (SEQ ID NO. 3), respectively. Primers were purchased from Operon Technologies (Alameda, Calif.).

All DNA sequence analysis was performed by the dideoxy nucleotide chain termination method of Sanger et al. (1977) with double stranded plasmid DNA as the template using a Sequenase kit (United States Biochemical Corp., Cleveland Ohio) as per the manufacturer's instructions. Primer annealing was as follows: 10 $\mu$g of double or single stranded DNA was denatured in 80 $\mu$l of 0.2M NaOH at room temperature for 5 minutes. Three pmol of primer and 8 $\mu$l of 3M sodium acetate were then added. 200 $\mu$l of 100% ethanol was then added and the mixture placed on dry ice. After 20 minutes the mixture was centrifuged in an Eppendorf 5415C microcentrifuge (Brinkman Instruments, Westbury, N.Y.) for 10 minutes, the ethanol was removed, the pellet carefully washed twice with 200 $\mu$l of 70% ice-cold ethanol and taken to dryness in a Savant Speed Vac Concentrator (Savant Instruments, Faringdale, N.Y.). 2 $\mu$l of 10×stock sequencing buffer and 8 $\mu$l of water were then added to the dried pellet and the labelling reaction performed.

20 cm or 33 cm×60 cm 6% acrylamide-7M urea sequencing gels (CBS Scientific Inc., Del Mar, Calif.) were used to obtain sequences starting typically from 20 to 30 bases from the priming site out to about 300 bases in a single loading. Similar results were also obtained using wedge gradient gels with a spacer to wedge ratio of 1:4 in a single loading. Priming was with $^{35}$S dATP (1000 Ci/mmole, DuPont NEN, Boston, Mass.). Gels were removed from the glass plates with 3 mm Whatman filter paper (Whatman Ltd., Madistone, England) and dried; a readable sequence could be obtained often after an 18–24 hour exposure using Kodak Biomax MR film.

Analysis of nucleotide sequences from one strand reading from the 3' direction to the 5' direction were performed using a Power Mac 7100/66 computer and the Wisconsin Sequence Analysis Package Version 8, program available from Genetics Computer Group, Madison, Wis.) About 50% of the fusions are in genes that show no significant homology to sequences in GenBank version 72. As only one strand was sequenced, the sequence results (SEQ ID NOS: 4–254) represented below in Table 3 have an accuracy of approximately 95%.

TABLE 3

| SEQ ID NO | LENGTH | PARTIAL 3'—5' SEQUENCES OF PROBES OF THE PRESENT INVENTION | | |
| --- | --- | --- | --- | --- |
| 4 | 390 | GATCCGGATG GAATGGCTCC AGCGCGTCGG TTTTCTCGCC | | |
| | | GACACCGAGG AATTTAATCG GCTTGCCGGT GATATGACGA | | |
| | | ATAGAGAGCG CCGCACCGCC ACGCGCATCA CCATCAACTT | | |
| | | TGGTCAGCAC CACGCCGGTT AACGGCAGCG CTTCGTTAAA | | |
| | | GGCTTTTGCG GTATTCGCCG CATCCTGACC GGTCATCGCA | | |
| | | TCGACGACAA ACAGCGTTTC TACTGGCTTG ATAGAAGCGT | | |
| | | GGACCTGTTT GATTTCGTCC ATCATCGCTT CGTCAACATG | | |
| | | CAGACGACCG GCGGTATCCA CCAGCAGCAC GTCGTAGAAT | | |
| | | TTGAGCTGCT TCTTGGCGGT TGACAGTATC ACGTTCTGCG | | |
| | | AAATCAGACG GAGAATCACG CAATTGTACA | | |
| 5 | 238 | GATCATAGAG GTGGATACGG CTTTTCAACG CCTGTTGGAC | | |
| | | GGCGTGCCAG TCGGCCTGTT CAAAACGCTG CTGCGCGCCG | | |
| | | GAAGTCACTT CCAGAAATCG ACCATACTGC GCGTCAAAGC | | |
| | | CTTGCAGGAT GGTTTGAGCA ATCAGTAATT CCAGGCCACG | | |
| | | CGGCATTTTT TTACCTCATC CGGCACCACG TCATGCCGGA | | |
| | | TGCGCGTTCG CTTATCCGGC CTACGCTATC TGTAGGCC | | |
| 6 | 309 | GATCGAGAGG ATGCGGTGGT GGATGCGCAT ATTACCGGAT | | |
| | | GACGGCGTGA ACGTGTTATG CGGCCTACCA GCCCAATGCG | | |
| | | CGATACCAAG CCGGATAAGC CGCCAACGCC CACCCCGGCC | | |
| | | CCGCCGCGTA TTTAATCAAG TTATTACCTT TGATCGCACC | | |
| | | CTTGAGGTCA GGCGCGTGAT AAGTTCGTAA GCACTTACTT | | |
| | | TTGTCATTTC AGCGATACGT TCAACCGGCA GACTTACCCA | | |
| | | TAGACACGAT CGCGGTATCT CGGTTGCCAA TTCGAATCTA | | |
| | | TCCATGGACG CGACATCGAC TACGACATT | | |

TABLE 3-continued

PARTIAL 3'—5'SEQUENCES OF PROBES OF THE PRESENT INVENTION

| SEQ ID NO | LENGTH | |
|---|---|---|
| 7 | 362 | GATCCGTTTT GACCATCCCG TGTTTGGTCG AAACCGTGCA GCCTTCTACC AGCGGCAGTA AGTCGGGCTG TACGCCTTCG CGTGAAACAT CCGGGCCGGA GGTTTCGGCA CGCTTACAAA TTTTGTCAAT TTCATCGATA AACACGATGC CGTGCTGTTC AACCGCGTCG ATAGGTCCTG TTTCAGCTCT TCCGGGTTGA CCAGTTTAGC AGCCTCTTCT TCAACCAACA GTTTCATCGC GTCTTTAATT TTCAGCTTAC GGGTTTCTGT TTCTGACCGC CCAGGTTCTG GAACATAGAC TGCACTGCTG TCATCTCTCA TGCCGAGCCA TATCTCTAGC CATCGGCGCA GTATTGACTT TA |
| 8 | 206 | GATCAAGAAT GTGTTCTCCC AGCGCATCCT TGATGGTTTC TCCCAGCACC TTGCCGAGCA TACTGACATT ACTAGCAACG CGGAATATTG TTCGTTCATA TGCCCCCAGA CGCCCCATCT TTAATGTAAT TGCCCTGTCT CTTTCATGCC ACAGCGCAGT GGCTGCGTGC GTATGCAGTT ATGCGAATGC TCGTGCTGCG ACTAAT |
| 9 | 250 | GATCGTCGGT GCGAATGGTG ACGTCGGCAA TCTCTTCGTA CAGCGGATTG CGTTCGTTAG CCAGCGCTTC CAGAACTTCG CGAGGCGGTG CTTCAACCTG CAACAGCGGG CGTTTTTTAT CACGCTGCGT GCGGCAGTTG TTTTTCGATC GGTCGTTTCA AGGTAGACCA CGACGCACGG CGAGAGACGG TTACGGTTTC ACAATTTTAC AGAGCCACAT CGGAACACAC ATACCTTTAT ATCTATACTT |
| 10 | 176 | GATCCAGGCT TCGCGTTCTG ATAGCTGTCA TACGGTACGG TGGTGATTTC CGGATGCTTA TCCATGATGA ATTTCTGGTG TCGTCGTACC GTTCTGTACG CCGACTTTCT TGCCTTTCAG TTGATCAACG CTGGTGTATT GCCTGCTGAC CACGAACAGC GTGAGTAGGG TATATG |
| 11 | 312 | GATCTTCCGC CCAGCCTGCG ACTTCTACTT TCGAGGCCTG GATTTCGAAA CTTTGCCCCT GTGCCGGCGA CGCGACAACC TTACCTGTTA CTACCACGGA GCAGCCTGTC GACAGGTGTA ATACTTCTTC ATTATAATTG GGCAGAGAAT TATTAATGAC AGCCTGTACA GGATCAAAGC AGGAGCCGTC ATAAACGGCG AGGAAGGAGA TGTCCAGCTT TTGAATCTCG GTCGGGTACG ACCCATCCCG CGCAGTGACT TCTTGGTCAA CGGCTACTGG CCTGGAGTAC TGCGGCTACG GCACACGTCA TA |
| 12 | 289 | GATCCCAGAT AATCGCCAGG ATCACCATCA CCACCGTTGG CATCAACCAA GCCAGTCCCT GTTCCGCCAG CGCAAACGCT GACTCCAGGC TGGCAGCATA TCGCCGAAGG ATGCTTTGAT GCCGTCAAGG ATACCAAAAA GCAGACTGAT AAACATGGCC GGCGCCGATG ATACGGGTGG AATTATGCCA CCATGAGCGG GTAAAACTTA ATACAACCAG TGCGATACAC GGCGGATAGA TAGCGTCATG ACGGAATTGG AGATTATCAG ATCGCTCAGT CGAGGTTGA |
| 13 | 240 | GATCAATAAT GTTATCCCGG CTTAACACTT CATCCGGGTG ATGCGCAAAA TACATCAGAA GATCGATCAG CCGTGGTTCA AGAGTAATCT GGCGTCCCTG ACGACTGATC TGACCAACAG AAGGTATAAC CAGCCACTCT CCAATGCGTA CAACAGGTTG CTGCATAAAA AGATGCCTAA CGAGCTAAGT CATACGTATA TACACGATTG CACAGACTTT TATCCTTTGT AAGAAGCTAA |
| 14 | 260 | GATCAGAACC TTAAAACAGC GTAGACACTT TTTTGGCTTT GTGAGAAATC CACGGACAAT TCCGCGAGCC AGTTATCGAC GTAGAACAGA GGAAGGGAGG AGCCCTTGCC GAAAAGGCCA TCCCATGGTG AATCGGGAAC GCTCCGGTTC CCGTTAATGC CTAATAATTA TCGTAATATA AACAACCGGA AATCAGTATA GGCCGCAATT TTGACGATTC ACCGAAATTG TTAGCGTGCT AATTACAGAG TACAGTTAGT |
| 15 | 314 | GATCGGCATA CAGCGCGTAC ACTTCATCCA GACGTTTGAG GGCGTTAACC ACTTCCGAAA CGGCCTCTTC AATCGACTCG CGTACCGTGT GTTCCGGGTT TAGCTGAGGT TCCTGCGGCA GGTAGCCAAT CTTAATGCCG GGCTGCGGGC GCGCTTCGCC CTCGATATCT TTATCGAGCC CCGCCATGAT GCGCAGCAGG GTAGACTTAC CGGCGCCGTT AAGGCCCAGC ACATCCGATT TGGGCCCAGG AGAGCTCAGG CAGATGTTTC AGATATGACG TTCAGACACT GCGAACCGAT GCTGATAGAT GAGC |
| 16 | 350 | GATCGCCATT CTGCTAACGA CTCTGACGCT GGCGCTGCTC TCCAGGCTGC ATCGGTTATA ACATTCTGGC GACACGGGCA AAACGCGGCT GTCGCCAGTC TCTGTCAGAA ACGGTAATCC ACCGCCATAA AGTAACGACG TCCGTCTTCG GTATAACCGT AGTCGTCGCG TTTGAGATCT TTATCGCCCA CGTTCAGAAC GCCCGCACGC AGTTTAACGT TTTTCGTCGC CTGCCATGCC GCGCCGGTAT CCCAGACCAC GTACCCGCCC GGCGTTTTTC GCTGTTTGCC TCTGTCGGCC CGCTTACGCC GGTATAATTC CTGATACGTA GATGACAGTT GAGCTGACCG |

TABLE 3-continued

PARTIAL 3'—5'SEQUENCES OF PROBES OF THE PRESENT INVENTION

| SEQ ID NO | LENGTH | SEQUENCE |
|---|---|---|
| 17 | 336 | GATCGTGCAA ATGCGCGCTA AAGGTGGCGG CGTCCATAAA GCCGGTGACT CGCGATTGCG GCTGTTCCTG GCCTTGGGTA TTAAAGAACA GAATGGTGGG CAGCCCGAGG ACTTGCAGAT GCTTTAACAG CGCGACATCC TGCGCATTGT TAGCGGTGAC GTTAGCCTGC AAGAGCACCG TGTCGCCGAG CGCCTGCTGG ACCCGCGGAT CGCTGAAGGT ATACTTTTCA AACTCTTTTA CAGGCCACGC ACCAGTCGGC GTAGAAATCA GCATAACGGT TTGCCTTTGG CCTGCGCCTG ATTGAGTTCA TCCACGTAGA ATAGCCGTGA ATTGAG |
| 18 | 286 | GATCCGCGAG GTGCGCCAGT TGCACCATCT CCAGCAATTG CGTCACTTTG TTTTAATCGC CGCCGCCGCA GTTGGGCGTC GCTCGCGCAG ACCGTAGCCA AAAGCGATGT TGTCAAACAC CGTCATATGG CGAAACAGCG CATAGTGCTG AAAACACAAA ACCGACTTTA CCTACTGGTG AGGCGCTAAC GTCGTACGTG GAAACGATAT ACCGTGGACT GTGTCAGCCC GGCAATAATC CCGGCTGTTT GCGGAACTAC GCACAGGACA TTGCGAGATA TTACGG |
| 19 | 325 | GATCGCGAAA GGCGTACATC TCACGGAATT TCCAACCGGT ATCAACGTGC AATAGCGGGA ACGGCAACGT ACCCGGATAA AACGCCTTAC GCGCCAGATG CAGCATGACG CTGGAGTCTT TACCAATGGA GTACAGCATG ACCGGATTAG CGAATTCCGC TGCCACTTCA CGATAATGTG ATACTTCGCA CAGTTGCGCA GTGGTGAGTC GTTTTGATCA TACGTCTTTG CATCGTTTTG CTAACTGATA CGACTAGGCG GTATATCGAT GATGTGTCTA GATACGCACA TCACACCGAT CCTGCAATTC ACGTACACGA TCTGC |
| 20 | 200 | GATCAGGTGC GGTCGGTAAT TGACAAAATA TGGGCAAATG GCCACGACAT TACCCCTTAA TTGATTGGCA GCAGCTCGTG GCTGATTGAT TTTAGCCGGA GCCGGACGCT CCGATTTTGG CGTCAGATAC CAATAACCCA ATCCATGAAT ACACACGACA AGTATACGGG TTACACACAG TATACATCGC AGATCGCTGT |
| 21 | 264 | GATCGGTTTT ACCCTTCGTC CCTTTGATAT AACGCGTGAC GCCGTTAACG TACCGCCAGT GCCGACGCCG AGATAAACAC ATCCACCTGA CCATCGGTCT CCAGAGTTTC CGGGCCGGTG GTTTTTCATG GATTCTCGGG TTGGCAGGGT TGCTGAACTG CTGGAGCAGG AGATATTTTT GCGGATCCGT GGCGACAATT TCTTCGGCTT TCTTGAATAG CGCCTTCATC CTGGCCTTGT CAGCACCAGA TTGGCTATGC TTAG |
| 22 | 324 | GATCAGAATC TATGTTGTCA CAGATTAATA GTTTATTATA TATTTCATCA AAATAATCGA CGTCAAGTTC TTTGTTTTTA TTTAGAGTGA ATACTTCCTG TCGTTTTTTA TCGTTTACAT AATCGACTAC CGTAACTGCA ACATTCTTAT TTTTTTGTTT CTCTATACAT AGTAATATGG TGTCAAGTTC AAATTTTATT TCTTCAAATC GCAAATCAAA GAAAAAATCT ATATTTTTAT TTAAAATCGT TGTCAATTAT CTTTAAAACG ATGTTTTACG TAACATTGTC GTATATATCG TCTGAGTCTA ATCAATATCA TAGT |
| 23 | 276 | GATCTTCGCC TACCGGCACC AGATTGGTTT GGTACAACAG AATGTCTGCC GCCATCAGCA CCGGGTAATC AAACAGGCCG GCGTTAATGT TTTCCGCATA GNNNCAGATT TATCTTTAAA CTGCGTCATA CGGCTCAGCT CGCCGAAATA GGTATAGCAG TTCAGCGCCC AGCCAAGCTG CGCATGTTCC GGCACATGGG ACTGAACGAA AATAGTGCTC TTTTAGGATC ATACCACATG CCAGGTACAG NNAGATTCCA GGCGTTTACG TAGTGT |
| 24 | 329 | GATCCGGCGC CGGAGCCACC ACGCCTTCAC GCGGGGCTCC GGGTTCGGCG CGGGCAGATT CATCAGCTTC GCCAGAATGC TCGCCAGCTT CAGGCGCATT TCCGGGCGGC GGACTATCAT ATCAATAGCC CCTTTTTCGA TCAGGAACTC ACTGCGCTGG AATCCTGGCG GCAGTTTTTC GCGAACGGTC TGTTCGATAA CGCGCGGGCC GGCGAAGAAT CGAGACTTTT GGCTCGGCGA TGTTGAGATC GCCAGCATCG CAAAACTGGC GGAAAAGGCC CATTGTCGAT CGTACTACGA AATGTAGGGC AGACGCTCTG CATTTAGAC |
| 25 | 222 | GATCCCTAAC ACCCGGTCAG TTCCCGACAG GCCGGTCTTT TCTACTAGCT GACCTATCAC AAAATTCACG ACAGCGCCGA TCGATAAGCG TCGCGATAAA CAGTACCGCG ATACGAATTC CCATTACGAA CCAGTTCGTC TTCAAAGCCC GTAAACCAGA CAGACAGGTA AGTAGTAGTAG TGACTGGCGA CAAAGAAGCA CACCCACGTA CCAGCATACG TC |
| 26 | 166 | GATCAGTATA CAACTATCAG TAATTCGACG ATAGACCGAA GTGTGCTTGC TGGCGCTTTA TCGTCAAGGA TAATTGCCGC TTTGACGGCC TTCGCGCTTC CTGCCAACTG GCTTCGTCTT TGTGCATGAA TCACCGCCAG CGGCTCTGCC GCTCGATNTG TCGATC |

TABLE 3-continued

PARTIAL 3'—5' SEQUENCES OF PROBES OF THE PRESENT INVENTION

| SEQ ID NO | LENGTH | |
|---|---|---|
| 27 | 333 | GATCGCTTAA CAGATAATGA CTGGCGCTGC GGGGCTCCAG TACGATATAG CCGCCTAGCA ACACGACAGG CGCGCTTTTA TGGTTCAGGT CGCGACGAAT GGTCATTTCA GAGACGCCCA ACAGGGTCGC GGCTTCTTTA AGATGAAGTT TATCGCTGCG TTTTAAGGCC TGCAGCAATT GACCAATAGC GTCGTCGCTC GGCTTTCCAT AGTTCCCCTG GAGAGTTAAA TAAGCGCTCC GCACCATACA GAGCGCTTAA TATTACTCTT TTTTGCGCTA TTTAGTCACG TACCCAGCCT TTTCGAATGG GCAATGCAAC AGAACGTACA CGT |
| 28 | 221 | GATCGCGCTC AATCGCTTCC GCCGCCAGTT TAGCCGCCAG CTCCGGCGTT TTTTCATGCA CCAGAGCTTT CTTAAGCGCT TTTGGCGTAG CACCACTTCT TTGGTTTGTA CTACCGGCGT GGTGGCCTTC CAGCGATAAG CCTCTTTCTT TACTGGCGGT TTCCAGCGGG ACGGNGGGNT GTACNNTCCG AAACCGAGGA GCGTCAGNAG AGTTATTACG G |
| 29 | 368 | GATCGTCGTA CCGCCAACCG AGCCGCCGGG TATGTGTCGT TAAACTCTGT CGCCAGACCA TAGTTAGAGG TAATAGAAGC CCCCCAGCCA AACTGGTCGT TAATCGGGGC GACAAAATGG ACGTTCGGCA CCCAGGCCGT CAGCGCGATG TTATCCGCAT CTAACGTCCG ACGAGATGGC GATGTCCCGC TAATATTAAC ATCAGGATCA ATATAAACGC GCCCGCTGAA AACGTCGGGC GGTCAAACAT GTATTACGCG GGTGCGCTAC GTACGCATCA TCTGCGATGC GCTCACGATA GCGCAGCAGA GAGAATCGTA CTGAGCTCGC GACAGTGTGA TGTCGATCGG ATCGCGCTTT GCAGTTTG |
| 30 | 288 | GATCTCCACA AACTGTTCCG GCTGAGCGAT AGCTTAAGTA GCGCATGTTT CCTCCAGGTA TGGAAATGCT CTGTGAGGCG GTAAGTCGAG CCCACGTACG GCCCCTGCTC CTTCTTACCC ATGCGCAGCA TCTTCTTCAT ACAGACGCGC CGCCGGGTTC GAGACCACAT TCGGGTGCAG CGGGTTAGTG CCCAGCGGCG TTTCATCGCT CGTAGTGTCA GGAACGCCTT CGCATTATCA TAGCAAACGA ACGTTCCAGC CCTTTCGCGT CATGAAAGAT GCGTCCGG |
| 31 | 254 | GATCAATAAC CGCATCGTTG TAGAAGTTCC CCTGCAATTT CANNNNATCC AGATAGTTGT TCTGGCTCAG GCCGACGGAA GAGAAGCCAC GGATAATCAC GAAGTCATAG GTATTGGAAG CGCCGCGCTG CTTACCGTTA CACCCGCGTG TAACCCAACG CTTCTTTACT GACTGGAATT GATGCATCTG CATCTCTTCG TTAGTGACCA CCGAAACCGA CTGTGCGTTT TTCGATAGTA TCAGTTTGTG TGCG |
| 32 | 176 | GATCTTGTTG GCTCGCCTCT CCCCTCGGAC AACACGGTAT AAAACGCGGT GATAGAGCCA CCGCCGTGGA TGCCATTACC GGCACGCTCG ACCAGCGCCG GCAGCTTTGC GAACACCGAG GGCGGATAAC CTTTGGTGGC TGGCGGTCGC GATTGCCAGC GCATTAGTGC ATTGAT |
| 33 | 338 | GATCGTGATA TTCAATGCAC GCCTGCAGCG TGTTTTCGAT AAGCGTGGCG ACCGTCATCG GGCCGACGCC GCCCGGTACT GGCGTGATGT ATGACGCGCG CGCCCGGGCT TCGTCAAACA CGACGACGCC AACGACCTTG CCATTTTCCA GACGGTTAAT ACCGACATCA ATCACAATTG CGCCTTCTTT AATCCATTCG CCGGGAATAA AGCCCGGTTT ACCTACGGCG ACAATGAGCA AATCAGCATG CTCGACATGG TGACGCAGAT CTTTGGTAAA GCGTGCGTAA CGGTAGTCGT ACAGCCAGCC AGCAACAGTC ATGCTCATTG GGCTCAAC |
| 34 | 319 | GATCTTGCAG CGCGCCGTGC CAGGCATAGC GCACCTGCTC ATTAAAGACG TTCGTTTTAC GTGAGTTCGG TTTCGGCGTC GGCTTCTGGC GTGCTGGCGC GTTGCCGCCG CCTGTTCCGC GCGAGACTTA CGCAGTCGAT CCAGCCGTGC GCGAACTGCC TGATTTGGTT AATCGCGTGG GCCTATTCAT TGGCCAGGCC ACCATGCAGA TGTCCATCGT CAGGACGAGC TGCCTATAGG AACGACGGGA CATAAGTCCA ATATGTGCGA GCGTCAGTAC CGTACCCTAA GTAAACTCTT CAACAGAAGT AAATGCCTT |
| 35 | 418 | GATCGATTTG CGCTGGCAGG TTGCTGCCGG TATTGACCTC TTTGTACATA TTCAGCGGCG CGTTCTGCGA GTAGCGCAGG TTATCTTCGA TATAGGTATT AAACACGCCT TTGGAGAGCG CGGCTTCATC ACCGCCGCCC GTCCAGACGC GTTGGCCTTT TTTACCCATG ATAATCGCCG TGCCGGTATC CTGGCAGGTC GGCAGAATGC TTTGGGCGAT CTGCAGGTGG CACTTTTCGG GGAAATGTGC GCGGAACCCC TATTTGTTTA TTTTTCTAAA TACATTCAAA TATGTATACG CTCATGAGAC AATAACCCTG ATAAATGCTT CAATAATATT GAAAAGGAAG AGTATGAGTA TCACATTCGG GCTATCTTTG GATTCTCGTT GACACAGAAC GAGGAAGAAG CGAGACAT |

TABLE 3-continued

PARTIAL 3'—5' SEQUENCES OF PROBES OF THE PRESENT INVENTION

| SEQ ID NO | LENGTH | |
|---|---|---|
| 36 | 350 | GATCAAGAGT CAGGGGTAAT TTTACCTTTT GCATAGGGCG CGCATATTAA CTTCGTAACG TCATATAGTC AAAGAAAAAG GCAGCCTGCG GTTGCCTTTT GCCAATAATT CGCACACATT GCGGGTTACA GACTTATTTT CGCTCAAGAC GAGTCAGTAT GACAGGCTTG AAGACCGAAG AGCTATGTTT AAGATGGCTC TCATCATTAC GCTATATCTG AGGGAAAAAA TATGCCCCGT CTCATCCTTG CGTCTACCTC TCCCTGGGCG TCGCGCGCTG CTGGAAAAGC TGACGATGCC TTCCGATGCG CGCGCGATGT GATGAACCCA TGCCGGGCAC GCGCTCAGTG |
| 37 | 270 | TGCGACAACA CACCCGCCAA AGCCGCCGCC GGTCATGCGC ACGGCGCCTC GATCGCCGAT GGTCGCTTTG ACGATGTCTA CCAGCGTGTC TATCTGCGGG ACGGTAATTT CGAAATCATC GCGCATTGAG GCATGGGACT CCGCCATCAG TTGGCCCATA CTTCGAAATC ACCTTTCTCC AGCAGGCTTG CCGCTTCAAC GGCGGGCATT TTCGGTCAAT ACATGGCGAA CCGTTTTCGG ATACCGGGAC AGTTCCGTGG CAACGGCATT |
| 38 | 280 | GATCCAGTGC TTTCGCCGCG TCATCCACAA TGACGTCAAA GCCAAAGGTT TCGGCGCGAG TACGCACGAC GTCCAGAGTT TGCGGATGGA CATCAGAGGC GACAAAGAAC CGGTTGGCAT TTTTCAGTTT GCTGACGGCT TTGCCATCGC CATCGCTTCA GCGGCGGCGT CGCTTCATCC AGCAGCGAGG CGAACGATGT CCAGCCCTGT AGTACACGCT ACTGTTGAGT TACAGACTCA AACTAAATCG TATAGATTTA GCCTACACTG ATTTACATTA |
| 39 | 275 | GATCATCGCC TTCAAATTGA CCTGCTTGAG ATCGAAAATG AGCTGCGCTA AGTCCTCGAT AGAGTAGATA GCGTGGTGCG GTGGCGGGGA GATCAGCGTC ACGCCCGGCA CTGAATACGC GAGTTTAGCG ATATACGGAG TGACTTTATC CCCCGGCAAC TGACCGCCTT CGCCGTTCGC CTCACTTTAA TCTGAATCAC ATCGGCATGA CAGTAGGTCG GTCACAAGCG CGACGACTCT ATCGCAATAT GTCAATCCGG TCCTACATAT CATTT |
| 40 | 333 | GATCTTTCGA CTCGATGTTG GCGACGAAGA TAAAGTTCGG CAGCAGCTTG CCCGCGTTGT CATAAACCGG GAAATACTTC TGGTCGCCCT TCATGGTGTA CACCAGCGCT TCGGCAGGCA CGGCGAGGAA TTTTCTCTTCG AATTTCGCCG TCAATACCAC CGGCCATTCC ACCAGCGAAG CTACTTCTTC CAGCAGGCTT TCGCTCAGGT CGGCATTACC GCCAATATTA CGTGCTGCTC TCAGCGTCCG TTTGATTTGG CTTAGGCTCG TAGTCGCATG ACTTACGGAC TCAGAGAATT GCGGTACTGT CAGATGTGAG GACCGTACAT AAG |
| 41 | 233 | GATCGGGCAT CGGCACGACA CCGGTATTCG GTTCGATAGT GCAGAACGGA AAGTTTGCCG CTTCAATACC GGCTTTTGTC AGCGCGTTGA ACAGGGTGGA TTTCCCGACG TTGGGCAGAC CGACGATACC GCATTTGAAT CCCATGATTT AACTCACCTT AATATCTTAA TAATCAACCT GTTATAGAAA ACAGATTGCA GAATGGAATA CTCGCTATTA TCACGCGCGC AAA |
| 42 | 302 | GATCAAGCGT GTCCGGCGAA AACGTTACGC GTTCTCGCAG CGATACAGGT GCCGTTTTAT GGTTAATACC GAGCGCTAAA AGGGTCATGT CTGCGGGAGT AGTACCAGCG TTGATATGGT TAGTCTGCTT GCATCATACA GGATGCGCGT GGTCAATAAA AGAGAGAGCC CCCTTTTGGA GTAATTGGCA GCGCTCGCTA ATTTGATGAT TTAAGCACACT TGAAAGTAGA CGATGTCACC AGGCGCCTAC ATTAAAGGCT ATACTGTACG ATAGCAAAAT TTCCGATCCG CCACTTTCAC TC |
| 43 | 262 | GATCTACTTT CGGGATGGCA GCGTATCTGC CGCAATACAC CCTGATGGAT GTTATGCCTG GATCTGATTA CTCTTCTTTG GGCGAAGTTT TCGACCCGGC TCTTTAACTT CTGCCCGGGT CTGAAGGTCA CCACGCGCCG TGCTGTAATA GGAATATCTT CACCCGTTTT CGGTTACGCC CCGGACGTTG ATTTTTATCA CGCAGATCGA AGTTACCAAA ACCAGAGAGT TCACCTGCTC ACGTTTCAGA GCACGACGAT CT |
| 44 | 153 | GATCAGGTCC ATATTTGTCT TTGCCTTTCT ACCCGACACG TTTCGGGTGT GCGATTCGGA TTAGTCCGCC AGAAATAGCG GGCCCATTGG CGGTTTTGGA AGGTCAAAAA GGTCAGGGTA ATCCACCGCA ACCAAATATA GCCCTTCCGC CTT |
| 45 | 169 | GGCGCGTTGG CAGATTTTGC CAGACGACGG GCGATTTCGG TTTTACCGAC GCCGGTCGGC CAATCATCAG AATATTTTTC GGCGTTACTT CGTGGCGCNN CTTCATCAAG CTGCATACAC GCACGTTACN ATCNNGACGG AACCTTTGTA TCTGCGATAA TNNTTGTAG |
| 46 | 282 | GATCGCTGTA GATTTTACAA GTCTTCTTCA GCGATACACG TCTGCACAGC AGGCCGAAAC CGGTGTTGAT GCCGTAGGAG TACGCCTTCA GGCAACGATA TCATTGACAA CGCGACGTGG CGTTAATACG TCAATGGCAT GGCCTTCCAG CGAAAGCTGT ACGATGAGAT ATGACATGAG AGAGACTTAA CTGCCCCAGA GTATATATTG TGTTCATATC AGCCTTTCCT CAACAACCAT CGTAAATTCA GACTTACTCA CACACATTCA CGTAGATCAT TC |

TABLE 3-continued

PARTIAL 3'—5' SEQUENCES OF PROBES OF THE PRESENT INVENTION

| SEQ ID NO | LENGTH | SEQUENCE |
|---|---|---|
| 47 | 258 | GATCGCGGGT CAGTGTACGC ACCGCTTCCG GCGTATTTTT CCCGCTATTA AAATAGAGCT TGTCGCCAAC AATCAGGTTA TCGAGATTAA TGACCAGCAG CGTATTTTTC TTCTCAGCGT CACTCATCGT TTGAGTAAAT TTGGGGGCCT AGCTTTCCCT CTTCTTCCCC GCTGGTGGCG ATAAAACGAA TCCCGTAATG GGTCGGTATA TCTTTCAGAC GGCGCAGTTC CAGCATAAGC CCTAATCCCG CGGCATTA |
| 48 | 315 | GATCGCGACA TGCGCAACAT CTACCAGTTT ACTTAACTGA CTAAACAGTA AGTCGACCGA CCGGGGACTG GCAACGGTCA ATTCAATATT TATATTCTGC GCATCGGTCG CGGCTTCCAT ATTCAATGGA GCACACCTGA AAACCACGAT GGCGCACCAC GCGTAAAACA CGTTCTAAGG TTTCTGGATT ATAGCGTGCC GATACATTGA CCTGATGTTG CATCATGATA TTTCACGATT TCAGAGTCAT GGCGCAGGCG CACACGCAGA CATTTGAAGT CTCGATGAGA CGAGAGACGC CTCAGTCACT GTCGA |
| 49 | 268 | GATCCAACGT CTGGCGTAAT GCCAGCATGT CGTACTGGGT GTTGTTGCCC AGCTCCGCAC GTGGGTCGCC TTTCGCCACC ACGTTGAACG CCAGACCATC TTTAATTTGC GGCGTCGGCC AGCATGGTAA AGCGGTTGCT GAGTACACGC GCTTCACGGA ATACCGTGGT GGCTTGAGCA CCGCTCACCT GCTTGAGTCG GCTGTTCAAC TCGGCGTAGT CCCCACATTA AGGCTGGTTG TACACGTCGT TGTTGGTGTA ACCGCGGT |
| 50 | 296 | GATCTAAAAT TCAAATACAG GAACAGGGAG TTCTGGTGCA GAGGGTACTA TGTCGATACG GTGGGTAAGA ACACGGCGAA GATGCAGGAC TACATAAAGC ACCAGCTTGA AGAGGATAAA ATGGGTGAGC AATTATCGAT CCCGTATCCG GGCAGCCCGT TTACGGCGTA AGTAACGAAG TTTGATCGAA ATGTCAGATC GTATGCGCTG TTAGGCGGCT GGTAGAGAGC CTTATACCAT CTGAAAACTC CGTATCCGAG ATATTATAGA CTATTGGCAA CCTGAATCTC TCGATT |
| 51 | 213 | GTACACAGAC GCCTTTCAGA TTGGCGATGA CGCATCCATT GAGAACACCC CATCGGTGGC GATCAGGACA TGACGCGCGC CGGCCTCACG CGCCTCTTTC AGCCGCGCTT CCAGCTCTGC CATATCGTTG TTGGCATACG CTTCGCTTTA CACAAACGCA CGCGTCAATG ATAGACTGGT TCAGCGCGTC GGAATATAGC GTTCGCGCAG CAA |
| 52 | 113 | GATCGAAACT CGCCACGTTA ATCACCGTCG CCACCACCGG CGGCCAGCGT CCGTAAAGCA GCGCAATCAC CACTACGGCC CAGGCAAATC GATGCATTAC CAGATTGGCG GCG |
| 53 | 337 | GATCTTCCGG GTTAAATTGC AACAATGCTT CGCTAACGCG CAGCCAGCTC CATTTGCGGT TCCTCCATCA GCGAGGATTT CAGCGTATCC AGTAGCTTAC GAATCACTTC GGCGTTATCC GCTTCGTCCA AATCTTCATT AAACAACTCG GCGACCGGAC TAATATTGCC TTTTAACCAG ACTTCCAGAG TATGTTCATC AAGCGTTTTC ACCGTTCGAA CGGTTAATCA GCCACATTTC CCCTTTCCAG CGATTCAATA CGCAAATCAA CTGCGTTGGG AAGATAACCT AGGCACAACG GCAAATCAAG ACGTTGCATA CATATAAATA GCGCCAC |
| 54 | 313 | GATCATAAAA CTTCCGCGTG TATATGTTGG TTGGAACCGT AGAGATATAG ACAGGTGGTT CTACACAGGC GTTTACCCCT ACCGTCGCAA ACATTTCTTT AATCAGGCTT TCTCTTTTTT CTTCTGATGG ATGCGAGTGA TTAAACTCAT ACATTAACGT TTTCCCACGA AGTCTTTTTT CCGGTAAGCC TTCGCATATA TCGGTAAATA GCTTGCCTGC TCTTATCTTT CGGTCATGGC ATGTTCATCG CGATCACTCC GTTATGATAT GTCTCGATAG CCTCGATCCA ATGATGCTAC GCATCATCAC TCA |
| 55 | 300 | GATCGAATTC AGATTCCATT ATCGCCATCA GATATTCCAG ACGTTCAGAT TAACGTCGGA CATCTCCAGT ACGGACTGTT TATCCGCCAG TTTCAGCGGC ATATGCGCGG CGATGGTGTC AGCCAGACGT GCAGGGTCGT CAATGCTATT GAGTGACGTC AGCACTTCCG GCGGAATTTT TTTGTTCAGC TTGATGTAGC CTTCGAACTG GCTGATAGCG GTACGACCAG CACTTCTTGT TCACGCTCAT CAATGGCTGG CGAATAAGGT ACTCGCTTCG CGAGAAATGT CGCGTGCAGA |
| 56 | 423 | GATCCCACTT CTTGAACTGC TCGAAGCAAA CGCCTTCCGG CAGATCATCG CGCGCCACAT ACAGCTGAAT GCGGCCGCCT ACGTCTTGCA GGGTAACAAA AGAGGCTTTA CCCATAATAC GGCGCGTCAT CATACGGCCC GCGACGGACA CTTCAATATT CAGCGCTTCC AGTTCTTCAG CTTCTTTCGC GTCAAACTCT GCGTGCAGTT GGTCTGAGGT ACGGTCAGAC GGAAATCGTT GGAACGGATA CCTGCTCACG CAGTCAGCCA GCTTTGCACG TGCCTTATTT ATTGTTAAGA TCGACTACTG TACGCCTGTC TTTGTCAGAC ATGTGATCTC ATAGCCTGGC TTTCAAACTT GCTCGATATG ATCAGACTAC GTCAGTACGC TGGATGCGTC ACAGTACAGC TTAATCGATC AGA |

TABLE 3-continued

PARTIAL 3'—5'SEQUENCES OF PROBES OF THE PRESENT INVENTION

| SEQ ID NO | LENGTH | |
|---|---|---|
| 57 | 173 | ACAGAATCTT TTTCACGACG TTCTCGTTAA TAACCGATAA GACGTGAGGA GTTTAGCAGA TTTAGTGCTT GATTTCGTGG CTTGTTTACA GTCAAAGAAG CCGGAGCAAA AGCCCCGGCA TCGGCAGGAA CNCTTATTTA TTAATAAAAT CTTCCCCAAC TAATATCTTT TTT |
| 58 | 218 | GATCCTCCGT GGCATAAGAA ATGCCGCCAA GAATCGTGAG TAAGATGTTG AAAGGATTGC GATAACATAC CCACAGATGC ACCCACCACG GCGAGGGTTT CTGTGCCGGA ACGGTTTTCG CCATGCTTTT CACGCGCNNT CACCTCGGCA GCGTTTAATC CTCGGTGCGT ATCAAAACCT GCAGAGAGTC TCTGCTCATG CGCGACTTCA GACAGTAG |
| 59 | 346 | GATCGAGAAA AGTGAGCATC CCTTCGATGG TAAGTTCGGT CTCATCCTCC ACACTTAATG TCGGATTGTT CCCGGAACCA TCCAGCTTAC GTGTCGCTAT CAGCAATACT CGGAATCCCT GCGCATTGTA ATCTTCGGTT TTCGCCAGCA GTAGCTCGCG GCGTGTTTCC GTCAAGCGCC ACCACACGAT CGCCTTCGCG AAGATGGGTG GCTACCATCA TCATCTCTTC AACGGCGCTT TGCAGATCAG GCATCTGTCT CATGCTGCGC ATCTCACAGA CGATACCGCG ACGTACAAGT CGATGCAGTC ATCGTTATGA GCCCTTGCGA TGTGCATGAC TGCAAC |
| 60 | 323 | GATCCTGACG AATGGCCACA ACGGAAGGCT CATTCAATAC GATGCCTTGT CCTTTTACAT AAATGAGGGT ATTCGCGGTA CCCAGGTCAA TGGACAGGTC ATTGGAAAAC ATGCCACGAA ATTTTTTCGA ACATACTAAG GGATTAATTC CTTGAAAGCT GGGGCGAAAA CAAAATGCGT TTACTTTACC AACCACACGC AGCAGCGACA AGCGCGAAAA TCATCTGCTA CGTGAATTAG TGCGTCGTTC TTTGTACAAT CTCGCTGAGT CAGCTGAAAA TCACGCGATC TGCTCGTGAC TTGAAGATCT CGATTCTCGA CAT |
| 61 | 276 | GATCGCGCGT GGTTTGCAGC GTCGGTTCCA CCACCAGTTG GTTAATGCGG TTCGTTTCCA GACCACCAAT CTCTTTCATA AAATCTGGCG CTTTGATACC CGCCGCCCAC ACCATCCAGA TCGGCCTGAA TATATTCACC TTCTTTCGTA TGCAGACCGC CTTCGGCGGC GCTGGTGACC ATAGTTTGCG TCAGCGCGAA CGCCAGTTTG GTCAGTTCAT TATGCGCGGC GTGGAGATAC GCGCGCACGA GGCAGATACG CGCAGTCACA CGAGTC |
| 62 | 166 | GGGCCAGAGG TATGACTCCA CCAGACCGTC AAAGACGGCG TTGCGTCGTG CTCAGCATAG AAGCCGCGCG CCTGCTCAAC GGTCAGGTGC AGCATTATTA GTGCCCAACA ATTTTGAACC CTGCAGCTTC AAACGCGCGA AAGATCGTCC AATACGTTCT CCGACC |
| 63 | 425 | GATCTTTAGC CGGGCAGACC TCTACGCATA AATTACAGCC AGTACAGTCT TCCGGCGCGA CCTGCAGCAC ATATTTCTGG CCGCGCATAT CGCGGACTTC ACGTCCAGCG AATGCAGACT GGCTGGCGCG TTCTCCATCG CCTGCGGGGA AACGACTTTC GCACGAATTG CCGAGTGAGG GCAGGCAGCG ACGCAGTGAT TACATTGTGT ACACAGTTCC TCTTTCCAGA CAGGAATCTC TTCGGCGATA TTGCGTTTTT CCCAGCGGTG GTGCCCATTG GCCATGTTCC GTCGGCGGCA GGGCGGAAAC AGGCAGTGCG TGCCGAGGCC CGCCAACATG GGCCGTAACG TTTCAGAAAT CGCAGTGAGA CGGCGGCATC CCATAGGATT ACGCTGAGAT CCAGATCTCC AACATCTCAT CTAAA |
| 64 | 333 | GATCTACCGG GTGAGCGTAT AACCNATCTT AATCCCTCCC GGTTAGGTTG ACATTAGGAT CCTGTTCCTT TCGGGTTATA CTGCGCTGAA CGCGGGTCCA GTCCAACGTG AATACGGCAG ATAAACCAGA CCAGCCAGTA ACACAAAAAT AAAAATTCGC AGCTTCCACA AAGCCAACCC AGCCGCTTTC GCGATAGAAG TCGACCATGC GAACAGATAC AGCGCTTCAA CGTCGAAGAT AACGAAGAAC ATGGCTACCA GGTAAAATTC GGAGACAGGC GTAAGGCGCG CCGGTGCGAC CATTCATCTC CATCCTTTGA ATTACGGACA GCA |
| 65 | 374 | TTATCAATAC CCGCATTTTT ACTGAAACCG GGCGTGATGT TTTTGGCTTT GACATTGCGA ATGACGAAAT GTTTGCCATT TTCTACGTGC ACAAGCTGTC GGCAATCAGA TCCGGTAATA TTGGCCACCA CAAAGTTTTT TACTGCCTGG TCTTCAGGAT AACTGTTGTC ATAGGTGCTA CCCGCCAGCC CGATCCCCCA GTTGATTTTG CCATTGGTAC AATTAATGCG TTCGATGACA TGATCGGAAA TCAGGATGTC GCGGTCGTGA TCGCGACATT CCACTCATGG CGTCCCTGT AATCGCTAAG CGCTATCGTA ATCGCGCGCA TCCATTGTTA TGAATCCTGC GAGATGGCGA GTGCGTGGTA CGGA |

TABLE 3-continued

PARTIAL 3'—5'SEQUENCES OF PROBES OF THE PRESENT INVENTION

| SEQ ID NO | LENGTH | SEQUENCE |
|---|---|---|
| 66 | 296 | GATCCTGAAA TGCCCATCCA CGCCAGCTTG GGTATAGAGC AATCTGGCAG TATAAGATTT GGGATGTATT TTGGCCGCAG CCGCAAAAAA CGCGTCTGGG CGATTCGGAC AACCAGAAAG AGGCGCTCTG TAATGCGGTC TGGGCTATGG GACGAATTTC CAGATAATAG TAAACGATTA ACCCTACACG AAAGCGTAAC AGAAGCGCAT AACGCCTTTA AAAACCACAG TAACACGCCT GCATTATAGT TTTTCTTACT CAACATCTAT CGTTCGCATA CCGGATGTAA TAGGCT |
| 67 | 178 | GATCGGCAAA GGTACCGGTG GTGCCGTCGT AGTTTTCTCC GCGCCGGGCG TTAACGTTCT GGCCCAGCAG GTTGACCTCA CGCGCGCCCT GGCCGCTAAC TGGGCGATTT CGAACCGGAT CATCGTCTCA GGGCCGGCTG ACTTCTTCGC CGCGGGTATA CGGCGCACAC GTAAGTAC |
| 68 | 327 | GATCAAAAGT TTTCTGCGCC GCCTCGTTCA TCAGTTTATA AGGATTGCTC TGATCCGCTG CCGTTGCTGC GCTTAATGGC GCAATGACCA GCAGGGCCAC CATCATCAGT CGTTTAAACA TGCCTCAATT CTCCTGAGAT TATTTCGTTT CGCCCGCGGG CTTGTGGCTT CAGTATGACC TTCCGTTGCG GGCTGGCGCA TCGCAGAATT CTTATTGTCG TCGCCTTCGT GTTATAAGGA ACTGCCAATC ATATCTCCAG CACATGCAGA CGGTCTGATC GTACTGCACG CTAGATAGAC GTCAGACTCA ACACAACGAG CTAGCGA |
| 69 | 375 | GATCCAGCAG GTTGATTTTT GTTTCTTTGT TAGGAACTAC CGGGGTACTG CTTTCAGGTG TGACAATTTG TTCAGACATA TGCTATTCCG GCCACGTTAT TACACGTTAT GGCCCCTGGA GGTTGAAAAA AGAAACGCCC CGGTAAGCTT ACTGCTCGTC CGGGGGCGCT GCATTGTACA AATTCTGGCG TAAGGAGTCC ACGTCTGCAC GCGCATTAGC AAAAATAATA TTTGAACCGA TAATTTATCG CCAACGCATT TACAGCGTGA AAGACGAAGG AGATTAACGG GTGGGGCCA CTCGCTTCAC GAGAAAAGCG ATTCGGCTGG CGATTCAGCG AATCGACGTG TGCGTTCAGT ACTATCACGT AGTCG |
| 70 | 298 | GATCGGACGG CGCCTTATCT TCTTCAATAT CGCGCGTACC GTAGAAACCT TCAGGCAAGG TCGCTCAGCG ACAGCCTGCT GGCTGAGTCC GAGTTGTTCA CGGGCATTGC GCAGACGAAC GCCGGTGGTT TGTGCTTCAT TTTGGTCGTG CGTTGCTTCA GTATTCATTC GCTACAGCTA ACGGTACGTG TAAATTAGGA TTCAGGCGCC GACGAGCGTA ATGCCGCCAC GCGCAAACAT CGTAGTACTT AGTCAGACAG TATACGTTAG CGCGCGATAC AGCTAGAACG CTAACTGT |
| 71 | 234 | GATCTCACCT TTTTTTAGCT GCGGCATCGC TTCCAGAGTG GCGACCGCCG GGTACGGGCA AGGTTCGCCA ACCATATCCA GACGGTAATC AGGGACGATA TTTTTCATAC AGATTCCTTA GCAGGCGTCA GCCCGCACGG CGAAAAAACG TTTTTTTCCC AGCCGATGAT TAACATTCAG TGGTAAATAA CAACAAAGTA GGTGACACGC AGACCGTAGG ACCAAGTATT CAGC |
| 72 | 317 | AGCTCTGATT TCGGTAGCGA TACGTCATCC ATCAGATTCG CCAGCGGATG GACAAACGGC AGGATGACCA GGCTGCCGAT CAATTTGAAC AATAGGCTGC CGAGCGCTAC CGGACGCGCG GCAGCATTGG CGGCGCTGTT ATTGAGCATC GCCAGCAGCC CCGATCCCCA GATTGCGCC GATGACCAGG CACAACGCCA CCGGGAACGA TATAATCCCG CCGCCGTCAG GTCGCCGTCA GCAACACCGC CGCCACTGGG AATAACTGAT AATAGCGAAC ATCCGGCCAA TAGCGCATCA GCATATGTGC CTGAGAG |
| 73 | 134 | GATCGAGGGC ACAGGAGAAA CGGGCATTTT CGCCGCAATT AGTTGACCTG ATCTCCCAAG ACCAAATTTT CCTCAGCCGG AATATACCAG AACTGGTCGC GATATCCGCA AGATCGCGCT TCACGGCGTC GCTT |
| 74 | 387 | GATCGTAATG TGCGGCCAGT TCAAAACCGA AGCGGCTATA TAACGCCGGA TCGCCCAGCG TCACGACCGC CGCGTAGCGA ACTCGTTGAG CGAATCCAGC CCTTCATACA CTAACTGGCG CGCCAGCCCT TGCCCGCGAT ACTTTTCATC GACCGCCAGC GCCATGCCGA CCCACTGTAA ATCTTCGCCT GCACATCAAC CGGGCTAAAG GCGACATAGC CACACTGACC TTCATCATCG TGCACAGTCG AGGTAGAAAA CATCTCACGA AATCGTGAAC AGCTTGCTTC GCATGTTTCG ATGACGGCGT ACACGCGATC AATACAGCGC ATCATAGATT TATGATAGAT GTATAGAGTG TGTCTAGAGT TTATCGCTAC ATCGAGT |
| 75 | 189 | GATCGTAAGG ATTGACGATT AACGCCGACG TCAGTTCATT CGCCGCTCCG CAAACTGTGA CAGTACCAGT ACTCCAGGGT TAGCGGGGTC CTGCGCGGCG ACAAACTGTT TGTGGACCAG GTTCATCCCG TCACTCAACG GGTTACTAGC CGACGTCTG AATAACGGAA TATACTTCAT TAACAGTTT |

TABLE 3-continued

| SEQ ID NO | LENGTH | PARTIAL 3'—5'SEQUENCES OF PROBES OF THE PRESENT INVENTION |
|---|---|---|
| 76 | 217 | GATCACGAAT ATTCATTATT CATCCTCCGT CGCCACGATA GTTCATGGCG ATAGGTAGCA TAGCAATGAA CTGATTATCC CTATCAACCT TTCTGATTAA TAATACATCA CAGAAGCGGA GCGGTTTCTC GTTTAACCCT TGAAGACACC GCCCGTTCAG AGGGTATCTC TCGAACCCGA AATACTAAGC CAACCGTGAC TTTGCGACTT GGTTTTT |
| 77 | 275 | GATCCCTTCT TTTGCTGATG CAGTAGCGGA CCAGGCTACC ACAAGGGGAA TGATGCAGAC TGCGAAAAAG TTTTTCATTT CAGAACCTGC CTTAATATTG GGCTAAAAGA CAAGTTTCAC GGTATAGGGT ATGATATAAC GATTCAATAA ACGAAGCCCA AAAAACGGTC TATTGTAACG CTGGGTTTCT GTAAGCGGGT AAAATGAGAT GAGATTTAAT AACATCAGAT ATCTCGGATG AATCACTCTC GAATCCGCAG CGTCCATCTA CGTAT |
| 78 | 101 | GATCTTCATA CAGGCCCAGA TAGCCGTCAT AAATGCCCAT GACTTCCAGC CCTTACGTCA ACGCTGCAAC ACAACACCGC GGATTTTTGA TTCATTCTCT T |
| 79 | 303 | GATCCGCACG GATAAAAACT CGTTTCCCGG CCAGATCCAG ATCGGTCATC TTAATTACAG ACATGGTGAA TCCTCTCAAT GATGCTTAAA GTTTTGTCGA CGCTGACGCG TGAGCCTGAA ACCAACTGCG GCCATCGCTA ACGTGGTGTC GAGCATCCTG TTAGCAAAGC CCCATTCATT ATCGCACCAG ACCTAGCGTC TTGATCAGTG GGCGCACTGA CCGGGTTGGG CATCACATGG CGTGGCTGGT AATTTGGACG GTGCATGTAC TCATGATGGC TTGGTTGGCC GGATTGCTTG CTT |
| 80 | 257 | GATCGTGACC CGGATAACGC TCATCATCTT TGGTCAGTTC CGGCGGCGTC ACGGCAAAAC CGCGGCGCCA CTGTTTAACC TGCTCGTCAC CATATTTTTC TGCCGTTTGC GCTTTATTCA GCCCCTGCAA CGGCCATAGT GACGTTCATT GAGTTTCCAG GATTTTTTCA CCGGCAGCCA CGCTGATCCA GTTCATCCAG TACGTTCACA GGCTATGGAT AGCGCGTTTC AAGTACGGAA GGTAGGCAAA TCAAGCG |
| 81 | 290 | GATCGAGCAG GCATTGCAGC AGCAGACTTT TGCCCTCCCC GCTGCCGCCA ACCAATGCCA CCATTTCGCC GGGCGCGATA TCAAAAGAGA CATTCTGTAA TAACGGCGAC CAGCGTCTCG CGCCATACCA GCGATAACGG CGCTTTCCAG CGTAACCTGT TGTAAACTCA GATACGTCAC TCCTTAGCAC AGCCGCTGAA TGGCGGAAAC TGTCGAAGAG CATCACAGCG TGAATAACAT TAGGCCGGGA ATAGACAGCA CAGTTCATGG CTAATAACGT ACCGTCGAGA |
| 82 | 233 | TGCAGATCCA CCTGGAACGG CGGGATGTTG ATCACCTGGG AGGCCAGACC GCTATTACGG CGCATTAACG CGCCATTACC TCTTCGATGT GGAATGGCTT CGTCACGTAG TCATCGGCCC GGAGCTGAGA ACCTCGACTT TATCCTGCCA GCCTTCGCGC GCGTTAACAC CAGAACCGGC AGTGAAACAT CACTCGTGCG CCCACGGGTA TTAAGGAAAG GCCGTCTTCA TCC |
| 83 | 284 | GATCTCATCA AAACGGTTGA GTACCAGCGC CAGGGTCATA CCCGCCTGGT TCAACGCCGT CAGGTGCGCC AGTTGTTGAC GGGCGGTCAC GTCAAGCCCG TCGAACGGTT CATCAAGGAT CAATAACTCT GGCTCAGACA TCAGCACCTG ACACAGCAGC GCTTTTCGCG TCTCGCCGGT AGAAAGGTAT TTAAAACGCC TGTCGAGTAA AGCGGAAATC CGCGAACTGC TGCGCCAGTA TCGCACAGCG CAGGATGGTG ACATATCCTG AATATTCGCG TAGT |
| 84 | 367 | GTTGCGATTA TCCCGCAGCG CCTGCTCGAA CAATTGGATT TGCTCAGTGC TTTCATGCCA TAACCAGAAG GTACTGATTA ACTGAACAC CAGCAGAATA AGACCAATTG TCAGCATTAA ACGCTGGCGA AGGGTCACTG CTCTTCGCTG AAAACGCATC AGGCTCACTT AGCTTTCCTC AGTGGCAACC AGCATGTAGC CAAACCCGCG AACCGTGCGA ATGCGACTTG CCGACTTTGT CGCGCAAATT ATGTATAGCA CTTCCAGAGT GTTGGTCGAG GGTTCGTTAT CCCAGTTGTG ATATCGTTAT AAAGAATTTC CGGTGCACGA CTGCCTGAGA CTAACCGTGA GAGCACGTAT CTAGCTC |
| 85 | 320 | GATCGTTGAT CGCCTGGATA ACAACCTGCT GCTGCTCGTG ACCGAATACC ACCGCGCCCA GCATAGTGTC TTCGCTCAGC AGTTCAGCTT CGGATTCCAC CATCAGCACA GCCGCTTCGG TACCGGCAAC CACCAGGGTC CAGCTTGCTT CTTTCAGCTC GTCTGGGTCG GGTTCAGCAC GTACTGGTCA TTGATGTAAC CTACGGCGCG CGATTGGGCC GTTGAACGGA ATGCGGACAG CGACAGCACG ATGCGATCAT CGCACGATGA TCAGGTACTG CGTACGAACG ACGTCCGATA ACTCGATGTA CAGCTCGGAA |

TABLE 3-continued

PARTIAL 3'—5'SEQUENCES OF PROBES OF THE PRESENT INVENTION

| SEQ ID NO | LENGTH | |
|---|---|---|
| 86 | 249 | GATCAATAAA TACTTTACGA ACTTCACTGG AGATTTCCCA TTTAGTGTCA TTTGGGCAGT TTATAAACAA ACGCGCGGTA GTATAAAGGC AAGCCAGACG CATTGATATA CCCGTTAACG CCGACGGGTG ATAAGGAGAT CGACCGTTAT GGCTTTTAAA CCTGGCAAAT AGGATTGCAT TATTCCAGCC ATGAAGCGCT GGCCATCGCG TTATTCACGC GCATCGGCTG ACACGCACTG TGCACTGCG |
| 87 | 275 | GATCGCCTTT TGCTGCCAAC GCTGCGGGAG AAAGAGCAGA AAGAGCGAAA ACAGCTGCGA CAGCCGCCAG AGTCGATTTG AGCATGAGAT TTCCTTAAAG AGAGCAGAAA TAAAGCAAGT GGAATGATTT TAAAGAGCCT TCTGGGCCAG GCAGCCTTTA CTATTTACGT ATATGAACAA TGTACGTTAC GACGACGCGT ATCTGCATAT GATGTGACAA CATAATAATA AATGCATGAC ATACTATACT ATATATTAGC TACAAGCTAT GCTCA |
| 88 | 325 | GATCGCCGCG AACCAGCAGA GCCACCAGCG GAGACTTGCT GTCTTTCACC GCTTTCACCA GCAGCGTTTT TACCGTTTTT TCAATTGGCA GGTTGAATTG TTCCACCAGC TCCGCGATGG TTTTGGCATT TGGCGTATCG ACCAGAGTCA TTTCCTGCGT CGCGCTGCGC GGCTTTGCGG GATAGCTTCT GCAGTTCAAT GTTAGCCGCG TAATCAGAAA CATCAGAGAA AACGATATCG TCTTGCGCTT TGGCAGCCTG GAATTCATGC TGGTTGGCGA TAGACGTATG CTGTACGGGA ATCAGCCATA GTGAGATACG CTATA |
| 89 | 230 | GATCGATACG ACGTTCAAAG GATTCAAACC GCGCCATGGC TTCATCCAGT TTGCCGCTGT CAAGCTGACG ACGGACATCG CGGGAAGAAC TCGCCGCCTG ATGACGCAGC ATCAGCGCCT GCGGGCGAGC GCGCGTGTTT CGCTGAGTTT GTTTTCCAGC GTCGCCAATC TCTTTCTTCA TGCGCGCAGT GTCATCACAG CGTGACTTCT GTTCAGCTAG CATAATCGTC |
| 90 | 146 | GATCCCATCG CTTTTTCAGA TATCATGCAC TTTTTGCACT CAATCTGCGG CAAATCCGAC CACTTTTTGC TCAGCCAGAA TGCAGTATTT CCGTCATACA TCGATTAGCT ACGACTCTAC GAACTACCTC GACCACAAGA TCACCG |
| 91 | 184 | GATCTTTGTT AATAACAGTG AGAGAACCGT ACGAATGTAG AAGAACTCCC GCCAGGCGGC AACATCTTTC ATAGTAGACC AAGCGTTAAC CCCTGCTGAT GTAAAAACGC TTCTATCTCT TGCGCACCAC GGAACGGAAG GTTGCGCGCC TTTAGCGCTT ACGGCAATAG CCGCGGCGGA TGGG |
| 92 | 311 | GATCAAACAC ATGAATACCG AGGCCTTTGA GTTTTTCAGT CGAGGCGTCC GAGCTGGAGA CCGCGCCTTC AATCTGGCCT TTCATTGTGC CCAGCGCATC AATAAAGTCT GCGGCCGTTG AGCCTGTACC AACGCCCACA ATGGTGCCGG GCTGTACTAT CTGAAGTGCC GCCCATCCTA CCGCTTTTTT CAGTTCATCT GCGTCATAGA TCGTTAGAAT GTGTGTGAAA TACGCCGCAT TATAGAACAT GTCCGGGAAA ATCTCGGTCG TACACAGCTA CGATTCGATT GCGCGCAATT TTGAGGGAAA A |
| 93 | 448 | GATCCTCGAT TAGGGGAGGC GCTAATTGAA TGTGGCGAGG TGTAAGAAAG CAGAAAAGCA AAGTGGGTTC TCGTTGCTCT GCATGTCGTC AAATTCAATT AAACGCATAA AAAAACCCCG CCGGGCGTTT TTCTTCAACT TCCAGGCGAT TACGGCGAAC GAAGTCGATG TGAGTCAGCT TCGGTTTGTA AGCGTGACCG TGTACAGCCT GAGCTTTAAC TTTTACTTCT TTACCGTCAA CAACGAGGGT CAGAACTTCG TGTAGAATTC AGCTTTAGCT TGCATGTTCA TCACCTGGTC GTGGTCAGTT CGATAGCAAT CGGGCTTCAG AACCGCGTAG ATGATTGCCG GACTGTAGCG CGCAGGCGGC AGCTCCTACA TGCTCTTACG TACTCTGCGT GATAGTAACA TTAATCTCTT ATATCTGCAG ACTGCACGAG ACTCGTCG |
| 94 | 359 | GATCATATCG ACGGTATCGG CGTAATTATT TTGCAGATGG CGTAACACAT CCAGATTATC TCCGGTCAGA AAAAGATTAT GGCTGTTTTT ATTTTCTGCC AGAGTATTGT GTTCCACGTC AGGAACGATA ACGGTAACGG ATTTTTCACC CGCCTGTTTT TTTGCCGTAA TCTTTGCCAA TAAAATCAAT CTGATAACCG CTAGTCAGCT CAATATTACG CGCTTTCAGG CGCTCAAATC TGGCGAGATC AATCCGCCTT TCGCGATCAG TTCGCCCTCT CGTTATAGCG GATCGCGGTA AAAATTCCGC GGTAATCGCA GTTGTAACTC AGACAGAAGC GCGTATTCGG CGCAGACGC |
| 95 | 298 | GATCCAGTTT AACCTCTGGC TGCCAAATCT TTCTGGAAAA CATGCGGTGC GTTTGGCGCT TCGAAAGAAA CATCCTGGTA TAGATACGTT GGATCTGGAA AGCCATTTCA GTGTTATTTT TGTTCTGACA TGTGTAAAAC CCTTTAGTGT TGTTCCTTAA ATACTTGAGT AACGCCTTAA CGCAACAGCG GATCCAGTCC ACCACGCGCA TCCAGCGATA CAAGTCGTCA CAAGCGCAAT GTGCTGTGCC TCAATCAAAT TTGCGACGTC GTCGCACTAC GTTGATATCT TTACGTCA |

TABLE 3-continued

PARTIAL 3'—5'SEQUENCES OF PROBES OF THE PRESENT INVENTION

| SEQ ID NO | LENGTH | SEQUENCE |
|---|---|---|
| 96 | 217 | GATCGTAAGA GTCAGAAATA AGCAGGCGTA ATGTTGTCAT AGTGGTTTTC CTTACCTTTA TTAAGCCGTC ATTTTACTCT TTTTCCTCAC GCTCTTCCTC TTCCGGAACA GGCTTGCTGG CCGTTAGCAG GAAGGGCGAC TGCTGCCAGC GGGTGCGTTT ACCTTGTAGC AAGGTGNNNC AGACACCACG CCTATCGCAG CGAGAGTAGC AGCATCA |
| 97 | 335 | GATCGAACTC TTTAAGCAGC ATCTTGGTAT GGAAAATATT TTCCTGATAC ACGTTTACAT CCACCATGTC ATACAGCGAC TTCATATCTT CCGACATAAA ATTCTGAATA GAATTAATCT CATGATCGAT AAAGTGCTTC ATACCGTTGA CGTCGCGTGT AAAGCCGCGC ACGCGTAATC GATGGTGACG ATATCGGACT CTAGCTGGTG GATCAGGTAA TTGAGCGCTT TTAGCGTGAA ATCACCCCGC AGGTTGACAC TTCGATCGTC GGCGGAAAGG TGCATAGCCC GCCTTCCGAT CGCTTCGATA GGTATCGACG CAGATATGCT CTATG |
| 98 | 352 | GATCGTCGTA GCTGCCGGCA TTGTGGTTGG GTAAATACTG GCGGCAAAAC GAGACTACGC CAGCGTCTAT CTCTACCATG GTGATGGTTT CGACGTTTTT ATGCCGGGTA ACTTCACGTA GCATTGCGCC GTCGCGCCGC CGATAATCAG AACGCTGTTT CGCATGACCG TCCGCCACAG CGGGGACATG GGTCATCATT TCATGATAAA TAAACTCGAC GCGTTCGGTC GGTCTGTACC AGCCGTCCAG CGCCATCACG CGGCCAAAAG CGGCTTTTCA AAGATGATTA AATCCTGGTG ATCGTTTTCA TGATACAGAA CTTGTCTACG GCAAGTCATG ACCAAACTGG TC |
| 99 | 127 | GATCTGTTTC GGGAAGTGAA CTTAAGGCCT CCGCAATATC ATTTATATAA ACTGACATGG CATTTTTAAA CTGCTCAGTA CTGCGTTTAC ATTTGTGGAA GATAGTCTCT GAGAGCAGAG TTTCTTT |
| 100 | 345 | GATCGGCAAC CTGCATTGCC AGTTCGCGGG TTGGCGTCAG GATCAGAATG CGCGGCGGCC CCGATTTTTT ACGCGGAAAG TCGAGCAGGT GCTGCAACGC CGGCAGCAGA TATGCCGCCG TTTTACCGGT GCCTGTCGGC GCAGAACCGA GTACATCACG GCCATCGAGC GCAGGCGTAA TGGCGGCGCT GAATGGCGTC GGGCGAGTGA AACCTTTATC CTGGAGGGCA TCCAGACAGG CTTTCGTCAG ATTCAAGTTC GGAAAAAGTG TTACAGTCAT GTCTACCTCT GTGTGGGCGC TGATTATAGA CTTACGCGCA TCTCATCTGT GATGATATCT CTCAG |
| 101 | 250 | GATCCGGGAC ATTCACGTTG AGAATACGCC CGGTACGCAA CGGCTCCCGG CTTAACCCTC GCAAAAGCGC ACAAGTCACG GCCGCAGCGA TACATAATGC TGATAGCCGT TAAGGGAGAC CGCTAATGCC GGAAAGCCGA GATGACGACC TTCATCGCGC GCACAGTACC GGAATAGATC AACATCATCG CCAGATTCGG ACCGCGTTAT ACCGGAAACG ACATATCGGT GACGATTAGC TTACGCAGAT |
| 102 | 333 | GATCCCGGCT TACGACGGTT GGCTGGATGA CGGTAAATAC TCATGGACTA AGCTGCCGAC ATTCTACGGC AAAACCGTCG AAGTCGGGCC GCTGGCGAAC ATGCTGTGTA AACTGGCTGC AGGTCGTGAA TCCACGCAGA CCAAGCTCAA TGAAATCATT GCGCTTTATC AGAAGCTGAC CGGCAAAACG TCTTGGAAAT TGGCGCAACT TCACTCTACG TGGGTCGATA CATCGGGCGT ACCGTTCACT GTTGTGAACT GCAAAACATA TTGCAGGATC ATACAGCTGA TTGTAATATC GGCAAGGATT ACACCAGTTT GAGACGGCAA TCG |
| 103 | 284 | GATCCAGCCA GACGGAACCC CACGGCGGCG GAGACGGCAG AGCGTAAGGG CCGATAAACA GACGCTGCCA GGCCTGTGCA ACGACTCTTC GCTGTGGGTC TTAAACATAG CCGCCACAGG GCAAGGCTCG GCATCAAGCG GCCACTGCGC CTGCAGTCGT CGTTTAATAG TCGTCCTGGA CCAGAGGAGC GGTTTCGTGG CTTTCCGCGA ATAATAAAAC AAGTGCCAAG AACAGTGTTA CTGCAAATCA TCTCGTTGTA AAAAGTGTAT TAAACATCCG TAAA |
| 104 | 249 | GATCAACGCA AACAATCAGA ACCTCTGCTT CATTTAGCAG CGTGTTCTCT GCGTTGACAA TGCGTTGCGT GAAAACCAAA GCGGTGCCAC GCATTGACGT AATTTCTGTT TGAGCTTCAA GCATATCGTC GAGCCGCGCA GGCCATAGTA TTCCAGCTTC ATCTTGCGCA CCACAAAGGC TACCCGCTCC GCAGCAGCAC CTGTTGCTGA AGTGATGGTG GACGTCAGCA TCTCGNNNTC TTCATAAAA |
| 105 | 248 | GATCCCTTTA CGACCAGGCG TCCCGGCGCC GTTATAGTGC CAGCCAAAAC CAAAGCCGCC GCCCGGTAAA CCAATCTGTT CCAGCATTGC GGCCAGCACG ACGACCATCC ATGACCACTG TTCGCATGCT GCATACGTTG TACGACCAGC CAGCGATGAT TTCGGTTCTG TCGTCGCATC TGTGGCAACG CGACTGGGTG GTGTAATCAA GATCATTTCG CAGGACTTGG TGCATTGTAG AATCGAGA |

TABLE 3-continued

PARTIAL 3'—5'SEQUENCES OF PROBES OF THE PRESENT INVENTION

| SEQ ID NO | LENGTH | SEQUENCE |
|---|---|---|
| 106 | 175 | GGCGGAGGAT TGCCACGTNG CAGCCTGCTA CGCCCGTCAG TTCTTTACGC AGGTTAGCCA CCAGTTCGTT TACCATGTGG CGGCTCCNTG TCAGTTTCCA GTTACCCATC ACTAAAGGAT GTGATTTATT TNTCCACGTT AGTAGCGAAT TAAGGAAGAT GGCCGCTCGT AGAGA |
| 107 | 307 | GATCATTATC TTAACCTAAA ACCGCTATAT TTATAAGTAT TATTACGAAT AATCTTAACC TGGGATATGT TATACTAATC GGACCAGAAA GATATTATTA CGACTTTAGT AAATGCTTTT TAAATATTAA ATAATAATTA ATTAAGATTT CTACCATTCA TTAATTATAC TTAACAATAG TTTCACACCC CGCGCCGGAA AGGTCTAACC TTCTCATTTA CCTTTAATAC TCAGTATTCC CGAATAGCCG ACCGACACTA ATGATGAATG CTTATCTCTC ATAAACCAGA TATTATGACA CATAACC |
| 108 | 234 | GATCAGGATA TGCCGCCGCC AGTAGCGATA GGGCGTCAAC CTCGTGCTTA TCGGTGATGA GCGGCGCGTT GGCCGGGGCT TTTAAAAACG AAAGCATTAT CCTTCCTTAA ACGTAACGCT GGGGCAACGA GACGCTCACC CGCGTACCGT GGGTACAAGA GATGGTTAGC GTCCGCCGAG CGACGACACG CGCTTCGCAT TCGGTCAGGC CGAAGCCTCT TGGTGAGACC GCCG |
| 109 | 352 | GATCGAGCGC GGAGAACGGT TCATCCAGCA GCAGTACCGG CTGTTCGCGT ACCAGGCAGC GCGCCAGCTA CCCGCTGACG CTGGCCGCCG GACAGTTCGC CCGGTAAACG CGTCATCAGA CTCTCAATGC CCATCTGATG TGCGATAGCT CCCGTTTTTC CCGCTGGCTG GCGTTGAGCG TTAACCCAGG GTTTAGCCCC AGACCGATAT TTTGCCTGCA CATTCAGGTG GCTGAATAAA TTATTCTCCT GAAACAGCAT TGAGACCGGA CGGCGTGAGG GCGGCGTAAG CTATGATCGT CGGCAATAGT AGCGTACGCT GGCCAGGCGC AAGAAACCGC ATAATCTCTC TT |
| 110 | 168 | GATCAGGGTC AGACGCTTGT GCGCCCATAC AACGTTTTGT TCCAGTTGGC CTTTCTCGTT AACGTTTTGG GAGCGCCAGA GCTGTTTAAC GCTCATGGGG CATTCCAGAA CGGGCAGTAT CTCTTCAAAG GACGTTATCG TTTGTCAACG GCGGACAGCA TTTTCAAA |
| 111 | 211 | GATCTTCGGG GCGCACCCAC GGGGTTTTTG CGCGGGGGAC GCCTGTGTTA TCAGCATTGT AGAAACTGCG ATAGATATTT CCGGTGAGGC AATTTTCGCT CGGCACGATG TGTCGCTTAT CCGGTATGTG GTGAGCAGTG TGCGCCGGGG CGTGTGATAG AGCCATTGCG CGATGGATCG TCTAGTGAGT TTCTCAGATA GGGGGTGACG A |
| 112 | 257 | GATCCGCAGA TCCATCTAAT CGGATTAGGC GCATACTGGT AAAGATTCAG CCCCCCCGCC AGCCCAATCG GATCCTGACT GACGAACCGT CCACACTCCG GTGCATAATA TCTGAACAGA TTGTAATGCA GCCTGTCTCG TCGTCAAAAT ACTGCCCCGG CAGCCGCAGA CCGGCTGGTG AAGTACGCCC GCTGTTGCTG ATGTCCGCCG CATTTCTCCA ACCCTGATAT ACCGCCACAC AGCGTCGTCG CGCGTAC |
| 113 | 359 | GATCCTGACT GGTACGACTT AACGTTTTAG GCTCGCCAAA ACTCAGCCCC GCCGCTTTCA TCGCTTCCGC GCCTTTGCCC GCTTTCAGCT CGACCAGCAG TTTTTCCGCA TCCAGCTTCG CCTGTTGTTC CGCTTTATTA TGCTTCACCA GGGCAGTGAC CTGTTCTTTC ACTTCTGCCA ACGGCTTCAC GGCTTCAGGT TTATGTTCGC TCACGCGTAC GACAAAAGCC CGGTCAACCA TCCACGGTGA TAATGTCTGA ATTCGGCCCG GCGTACCGTT TGCACAGACG CATAAGATAG CATCGGCTAA CGTTGAAGTC AGCCTTCGGT AAGGTGTACG GCTAACAGCG GTTACGCTT |
| 114 | 427 | GATCGCGTAC CGCCAGTAAC GCCGCCGCTT TACCGTCAAT CGCCAGCAGG ACCGGAGTCG AGCCTTGCGA GGCCTGCGCG GTGATTTCCG CCGTCATGTC ATCCGTGGCG ACGTGCTGTT CGTTCAGCAA CGCCTGGTTC CCCAGAAGCA GTTGATGACC TTCCGCTTCA CCGCTGACGC CCAGTCCGCG CAGCTTCTGA AACCGTTCAC CTGCGGCAGT TTATCATCGC CGGCTTTTTC CAGAGAATCG CATGGGCCAG CGGGTGGCTG GAGCTTGTTC GAGCGCGGCA GCCAGACGTA ATGCCTGAGC TTCTCAACGC GTTAAAGGTT TTATCGCACA CTTGCGGCTT GCTCGTCAGC GTCCGGTTTA TCAAACTGAG GTATCAACGT ACTGGCGCGT GCAGGATGGC ATGTACAGAG CGATGAG |
| 115 | 299 | GATCTGGAGG TAGAGGTTAT CGAGGCCAGC GGTAAAACCT CACGTTTCAC CGTGCCTTAT TCTTCCGAGC CGGATTCGGT TCGCCCCGGT AACTGGCACT ATTCGCTGGC CTTCGGCAGG GTTCGTCAGT ACTACGATAT TGAAAATCGT TTCTTTGAGG GAACGTTCCA GCACGGCGTT AATAACACCA TTACCCTCAA CCTCGGTTCA CGAATTGCGC ACGGTTACCA GGCATGGCTG GCGGGCGGCG TCTGGGCCAC CGGTATGGGC GCGTTCGGCC TTAACGTCAC CTGGTCGAA |

TABLE 3-continued

PARTIAL 3'—5'SEQUENCES OF PROBES OF THE PRESENT INVENTION

| SEQ ID NO | LENGTH | |
|---|---|---|
| 116 | 339 | GATCAGAGTA AAACCTGGCT GCTATGGTGC GAACGTGGCG<br>TAATGAGTCG CCTGCAGGCC TCTATCTGCG CGACGAGGGG<br>TTTGCCAATG TGAAGGTGTA TCGTCCGTAA TTCCTTTGCC<br>GGGTGGCGGC TATGTCCTAC CCGGCCTATC GTTTTATTTC<br>TGCCCCAACC GTTTTGCAAT GCGCTCCAGC TTCATCATCA<br>GCAGCAGCGT AATGGCCACC AGCACAATGG TCAGCGCGGC<br>GTCAGCATAT TTCACGTCGG TCAAGCTAAA GATAGCCACC<br>GGCAGCGTCG TCAGCCGGCG ATAATCATCA TCGTGGCCAA<br>CTCCCATGAG AGCATAACT |
| 117 | 378 | GATCGATATC AGGGAGGAAG TGGTTGCCCG CCACCAGCGT<br>ATCGGTACTG ATCGCCAGGG TCTGCTTTTC AGGAATATCA<br>GGAGCGCGCA ATCGTCGCCA ATACCGGTTT CAACATCAAG<br>ACGAGAGCTT CTTACACGGT CAAAATAACG GGCAATCAGG<br>GAAAACTCGC CACATGCCAT ACGTTATGCC TCAGCAGAAA<br>AAAAGAAAAG GCCGGAGACG CGGGTATCGA GCGCCCGCTA<br>TCTTTCCGGC CTGTGAATCA CTTTTTGTTG GGACGAATCA<br>CCGGAGCTGC TTTATCAGTA CGCGTTGACG ATTTGTGGCT<br>GTCTTCACGC GCCAAAGTTT GAGTTCATCG CTTCGTTGAT<br>GGCCATTATA AGCCAATC |
| 118 | 266 | GATCTCTTAC GATAAAGAGC ACATTATCAA CCTTGGCGCG<br>CCAGATTGGT ACGGAAGATT TTGCCCGTGC GATGCCTGAA<br>TACTGTGGCG TGATTTCAAA AAGTCCGACG GTGAAAGCCA<br>TTAAAGCGAA AATTGAAGCC GAAGAAGAAA ACTTCGACTT<br>CAGTATTCTC GATAAGGTGG TAGAAGAGGC GAACAACGTC<br>GATATTCGTG AAATCGCCAG CAGACCCAGC AGGAGGTGGT<br>GGAGTAGAAC GTGATGATCG GTTTCT |
| 119 | 345 | GATCATCTTC CACTTCCAGA TGCACCGTCA CATCCGGGTT<br>AGTGAGCTTC ACGCGCGCCG ATTCAATATG CTGATTTAAT<br>CCGCCGCCAA CATAGCGCTC CACTTCAATG GAGCTAAACT<br>CATGCTTACC GCGACGTTTT ACCCGCACGC AGAAGGTTTT<br>GCCTTCAAGC TGTTCGCGAT ACTGCGCCAA ACGCTTTCTC<br>GAAAATGTCG TGCATATCGG TGAACGGCAC ATCTCGACTT<br>CAAGAATATG TGAATCCCGG GATCGTGGTC AGCGCTCGGA<br>ATCACAGACG CTGGTTTCAC TTGCGCGACT CATTTACAGT<br>CAGACACGTG TAGTGCTTAA CTCAG |
| 120 | 321 | GATCATCCTG GAGGTCTTTA TGGCTGATTT CACTCTCTCA<br>AAATCGCTGT TCAGCGGGAA GCATCGAGAA ACCTCCTCTA<br>CGCCCGGAAA TATTGCTTAC GCCATATTTG TACTGTTTTG<br>CTTCTGGGCC GGAGCGCAAC TCTTAAACCT GCTGGTTCAT<br>GCGCCGGGCA TCTATGAGCA TCTGATCAG GTACAGGATA<br>CAGGTCGACC GCGGGTAGAG ATTGGGCTGG GCGACGGACG<br>ATTTTGGCTG GTCCTTCTCA GGCGCTATTA GTACGCGGTT<br>CATGCAGTAC ATACTACCTG AAGTCACGAT GCACCGAATA G |
| 121 | 216 | GATCGGCGCG CGTATCTCAG GCATGTGCGC CGCCAGTTGG<br>GAAACGCGCC CGCCGGGGCC CTCAATTTCA TACGCAGAAT<br>ATCCGCGCGC GCCGACCGCG CCGGCAACGG CGCGGCAGAC<br>ATTGACGCCG GCGGGCAGCT CGCGGGCTGT GGCAGAAGGG<br>CGTCACGCTG CCAGGCCTCG TCTGGATAGA TTGATATTCT<br>CGACCACATC CCGAAA |
| 122 | 292 | GATCGGCAAA CAGATAGTCC TGCGACGCAT TAAATCCAGG<br>CATTGCCGAG GAGCACGCCG AAGCGGATAC GCCAGGCGGG<br>CAGGCCATAC CTACGGTATT TGTCAGACCA AACGCCTGCG<br>GGTTGGCAAG AATTTCCTTA AAGAGGCCGT TGATATCGGC<br>ACGGGCTATA TTGCCGCCGT GTTGCTCCAG CCCCTTCTCT<br>TCCATCTGAT TATAATAATC GGTCAGAGCT GACGCTGCCC<br>TGCCGCCGTT CATAGTTGCA GAGTGTCACG AGCAGTGTGA<br>TAATGATGGG TT |
| 123 | 109 | GATCAGCGCC GCGCTACGTT AATAGCCGGT TGCGACGACC<br>GTGGACGCTA GCAGAGTCGC GGATGACTTC CGTATCGGTT<br>GGTCCACGCG TGAAATTAGT TGCGCGACA |
| 124 | 258 | GATCGGTCGC ACGCCGGAAT ATCTGGGGAA AAAAATCGGC<br>GTGCGTGAAA TGAAAATGAC CGCGCTGGCG ATTCTGGTCA<br>CGCCGATGCT GGTCTTGTTG GGTTCGGCCT GGCGATGATG<br>AACGGATGCC GGACGCAGCG CAATGCTGAA CCCTGGCCGC<br>ACGGTTTTAG CGAAGTGCTA TATGCCGTCT TCCTCTGCCG<br>CCAACAACAA CGTAGATTTT TAGTCTACCT AACTACTTCT<br>GAACTACGGC ATCTCGAC |

TABLE 3-continued

PARTIAL 3'—5'SEQUENCES OF PROBES OF THE PRESENT INVENTION

| SEQ ID NO | LENGTH | SEQUENCE |
|---|---|---|
| 125 | 384 | GATCGTTGGT CTTTAAGGCC GCCGCCAAAT CGCTGTCGAC CTGCTTGTTG CTGTAAAAAG CGGTATTAAA CTGCGTCGGC GGCCAGTTTT GTGATGCGAA GAGCGGCGAT AACGCCCAGT CAGCTTCGCC CGTCAGACGC CGACCAGCCT GTATAGAACA TTCGCACGCG CTCTCTTTTT GCCCTTTGCC CTCGACTTCC GCGGCGGCTG GCCGGCGTAC ATCGCGGTTA TCCGGGCTTT AACGACCAAT CTGCGCCAGT TGCTGTTGGG TAAACTGCAA GAGTTTTTGG GTGCTATGGT TGTGCATGAC ACAGCGTGTA CTGAACGTCT GATACCGCTT TCACGTCCCC TAGCGATCAT GGCCAGTGAA GTTGCATAGC TAGA |
| 126 | 448 | GATCATACCT TGCTTGATGA CTGCGCCACT AAAAACCTGA CGCCGGCGAA AACCCACTGG GCGCGCCCGC TTGATGCGCC GCCCTACTAC GGTTATGCGC TGCGACCCGG CATCACGTTT ACCTACCTGG GTCTGAAAGT CAATGAACGT GCCGCGGTGC ATTTGCCGGT CATCAAGCCG CAACCTGTTT GTTGCCGGCG AGATGATGGC AGGAAATGTT CTGGGCAAGG GGTATACCGC AGCGTAGGCA TGTCTATCGG CACAACCTTT GGCCGCATTG CAATAGAAGC CGCCCGCGCA CAAGGAGGCG CACGATGAAA CAGCTTGAAA ATTATCATTG AGGCACGTGC TTACGAACGA AGCGAGGTGA ACTGTCATGC AGTGTGTACG TGTGTGCTAC TCGAAGGTTT GCGGATTCGC ATGACAGGTG ATGTAGCGAT ATATCGAT |
| 127 | 392 | GATCCCCAGG AGGTCTGGTT TGTCAAATCG CCGAAATCCT TTTTAGGCGC CACGGGCCTG AAACCGCAGC AGGTCGCGCT GTTTGAAGAT TTAGTCTGCG CCATGATGGT ACATATTCGT CATACGGCGC ACAGCCAATT GCCGGACCGA TTACCCAGGC AGTGATCTGC AGGTGGCACT TTTCGGGGAA ATGTGCGCGA ACCCTATTTG TTTATTTTTC TAAATACATT CAAATATGTA TCGCTCATGA GACAATAACC TGACAAATGC TTCAATAATA TTGAAAAGGA AGAGTATGAG TATTCAACAT TTCGTGTCGC TTATCCTTTT TCGCATTTGC TTCCTGTTTG CTCACCAGAA CGCTGGTGAA GTAAAGATGC CTGAAGATCA GT |
| 128 | 327 | GATCTTGTCA AGCTGGTCAG CATATCCCGG ATATCCTCCG CCTCCCCCCC CGCCACTCCG CGCGGCTTAT GAATCATCAT CATGGCGTTT TCCGGCATAA TGACGGGATT ACCTACCATC GCAATAGCGG ATGCCATTGA GCAGGCCATT CCATCGATAT ACACCGTTTT TTTCGCCGGA TGATTTTTCA GGAGGTTATA AATGCTATT CCGTCCAGTA CTGCTCCGCC AGTGAATGAA TATGCAGATT TATACGGTTA ATCTGTCCAG TGCAGCCAGT TCTCTGCAAA CCAGCGAGCC GAAATTCCCA TCTCAATCTG TCATAAT |
| 129 | 306 | GATCCGCAGG AGAAAACACG ATTGTACAAA GAGGCGCAGG ATATTATCTG GAAAGAGTCG CCCTGGATAC CGTTGGTGGT GGAGAAATTG GTTTCTGCTC ACAGTAAAAA TTTGACCGGT TTCTGGATTA TGCCGGATAC CGGTTTCAGC TTTGACGATG CGGATTTAAG TAAGTAATGC GATGGGCTG GATGGCGCGC GGTTGTCGCC ATCCGTAAAA GGTTCGTGTA TGCTAACTAT GTTCTCAGCG CTGCTGGATT ATTCTACGTG TTGATTGTGC AGTGCTGGTG TTTATTGTCA TTGTCC |
| 126 | 448 | GATCATACCT TGCTTGATGA CTGCGCCACT AAAAACCTGA CGCCGGCGAA AACCCACTGG GCGCGCCCGC TTGATGCGCC GCCCTACTAC GGTTATGCGC TGCGACCCGG CATCACGTTT ACCTACCTGG GTCTGAAAGT CAATGAACGT GCCGCGGTGC ATTTGCCGGT CATCAAGCCG CAACCTGTTT GTTGCCGGCG AGATGATGGC AGGAAATGTT CTGGGCAAGG GGTATACCGC AGCGTAGGCA TGTCTATCGG CACAACCTTT GGCCGCATTG CAATAGAAGC CGCCCGCGCA CAAGGAGGCG CACGATGAAA CAGCTTGAAA ATTATCATTG AGGCACGTGC TTACGAACGA AGCGAGGTGA ACTGTCATGC AGTGTGTACG TGTGTGCTAC TCGAAGGTTT GCGGATTCGC ATGACAGGTG ATGTAGCGAT ATATCGAT |
| 127 | 392 | GATCCCCAGG AGGTCTGGTT TGTCAAATCG CCGAAATCCT TTTTAGGCGC CACGGGCCTG AAACCGCAGC AGGTCGCGCT GTTTGAAGAT TTAGTCTGCG CCATGATGGT ACATATTCGT CATACGGCGC ACAGCCAATT GCCGGACCGA TTACCCAGGC AGTGATCTGC AGGTGGCACT TTTCGGGGAA ATGTGCGCGA ACCCTATTTG TTTATTTTTC TAAATACATT CAAATATGTA TCGCTCATGA GACAATAACC TGACAAATGC TTCAATAATA TTGAAAAGGA AGAGTATGAG TATTCAACAT TTCGTGTCGC TTATCCTTTT TCGCATTTGC TTCCTGTTTG CTCACCAGAA CGCTGGTGAA GTAAAGATGC CTGAAGATCA GT |

TABLE 3-continued

| SEQ ID NO | LENGTH | PARTIAL 3'—5'SEQUENCES OF PROBES OF THE PRESENT INVENTION |
|---|---|---|
| 128 | 327 | GATCTTGTCA AGCTGGTCAG CATATCCCGG ATATCCTCCG CCTCCCCCCC CGCCACTCCG CGCGGCTTAT GAATCATCAT CATGGCGTTT TCCGGCATAA TGACGGGATT ACCTACCATC GCAATAGCGG ATGCCATTGA GCAGGCCATT CCATCGATAT ACACCGTTTT TTTCGCCGGA TGATTTTTCA GGAGGTTATA AATGGCTATT CCGTCCAGTA CTGCTCCGCC AGTGAATGAA TATGCAGATT TATACGGTTA ATCTGTCCAG TGCAGCCAGT TCTCTGCAAA CCAGCGAGCC GAAATTCCCA TCTCAATCTG TCATAAT |
| 129 | 306 | GATCCGCAGG AGAAAACACG ATTGTACAAA GAGGCGCAGG ATATTATCTG GAAAGAGTCG CCCTGGATAC CGTTGGTGGT GGAGAAATTG GTTTCTGCTC ACAGTAAAAA TTTGACCGGT TTCTGGATTA TGCCGGATAC CGGTTTCAGC TTTGACGATG CGGATTTAAG TAAGTAATGC GATGGGGCTG GATGGCGCGC GGTTGTCGCC ATCCGTAAAA GGTTCGTGTA TGCTAACTAT GTTCTCAGCG CTGCTGGATT ATTCTACGTG TTGATTGTGC AGTGCTGGTG TTTATTGTCA TTGTCC |
| 130 | 301 | GATCTCAGCG ATGTTCAGTT AAACGCTGTG CCGGATGCGG CGTAAACGTC TTACCCTGCC AACGGGTTGG GTAAGCCGAA TAAGCGCCGC TCCATCCGGC AGCATTCACA TAAAGTCCGG CACCAGACGC TGTAACGCGC CTTGCGCAGC AGCGCCGTCG CACACTCAAT ATCGGGCGCA AAAAAACGAT CCTGCGTATA GTGCGCCTCC TGCTCGCGCA GTGTCTGCCG CGCCTGTTCC AGTAACGGGC TGGAGGTTAA CCTTCCGTAA TTATCCTGAC AGCAGCAGCA TCACGCATAT G |
| 131 | 329 | GATCGCCGGT CAGTTCCTCC ATTAAGAGCG GCGCGCGCGC CAGCATCTCC ATGCAGAAGA GCCGCGACGC CTGCGGATAA TCACGCGAAA CTTCCAGCTT GAGACGGATA TACTCTTTGA TGGCCTCCAT AGGGGAAAAT TCTGCGCGAA ACGCTTGAGC GGCGCACGAG ACATCCAGAA TCTCGTCGCA TTACCGCGAC ATACAGCGCC TCTTTCGAGG GATAATAATA AAGCAGATTG GTTTGGAGAC GCTGCCGTAG CGGCGACTGC TCAAGACGCG CGATGATGCA TACTGGAAAC ACGAGCGCGT AGATAGCTGC GTTGCACGG |
| 132 | 266 | GATCCGCCCA CGCGTTAAGG GCCGTAAACA GAGCGTCATT CATCATTACC GCTGGATTCA CCGCCCTTCG TTCTTCTTCT GTTAACACCA CGCGTAATCG CAGACAGGCC GGGCCGCCGC CGTTGGCCAT ACTTTCTCGC AAATCAAACA CCTGCATCGC GCTGATGGGG TTATCCTCCG CCACCAGCTT ATTCAGATAG CGTCCAGACG CGACATGGTC TGACTTCCGC GCACCTACGG TTGAGCCGTG TTCGCTTGCA CTGCTT |
| 133 | 319 | GATCAAATGC AGGCAGTAAA AGGGCGTCAT CAAGATTATC GGTACACTGT GTAGCGGCGG TTTGCAGAGT ACCATGTAGC GCCGGATAAT TATGCCGGGT CAGGTTGACA CCGTGCGTAC CGTTAATAGC TTCAAAGGCG TCGCAAAACG CGCGGTGTTT TTCTGCGGTG ACGGGGTCTC CCGGCGCTTC AAAAGTTCGC ATCAAATGCG GGCGATGCTC TGATTCTGGT ACTTATCGTA CAAAACGACG ATCGCTCTCT CATGATATAC GCATATAGCA TCATGCCTGT CCGTGCATAG TCGTAACTAG AGACATCAC |
| 134 | 438 | GATCAACCTG AACTCAACGG ACCCTGTACC GTCTAAAACG CCCTTAGCGT GAGTGATGCG GATTCGTATA ACAAAAAAGG CACCGTCACC GTTTATGACA GCCAGGGTAA TGCCCATGAC ATGAACGTCT ATTTTGTGAA AACCAAAGAT AATGAATGGG CCGTGTACAC CCATGACAGC AGCGATCCTG CAGCCACTGC GCCAACAACG GCGTCCACTA CGCTGAAATT CAATGAAAAC GGGATTCTGG AGTCTGGCGG TACGGTGAAC ATCACCACCG GTACGATTAA TGGCGGAGCC ACCTTCTCCT CAGCTTCTTA CTCATGCAGC AGACACGGGC TATACATGGA CATCAAACGG CTATAGGGGA CTGTGAGCTA CAGATTACAC TGATGGCACG TGTTGGCACT ACACGCGCGT TCGGCGATGT GTATGAAC |
| 135 | 363 | GATCTTATCC TTCCGCTACA AAATCAACTG CGCCATCTGA CGCATATTGT CGGCGTGGAT AAACTGGCGG CTGCCACCAC AGCGCTTGCG TTAGTCAAAT CATCGACCGC AGCGAACCGT TGCAGTCAGA CATTAACATT CACGGTGATG AACTGGCGGC AGTGCTGTTT ACCTCCGGCA CAGAAGGAAT GCCGAAAGGG TGATGTTGAC CCACAATAAT ATTCTTGCCA GCGAACGGGC GTATTGGGGG TTGAATTTAA CCTGGCAAGA TGTGTTCCTG ATGCTGGCGC ACTGGGAGAC CGGATTTTAA GGAGGCTTTT ATGGGGTAGT ATTGCTGGAC ATCTTACCAG AGCTCTACTA TAG |

TABLE 3-continued

PARTIAL 3'—5' SEQUENCES OF PROBES OF THE PRESENT INVENTION

| SEQ ID NO | LENGTH | SEQUENCE |
|---|---|---|
| 136 | 347 | GATCGATTTT CCCCTCCATG TTTTCATAGG GGAACAGGTT CGGGTTAAAA ACCACCTGAC GGATATCGCA CAAAAAGCCA ATCCGCTCCG CCCAGTAACC GCCCAGCCCC ACGCCACAGA TTAAAGGGCG CTCGTCCACA TTCAACTGCA ACATTTTGTC CACTTCTTTC AGCAGATGCT GCATATCGTG CTTAGGATGC CGCGTACTGT AGCTTACCAG CCGAACATCG GGTCGATAAA CTGGTAATTG CGAACACTTT TTCATGGTGC GCGGACTATA TGAGTCAAAA CGTGTGATAT ATATCATCTG GCACCTCACG AGACTGAGTG ATGCGTGCGT TTCTGCA |
| 137 | 278 | GATCCCAGAC AATACCGTTA CTGTTATCCA ACGATACCCC TGCCAGTGAG GTACGCAGGA ATCCATATTG GGTGTGATGC GCGTAAGAAA CGCCCGCCAT CATAGTACTT TTACGCCTGT CCAGACGACG CAACTGATGG TCATCGCTGT CGCCCGGTTT GAAGTACATC GGGGACCAGT ATGCCATGAT TGACAACTTA TCGGCATTGT CATTCACAAG TAGTACCGCG CCAGACACGA CAGAGTTNTT CATAGGCATG ACGATCGATA ACAGCTAT |
| 138 | 385 | GATCGTTATG AATCGCTTGC GTGATTTCCA GCGTCACCGG GTCGAGACGA TAAACTACGC CGCCTTTATC CAGTTTACGG CTTTGCGATG TAGCCAGCCA GAGCGCGTTT TCTTGCTGAC TCCAGGCCAT CTCATAACGC CTTTGCCTAC CGCTTTACGC AGCATGTCTT CCGCGCCAGC GTGCTAAATG AGGATGCGAC GAGGAGCGAA CCTAACAATA AAGAACCACG CAGGCTGGCG AAAAAAGATG ACGTAAGTGC ATGACGACTC CTTTGATAAA ACGTGTATAG CTGCTTCACA CTACTTCGCT GCGTGGATCT GCAGGTGGCA CTTTTCGGGA AGTGCGCGAC CCTATTGTAT TTCTAATACT CAATATGATC GTTAT |
| 139 | 282 | GATCAGCGGC TATGGCGGTC CGGAAGGCGC GAAGATGGCA CGCCGGCGGG CACAGTTTGG TTTGCCTGGA ATATTAACAA TACAACTTTT ACAAGCCGAC AACATTTCAA CGGAGATTGT CAGGAAGTAT TGGAAAAATG CGTACGCTTC GCCCTCGCTG AATTGCTTTT CTGTTAACGA AGAAAGCATA ACATAATTTC ACTGACGTCA GATACTCCGG CTAGATAAAT CGAGCTTACC GCGTGTTCGG AATTCGATGA TTCGGATATC GGTCGCCATC GT |
| 140 | 179 | GATCGGCGAC TACAAAACCA ATCACCGCGG CTTTACCATC GAGTTCCATA TGCGTACGTT TTATCGCTGG GAGTATGGCG AGAATATGTC CCCGGCCGGA TAGAACCGGT TAAAGAGACC ATGCGTTACT TTTTCATGGC GGTATACATG CACAGTTGCT TGGTGGCATG ACATTGGAA |
| 141 | 261 | GATCAGTAAC AGGACGGTAG CAAAATTCGC ACTGAGCCCG GCGACATTCT GAACGAACGG TTCAATATAG CTATAACTGT GTAATGCGCA GTCACCACAA CGACGGTCAG TACATAGAGG CTCATCAGCG CCGGGCGTCT GAATAGCAAA AGGTAAACTT TTTAGTGAGC CGGAATGCTC GTCTGGCAAT TTCGGTAGAG CTTATCAGAA TAGCAGCGTA TATCTCCATG CGATGCAAAG TGGCCCAGCA AATCTGACAC T |
| 142 | 225 | GATCATTTTG GTGCCGGTGT CAGCCTGCTG ATGTCCACTG GTCAGCGCAA CGGAATAGAA CTCGCCGATA TAATTATCAC CGCGCAGAAT GCAGCTCGGG TATTTCCAGG TAATCGCCGA ACCGGTTTCC GACTGGGTCA ACGACATCTT GCTGTTTTCC CTTCGCACAA GCCCGCTTGG TCACAAAGTT CAGATCGCCG TGTGTGTGCC GGACAGTTGA CGTGA |
| 143 | 301 | GATCATCCTC GGCGCGGGAG TGAATCACTG GTATCACATG GATATGAATT ACCGTGGGAT GATTAACATG CTGGTGTTCT GCGGCTGTGT TGGACAAACC GGCGGCGGCT GGCCGCACTA TGTCGGCCAG GAGAAGCTGC GGCCGCAAAC CGGCTGGCTG CCGCTGGCTT CGCGCTGGAC TGGAATCGCC GCCGCTCAGA TGAACAGTAC TCGTTTTCTA CACCATGCCA GCCAGTGGCC TATGAAACTG ACTGCGCAAG AGTTGCTGTG CGCTGCGATC GCTAATTCGA CTATCGATTA C |
| 144 | 272 | GATCATGTGG GTTTAACCCG TTGATTAAAC ATTGGATTAC GGAATAGCAA TTGCTTATTT TATTTGTCAT ACAAATAAGT ATAATACCCG CTTCCGATGT AGACCCGTCC TCCTTCGCCT GCGTCACGGG TCCTGGTTAT ACGCAGGCGT TTCTGTATGG AATACGCCAT CCCCTCTGAT AGATGCCTTG TTGCCTTAAG CAGTTAACCC GCCTGAAGCA AACGACAAGA CGGCAGACGC TTACCGGCAT ACGACACGGA TGCTTCAGAA GA |
| 145 | 358 | GATCTGCGCA CATCATTCGG GTCATCGCTA AATTTTTCAC TTTTAATTCG CCGTCCGACA GTTTTCCTTC GCCGGTGAAT TGATTGCACA TTTTGCCGGA TACCGTCATG TCCTCGCCAA GGCTAGAGCT CCGGGCCGGT GACCGTTTTA CCGTTTACGC TTTCCAGAAC AAAGCGGTGG TGCTCCAGTT CGTCGCGTTT GACGGACACT TTTCACTGCT CACACACCTG TCATTATGAT GCTCAGGGCG ACCAGCGTGA TTTCTTCATT GATATTCTCT GTAATCTGAT AGGTTAACAC TGACTATAGT AATGATATGA CCGGATAGAT CTTCAGGGTA TCCGAAAATC GTCCCTGA |

TABLE 3-continued

PARTIAL 3'—5'SEQUENCES OF PROBES OF THE PRESENT INVENTION

| SEQ ID NO | LENGTH | SEQUENCE |
|---|---|---|
| 146 | 224 | GATCTGTTGT TACAGCATGG AATGCGCCGT CCTCCTCACC GGCCAGGCAA ACGGCGCGAT CGTATCGAAC TGTGCGCCGC GCCGAAAGAA GGGGGGCTTA GCCCTTCTTT CGGCGTCTTA CGCAGCGTAG CCAGCATATT AGCATTGCCT AACTGCATTA TTGTCTGCGG CGGGGATTTT ACTACGTAGC GCAATTTGGC ACGTCTAGAA ATTCGTAAAG GTTC |
| 147 | 268 | GATCCTGAAT CGCCACGACA CGGGCGCCAG GCCTGCAAAC AGACGCGCGG CTTCGCTGCC GACGTTACCA AAACCCTGAA CCGCAACGCG AGCGCCTTCA ACAGCAATAT TCGCCCGACG TGCGGCTTCC AGCCCGCTGA CGAAAACGCC GCGCCCCGTC GCTTTTTCAC GGCCCAGCGA ACCGCCAAGA TGGATAGGCT TACCGGTGAC GTAAGATAGT GACCGTGTGC ATGATTCATG GAATACGTAT CATATCATCA ATATTACT |
| 148 | 314 | GATCCTGAAA AATACCAATT TTCAGCGGGC GAGCTTCGCC TTCCGCACTA AAACAGTGAG GAAAACGCTC GGCCAGAAAC GCGATAACTT CTTTACTGCT ATTCAACTTA GGTTGATTTT CCATGAAATT TCCTGATTAC AACGGACGTA GCCAACAAGC AGCAGGCATG AACAGGCGTC ATTATAATGA CGCCATCAGT AATTGCTACG TTATCCGTTG ATTATCCTGC GACGTCGCAA AGATTTTTTG TATCCGTCGT GCAGCACGTT CAGCTGTCAC CAGCGTACCA GGCGTGTCAT CTCTCGTAAC GCAA |
| 149 | 379 | GATCCAGAAT ATATAAAACC CCATTAACNC CAGCGCGCTT AATAACCATG TGGTCATCTG CGCTCCGTGG CTGGTTACGT TGTTATAAAT AAGGATGGCG ACCAGCCCAA CGAAGATAAC GCTGTCTACG CGACCGCGGC GGAGAGGGCT ATAGAAAGCA GAGTGGGGCC ATTGCGACGG GGCATGATGA ACTGATCGTA GAGAGCGTAA GCCAATAATT CGGCAATAAA GAGAATCAGC ACCAGGTCCG TGATAGTCAT TTATCTCAGA GAAATAAAAA ACGGGCGTTT GCGTAGTGTA CAACAGCCTT ACTGGCCAGC AGTCTACGAG TAGCCGGCGA TACCAATGAC GAGAGCCACG ATATCACAGC GTACTTCTA |
| 150 | 355 | GATCCAACAA GCGGCTGGCG CCATAGCCGC CGCGAACCGG CATGACGATT GTATCCGGCG ACGTTAGCGA GGCCAGCGAA TTAACATCGG CCAGCCGTTC CGCGTCCGTA CCGGCAAAAC GCTGAAAGGG CGACGAATCA CCTCGTCATT CTCCACCTGA TGACCCGCGT CAGTCAGGCG CTGAACGCCG CGTAACGGCT GTTGGTTAAT ACAGTAGCCC GACTGGGCGA TTAATGAAAC AGAGACATGG TAATTCCTTG CTGACAATAG AATCGAATGT ATATCATGCG CATATATAGG CGATGTCTCG TGTCGCAGTT CTGATCGGAC AGGAGGCACT AGCTCGGGGT ACTTT |
| 151 | 278 | GATCCTTATT CCCGATGTGT TCACCTTTAA TATTCTCCAC TCGCGCGTGG AGGAGATGAG CGGCGTTCCG GTCGTTCCGC TATATGACAC GCCGCTATCA GGGATTAACC GTCTGCTTAA ACGGGCAGAA GATATCGTGC TGGCGTCGCT GATTCTGCTG CTCATCTCAC CGGTACTGTG CTGCATTGCG CTGGCGGTCA ATTGAGCTCG CCGGGCCGTG ATTTGCCGCA GACGCTACGG ATGGCAGGCA AGCGATCAAG CTGAAGTCGT CATAGGAG |
| 152 | 394 | GATCAAAATA AAACTTTAAT CCCACTGGGG CAAGAGAGTG ATGTGGTGAC GCTCAGTCCG GGTCAGGCGT CGGCGCATCT GCAATTTTAC GCGCGTTATC TTGCCGATGG CGGCGCGGTA ACGCCGGGGA CGCCAATGCC TCCGCAACCT TCATTCTTGC CTATGAATAA GTTCTTTTTA CGCTGCGCGC ATATATTGGT GCTTGCTTCC CATATCATGG GCGCAGGCTG GCGTGGTAAT TGGCGGTACT CGCTTTATCT ATCATGCGGG CGCCCGGCAT TAAGCGTACC GGTAAGTAAC CGTTCAGAAG TCGTTCTGTT AATTGATACG CATATTTACT GGTGGGTCGG TTACGGAACA AAACGATGGA TATAGTCCTG TGTAGTGATA TGCT |
| 153 | 324 | GATCGTTAGC AAGGTTTGCT GCGTCATCTG CTGGGTTTCA CGCAATGTGT GCGCGTTAAG CATCACAAAA TGGCTGGCGC GCGTCGCCCA GTGGGCATTG ATTTGTAATT CAAGCATACA AACCAGGTTG CGGTTGATGG TCTGAATGGC CTCGAAAATA GATTTTTGTA TCCGGGTTTC TTTACTGGCA GGCGTTATCA GCCCGCGCAT TTTGACGACA TCGTTCAGCA ACCGTTGCAA ATGTTATCCA ACCGGGGAGT CAGCAATCGC GACAGCTGCC TTGATACCCA GTTACCTGAC CGATCCGGAT GATCCGATCG GAAA |
| 154 | 308 | GATGGCTGGG AAGACGGGTG CCGTTCTGGT TAAGCGTATT CAGCTCTTCG CGCGGGAAAT AGCCTTTAAT CGCCAGGGTA CTGTACAACG CGGGGCCCGC ATGGCCTTTC GACAGTACGA AGTAATCGCG TTCCGGCCAG TCCGGGTCGG AGGGTCGATT TTCATCACCG CGCCGTACAG AACCGCCAGA GTCTCCACTA CCGACATGCT GCCGCCATAG TGACCAAAAG CCAAAGATGG TTTAAGGATT TGACGGTGGA CCGAATATCG ACAGTTGGGG GATTTCGGTT ACGTTCATTC TTCCTGAA |

TABLE 3-continued

| SEQ ID NO | LENGTH | PARTIAL 3'—5'SEQUENCES OF PROBES OF THE PRESENT INVENTION |
|---|---|---|
| 155 | 333 | GATCGTGGTC CAGCTTATGA ACGGTATAAC TGAGGGCGGA CGGCGTTTTA AATAATTTTG CCGACGCCGC CGCGAACGTG CCTTCTTTTT CTAACGCATC AAGAATAATC AGAACGTCCA GCAGTGGTTT CATACTCGTC CCCTTGCCGC TATATGGCGA CCACCTGCTG GACAGCGACT CACTCCATCG GCATCACCAA CGGATCGGGA TATTGATATT CAAATCCCAG CTCATTACAA ATCGGCTACC GTCGATAATC TTCCCTTTTG CCGTTGTCGG TGGTACGAAA ATCGCGGCGG CGATTCCCAG CAAGCGTATT GCGATAAACA CTG |
| 156 | 334 | GATCCACCCA CGTCAtCAGT TGTTCAAAAC CCTGCTTCAC GGTGTGTTCC CATGGACCGA CCATGTGGAA AGCGGCTATC TTGCGTTTTT GTGGCTGCCT GATTTCGTAA TCCATGCTGC CTCCGTCACT TCACAATGCT GTATGAATGT ACAGTATAAT TACAGCCTTT TACGGTCACA AGGACAGCGT GATCATTTTG TGAGCAACCT CGCAATCCCG CCCTTTTGAC ACCTCAGATG ACGGTGAACG GTGTGTGTGA CAACGGCTTA CGCTTTATGT GAAAATAGTC GTCAGACGAG AGAACATACC GCCTTTACCA CGATTCAGAG TGAC |
| 157 | 152 | CGTTTGCTAT CGACCTGCAG ATCGGAACGG ATTGGCGTCA CGTGATGGAT AAGACCGTGT TCTTCAATGT TATCTCGGCG ACACGAGCGC ATCCGGCGAA ATATCGACCG CATCAACCTC TGCGTCGGGA AAGCATAACA CAGGCATGGC AT |
| 158 | 204 | GATCGAACGC GCGTTGCAGC AGCGCCCGGC TATTTTCTAC CCGTGTCGTA TCGCCGAAGT TGTGCCATAA CCCCAGCGAA ATAGCGGGAA GTTTGACGCC GCTGCGTCCG CAGCACGATA CTCCATTGTG TGATAACGAT TCTCATCGGG CTGATAAATC ATGACCTTTC CCCTGTGGCG AGAATAATAT GTGTACGGTT ACTC |
| 159 | 283 | GATCTTACCG AGTGGGAAAC TAATCCGCAA TCGACCCGCT ATCTGACGTT TCTCAAAGGT CGGGTAGGGC GCAAGGTCCG CTGACTTCTT TATGGATTTC CTCGGCGCCA CGGAAGGGTT GAACGCCAAA GCGCAGAATC GCGGCCTGTT GCAGGCAGTG GATGATTTCA CCGCAGAAGC GCAGTTGGAT AAAGCGGAAC GTCAGAACGT GCGCCACGAG GTGTACAGCT ACTGCAATGA GCAATTACAG AGGGAGAATG AGCTGGATCG CTGTCTAAGA GCT |
| 160 | 302 | GATCGCGTTC GCCAGGCAAA ATATTACCGT GCTCAAGAAT ACCGCTGCGC ACGGCATCCT TTACCGTCTG GGCGAATTTC ATGTATAGCG GCGTATTATC CGCCGCTGAA ATTCGTTCAT TCAGTTGCGC GATGAGCCGG GTATGCGCTT GTTCCATTTA TCTTTCCTGA CGACGGGTCT GTAGGCAGTA TACTACCACC ACGCGTGGAA ATGATGTACC GGACCAATGC CCTTCCCCAC TTCCAGCCGT GTACGCTGGC AGCGCCGAAG CATGCCTTGC TCGTTTACCG TCTCTCCCAA CT |
| 161 | 233 | GATCCTGAAT GAAAATCTCA CTGCTCGGCT TGTTGGTCAG TTCGGCCATG GTCTGGCGCA CGTGCTCCAG CATGCCGCCG ATATTGGTCC CGGCCTCGCC GTGACGTTGT CGAGCTTGCC GCAACCGTCC ACCGCTTTGC TGATGGCTTC GGACGCCGGC GGCAACATCC ACACAGCGCA CCGAGACCCT GAGCCTGACG CTACCGGATC CGGCGGTATG AGCGGTTAGC GAG |
| 162 | 236 | GATCTGTTCC GTCTGACGGC GGGTAAACTG ACCGGCCTGG ACCGAATGGG GCCAAAGTCC GCGCAAAATG TTGTTAACGC GCTGGAAAAA TCCAAAACGA CGACCTTTGC GCGTTTTCTC TATGCGCTGG GCATCCGTGA AGTGGGTGAA GTGACGGCGG CGGGGCTGGC GGCTTATTTC GGTACGCTGG AGGCGCTGCA GGCCTCCGAC CATTGACGAG TTCGAGAAGT ACTACT |
| 163 | 334 | GATCGCGTGT CGGTGCGTGA TTTAAGCCGT GGCTTAATCG TGGATTCCGG TAACGATGCC TGTGTGGCGC TGGCGGATTA TATCGCGGGC GGGCAGCCGC AGTTTGTGGC GATGATGAAC AGCTATGTGA AAAAACTCAA TTTACAGGAT ACCCATTTTG AAACCGTCCA CGGTCTTGGA TGCGCCGGGA CAACATAGCT CCGCGTATGA CCTGGCGTAC TCTACGGCGA TTATTCACCG GCCGAAGCCT TGAATTTATC ACATGTACAC GAGAAAAGCC TTGACCTTGA ACCGATTAGA GCAGAACCGA ACGCTTGATG GATAGACACG AATG |
| 164 | 308 | GATCGTAGTG GAGAGTGTCG CCGAACGTCT GGTGCAGCAA ATGCAAACCT TCGGCGCGCT GCTGTTAAGC CCTGCCGATA CCGACAAACT CCGCGCCGTC TGCCTGCCTG AAGGCCAGGC GAATAAAAAA CTGGTCGGCA AGAGCCCATC GGCCATGCTG GAAGCCGCCG GGATCGTCTG TCCCTGCAAA AGCGCCGCGT CTGCTGATTG CGCTGGTTAA CGTCTGACGA TCCGTGGGTA CCAGCGAACA GTTGATTGCC GATGCTGCCA GTGTAAAGTC AGCGATTCGA TAGTGTGTGG CGCCTGAG |

TABLE 3-continued

| SEQ ID NO | LENGTH | PARTIAL 3'–5'SEQUENCES OF PROBES OF THE PRESENT INVENTION |
|---|---|---|
| 165 | 362 | GATCCCATCG CGAATATCGG TAAAACAGCG CTTCTGCTGA CCGCCGTCGA TAAGCTTGAT CGGCGTTCCT TCTACCAGGT TCAGAATCAA CTGCGTTATC GCGCGTGAAC TGCCGATACG CGCCGCGTTC AGGCTATCCA GCCGCGGCCC CATCCAGTTA AAGGGACGGA AAAGCGTGAA GCCAATCCCT CTTTTTGCCA TAAGCCCAAA TCACCCGTCG AGAAGCTGTT TGGAAACGGA GTAAATCAGG GCTTATTCAC CGGCCCGACG ATCAGATTGA TTGTGTTGTA AAGAGGCTCT AATCGGTCAC ATTAGAGAGA GGAAACATTT AGTATTAGAT AAGATACCGA GTTTAATAGT AA |
| 166 | 71 | ATCGCGTTGT GTTGCCGAGC ATTTATTACA AGGCGCTTCT GTGTGNCNCT CGAATGGTGC NGCAAGACTG C |
| 167 | 363 | GATCGTGTCG CAATTCTTAA TGCCATAGAG GGTAATCATA TTGAATCCTT TAACGCGAAA TTCGAATAAA TAATCAATAG TATCGTCTGC GGGATAATAA GTGTGGCCGT TTATGGTTAT TTATCCAGCG CTGATCGGCA ATCAATATAA CATTGTTGAG TGAATGTGAA TAATGATTCC TTTTCGTTCC AGATGTGGCT TGTTTATACT TCGCCGGTAT AATCCTATTT GGGCAAATGC AATTGTGTTT ACCATTGATA AGGTAGGTAG GAAAGGTATA TGTGCTAATA TGGCGTAGTC ACATAATTAG TCTACGGCCA TGATCAGACG CAACAGGATC GACTCGTATG ACTTTACGAC CGC |
| 168 | 329 | GATCCGGCGC TGATTTTCAC CATCACGTTT TTCATCGGCT GACCTGCGGC GTCTTTCACG TCGATGGTGG CGGCCATCTG CTCGCCCTTC TTCGCCTTTG CGCTTCCGGT GGTTTCATCC TGGCCTGCCA GCGTCAGCTC AGGCTGGCGG CGGCGCTGCG GGCGAGGCAA GACAGGTCTG CATGTAGTAC ATCGAGGTGC TGGTCGTCGT TTGACATCAT TGCCGTCGTT AAACAGGTTG ACCGCCGCAT AGAGCGACTT GTGCCGTCTG ACGATATCAC GTAATCCCGC CACAGTAGCG CTGAGCTGTG TGCTGACTGT ATGCACTAG |
| 169 | 198 | GATCTGGCGG GCGCGTGAAA ATATGTTGCT GGCCTCCTGT ATGGCGGGAA TGGCCTTTTC CAGCGCCGGT CTGGGGCTGT GTCATGCGAT GGCACACCAG CCTGGGGGGC GCTGCATATT CCGACGGCCA GGCCAACCGA TCGTCGTCGC AACAGTCATG GGCTTTAACG GATCAGTTTA CGGAAAGTTC AGTAATAT |
| 170 | 273 | GATCAACATC AATAACTAAA ACTCTTTTAC CAAGATAGTT AGCCATGAAC TCAGCAATGC CAACACATAG AGTTGTTTTT CCTACCCCGC CTTTCATATT AATAAAGCTA ATTACCGATG CTGGCATAAT TATTCCTTGC TATGTTGAGA ATGAGTCATT TTGATAATTA CTCGAGCTTT TATCTTAATC TTCGCGCGTT CGAATCCTTC CCTTCATGTA CTTCTCGTAC ATGGCATCCA GTTCCTTGAG ACGAGATAAT ACCCGAAGAA AAT |
| 171 | 244 | GATCGCTGGT TCTGGCGGCA CCCTGGCGCC AACCCAAGCA ACGTCGCGCG CGCGGCATGG CAGGATCTTA CCGCCGGGCG CGTTATTATT TCCGGCGGCA GTACGCTGAC TATGCAGGTG GCGAGACTGC TGGACCCCGC ATTCGCGCAC GTTCGGCGGT AAAATCCGCC AGCTTTGGAG CCCTCCAGCT TGAATGGCAT TTGTCCAAGC GCGATATCCT GACGCGTGTA CTGAACCGAG AGTG |
| 172 | 247 | GATCGCGCAG CGCTCTCATA GCACAAAACG AGGTTTTCCA TTCTGTTATG TTCCCTGGCG ACGATAAACG TTCGATTGTC TCATGGCGCT GGTGAACCTT ATTTTTTAAC GGAGATGTTG AATGGCGGTA GAGGTTGTAC GTAATGGCCA AACCCGGCGG CGGATCTCGA ATATTGATTC GGCAATATTC GTTCTATCTT GGAAAAGGAG CGCTGTACCG GAACGGAATA AAACTGCGAT GTGCAGA |
| 173 | 300 | GATCAGCTTG CCGCACTGTA TGCCTCCAGC GACGGCAATA AAATCCACAC CGTATCCGGC TGGCCGACTG AGTATGACTA CTGGTCATCC ACCTTCGCCA GCGCCGCTAC ATGGCAGGCG GTATCACTGG CTGCGGGCGG CTATACCGCT TCCGGCGATG CGGTCGGACT ACGTGAGCTG TCTGGTCAGC AAAAATCGAC GCGCGTCTAT CACCATTGAG CCGGTGGATG CGCATTGTGT ATACGCAACA GCGAACACGC GTGAAGGTGA AAGGCATACG TCAGCTTAAG TGACGTAAGA |
| 174 | 337 | GATCCGGACC GTGCCTTATA CCCTGAAAAA GGGGGAGACG GTGGCGCAGG CGCACGGCCT GACCGTCCCA CAGCTGAAAA AACTGAACGG GCTCCGCACT TTCGCCCGCG GCTTTGACCA CCTGCAGGCC GGCGACGAGC TTGACGTTGC CGGCGGTCCC GCTGACCGGC GGGAAAGGTG ACAATAACCG CCATGACGTC CGCGGTCCGT TTGCTGCTGA CCGGGAAAAT GAGGACGATC GCAGGCAGCA GATGGCCGGC ATGGCTCACA GGCGGCAGCT TCTGCCAGCC ATCGGACGTT AGGCCGCCGC GGATGGTTCG TATTCGCGTT GACATGT |

TABLE 3-continued

PARTIAL 3'—5'SEQUENCES OF PROBES OF THE PRESENT INVENTION

| SEQ ID NO | LENGTH | SEQUENCE |
|---|---|---|
| 175 | 424 | GATCAATGAA GCTTTGTGGG AAGTCTTGAC TTTCGTCGAT AAATACGTAA TCAAGTGCCT TTTTATCAGC TCTCCCACTA TTATTTATAT CTGCAATGGC TTTCTTACAT AGGGCATCAA AATCGCCATT ACCAAATCCC CCAAATGGAA TTTCGCTAAT AATGGCATAT ATATCTGGTA CATTCCAGAA AAAGGTTCTT TACGTCAAAC CCCAAGAGTT GAAGCAAAAA AGTTTTTGTA CCCCATTCTA TCTGTTTTTC GACTCGCATA AATCGAAAAA CTCAGGGATT CTGGTTCTCA TTGTGGAGCA GATTATAAGC AGTAATGCAT CTAGATACGG TTTGATACTC TCTAGTGTAG TATCAGTTAC TGACAGCTAC TGCATAACCC TTTCAGCACT GAGACACGTG CGCAAATGTG TAAA |
| 190 | 176 | GATCATTTGA TTAAAACCTC ACACCGCAAG ATGCGACTTT TTGTAAACCT GCTTTACCGC TGACACATTT CTCCGCATTA CTGCGGAACA AGGCTTAAAA AGCGTATCCG AACGTATAAC CCTCCAACGT TCGCTACGGG AAAAATGGGG ATGAGTACTG GAAGGTCGCA TATATGACCA AGCCAGACAT |
| 177 | 441 | GATCCATGCC TGTGATGCCT GGATGTCCCG AATACTTGAA GGTTTGATCG AACGGCAGGC CAGTAATGGC AACGCCACTA TTCTGTTATC TGCGACGCTA TCGCAGCAGC AGCGAGATAA GCTGGTGGCG GCATTTTCCC GTGGGGTGAG GCGTAGTGTG CAGGCGCGTT GCTAGGCATG ACGATTATCC CTGGCTGACT CAGGTCACAC AAACAGAGCT GATTTCTCAG CGGGTTGATA CACGCAAAGA GGTTGAGCGT TCGGTAGATA TTGGCTGGCT ACATAGTGAA GAGGCGTGTC TGAACGTATA GTGAGCAGTG AAAGAACTGT ATCGCTGATA CGTACTCGTG ATGATCGATC GATCTACCGA GCTACTCACT GGTAGGGCAG AACTTACTCA AGGCTCTCAG GCGTCTAACA GGCGTCTAAC ACGTGGAAGT T |
| 178 | 370 | GATCGTCGTT ACCGGCGACG GTTAAAGCAA ACTGGGCATC AATGGGCCGT AAGAGTTTTT GTTCAACGGC CTCCAGCAAC CGCTCCTGGA TTGTCATTGC GCCTCCTCAC TCATTTCACC TGCAAACATA TCATCCAGTT GGTTAATTAA CGCCGCCGCA GGACGAGTGG TAAAAATACC CTGCTGCGGA CTGTCGCCAT CCACCCCGCG TAAAAAGAGA TAGATGACTG CCGCCGAAAT GGCGTTCATA GTCGTAATTC GTCATTCGAT GACGAAGGTA ACGGTGCAAT GCCAGCGTAT AAAGCTGGTA CTGCAAATAT AGCGATCGCG TGCTCCGCGC AGCCATGCGT CTGGATAGCG CTATCTGCCG |
| 179 | 212 | GATCCGGGTA CTATGAGCCC AATCCAACAC GGGGAAGTGT TCGTTACTGA AGACGGCGCT GAAACCGACC TGGACCTGGG GCACTACGAG CGTTTCATCC GACCAAGATG TCTCGCCGCA ACAACTTCAC GACTGGCCGC ATCTACTCGA CGTTTCTGCG TAAAGAACGG TGACTATCTG GGACGACAGT ATCTAATATA CGGATTAAGA GG |
| 180 | 367 | GATCTTCTTC ACGTCTGGCT TCATCACTCT GATGAACGAT ATGCTCGGTC AGATGACCTT TAATCACCTC GCGCATTAAG CCATTTACCG CGCCGCGAAT CGCCGCGATC TGTTGTAACA CGGCCGCGCA TTCATGCGGT TCATCCAGCA TTTTTTTTAG CCGCTATCAC CTGTCCCTGA ATCTTGCTGG TTCTGGCTTT AAGCTTTTGT TTGTCCCGGA TGGTATGTGA CATTACAACA CCTCACTAAA CATTAACGAA TACAAATTAT AGCATTACCA GATGCTACTG GGGGTAGTA TCTATACTGG GGGGAGTAGA ATCGACGCCC ACATAAAACA ACTAAGAATC ACTCATGGGT GAATTTC |
| 181 | 196 | GTATCACGTT TGATGCGGCT GTTATCGTCC AGATAGCCGG TGCGATAGGC AAAATAATGC GGCAATGAAA GCGCCAATCG CCAGGGGGGA TCCCCACAAT ATATGCCAGC ACGACCCCGG GGAATACCGC ATGACTCATT GCATCGCATT CGCGCTTTTA CACTAAAACC CGCGTAGGAG ATCGCAATCG GACTAG |
| 182 | 266 | GATCTGTCGC GTTTTCGCCA GAATAGCGCG CGGAATAGAT ACCCGGCGCG CCGCCTAAAA CGTCAACGGC CAGACCGGAG TCATCGGCAA TGGCGGGCAG GCCGGTCATT TTGGCGGCAT GGCGCGCTTT GAGAATCGCG TTTTCAATAA ACGTCAGGCC GGTTTCTTCC GCGGAATCGA CGCCCAGTTC CGTTTGCGCT ACCACATCAA GCCAAAATCG CTTAACAGCG AGCNNCACTT ACGCGTNTGC GAGACACTTT NCTGAG |
| 183 | 351 | GATCATCATC ATTCCGCAGC CAAACGCGCG GCTTTTACCG AACCCCTGCG CCAGACGTTG CAGGAAAAGC GCGGGTTCGT TAATCACCAG CACGCCGGTA TAGTCCACGC TGCTAAACTG AATCATCTGG CCGATCTTTT CCCGCGACGT ATCTGCCTGC CTGCCGATAA GCATCAACGC TCGGCTCGGC AGAGTAAAGC CATTTTGCCT CCCCCTGCGC GCCAACCACG CAGGCGCTGC TGCTGATAAG ACCAAATATG CTGGCTATCA CCTGCGTTTA GTGGCGATTT AGACTCATCA GCAAATCGTG AGTTGCGTTT TGCAACGAGA TTGGGAGGTT AACGAGATGA A |

TABLE 3-continued

PARTIAL 3'—5'SEQUENCES OF PROBES OF THE PRESENT INVENTION

| SEQ ID NO | LENGTH | Sequence |
|---|---|---|
| 184 | 398 | GATCATGTGG TGATCTGCGC CGGACAGGAA CCTCGCCGCG AGCTGGCGGA CCCGTTACGC GCCGCAGGTA AAACGGTACA TCTTATCGGC GGATGCGATG TCGCGATGGA GCTGGATGCC CGACGGCGAT TGCCAGGGCA CCCGACTGGC ACTGGAGATT TAACGACTTT GCCTGATGGC GCTACGCTTA TCGGGCTTAC GCCGTCATAC CGGTTTTATA GGCCGGTATG ACGCTTGAGC GCTTATCGAC GGCGTCCTGC TTCACCGCTT TCAAAATGAC AAATTTATTG TTGGTGCTAT CGTCGCGCAA TTACCGAAAT CTTCTTCAGC TGTGGAAATA GTCAGATGGC GTTCGCACAT ATACAGTTGC CGTGATTAGC ACACGCTATG CAATTCAG |
| 185 | 347 | GATCGCTATT GGTATGGCCC CACTTGCCGT ATTTCACCGG AAGCGCCGGT GCCCGTGGTT AAGGTAAATA CCGTTGAGGA ACGCCCGGGC GGCGCGGCGA ACGTGGCGAT GAACATTGCG TGCTCTGGGA GCGAACGCCG TCTGGTCGGC CTGACGGGTT ATTGATGACG CCGCGGCGCC TGAGCAAAAC GCTGGCGGAG GTCAATGTGA AGTGCCGACT TCGTTTCTGT GCCGACGCAT CCGACGATTA CCAAACTGCG AGTACTATCT ACGTAATCAG CAGCTCATTC GTTTGATTTG AAGAAGGCTT TGAGGATGAC CGCAAGCCGT TGCATGAGCT ATAACCA |
| 186 | 294 | GATCGGCGTG CTGGCGGCGA CCTGGCCGCG GGAAATACCC TGGAAGAGGC GTGTTATTTC GCCAATGCGG CGGCGGGCGT AGTGGTAGGT AAACTCGGGA CGTCAACGGT TTCCCCTATT GAGCTGGAAA ACGCAGTGCG CGGACGGATA CCGGCTTCGG CGTTATGACC GAAGAGGAGT TGAGACAGGC CGTCGCCAGC GCGTAAGTCG CGAGAAGTGT CATGACCAAC GCGTTCGATA TCTGACGGCA TTATGACGCA ACTGGACCTA TCGGATACTT ACTAGACTAC ATAC |
| 187 | 352 | GATCCGCATT GTCAGGGATA TCGCCCTGAA CGCGAGCTAC GCCGGCATCT GCTGCTGATT ATTGCCATTG ATCACCGCCA GCTTAACGGC CCGTCGCCCT GGAGCTGTAC CGTAATGTCA CCAGCAAACT TCAGCGTCGC GTCAGTAGGC TAGTGGCGAC CAGCAGTTCG GCAGTACGTT TTCACCGGCT GCGGATAGTT ATGATTGTCG AGGATCTGTT GCAAGGTTTC CGAAACAGTT ACCAGCTCGC CGCGAACACA AAGTTTTCAA ACAGATAACG ATGTAATTGG TCATGTTGCG CATAATCATC TCTCTTCAGT ACATTATTCA CTATACGTGT TTAAATCGTA CA |
| 188 | 290 | GATCCTTACC GTTTTGGTCC ATTAATACAG GAAATGGATG CCTGGCTATT GACGGAAGGC ACCCACCTGC GTCCTTATGA AACGCTGGGC GCGCACGCCG ATACGATGGA TGGCGTCACC GGCACCCGTT TCTCCGTCTG GGCGCCTAAT GCTCGTCGCG TTTCGGTTGT CGGGCAATTC AACTATTGGG ATGCGCCGTC GCACCCGTAT GCGTCTGCGC AAAGAGAGCG TATTTGGGAG CTGTTATCCC GGCATAATGG ACACTGATAA TCGAGCTCGT ATCGCAAGAA |
| 189 | 213 | GATCTTCAGC AACCACGACA GGAATGCCCG TCTCTTCCAT TAACAGACGG TCAAGGTTAC GCAGCAGGCG CCGCCCCGGT GAGCACCATA CCGCGCTCGG AGATGTCTGA CGCAGCTCCG GCGGACACTG TTCCGGCGCA CCATTACCGC GCTGACGATA CCGGTCAACG GTTCCTTGCA ACGTTCCAGA ATCTCGTTTG CGTTCAGGGT AAA |
| 190 | 256 | GATCGCTTTG GTTAAATCCC CGCCGCCAGT GTCGGCGCGA CCAGAGCGGA ACGTGACGAT TCTGTCGGGA AGCTGCAAGC CAGTGCTGCG GCGGCCATGA GGACTTCCTG CAACAGTAGA CGCGCCAGTG CGGCGGCAAT TTCGCTGCGG CGGGTAAATT TAAGCTGATG CACCAGTAAA CTCAAGGCGG TGTATAGTCA CTGACGCTCA CCAGACTTGC AGGGTGGCGG TTTTTTCAGG CAGCGACCGC ATGGGG |
| 191 | 247 | GATCGTGGCT GCCGGTGCTG TCGGTGTAGC CACCACATTG ACGGCGGTCT TGGGATACTC TTTCAGCACC ATCGCCACGG CGGTCAGCGT CTTAGCGCCT GCCGGCTTTC AGCGTCGGCT GCTGCTGTCG AAGGTGACAT TATTCGGCAT ATTAGAATGA CTACTTACTC GCCCGCCTTC GGCTCACGCT AACGCCTGTG CCCCGATTTG TAGAGTTTGC TTCTGTACGT AGAGTAACCA GCGCGCA |
| 192 | 402 | GATCCATTTT AACTTTAGCG GCCCTTTTGG CGAGGAGATG ACTCAGCAAC TGGTCGGGCT GGCGGAGTCT ATCAATGAGG AGCCGGGCTT CATCTGGAAA ATCTGGACAG AAAGCGAGAA AAACCAGCAA GCTGGCGGTA TTTACTTGTT TGAATCCGAA GAAACGGCGC AGGCTTATAT TAAAAAACAC ACTGCGCGTC TTCGAAAAAT CTTGGCGTTG ATGAGGTGAC GTTTACATTA TTTGGCGTGA ACGACGCGCT GACGAAAATA AATCACGGCA ACCTTTGCCG CTAAATCACA TAACGCAGGT TCTGTTCCGG TGCTGCTGAC CGCAACGGTA ATCTTTATAC CGGGCGAGTA CCTAAGAGGC TTTATGGACG ACAGCGACAC GACGTTTCAG CG |

TABLE 3-continued

| SEQ ID NO | LENGTH | PARTIAL 3'—5'SEQUENCES OF PROBES OF THE PRESENT INVENTION |
|---|---|---|
| 193 | 240 | GATCGCGAAG CCGCACAACG TAAGCAGGGG TTATGTAGTG TGTTCTTCAA CACCACGCTA TTCATGCCGT ACCGCAGGTA GATGTCCCCC TTAGGAGCAT CGCTTACGCT GGGAACAGCG TTTAAGCAGC TTTTTGACAA GGGAGCTTTG ATGTATTGTT TGCAGTTCTA GACCTGACAC GGGCGATGAA TAGGAGCAAA GCGTGGTTTA CACATCCATA TTGCTATGTT ACACTATTAC |
| 194 | 248 | GATCCCCTCT ATACCGCAGA CAACACAAGG CGCGCTTGCT AACGCGGTGT TACAGGGCGA AATCTTTCTA CAGCGCGAGG GACATATCCA GCAACGGATG GGCGGGATGA ATGCGCGCTC GAAAGTCGCA GGAATGTTAA TGCGCCAGGA TAACGCCCTC CGCTAAATTC TTGGTATTTT ATTTGGCTGG CCGACGTCGC AAATTAGCCA AAGTTAGCCA ACTTCTAGCT GATTCATCTA CGATAATT |
| 195 | 304 | GATCGGGGTT CAGCTCAAAT TTTTCAATCG CCCAGGCAAC ACCATCTTCA AGGTTCGATT TAGTCACAAA GTTAGCCACC TCTTTGACCG ACGGAATGGC GTTGTCCATT GCCACGCCCA TACCGGCGTA TTCGATCATC GCAATGTCGT TTTCCTTGAT CGCCATCACC TCCTCTGCTT AATACCCAGC GCCTCGACCA GTGATTTACG CCAGTGCCTT TATTAACCGT TATCGAGGAT TCAAGGAAAT ACGACACTTA CGCACGGTAC TTCTCATTGC GAACGCATGC GCGAACGCAG TCAT |
| 196 | 301 | GATCTGCGCC CCAGCGTTTG CAGCAGAAAA TAAAAGCCGA AAATCACCAC TAAACAGGCG ATCAACACGT AGAGAAGCAA CCTCCCAATC AATTTCATGG TCTTCCATCC CGTGAAATGC ACATAGGGGA TTTATGCACG ATTTGCGTGC AATCCTCAAG ACAGGAATGG TGAAAGAGCG TTACAGCAGC GGCGAATCGT GTCGCGCGCA GGGTTTTTAC GGTTTTTCGG CGGAGAATCA GTCAGCACGA TAGCGTGATG CGCAGCGATC GATGAGAGCG ATTTACCATC GGACTGAGAT T |
| 197 | 366 | GATCCAATCC TGAACGCCGA ATTTTCACCA CAGGGCGTTG CGCTACGCCA GTTCACTACC CGCTGGGAAG GCGGTATGGT CAGAACTTCC GGCGCCTGGT TACGCGAAGG CAAAGCGCTT ATTCTGGACG ATACCGCTAT CGCCGGGCTG GAGTATACGC TGCCGGAAAA CTGGAAGCAG TTATGGATGA AGCCGCTGCC CGACTGGTTG AACAGCTGAC GCTGAAAAAT TCAGGCAGCG CAATCTGGTG ATTGATATCG ACCCGGCCTT CCGTGCAAAT CACCGCTCTG ACGCTACGCG CAAACTGAGC TGTACAACCA TCATCAATGG GCTCTGAGCG CATCGACTAC GGCAGCGGAA CTTTAC |
| 198 | 310 | GATCGCTACC CAATTCCGCG CCCACACAGC CTGCTTTAAT CCATTGCGCT AGGTTTTCCG GCGTCACGCG CCGACGCAAA TAGCGGAACA TCCGGCGGAA GTACCGCTTT CAGCGCGCTG ATGTAGCCCG GACCAAACGC CGACGACGGG AAAATTTTTA ACTTCTGTGC TCTCTGCATC CAGCGCAGAA AAGGCTTCCG TTGCCGTCGC GCAGCCGACA CACGTCATGC CATAGCTCAC CGCCGCGAAT CACTCGGTTG ATATCGCGTA CATCACTTCG CCATCGCACG TGTTCTTCGT TAGCTGTACA |
| 199 | 348 | TCGAAAATAC GTATACCCTG ACAGTGAAAG CAACCGATGT TGCAGGCAAC ACGGCGACGG AAACGCTCAA TTTTATCATT GATACCACAT TGTGGACACC GACCATCACG CTGGATAGCG CAGATGATAG CGGCACCGCC AACGATAATA AGACTAACGT TAAAACGCCC GGGTTTTATT ATCGGCGGTA TTGATTGATT CTGACGTGAC TCAGGTCGTC GTGCAGGTGA TGCGCGATGG TCACAGCGAG GAGGTGGAGC TGACCGAGAC TAACGGGCAG TGGCGTTTGT ACCGGCACGC GTGGACTGAT AGGCGACTAT CGCGTACGTA GTGAAGATAG CGTATATA |
| 200 | 279 | GATCGGATAA CGACTCCGCG GTGGATGCGC AAATGTTGCT TGGCCTGATT TACGCCAACG GTGGGCATTG CCGCCGATGA TGAAAAAGCC GCCTGGTATT TCAAACGCAG TTCCGCCATT TCCGTACCGG CTATCAGAAT ACTGCGGGAA TGATGTTTTA AACGGTGGAA CCGGGCTTTA TTGAAAAGAA TAAGCAGAAG GTGTTGCACT GGTTGGATCT AGCTGTCTGG AGGTTTGATA CCGATACCGT TGCAAGATTC GAACGCTACG ATGCTATTT |
| 201 | 272 | GATCGCCAGG GACGATGGCG AGCTGGGCCC CTTGTAAATC GTTTTTGGTG AGGCCGAGAT GAAAAACATC AGACTTGGAC ATATAAAACT CCTCTGTGAA TCGGGTTTGT CAGAAGAAGA AAGAGACACT TTACCTAAGG ATAAAGATAT TTTGGTGCAT CATCACTATG CGTAAAACAA TTGCGTGTTC CATTAAAAAG AGATGCCCCA TCACAATAAA TAATCAATAT GCAGGCATTG CACAAAGCAT AGGCGTTTAG GCATGTGTTG TA |

TABLE 3-continued

| SEQ ID NO | LENGTH | PARTIAL 3'—5'SEQUENCES OF PROBES OF THE PRESENT INVENTION |
|---|---|---|
| 202 | 401 | GATCCAATAA TGACTGCATT GCCTCATACC CCATACGTAA CGCGCTATAC AAAATATAGA TGCCGATACC TAACGCAAAC AGGGCATCCG CACGATGCCA ACCGTACCAG GATAACCCCA GCGCGATAAG AATCGCTCCG TTCATCATAA CATCAGACTG ATAATGAAGC ATATCGCCCG TACCGCCTGA CTTTGGGTCT TGCCGTACCAC CCAGCGCTGA AACGTGACCA GTATAATAGT GCATATCAGA GCATGACGGT AACGCCAATC CCACGCGGGG TCGTTCATTG GCGTGGCTTT AATCAGATTC TGAATACTGG TCAAAAACAG AAACACGCGA ACCGGAAATA ACTACTTTGC GCGCGCAGGC ACTCGTTTAC GTGCCAAGGG TTAATGGTGG G |
| 203 | 169 | GATCCAAAGT CGTTAAATAA CGGCGGGAAA AGCCTCCACG CCATGGAAGT GCCCCGGAAA TCGCCCCGAC CATGGTGGCG ACAGTATCAG TATCATTGCC GATATTAACC GCCGGAGATA ATAGCATCTA CGGCAGAATT CGGACAACAC GCGAACAGGC CAAAGCGGC |
| 204 | 253 | GATCCAAAGT CGTTAAATAA TCGGCGGGAA AAGCCTCCAC GCCATGGAAT GCGCCGGAAA TCACCCCGAC CATGGTGGCG ACAGTATCAG TATCATTGCC GATATTAACG CCGGAGATAA TAGCATCTAC GGCAGAATTC GGACAACACG CGAACAGGCC AAAGGGCCGG CACCGCTTCA CTCACGTGCA GCCGGAGCAA TATATAGCAG TTCACGCGCG TTCCATGGAT GAGCTTCGAT ATAGCTCAGT ATG |
| 205 | 198 | GATCGTACAG ACCCGCGTTG TCATAACCAC GGGTTTTTAG TTCCGCCACA CGCTCGCCCG CCAGCGTTTT CATATCCTCT TTCGAGCCAA AATGAATGGC GCCGGTTGGA CAGGTCTTCA CGTCAGGCCG GTTCTTGCCG ACGTGTCACG CGGTCAACGC ACAGCGTACA TTATGACGTC GTTGTCTTCC GGTTGAGG |
| 206 | 411 | GATCGGAATG CCTTTGAACA GCGGCAGGTC TTCCAGCGGC AGTCCGCCGG TCACGGTCAC TTTAAAGCCC ATATCGGACA GCCGCTTAAT CGCGGTAATA TCCGCCTCGC CCCACGCCAC GGCTGCCGCC TGGGGTCACG GCTGCGGTGA TAAACCACTT GCTGAATACC CGCATCACGC CACTGCTGCG CCTGTTCCCA GGTCCAGTAA CCGGTCAGTT CGATCTGCAC GTCGCCGTTG AACTCTTTCG CCACATCCAG GGCTTTTGCG GTGTTGATAT CGCACAGCAA ATCACGGTAC CAGTACGGTT GGCTTCGAAA CACATACGGG AGAGGATTTA CGAATGCATT GGGAGAGATT GGGTAGGTCA GTAGACGAGA ATGCAGAGAT GGCATGAAGA TTGAAGGGTA G |
| 207 | 402 | GATCCTGAGC CGGGTAGCCA GTATTTGCAG GCAGCAGAGG CAGGTGACAG ACGCGCACAA TATTTTCTGG CCGACAGTTG GTTGAGCTAT GGCGATTTGA ACAAAGCTGA ATACTGGGCG CAAAAAGCCG CCGACAGTGG CGACGCCGAC GCCCTGCGCG CTACTGGCCG AAATCAAAAT CACTAATCCG GTAAGCCTGG ATTATCCCGA CGCGAAAAAG CTGGCTGAAA AGGCGGCTAA CGCGGCAGTA AAGCGGGAGA AATTACGTGG CGCGGATCCT GGTCAACACC CAGGCCGGGC CGGACTACCA AAGCCATCTC GCTGCTGCAA AAGGCCTCTG AAGATCTGGA TACGACTCGC GTGATCGCAA TGTGCTTGCT ATTGACTGGG CATCTCGTTA AA |
| 208 | 288 | GATCAAACGC GCTGGCGTAA TCGCTACTGG GTTGATAGCG AAGGCCAAAT TCGCCAGACG GAACAGTATC TGGGCGCGAA TTACTTTCCG GTGAAAACCA CGATGATTAA GGCGGCAAAA TCATGATGAA AAGGACGATA AGCGCGCTGG CGTGGCCTTT GTCGCGTCAT CCGCCTTTGC CAGCGGCACT GTTACCGTTT TTACCCAGGG TAATAGCGAG CTAAAACGCT GACAGACGCT GAGCGCTCGC TCGATTAGTG GACAGCGCGC TGCACGAGCT GGTGGCTG |
| 209 | 169 | GATCAGGGAA CCTGTACCTC TTAAAGAGAA GTTCGATACC CCCAACGGTC TGGCGCAGTT CTTCACCTGC GACTGGGTAG CGCCTATCGA TAAACTCACC GAAGAGTACC CGATGGTACT GTCGACGGTC CGAGTCGCCA CTACTCTCCG TCAATGACCG GTAACTGTC |
| 210 | 311 | GATCATCTTC GTCCTGCTCT TCCTGACTCA GCGCACTGTT TACGACAATA CTGTCCGCAT CTCGTTGTGC GATTTTATCG GCGACGTCGC GGGAATAATC GCATATTCAC ATTCACCGCT GTTATTGATA ACCAGACGGC AATCGCAGAC GCCCATTAAT CAGTTGCGTC TGAGTGAGCT TATCCACGTC TATTTTTTTG ATGACGTTAT TATCGGTGAA GTTAAAACCA ATATCGCCTT TAGATACATT GATTCTATTC ATTTCAATAA GTTGCTTAAC CTGAGCTTTA AACTCTTCGC TAAAACCGCT G |

TABLE 3-continued

| SEQ ID NO | LENGTH | PARTIAL 3'—5'SEQUENCES OF PROBES OF THE PRESENT INVENTION |
|---|---|---|
| 211 | 368 | GATCAGTATC ATCAGTAATG GCCAGCGTTG CAGTATTCTG AATAGCCAGT GAGGTTTTCA GCGGGAAAAT GGCGAGGGTA TACGGAACCG GTTCGGTGGT GCCTTTTGTA GCAACGGTAA ACATTTCCAT ATTGCCGTTT TTGATAATCC GGTGGAAGAC TTCTGCCAGA CTGGGCTATC AACGGTTCCT GAGATAGCGT CAGATTTTAC ACCATCAGCG GTAACGTCGC GTATCGGTAT AAATAGAGAA CGCGCCGATT TTTACACCTT CGGTTGTTTG CCAACGCGAG ACATTGTGGA TCAGATACTA TACTATAGTC ATATCGCATG GCTATGAGAT ACGAGTGCCT GGTGGTGTGC ACGTATGA |
| 212 | 258 | GATCATCCAC TCATCTTTGC CGGTTGAGCC CGATAGTTAC CCGTTCAATA CCGGCATCAA TCGCCCCCGT TTTATTCACC ACCCCCAGAA AGCCGCCGAT AATCAAGACA AACAGCCGCG ACGTCAATGG CGCCGGCGGT GTAGGTTTCT GGGTTATAGA GGCCGTCAAT CGGCGCCAGC AAAACAGCGG TAATCCTTTC CGGATGCGCA CGGGGCATAC GCTCCGCACC GACTTTCAGA GCTGCTATCG ATTGATTT |
| 213 | 322 | GATCATTGTC ACGCCATTTT TTTAAATTAT TAGTATGGCG TGTGGAGACG CGTATCTGCT CACCAATATA CGTATTGTCC ATAGGCGTAG ACAAGCTCCA TTGCTACAAA GATAATTTTA TTTAAGTGTC AGGAAAATTC CGGACAAATC CCTTTTTTAA TAAAAATACA CACTCTCGGC ATGGGATAAT ACTTAATTAA CTTTTGTTAG CGTTTTGAAA TTAAAAACAG CGCAGAGGTA ATAATAGAAA ATAACGTTAA CAGGCTGGGT GAGTATATTT GACTGACACA ATTCCAGGTG TATATGTATG CGTTTATGCA TG |
| 214 | 320 | GATCATCCGC AGAAGAAAAA ATATGGCCGC GTAGAGATGG TGGGGCCGTT CTCCGTTCGC GACGGAGAGG ATAATTACCA GCTTTACTTG ATTCGACCGG CCAGCAGTTC GCAATCCGAT TTTATTAATC TGCTGTTTGA CCGCCCGCTT CTGTTGCTCA TTGTCACGAT GCTGGTCAGT TCGGCGCTCT TGCCTATGGC TGGCATGGAG TCTGGCGAAA CCGGCGCGTA AGTTGAAAAA CGGGCTGATG AAGTGGCGCA AGGCAACCTG CGTCAGATCC GGAGTGGAGG GGAGAGTTCT GGTGCAGTTT AACAGATCTA |
| 215 | 277 | GATCAGATGG ACCACAACGA GCACCGAAAA CAAAACGGCG CTGACCATCA GAATGACGGT AGTGCCGAGT TTCATGGGGC GTTTGCGTAA CGCCGGCATG GCAGGGAGTG TTTCATAGTG GACCTGAGCG ACGAATCGTA AGGTTATTAT CCCTGATGAG GCTCTAATTC AAAGGCATAG GCAGTCGTCC AGTGTGAAAG CCGCTGCTGC AGGCCGCTAC TGCATCGTAT ATCGGACGAG ATTTCAATCA ATAACACGCA ATTTCCGCAT CCAACCG |
| 216 | 330 | GATCCTGAAA CGCTGACCAG ACGCCGAGCG CGCCGTACCA CGAATCTCCG GTGGCACTCT GCGCACAACC TCTACGCCCA GCGATGGGAA CATCAGCGAA CAGCCGCAGC CGGTAATCGC CGCGCCAATC AGCGAGCCTG CTGACGGAGC GGCCCACATT ACCGCCAGTC CGGTCCCTCT ACCAGTAGTG AAAAGGTTGC ACCGTGCGCG CGTAACGGTC GGGAAATTTG GCGCAGAAAA GCGGACAGCG ATAAACGCAT CAACACTATG AAACGGTGAT ACAGTAGTGT GACAGAGTGT ATCTAGTGAC ATCTGACAAC TTCTCTCAGC |
| 217 | 223 | GATCTGGGCG AAATCGCGCG GAGTCTGGCG GCGGGCGATA TCATTACCCA CTGTTACAAC GGTAAGCCGA ACCGTATCTT CGGCCTGACG GCGAGCTGCG GCCTCGGTGA CACGAGCGCT GGCCGGCGGC GAGGCTATGG AGTCGGCATG GTACCGCCAG TCCTGAGCTT TGCGTGGCTA ACTCGCTATA GCTGGATTTA CCGCATACAT CAGTCGATAT CTC |
| 218 | 316 | GATCGCCACC GTTTTGTGAT GCGCGCCAAT TTGGGCTGGA TAGAAACCGG TGATTTCGAC AAAGTTCCGC CGGATTTACG TTTCTTCGCC GGGGGGACCG CAGTATTCGC GGCTATAAAT ACAAATCTAT TTCGCCTAAA GATAGCGACG GCAATCTTAA AGGCGCCTCA AAACTGGCAA CCGGATCGCT GGAGTACCAG TATAACGTCA CCGGTAAATG GTGGGGCAG TGTTTGTCGA TAGCGCGAGC GTGAGTGATA TCGCGTAGCA TTCAAACCGG ACGCCGACCG ACCGACCGTG GCTTCAACCT ATTCAC |
| 219 | 182 | GATCTGGGGT GGGGATTGT TGATGGTGTG TGGAGCGCTG CTGAGCGGAT GGCGGGGGAG GAAGCATCCT GAGTTATTGC CTGATGGCGC TGCGCTTATC AGGCCTACGA GTGAAAAGCA TGGTAGGCCG GATAAGGCGT TCACCGCATC CCGAAAACGA TGTTACTTTT GGCTTTACTG AT |

TABLE 3-continued

| SEQ ID NO | LENGTH | PARTIAL 3'—5'SEQUENCES OF PROBES OF THE PRESENT INVENTION |
|---|---|---|
| 220 | 419 | TGCAGATCAA AACAGCGACG GCTGGCAAAA GCGGTAAAGG TTTACGACCG GTCAGCGCCC CAGCCGCCGC CGTGCCAATC ACATTCGCCT CCATAATACC GCAGTTAATG ACATGCTGCG GGTAGTCACG CGCCACGCTG TCATCGCCAT TGAGCTCATT AATCAGCCTC AGGATATGGC TTCAGCCTCA AGCGCAATAA TTGGGCTTCC GGCCTCAATC TGCCCGGCGA TAAAACCGGC GTAAACTTTG CGCATTTCGA TATCGTCTTT AAGCCCTGGG AAGCTTAATC ATGCATGACC TCCAGTTGAT GAATGGCCTC ATTGAACGTT GCTTATCGCA TCGTCAGCGT AAGTGGTGAG AATTCGTTAA CTGCTCAGGC ATGCACCCTG CCTTATGCTG TCAAGGATCA CACCGTGCT |
| 221 | 126 | GATCTTATGA CATTGTGAGT ATCCATCGCT TTTTGTACTG AGCTGTAGGC AACTCCGACA GCTTTTGCTC AGCAGCTGTT GTTTCTCATA AGCTAGTGAC CAAGCTGCTG CTACCACAGG TCTGGG |
| 222 | 192 | GATCCTGCAC GCACGGGCGC ACAGCACCGA CAAGCTGTCC AGCTACTTGA CACAGCGCCA GCGCGTGCTA GCGAGCGAAC CCGCAGGTGG CACATGGCGG GGACGGCGAG CAGGAGACAG GCTAGAACGC TTTATGTGCG CACTATGCTA TCAAATAGGC CGTCCGGCTG CACGCCGACA CTACCCTGAC AA |
| 223 | 331 | GATCACCGCA TCGCGAACTG GTTACGGGCC TGTGGAGCGT ATTTTTTGAT GTTATTGGTA TTCATAGAAA ATCCTGCAAA GGGCAGCAGA GCGCTGCCCT GAAATGGGGG TTACTGAAGA CGAATCCGGT CACCTGCCTC AATAGCTGCC AGCAGCGAAG TACGAAGCGT ATCCAGCGCT TTTTCCACCT GTTCGGCGGT TTCCAGCACT TCGCCACCGG TGGCTTTGCG CATCTCGCTG GCGACATTCA CCAGATGCGT TTTTTCGGTA CCGGTTGGAT AACGGTTCTC TACCACAACA TAAGCTCGTT GTGACTCGGC GCCTTAGCTT A |
| 224 | 410 | GATCTAACGT ATCACGACTA AACGTAAGGG TAAAGCGGCT GGCGTATCGT CCGGGCATAA AGTCATATCG CCTGAACAGA TAACATCTCA CTGACTTTGA AACGCGATTT TATAATTTGC TGCCCAAAAA TACGTGGCGC TGAAAGGCGC ATTTTTGATG CAAATCATTT ATTACTGTGA TAACACTGCG CGCGATAAAA CATTAATATA TTCACATAGT AATATGTTCT ATTGGAATGG TTGTTTCGAT ATGACAAAGT CTAAAAAACC ATTGATGTGA AAAGGAATAA GAATTGTCTA TATTCCGATT CGGTGGAATT AAGTATTCTC GGATAAAATA GAATGATATT GATATTCTTT TGATATGGTC TATAGCGCTA TGTATCAGAC GCGTGATCGT CGGAGATCAG |
| 225 | 185 | GATCTTCGAC TGCCGCGCTT CCGCGACAGC GACATACGGG TGTTCTTTGT CGGTGACGTT TATCCGTTGT CGTGACCTTC ATCCGGTGGT GAAACCTGAG CCGAATAATA CTGTACACCA CCACCAGGAC AGAATACTCA AACCACGTTC ATGTGATTGT TGCACCACAT ATTCATTGTT GGAAC |
| 226 | 276 | GATCCGCTGA CAGATGTCGT GTACAGCATT CTTTAGAGTG GAACGGTGAC CGTACCGCAA AGCTGTGAAA TCAACGCCGG ACAAACGATT CTGGTAAATT TCGGCGCATT ATACAGCGGC AATTTCAACC ATGCAGGCCA AAAGCCGGAG GGGGTACGAG CGAAAAAATT CAGTCGCTTC CGGTAAAGTG CAGCGGTCTG GATTCGCAGG TCAATTTAAC AATGCGTCTT ATCGCTCCGC GGATAGCACG TCCAGCTATC GCTCGATATG CGATGT |
| 227 | 383 | GATCACCGAC CGGACGGTCC GTACCTGGAT TGGGGAGGCG GTTGAGTCCG CAGCGGCTGA CGACGTGACG TTCTCAGACC CGGTGACACC CCATACTTCC GCCACTCCTA TGCGATGCAC ATGCTGTACG CGGCATACCG CTGAAGGTGC TGCAGGCGCT GATGGGACAC AAATCGGTGA GCCTGACGAG TGTACCGAAA GTGTTTGCGC TTGATGTTGC CGCACGACAC CGGGTGCAGT TTCAGATGCC GGGTGCTGAT GCAGTGGCTA TGCTCAAAGG AGGTTCATAG AGACGTGTAT GCATTTTCAG CTTCGCTGCA CAGCATCGAA CGGAGTTTAC GCGTTTATCA GCCATGTCTG CGCACAGAGG AGTGTGCTCG AAA |
| 228 | 357 | ACTTGCCGGT AATTTCCATC CCTTCCAGCA CCGCCATCTC TTTACCCTCA ATGGCGATGG ACAGTTTATC CAGCGTTAAC TTTTGGTCGC CCCACGTTCG CCAAAGCTTG CCAGTTTACT GGTACCGTCG GTTTTCAAAT TATTAAAGGT GAGTTGGACC TTCTGATTAT ATTCGTTAAC GGCATCGACC AGGCCGCTCT CGCGCTTCGC CTGACAGCGA AACCACATTA CCGTCTTTAT CGGGCGTTAA CGGGAACTCG GCGCCGCTAA AGGCACCTTT ACCGGCATTC TCTGAGTTAA CCGGCTTGAG AGAGATATCG GAGCGGTATC GCCGCCATAC ATGCGGTATT GATACAA |

TABLE 3-continued

| SEQ ID NO | LENGTH | PARTIAL 3'—5'SEQUENCES OF PROBES OF THE PRESENT INVENTION |
|---|---|---|
| 229 | 225 | GATCTATTTC GGACAGCCAA AAGGCCGTGA AGGCAGCGGT CAGTACAAAA AGCCTTTGAT ACCGAAGTTT ATCACCGGCT TTGAGATCGA GCGCAGTTGC CCGTATGCCT TTGAATCGGC GCGTTAAACC GGCCGTAAAG TACCCTCTAT TGATAAAGCC AACTACTGCA AGCTCTATCT GTGGCGTGAA TACGTCAATA GTGGAAAACG TATCCGATGT GAACT |
| 230 | 275 | GATCGTTAAA CAGATTGACC AGTTCGCCAC ACTCTTCCAG ATTAAACCCC ACCTGCCTCG CCTGTCGCAG CAACGTCAGC TCGTTTAAAT GCTTCTGCGT GTAGGTGCGA TAACCATTTT CGCTACGTAA TGGCGGCGTC ACCAGCCCTT TCTCTTCATA AAACCGAATG GCTTTGTGGT TAGCGTTTTG GCACATCGCT ATATCATATT GCCCTGCCTA CTGCTGAGTT ACTATACGGG TACTACGTCT AGAGATCGCG AAAAGGTTAC AGTAC |
| 231 | 233 | GATCGACGTC GCCTGATTTA AGACCCGCAA GCAACATCGT ATTGTTCATG GTCGCGACCT GTAACGAGGT CGATTTTTGC TGTTGATGGA ACCGCCCAAT AGCCGCCGGG AGTATACCCA GCGCAGGTGG GGAGCGGCAA CACGCACCAT CGGCGCTAGC TCCTCTTTGG CGATTCGATC GGATCCTGGC GGTGGTATTC ATGATCTAAT CCTTTTATCG ATGAGTAAAA TTG |
| 232 | 358 | GATCGGCGGA GAATCCCAGA CAGGCCAGGT CTTTCAGCTC GTCGCGGGTC ATCGGGCCGG TAGTATCCTG AGAACCGACG GAGGTCATTT TCGGTTCGCA GTACGCGCCC GGACGGATAC CTTTCACACC ACAGGCGCGA CCGACCATTT TCTGTGCCAG CGAGAAGCCA CGGCTGCTTT CCGCCACGTC TTTTGCTGAC GGAAAACGTC TGAGTGCGCA GCCAGCGCTT CACGCTTTTG TGCTAGCACG CGATATCACG ATACACACGC ACGACTCGTC ATCAGCACGT CGTTCAGTCG AGTGCAGTAG CGCGTCATGA TGCGTACTGC TTGACGTAGA CTATCATGCC ATATCAGT |
| 233 | 302 | GATCCACAGG TAGCGTGATG CGTTTTAGTT CCCCCTGCTG CTCAAGTAGC GTCAGGCCGT CGCGTAAATC GTGATATTTC ATGGCGTCCA TTGTAGCCTC TTGGTAAGCG CATCATTATA CGGCGTTCAT CATCGGGATG CTGTATTTTT GTTAAATTAG CGTGAACTCT GGCAACCAAC GCTAATCCAG ATACGGCTTA AAGGATGAAG TGTATATTAA CTTCGCGCAT GGCTTTTGCT ATGCTTGCGC CCCGAACAGC GATAAGAGTC ATATGCATCT GGTATTTACT GTACTGCAAA CG |
| 234 | 374 | GATCGTCACC TCCACCCTCG CGCGCGGGGC GGTGAAGCTC TCGAAACAGA AAGTTATCGT GAAGCACCTT GATGCGATTC AGAACTTCGG CGCGATGGAT ATCTGTGCAC TGATAAAACC GGCAACTCTG ACGCAGGATA AAATTGTGCT GGAGAAATCA CACGATATTT CTGGTAAGCC CAGCGAGCAT GTCTGCATTG CGCCTTGCTG ACACATTATC AGACCGTCTA AAAAAATTTC TGATACGCGT CTGAGAGTAG ACAACGCGGT CACCTCGACG TGCAGAAAAT CGATAGATCC GTTATTTAGC GTGCGATGTC GTAGTGTGCG AGATCGACGT GCATCAGCTG GATCTGCAAG CTAACGAGAC TCAC |
| 235 | 355 | GATCGGACTT TATTCGCGCG ATAGTCACGG AAAAAATGGT TTAACTTTGC TAATTCATCC TGAATGTAGG CTCTTCCATC GAAAAACTCC GCCTTGATTG ACTCTCCGGT ATGGAGATTG TTTAACGTCA AAAATGCGCG CCGTGGGGTC GAGAGTGTGG CAAACGCTGA GCGCGGGCAG GATGGCGGCG CGAGAGCGAC ACCACCAAGC GCCAGAGCTT GCGCGATTAG CGTCAAATTT GTCATGATAA TCAGGTCTAC AGGTCAATGT TATCGTTAAT ACACTTCTAC CTTTAAGCAG ACATGATACG CTGACACGAC TCTACGCGTG ATAGTGTGAT ACTTGGCACA GACTA |
| 236 | 363 | GATCGTCACG TGATTTGCCC GTCACGCGAA TCTCTTCCCC CTGAATTTGC GCCTGCACCT TCAGTTTGCT GTCTTTAATC AGCTTGACGA TTTTCTTCTG CACGGCGCTT TCAATGCCCT GCTTCAGCTT CGCTTCCACA TACCAGGTTT TACCGCTATG CACGAACTCG TCCGGTACAT CCAGCGAAGC GCTTCAATAC CGCGTTTAAG CAGCTTGGCG CGCAGAATAT CGAGCAACTG ATTGACCTGG AAATCGGACT CGCTCAGCAC TTGATGGTTT ATTGGCATCG TTCAGTTCAT AGTGCTCTAC GCACGGAGTC AAACAGACTC ACTGGAGCTA TCACACGTAC GCGCTCTCGA GAT |
| 237 | 320 | GATCGTTAAT TAGGCGCTGG GCGTGCTGGA GCAGTAATTT ACCGCCTTCC GAGGGGCGTA GTCCTTTACT GTGGCGCTCA AAAAGCGTGA TGCCTATCTC ATCTTCGAGT TGAGATAGCC ACTTCGATAG CGCCGCCTGG GAGATATTCA TCATCCGGGC GACGTGTCCG TTCAAGGGTT GGCCCTGTTC GGCCCAGCGC AACCAGCGTT TGCGGTGATG TAATTTCAAT TTCTCCCGTT CCATTCGCTA TAACCTCAGG TTATGTCTCT CCTGAAACCA TTGTACTTTA TCCTCCTCTA CACTCGTACT GCACTAACAC |

TABLE 3-continued

PARTIAL 3'—5'SEQUENCES OF PROBES OF THE PRESENT INVENTION

| SEQ ID NO | LENGTH | SEQUENCE |
|---|---|---|
| 238 | 406 | GATCCTGCAA CGCTTTCGAC CCGGTCGAAA TAATGACTTT TTTCCCGGCG CGCAACGCCG AGCGAGGTAA GCATAGGTCT TCCCGGTTCC GGTGCCGGCT TCAACAACCA GAGGCTGCGC ATTTTCAATC GCTTGTGTTA CGGCAACCGC CATTTGTCGC TGTGGTTCGC GCGGTTTAAA GCCGGTTATC GCTTTGGCCA GTTGGCATCT GCTGCAAAAT CGTCCGTCAC ACTGCCCCCT GTTAATTTGC ACAGGGATTA TGTCAGGGTA GAAAGGCTTA CACAGTTACA GAGGTGACGG CGGCACATTG TGCAGTCTTG AACCATTCAA ATGAAAAGCA AATGAGGAAT AAGTAATGTC TATCGTGCGT ATGATGCGAG ATCGTGTCAG ACGTGTGACT CAATAT |
| 239 | 263 | GATCCTACCG GCCCCCACGC TTTGATTTGA ATAATAGAGG CTACCGACGA CAGCGACATG CTGATAATGT GCTGCGTATC CTGCGCCGGT AAACCCAACG CCTGGCAGAT TAACAGCGCT GGCTGATTAC CGCGACAAAC ATGCCACGAG ATGCTGACAA GCGCAAAAGG TTGAGGAGCG CGGCGATCTT CAAGACGGTA AATTAATCGC TGCACAATTG TACGCGACGA TGCATCTCGC ATGCGTCTAC GACATAGACA TCT |
| 240 | 364 | GATCAACGCC TAATTTGGCC GCACAATCCA GAGAGACCTG CGGGTGCGGT TTGCTGTAGG GCAATTTTTC TGCAGAAGCC AGCGCGTCAA AACTGTCGCG CAGTTCAAAC ATGGTGAGCA CTTTTTCCAG CATATGCAGC GGCGATGCCG AGGCAAGCCC CACTAATAGC CCCTGCGCTT TACACAGCGC CACAGCTTCG CGCACACCCG GCAAAAGAGG GCGCTCTCTT TCGATAAGCG TAATCGCGCG GGCAATAACA CGGTTTGTCA CTTCTGGCGA TCGGGCGTTC ACGTTGCTGC GCAACAGAGA TCGACAACCA TATCATGCGT AGCAAGCTGT TGCAGCTCAT GGCCGAGTAT ATCT |
| 241 | 221 | GATCATTTTA ATGCTGTGTC TTGCCATTTT TTTCTCCATA AATTTCAAAA GGAAATCATG CCTGATGCGC ATTGCGACGG CGTGAGTACC ATTCAAGGAT TTGGTGACGA TGCAAACTGA TGGAACGACC AACGACAACA ACAATGAGAA GCGCACCGGA CAATGCGCTG GAATTGATTC GGCACTCCGG CCATCTGTAG CCCTCGTGTA AATCCACCAG C |
| 242 | 280 | GATCATCGAC GTATGTCCTT TCCAGATATT CCGCCCGCCG CCAGCCCACT CAAACACGG GGGGCGCCGG CAAAAAAGCG AAAGACATCC ACCGATTGCC GGAATTTATA TTAATTACGC CAGTGCAAAG GCTTATTGCA GTTTTGCGAT TCAAGCCGGG CGAACTCAAG GGCGTTTTGC TCGATGCTGT CCGCAGTTTT AACAGACATT CCGCCCGTGC TTTGGGTGTG GTCTGCCCAT TCGGAAACGC GTTATCGGCG GCTGATCGCA GCGTAACCTG |
| 243 | 277 | CACTATAACA ACGGCGCGGC GGTACCTGGG CGACGTCGCC AGCGTCACCG ACTCGGTGCA GGATGTCCGT AACGCCGGGA TGACGAACGC TAAACCCGCT ATTTTGTTGA TGATCCGCAA GCTGCCGGAG TGGAATTCCA CATGTGGAAT TCCCATGTCA GCCGTTAAGT GTTCCTGTGT CACTCAAAAT TGCTTTGAGA GGCTCTAAGG GTTCTCAGTG CGTTACATCC CTAAGCTTGT TGTCACAACC GTAACTAAAC TTAAACCTAT ATATCCT |
| 244 | 380 | TGCAGATCAT TGCCTGATGT TCTACGGTCG CAAAATGCAC CAGNNNNCAG AACAACGACA GCGACAACAA TACGGCTGAA GCGCTTTAAT CGCGCTAACT CCTTTTTCTC AAAGCCCCTT TCCGTTCACC TGCTATAGCG TNGAGGGGCC CACTTACCAG GAACAAGACT ATGAACGTTA TTGCTATCAT GAACCACATG GGCGTCTACT TTAAAGAAGA GCCTATTCGT GAACTGCATC GTGCACTGGA AGGTTTAAAT TTCGTATCGT CTATCAAAAC GACCGAGAAG ACCTGCTGAA GCTGATTGAA ATAACTCCGC CTTTNNGTCA TTTCGACTGG GATAATATAC CTTGAGCTTC GAGAGAGATA GCAGTGAGCG |
| 245 | 353 | GATCTGATTA TCGACGCGCT GCTTGGCACC GGCATAGCCC AGGCACCGCG CGACCCGGTA GCCGGTCTGA TTGAACAGGC GAACGCATCC TGCGCCGGTT GTCGCCGTCG ATATCCCGTC AGGTCTGCTG GCGCAAACGG GCGCACGCCT GGCGGGTGAT AAGCGCGCGC ATACGGTCAC GTTTATCGCC CTGAAACCAG GCCTGCTGAC CGGCAAAGTG CGTGAGCTTA CCGGCATATT GCATTATGAC GTTGGGACTG GAAGGCTGGC TGGCGAGCAG ACGCGCGTCG GTTTTGAAGA GAGTTGGGGC AATGGCTAAC GCGTGACGAC TGATAGGGAT ATGTGTAGAT ATG |
| 246 | 376 | CACCCGGCTG ACTGCCGTAT AATCCAGCTT TTTACGCGGG TCCGCGGAGG GTTTTGCCGT CACAGAGAGC GTATTCTGCG AGTTTATGGT TGTCTTACCT AACGGATAGC CTTCGCTATC ATAGCGGTAC TCGACCCTTC ATCTCTTTGC CCGTCGCCGA TACCACAAAA CCGTTGTCGT CCGTTTCCCA GGTCACGCCC GCCGAACGAA CGCCGCCAGC TGGCACTTCC CCTGTAACTG CACCTTTTTT TCCAGCGTCT GAGCATCCCG GTAATAATTG GCATCCAGCA CGAGTGCCAG CCCCGTATTT ATCTCCAGAT CGTGTAACTC AAGCGTATCA AACAGCCTT CCTGTGAAAG CGTACCGCGA CCTCTA |

TABLE 3-continued

PARTIAL 3'—5'SEQUENCES OF PROBES OF THE PRESENT INVENTION

| SEQ ID NO | LENGTH | |
|---|---|---|
| 247 | 248 | GATCAAGACG CGAATCCCCG ACGCGCCGAT AACGCCGTAC AACAGCAGCG AGACGCCGCC CATCACGGGT AACGGGATAA TCTGAATCGC CGCCGCCAGT TTGCCAACGC AGGAAAGCAT GTAATAACGA AAATCGCGTC GCCGCCGATA ACCCAGGTAC TGTAAACGTC GGTGATCGCC ATGACGCCAA TATTTTCCAT AGTGTATCGG CGTGAGTAGA ACCGAATATC GTCGACATCT AGCACATC |
| 248 | 253 | TTTCGACAAA GCGCGCCGCC GAGATATTCG CCATGATCAT GCACTCTTCG ATAAGCTTAT GCGCGTCATT ACGCTGGGTC TGTTCGATAC GCTCAATGCG ACGTTCGGCG TTAAAGATAA ACTTCGCCTC TTCGCACACA AACGAGATCC CCCCGCGCTC TTCACGCGCT TTATCCAGCA CTTTGTAGAG GTTGTGCAGC TCTTCAATAT GCTTCACAGC GCGCATATGT CACGCAGATC TGATCGCTGC AGC |
| 249 | 414 | GATCAAACAC CAGACGACCG CGACGCGCAC GACCATCGGT GGTATCTAAC TCAAATTTCA TTATCACTCC TGCGTCAGAA AAACAGTCCG ACGTTTAACG ACTCGCTACG GAATGATTCC ATAGCTAATA AATTCCCGAA GACGTCATCG GCGCAGAGTT TGGGGTCGAC CAGCGCACAG CCACCGGAGC GTACACGCAG TACGTGAGGA TGGCGAGCAC TGCCGCGTCA AATGCAGTGA GATAGCTCTA CGACGTCAGA ATAGCTGCGA TGTACGTGAT AACTGCTCCG TAGCTAAAAG CATTTGTCTA CGCAGTCTAT AGGCATCATG TGTGTGATAC GCATGCGAAC AGCATACACG TGATCGCAGA TGAGTGTGAT CAGGCATATA CTGACGAACT GATATAGATT CGTG |
| 250 | 112 | GATCTTCCGG GTTCACGGCC ACGCGGTAAT TCTGCCGAGA ATAGTTTTCG GGCGGGTGGT GGCGACAACC AGAAATCTTA CCGTCGCGGT TTTCGCGCCG TCGCCAGCG GA |
| 251 | 345 | GATCGTTAAA TGTGCGGTAA TCCTGTGATG AATACCGATA CGCAGCCAGA CCAAACCGAG TTAATGTTTG GGTCAGGTAT TTATTATAAG CAATCTGATA ACTCTGACCA TCAAATACGA CGCCATTATC CTGTTTACTG TGCGCTCGCG TAGCTCAAGC GAAATGGCGC CAATCCGGGT ATTCCACCCC GTGCCGAGGG TAAACGCATT ATAATGGTTC GATAGCATCG TACGCATAAG CGTCAACAGG TTATTAGGCA TACTGATACT GATTGGTAAA TCGGCTGATA TCGGCGCTTC AATTATGACT ACGCGCGAAA TCATACTGAG CCGTCCAGTC CATTC |
| 252 | 203 | GATCGGTCGC CGCCTTACCT TTTTCCAGTA CACTGAGCAG TTCGCTCAGC AGTTGTTCAA CAGCTCCATC ACTAGAGCGG GAGAGTTCTG GCATAAATCA AAATCTGTTT GTTCATGAAA CGGCAACACA TTAACCGCAG CAACAGTTTT TTTCTGCATT TTTCGGCCTA AATCATCGCC TTACGATACT CTGAATACAG GGG |
| 253 | 273 | GATCGTAATC ATTCACTTCG GTCAGCAGCT CGAGCACTAA CGCGTCGAGC ACGCCTTCCA TCGGCGCCAG TAAAACACGC ATATCGGTAT CCACAGCAAA AAAAGAGGCG CTATCATAAC GCCTCTCTGC GATGAGCAAA ACTTTTTTGC CGGGTGGCGG CGCAAACGCA CGCTACGTAC GTAAGTGCTC ACGCGGCTTC AAGACCAGTT ATTTTTCCAG CCGACCAGCC ATTCGAACCG CGATAAGCTC TGCGATCCTT TCCAAGTATG CTG |
| 254 | 154 | GATCTTCTCG CTTTCTTCAG GGCTTACTCC CGTCTCTTCT TCATCGACCG TGATCAAAAT ACCGTCTTTA TCCACCAAGA AGCCGACTTC AATCTTCGTA TGATCAAAAT ACCGTCTTTA TCCACCAAGA AGCCGACTTC AATCTTCGTA TGAAAATAGC TCACCATTAC GAACTATATT TTTCATCTCT CTTTCCAGCT TTTT |

There are many examples where highly-linked virulence genes are involved in the same stage of pathogenesis. Consequently, identifying the map location of the coding sequences of the present invention to a particular region of the bacterial chromosome is informational.

Mapping Protocol

A bacteriophage P22 lysate is made on the fusion strain of interest and used to transduce a recipient strain such as wild type *S. typhimurium* strain ATTC No. 14028. The resulting tetracycline sensitive, ampicillin resistant fusion strains are grown overnight in LB Amp and then transduced on LB Tet X-gal plates using a bacteriophage P22 lysate made on a pool of random Tn10d-Tc$^r$ insertions. White Tet resistant colonies represent either spontaneous Amp sensitives where the fusion has segregated by homologous recombination between the direct repeats of the cloned fragment or replacement of the region brought in next to the Tn10d-Tc$^r$-element.

To verify and measure the linkage of each candidate to the parent fusion, white Tet resistant clones are made phage free and phage sensitive. Bacteriophage P22 lysates are grown on them and used to transduce the parent fusion containing strains again to Tet resistance on LB Tet X-gal plates. Linkage is visually present by an increase in the number of white colonies. Strains containing the Tn10d-Tc$^r$ insertions next to the fusion locus are used in the next step, mapping by the method of Benson & Goldman, see Benson N. R., et al., *J. of Bacteriol.*, 174:1643–1681 (1992).

A selection exists for the loss of the tetracycline resistance determinant of Tn10d-Tc see, Maloy, J. R., et al., *J. of Bacteriol.*, 145:1110–1112 (1981). Plates containing fusaric acid will allow the growth of tetracycline sensitive strains over tetracycline resistant strains. In conjunction with this, a set of Mud P22 phage lysates which each package a small, defined region of the chromosome is used to transduce each Tn10d-Tc containing strain to Tet-sensitivity (available from Salmonella Genetic Stock Center, Calgary, Canada). The lysate that produces the most Tet sensitive colonies packages the region where the Tn10 lies in the chromosome and by inference, the location of the original IVET fusion.

After assigning each fusion to an internal donor, lysates grown on all the Tn10d-Tc containing strains in an interval are used to transduce all the strains with IVET fusions in them to Tet resistance on a Tet X-gal plate to test for linkage of each of the fusions to the others as well as Tn10 insertions in known genes already mapped on the chromosome to provide anchor points if possible.

In addition to the map locations of each coding sequence of the present invention, the defined sequence data presented previously has been compared to published sequences and known genes having homology to the coding sequences of the present invention are cited in Table 4 below.

Table 4 below represents (i) the known map locations of each coding sequence of the present invention; (ii) known genes that share homologous regions with the coding sequences of the present invention; (iii) the type of IVET plasmid that the coding sequences of the present invention were originally cloned into; and (iv) the type of tissue each coding sequence of the present invention was derived from. It is to be understood that while each coding sequence of the present invention was derived from a specific internal organ or macrophage, that does not imply that a gene transcribed or genes cotranscribed with each coding sequence are specific to that particular tissue type. For example, SEQ ID NO. 82 was derived from both intestinal and splenic tissues.

TABLE 4

| Seq ID # | Vector | Gene | Between Loci: | Tissue |
|---|---|---|---|---|
| 14 | pIVET1 | cfa | aroD-pyrF | intestine |
| 80 | pIVET1 | pgm | cobD-putA | intestine |
| 13 | pIVET1 | cadC | cysA-purG | intestine |
| 247 | pIVET2 | uraA | cysA-purG | intestine |
| 8 | pIVET1 and 2 | argE | ilvA-melA | intestine |
| 76 | pIVET2 | oxyR | ilvA-melA | intestine |
| 106 | pIVET1 | tpi | ilvA-melA | intestine |
| 210 | pIVET1 | unk | ilvA-zjh | intestine |
| 213 | pIVET1 and 8 | unk | melA-zjh | intestine |
| 221 | pIVET1 | unk | melA-zjh | intestine |
| 104 | pIVET1 | tolQRA | nadA-putA | intestine |
| 10 | pIVET1 | artI | nadA-putA | intestine |
| 88 | pIVET1 | proS | nadC-proA | intestine |
| 31 | pIVET1 | fhuA | nadC-proA | intestine |
| 28 | pIVET1 | dnaZX | proA-purA | intestine |
| 55 | pIVET1 | lon | proA-purE | intestine |
| 249 | pIVET1 | vacC | proA-purE | intestine |
| 38 | pIVET1 | gcvP | proU-zgf | intestine |
| 79 | pIVET1 | pgk | proU-zgf | intestine |
| 101 | pIVET1 | surE | proU-zgf | intestine |
| 102 | pIVET2 | TGI/hyb | proU-zgf | intestine |
| 92 | pIVET1 | rpiA | purG-proU | intestine |
| 82 | pIVET1 | phoPQ | putA-aroD | intestine |
| 91 | pIVET1 | rbs | pyrE-ilvA | intestine |
| 195 | pIVET1 | unk | pyrE-ilvA | intestine |
| 198 | pIVET2 | unk | pyrE-ilvA | intestine |
| 196 | pIVET1 | unk | pyrE-ilvA | intestine |
| 111 | pIVET2 | unk | thr-nadC | intestine |
| 32 | pIVET2 | flagellar pr | tre-zea | intestine |
| 75 | pIVET1 | otsA | tre-zea | intestine |
| 148 | pIVET1 | unk | tre-zea | intestine |
| 6 | pIVET1 | alr | unmapped | intestine |
| 19 | pIVET1 | cysD | unmapped | intestine |
| 29 | pIVET1 | fadL | unmapped | intestine |
| 62 | pIVET1 | ndk | cysA-purG | intestine |
| 68 | pIVET1 | orf211 | unmapped | intestine |
| 232 | pIVET1 | unk | unmapped | intestine |
| 233 | pIVET1 | unk | unmapped | intestine |
| 234 | pIVET1 | unk | unmapped | intestine |
| 235 | pIVET1 | unk | unmapped | intestine |
| 236 | pIVET1 | unk | unmapped | intestine |
| 44 | pIVET1 | hisT | zea-cysA | intestine |
| 64 | pIVET1 | nuo | zea-cysA | intestine |
| 157 | pIVET1 | unk | zea-cysA | intestine |
| 107 | pIVET1 | unk | zea-cysA | intestine |
| 165 | pIVET2 | unk | zea-cysA | intestine |
| 252 | pIVET1 | yejL | zea-cysA | intestine |
| 39 | pIVET1 and 2 | gltB | zgf-zgi | intestine |
| 54 | pIVET1 | lacA | zgf-zgi | intestine |
| 85 | pIVET1 | pnp | zgf-zgi | intestine |
| 20 | pIVET2 | cysG | zgi-envZ | intestine |
| 34 | pIVET1 | ftsX | zgi-envZ | intestine |
| 40 | pIVET1 | glyS | zgi-envZ | intestine |
| 60 | pIVET1 | mreB | zgi-envZ | intestine |
| 87 | pIVET1 | ppi | zgi-envZ | intestine |
| 224 | pIVET1 | unk | zjh-thr | intestine |
| 250 | pIVET1 | valS | zjh-thr | intestine |
| 125 | pIVET2 | unk | cobD-nadA | liver |
| 205 | pIVET1 | unk | ilvA-melA | liver |
| 57 | pIVET1 | mdh | zgi-envZ | liver |
| 43 | pIVET1 | unk | aroD-pyrF | liver |
| 126 | pIVET8 | unk | cobD-putA | liver |
| 70 | pIVET1 | orf337 | cysA-purG | liver |
| 247 | pIVET2 | uraA | cysA-purG | liver |
| 45 | pIVET1 | hslU | ilvA-melA | liver |
| 106 | pIVET1 | tpi | ilvA-melA | liver |
| 202 | pIVET1 | unk | ilvA-melA | liver |
| 12 | pIVET1 | brnQ | proA-purE | liver |
| 90 | pIVET1 | purA-like | proA-purE | liver |
| 73 | pIVET2 | orfA | zea-cysA | liver |
| 23 | pIVET1 | dam/trpS | zgi-envZ | liver |
| 250 | pIVET1 | valS | valS-thr | liver |
| 138 | pIVET8 | unk | aroD-pyrF | macrophage |
| 139 | pIVET8 | unk | aroD-pyrF | macrophage |
| 246 | pIVET8 | unk | aroD-pyrF | macrophage |
| 37 | pIVET8 | galK | cobD-nadA | macrophage |
| 124 | pIVET8 | unk | cobD-nadA | macrophage |
| 167 | pIVET8 | unk | cysA-purG | macrophage |
| 169 | pIVET8 | unk | cysA-purG | macrophage |
| 168 | pIVET8 | unk | cysA-purG | macrophage |
| 72 | pIVET8 | orf543 | ilvA-melA | macrophage |
| 84 | pIVET8 | pmrB | ilvA-melA | macrophage |
| 199 | pIVET8 | unk | ilvA-melA | macrophage |
| 200 | pIVET8 | unk | ilvA-melA | macrophage |
| 207 | pIVET8 | unk | ilvA-melA | macrophage |
| 17 | pIVET8 | cutA2 | melA-zjh | macrophage |
| 58 | pIVET8 | mgtA | melA-zjh | macrophage |
| 211 | pIVET8 | unk | melA-zjh | macrophage |
| 212 | pIVET8 | unk | melA-zjh | macrophage |
| 50 | pIVET8 | IS200 | nadA-putA | macrophage |
| 83 | pIVET8 | phrA | nadA-putA | macrophage |
| 127 | pIVET8 | unk | nadA-putA | macrophage |
| 128 | pIVET8 | unk | nadA-putA | macrophage |
| 129 | pIVET8 | unk | nadA-putA | macrophage |
| 98 | pIVET8 | speE | nadC-proA | macrophage |
| 94 | pIVET8 | S.t.res/mod | proA-purE | macrophage |
| 114 | pIVET8 | unk | proA-purE | macrophage |
| 115 | pIVET8 | unk | proA-purE | macrophage |
| 118 | pIVET8 | unk | proA-purE | macrophage |
| 116 | pIVET8 | unk | proA-purE | macrophage |
| 117 | pIVET1 | unk | proA-purE | macrophage |
| 178 | pIVET8 | recD | proU-zgf | macrophage |
| 177 | pIVET8 | unk | proU-zgf | macrophage |
| 179 | pIVET8 | unk | proU-zgf | macrophage |
| 180 | pIVET8 | unk | proU-zgf | macrophage |
| 121 | pIVET8 | unk | purE-cobD | macrophage |
| 33 | pIVET8 | folD | purE-cobD | macrophage |
| 174 | pIVET8 | unk | purG-proU | macrophage |
| 131 | pIVET8 | unk | putA-aroD | macrophage |
| 132 | pIVET8 | unk | putA-aroD | macrophage |

TABLE 4-continued

| Seq ID # | Vector | Gene | Between Loci: | Tissue |
|---|---|---|---|---|
| 105 | pIVET8 | torA | pyrE-ilvA | macrophage |
| 194 | pIVET8 | unk | pyrE-ilvA | macrophage |
| 53 | pIVET8 | kdsA | pyrF-tre | macrophage |
| 144 | pIVET8 | unk | pyrF-tre | macrophage |
| 110 | pIVET8 | unk | thr-nadC | macrophage |
| 109 | pIVET8 | unk | thr-nadC | macrophage |
| 71 | pIVET8 | orf48 | tre-zea | macrophage |
| 146 | pIVET8 | unk | tre-zea | macrophage |
| 228 | pIVET8 | unk | unmapped | macrophage |
| 229 | pIVET8 | unk | unmapped | macrophage |
| 16 | pIVET8 | col I rec. | zea-cysA | macrophage |
| 18 | pIVET8 | cysA | zea-cysA | macrophage |
| 66 | pIVET8 | orf179 | zea-cysA | macrophage |
| 93 | pIVET8 | rplY | zea-cysA | macrophage |
| 151 | pIVET8 | unk | zea-cysA | macrophage |
| 152 | pIVET8 | unk | zea-cysA | macrophage |
| 153 | pIVET8 | unk | zea-cysA | macrophage |
| 155 | pIVET8 | unk | zea-cysA | macrophage |
| 154 | pIVET8 | unk | zea-cysA | macrophage |
| 184 | pIVET8 | unk | zgf-zgi | macrophage |
| 185 | pIVET8 | unk | zgf-zgi | macrophage |
| 49 | pIVET8 | IS2/IS30 | zgi-envZ | macrophage |
| 86 | pIVET8 | ponA | zgi-envZ | macrophage |
| 188 | pIVET8 | unk | zgi-envZ | macrophage |
| 222 | pIVET8 | unk | zjh-thr | macrophage |
| 223 | pIVET8 | unk | zjh-thr | macrophage |
| 14 | pIVET1 | cfa | aroD-pyrF | spleen |
| 30 | pIVET8 | fdnGHI | aroD-pyrF | spleen |
| 63 | pIVET8 | nifJ | aroD-pyrF | spleen |
| 140 | pIVET8 | unk | aroD-pyrF | spleen |
| 141 | pIVET8 | unk | aroD-pyrF | spleen |
| 142 | pIVET8 | unk | aroD-pyrF | spleen |
| 143 | pIVET8 | unk | aroD-pyrF | spleen |
| 43 | pIVET1 | unk | aroD-pyrF | spleen |
| 251 | pIVET1 | yehB | aroD-pyrF | spleen |
| 52 | pIVET8 | kdpD | cobD-nadA | spleen |
| 67 | pIVET1 | orf2 | cobD-nadA | spleen |
| 80 | pIVET1 | pgm | cobD-putA | spleen |
| 126 | pIVET8 | unk | cobD-putA | spleen |
| 13 | pIVET1 | cadC | cysA-purG | spleen |
| 70 | pIVET1 | orf337 | cysA-purG | spleen |
| 69 | pIVET1 | orf384 | cysA-purG | spleen |
| 170 | pIVET1 | unk | cysA-purG | spleen |
| 171 | pIVET8 | unk | cysA-purG | spleen |
| 172 | pIVET8 | unk | cysA-purG | spleen |
| 173 | pIVET2 | unk | cysA-purG | spleen |
| 168 | pIVET8 | unk | cysA-purG | spleen |
| 247 | pIVET2 | uraA | cysA-purG | spleen |
| 5 | pIVET8 | aceK | ilvA-metA | spleen |
| 7 | pIVET1 | arg.perm. | ilvA-melA | spleen |
| 45 | pIVET1 | hslU | ilvA-melA | spleen |
| 48 | pIVET8 | ilv | ilvA-melA | spleen |
| 78 | pIVET1 | pfkA | ilvA-melA | spleen |
| 106 | pIVET1 | tpi | ilvA-melA | spleen |
| 199 | pIVET8 | unk | ilvA-melA | spleen |
| 200 | pIVET1 | unk | ilvA-melA | spleen |
| 201 | pIVET1 | unk | ilvA-melA | spleen |
| 203 | pIVET1 | unk | ilvA-melA | spleen |
| 204 | pIVET1 | unk | ilvA-melA | spleen |
| 206 | pIVET8 | unk | ilvA-melA | spleen |
| 208 | pIVET8 | unk | ilvA-melA | spleen |
| 209 | pIVET2 | unk | ilvA-melA | spleen |
| 202 | pIVET1 | unk | ilvA-melA | spleen |
| 207 | pIVET8 | unk | ilvA-melA | spleen |
| 35 | pIVET8 | fumB | melA-zjh | spleen |
| 58 | pIVET8 | mgtA | melA-zjh | spleen |
| 214 | pIVET8 | unk | melA-zjh | spleen |
| 215 | pIVET8 | unk | melA-zjh | spleen |
| 216 | pIVET8 | unk | melA-zjh | spleen |
| 217 | pIVET8 | unk | melA-zjh | spleen |
| 218 | pIVET8 | unk | melA-zjh | spleen |
| 219 | pIVET2 | unk | melA-zjh | spleen |
| 220 | pIVET1 | unk | melA-zjh | spleen |
| 213 | pIVET8 | unk | melA-zjh | spleen |
| 221 | pIVET1 | unk | melA-zjh | spleen |
| 248 | pIVET1 | vacB | melA-zjh | spleen |
| 11 | pIVET1 | asnS | nadA-putA | spleen |
| 27 | pIVET1 | deoR | nadA-putA | spleen |
| 46 | pIVET8 | hutH | nadA-putA | spleen |
| 130 | pIVET8 | unk | nadA-putA | spleen |
| 88 | pIVET1 | proS | nadC-proA | spleen |
| 97 | pIVET8 | speD | nadC-proA | spleen |
| 98 | pIVET8 | speE | nadC-proA | spleen |
| 77 | pIVET8 | tia-like | nadC-proA | spleen |
| 112 | pIVET1 | unk | nadC-proA | spleen |
| 113 | pIVET1 | unk | nadC-proA | spleen |
| 12 | pIVET1 | brnQ | proA-purE | spleen |
| 55 | pIVET1 | lon | proA-purE | spleen |
| 90 | pIVET1 | purA-like | proA-purE | spleen |
| 116 | pIVET8 | unk | proA-purE | spleen |
| 117 | pIVET8 | unk | proA-purE | spleen |
| 119 | pIVET1 | unk | proA-purE | spleen |
| 120 | pIVET8 | unk | proA-purE | spleen |
| 38 | pIVET1 | gcvP | proU-zgf | spleen |
| 56 | pIVET1 | lysS | proU-zgf | spleen |
| 102 | pIVET2 | TGl/hyb | proU-zgf | spleen |
| 181 | pIVET1 | unk | proU-zgf | spleen |
| 182 | pIVET1 | unk | proU-zgf | spleen |
| 183 | pIVET8 | unk | proU-zgf | spleen |
| 122 | pIVET8 | unk | purE-cobD | spleen |
| 123 | pIVET2 | unk | purE-cobD | spleen |
| 4 | pIVET1 | 48k prot | purG-proU | spleen |
| 92 | pIVET1 | rpiA | purG-proU | spleen |
| 100 | pIVET1 | srmB | purG-proU | spleen |
| 22 | pIVET1 | unk | purG-proU | spleen |
| 175 | pIVET1 | unk | purG-proU | spleen |
| 176 | pIVET8 | unk | purG-proU | spleen |
| 36 | pIVET1 | g30k | putA-aroD | spleen |
| 61 | pIVET1 | ndh | putA-aroD | spleen |
| 82 | pIVET1 | phoPQ | putA-aroD | spleen |
| 133 | pIVET1 | unk | putA-aroD | spleen |
| 134 | pIVET8 | unk | putA-aroD | spleen |
| 135 | pIVET8 | unk | putA-aroD | spleen |
| 136 | pIVET1 | unk | putA-aroD | spleen |
| 137 | pIVET1 | unk | putA-aroD | spleen |
| 103 | pIVET8 | unk (cbiJ/thr) | putA-pyrF | spleen |
| 59 | pIVET8 | mgtB | pyrE-ilvA | spleen |
| 91 | pIVET1 | rbs | pyrE-ilvA | spleen |
| 105 | pIVET8 | torA | pyrE-ilvA | spleen |
| 108 | pIVET8 | uhpB | pyrE-ilvA | spleen |
| 197 | pIVET8 | unk | pyrE-ilvA | spleen |
| 196 | pIVET1 | unk | pyrE-ilvA | spleen |
| 41 | pIVET1 | gtpl | pyrF-tre | spleen |
| 42 | pIVET1 | hemA | pyrF-tre | spleen |
| 145 | pIVET1 | unk | pyrF-tre | spleen |
| 109 | pIVET8 | unk | thr-nadC | spleen |
| 32 | pIVET2 | flagellar pr | tre-zea | spleen |
| 147 | pIVET1 | unk | tre-Zea | spleen |
| 149 | pIVET8 | unk | tre-Zea | spleen |
| 150 | pIVET8 | unk | tre-Zea | spleen |
| 62 | pIVET1 | ndk | unmapped | spleen |
| 65 | pIVET8 | orf1.3 | unmapped | spleen |
| 68 | pIVET1 | orf211 | unmapped | spleen |
| 81 | pIVET8 | phnK | unmapped | spleen |
| 89 | pIVET8 | pspA | unmapped | spleen |
| 230 | pIVET1 | unk | unmapped | spleen |
| 231 | pIVET1 | unk | unmapped | spleen |
| 237 | pIVET8 | unk | unmapped | spleen |
| 238 | pIVET8 | unk | unmapped | spleen |
| 239 | pIVET8 | unk | unmapped | spleen |
| 240 | pIVET8 | unk | unmapped | spleen |
| 241 | pIVET8 | unk | unmapped | spleen |
| 242 | pIVET8 | unk | unmapped | spleen |
| 243 | pIVET8 | unk | unmapped | spleen |
| 244 | pIVET8 | unk | unmapped | spleen |
| 245 | pIVET8 | unk | unmapped | spleen |
| 99 | pIVET8 | spvB | virulence plasmid | spleen |
| 227 | pIVET8 | unk | virulence plasmid | spleen |
| 18 | pIVET8 | cysA | zea-cysA | spleen |
| 21 | pIVET1 | cysK | zea-cysA | spleen |

TABLE 4-continued

| Seq ID # | Vector | Gene | Between Loci: | Tissue |
|---|---|---|---|---|
| 24 | pIVET1 | dedB | zea-cysA | spleen |
| 25 | pIVET1 | dedE | zea-cysA | spleen |
| 44 | pIVET1 | hisT | zea-cysA | spleen |
| 66 | pIVET8 | orf179 | zea-cysA | spleen |
| 73 | pIVET2 | orfA | zea-cysA | spleen |
| 74 | pIVET1 | orf f167 | zea-cysA | spleen |
| 154 | pIVET8 | unk | zea-cysA | spleen |
| 156 | pIVET1 | unk | zea-cysA | spleen |
| 158 | pIVET8 | unk | zea-cysA | spleen |
| 159 | pIVET8 | unk | zea-cysA | spleen |
| 160 | pIVET8 | unk | zea-cysA | spleen |
| 161 | pIVET8 | unk | zea-cysA | spleen |
| 162 | pIVET8 | unk | zea-cysA | spleen |
| 163 | pIVET8 | unk | zea-cysA | spleen |
| 164 | pIVET8 | unk | zea-cysA | spleen |
| 166 | pIVET1 | unk | zea-cysA | spleen |
| 107 | pIVET1 | unk | zea-cysA | spleen |
| 165 | pIVET2 | unk | zea-cysA | spleen |
| 252 | pIVET1 | yejL | zea-cysA | spleen |
| 253 | pIVET8 | yohI | zea-cysA | spleen |
| 187 | pIVET1 | unk | zgf-envZ | spleen |
| 39 | pIVET8 | gltB | zgf-zgi | spleen |
| 47 | pIVET8 | iap | zgf-zgi | spleen |
| 54 | pIVET1 | lacA | zgf-zgi | spleen |
| 185 | pIVET8 | unk | zgf-zgi | spleen |
| 186 | pIVET8 | unk | zgf-zgi | spleen |
| 9 | pIVET1 | aroK | zgi-envZ | spleen |
| 20 | pIVET2 | cysG | zgi-envZ | spleen |
| 23 | pIVET1 | dam/trpS | zgi-envZ | spleen |
| 34 | pIVET1 | ftsX | zgi-envZ | spleen |
| 40 | pIVET1 | glyS | zgi-envZ | spleen |
| 51 | pIVET1 | kbl | zgi-envZ | spleen |
| 60 | pIVET1 | mreB | zgi-envZ | spleen |
| 189 | pIVET1 | unk | zgi-envZ | spleen |
| 190 | pIVET8 | unk | zgi-envZ | spleen |
| 191 | pIVET8 | unk | zgi-envZ | spleen |
| 192 | pIVET8 | unk | zgi-envZ | spleen |
| 193 | pIVET8 | unk | zgi-envZ | spleen |
| 95 | pIVET1 | secB | zgi-pyrE | spleen |
| 15 | pIVET1 | chvD hom. | zjh-thr | spleen |
| 26 | pIVET1 | deoAB | zjh-thr | spleen |
| 96 | pIVET1 | serB/smp | zjh-thr | spleen |
| 225 | pIVET8 | unk | zjh-thr | spleen |
| 226 | pIVET8 | unk | zjh-thr | spleen |
| 224 | pIVET1 | unk | zjh-thr | spleen |

The examples which follow are not intended to limit the scope of the present invention but rather exemplify how the coding sequences disclosed are useful in identifying and isolating microbial virulence genes, the products of which will provide potential targets for the development of antimicrobial agents or vaccines.

EXAMPLE 1

Identification of Known Genes That Are or Have Been Implicated in Salmonella Virulence As discussed previously the defined portions of the coding sequences of the present invention have been compared to published sequences, and genes that were both previously known or believed to be implicated in Salmonella virulence have been identified. Several known Salmonella spp. virulence genes have been identified using the coding sequences of the present invention, shown in Table 5, thus validating the method and probes of the present invention.

TABLE 5

Genes of Salmonella Virulence

| SEQ ID NO. | GENE | FUNCTION | ROLE IN PATHOGENESIS |
|---|---|---|---|
| 82 | phoPQ | virulence regulator | invasion, macrophage survival |
| 99 | spvB | plasmid virulence | systemic survival |
| 178 | recBCD | recombination/repair | macrophage survival |
| 199 | pmrAB | polymyxin resistance | neutrophil survival |
| 13 | cadC | lysine decarboxylase | acid tolerance |
| 76 | oxyR | oxidative stress regulator | macrophage survival |
| 31 | fhuA | $Fe^{++}$ transport | $Fe^{++}$ accumulation |
| 58/59 | mgtA/BC | $Mg^{++}$ transport | $Mg^{++}$ sensor |

Examples of genes known to be involved in virulence include phoPQ, the two-component global regulator of Salmonella spp. virulence involved in invasion, macrophage survival, and defensin resistance, as well as spvB, a Salmonella plasmid virulence gene whose function is to facilitate growth at systemic sites of infection. phoPQ gene products are involved in both early and late stages of infection since phoPQ mutants confer a defect after either oral or intraperitoneal delivery. Accordingly, phoPQ in vivo induced fusions were isolated from the spleen after either oral or intraperitoneal infection. In contrast, mutants that lack the Salmonella spp. virulence plasmid are defective in late stages of infection; consistent with this infection profile, spvB fusions were isolated from the spleen after intraperitoneal delivery.

Another class of in vivo induced fusions reside in recBCD, encoding exonuclease V, the primary recombination and repair enzyme in bacteria. recBCD has been shown to be required for full virulence and has been implicated in superoxide resistance in cultured macrophages. Correspondingly, the recBCD fusion was isolated from cultured macrophages, presumably reflecting the pathogen's protective recombination and repair response to DNA damage resulting from the macrophage oxidative burst.

The next three classes of in vivo induced genes shown in Table 5 (pmrAB, cadC and oxyR) are in regulatory loci that may be implicated in Salmonella virulence due to the biochemical functions that are associated with their expression. Examples include pmrAB, a two-component regulator that controls resistance to cationic antibacterial proteins (CAP) of human neutrophils and to the drug, polymyxin B. The apparent in vivo induction of pmrAB may be involved in resistance to similar, as yet undefined, murine macrophage-derived antibacterial proteins.

cadC is an in vivo induced regulatory locus that controls lysine decarboxylation. These fusions were isolated from the intestine after an oral infection and from the spleen after an intraperitoneal infection. Decarboxylation of basic amino acids produces primary amines which may increase the pH of host cell organelles such as the phagosome. The fact that cadC was isolated from different host tissues suggests that it may function to increase the pH of several different host cell organelles (e.g., in response to the low pH of the stomach or phagosome). Moreover, CadC is topologically similar to ToxR, the global regulator of virulence in Vibrio cholerae. Both cadC and toxR respond to low pH and media composition, but it is not known whether toxR regulates polyamine synthesis in Vibrio cholerae or whether cadC regulates other virulence genes in Salmonella spp.

Last, oxyR, a regulator of the oxidative stress response was recovered from the mouse intestine, a tissue which is thought to be relatively anaerobic. The apparent in vivo induction of oxyR may be in response to the oxidative burst of macrophages present in mucosal associated lymphoid tissue (MALT) that line the intestinal epithelium. Alternatively, this may be a developmental response: oxyR may be inducing bacterial oxidative protective systems within the lumen of the intestine in anticipation of encountering macrophages in some later stage in the infection cycle, such as in the blood or spleen.

EXAMPLE 2

Virulence Genes of Other Pathogens Not Previously Known to Exist in Salmonella spp.

The coding sequence of the present invention have been compared to published sequences and virulence genes of other pathogens not previously known to exist in Salmonella spp. have been identified, see Table 6.

TABLE 6

Virulence Genes of Other Pathogens

| SEQ. ID NO. | GENE | FUNCTION | ROLE IN PATHOGENESIS |
|---|---|---|---|
| 248/249 | vacB/C | ipa/icsA expression | invasion/intercellular spread Shigella spp.; EIEC |
| 254 | cpxA | virF expression | invasion/intercellular spread Shigella spp. |
| 251 | yehB | pilin assembly | adherence K. pneumonia; H. influenzae; EIEC |
| 77 | tia | gut epithelial invasion | adherence; invasion EIEC |
| 15 | chvD | virG expression (plant virulence | signal transduction A. tumefaciens | in vivo induced fusions to virulence genes of other pathogens not previously known to exist in Salmonella spp. and enteroinvasive *E. coli* (EIEC). vacB mutants are defective in the synthesis of invasion plasmid antigens (ipa) and intercellular spread (ics) gene products, which are required for invasion and lateral spread within host cells. The affected genes are transcribed at normal levels but the corresponding proteins are not detected. vacB fusions were isolated from the spleen after an oral or intraperitoneal infection, suggesting that vacB is needed at both early and late stages of infection, possibly for invasion of the intestinal epithelium and for invasion at systemic sites of infection (e.g., invasion of splenic macrophages in a manner that may not activate phagocyte killing mechanisms). vacC is homologous to *E. coli* tgt, which encodes a transglycosylase that modifies tRNA molecules. In contrast to vacB, Shigella spp. vacC mutants show reduced transcription of the ipa genes; they do not form plaques on cultured mammalian cells and exhibit reduced survival in stationary phase. Some tRNA modifications (encoded by miaA and tgt) are sensitive to environmental signals such as $Fe^{++}$, $O_2$, and growth state. The in vivo induction of environmentally-sensitive tRNA modifications may contribute to the changes in bacterial gene expression (by attenuation) and/or protein synthesis (by altered codon preference) that may occur in host tissues (note that [chorismate], produced by a metabolic in vivo induced gene, aroK, is also involved in tRNA modification).

A third class of fusions map to the *E. coli* yehB locus, which has sequence similarity to proteins involved in pilin assembly in many pathogens, including mrkC of *Klebsiella pneumoniae* hifC of *Haemophilus influenzae*, and CS3 pilin assembly components of enterotoxigenic *Escherichia coli*.

yehB fusions were isolated from the spleen after an intraperitoneal infection and may represent a new class of Salmonella spp. surface properties that are induced at systemic sites of infection.

Recently, it has been shown that *Pseudomonas aeruginosa* encodes virulence factors that are required for infection of both plants and animals. Similarly, one class of in vivo induced fusions isolated from the spleen after an oral infection resides in a gene that has amino acid sequence identity to chvD, a chromosomal virulence gene involved in signal transduction in the plant pathogen, *A. tumefaciens*. Under conditions of low pH and phosphate starvation, chvD is required for the induction of transcription of virG, the regulatory component of the virA/G two-component regulatory system in *A. tumefaciens*. The apparent in vivo induction of a chvD homolog in *S. typhimurium* may represent another example of a sensory virulence determinant shared by animal and plant pathogens.

EXAMPLE 3

Unknown Genes

Unknown coding regions of promoters that are induced in vivo have also been identified and are represented by SEQ ID NOS. 22, 43, 103, 107, 109–177 and 179–253.

One can imagine that pathogens possess many functions that are required during infection, but are not easily detected on laboratory media or identified by biochemical assay. The coding sequences of the present invention allows for the identification of previously unknown genes and provides a means to associate them with a phenotype, induction in the host. Indeed, the functions of >40% of the in vivo induced genes are unknown. The members of this class have either no homology with the DNA data base or encode open reading frames with no assigned function. Defined regions of the coding sequences of the present invention sharing homology to unknown genes have been isolated from all IVET vectors (pIVET1, 2, and 8) made according to the present invention and routes of delivery (oral, intraperitoneal) and host tissues (intestine, spleen, liver) tested. These unknown fusions have been mapped (shown in Table 4) to determine whether they cluster to a specific region of the *S. typhimurium* chromosome possibly functioning in the same stage of pathogenesis. Thus, by combining the knowledge of the in vivo induction phenotype, the host tissue from which the coding sequences of the present invention were recovered, and the chromosomal map positions, one has the means to begin investigating not only novel virulence factors but also bacterial sensory and biochemical pathways that remain undefined. Coding sequences of the present invention having homology to unknown genes are found throughout the chromosome. However, clusters of in vivo induced fusions in adjacent genes do occur in some locations. For example, two unknown in vivo induced fusions reside in the previously reported open reading frames, orf384 and orf337, in vivo induced A (SEQ ID NO. 69) and B (SEQ ID NO. 70) lie in transcription units that are highly linked to the metabolic in vivo induced gene, ndk discussed further below.

EXAMPLE 4

Method of Using the Coding Sequences of the Present Invention to Identify Genes Involved in Virulence Each in vivo induced clone can be used to isolate mutations in the gene identified by sequence analysis. Insertion mutations generated by transposable elements (Mahan, et al., *J. of Bacteriol*, 175(21):7086–7091 (1993)) that disrupt an operon will reduce the transcription of the lac gene. These insertions will have a light blue color on LB plates supplemented with X-gal. Some of these will be insertions in the in vivo induced gene, identified by sequence analysis. In addition, genes that are downstream of the operon promoter, but proximal to the ivi lac fusion may be disrupted; this will result in reduced transcription of the lac genes, again resulting in a light blue phenotype on X-gal containing plates. Sequence analysis of the DNA surrounding the insertion will identify new genes cotranscribed with the original in vivo induced gene.

As an example, tia (SEQ ID NO. 77) is an in vivo induced gene identified by the method of the present invention which encodes a product with protein sequence similarity (as translated from the DNA sequence) to an *E. coli* protein that directs invasion of gut epithelial cells in tissue culture cells. The coding sequence of the present invention containing the tia fusion was used to isolate insertions that disrupt the tia coding sequence by looking for transposon insertions that reduce the transcription of the lac gene. Among the mutations isolated by this method are transposon insertions in tia and also in a gene promoter proximal to tia. This gene, having the partially defined sequence 3'-CGCTGTCCTG GTGTTAAGAC TTTGCTTAAA TCAAAATAAT ATT-TAACCCG ATAATAGCGA GCCTGTTGTT CTATGT-TACT GAAGGCTGCA AGCTGCTGTT TTACGGCGGC GTCATCCCAT TTACCGGATT TAATCACCTC TAT-CAGCGCA CCGTCTTTAA TTCCCTTCAT AGAAATCTGA CTGACGTCGG TTTCCAGTTG TTG-GTGAAGT TTTTTGATCC GGGTAATCTG ATCGTTTGTC AGCTTCAGAT GCTGGACAAT AGGATCCTGG GCGGGCAGGG GGAGGATTGG GGA-CAGCGTG CAAGCAAAAG AAACGCGCAG AGTCGCTGCA GTAAGTGGGC ATACGTTT-5' (SEQ ID NO. 255) encodes a protein product with sequence similarities to pfEMP, a protein encoded by *Plasmodium falciparum* (the causative agent of malaria) during infection of red blood cells. Thus, the identified sequences of the present invention described here can and do lead to the identification of other genes specifically induced by the bacterium during infection. Each in vivo induced clone contains one or more genes transcribed from a single promoter, thus insertion mutations that are proximal to the operon promoter are capable of disrupting and reducing the transcription of distally positioned genes including the lac gene. In the alternative to using this insertional mutagenesis technique to identify other non-sequential genes that are cotranscribed with the genes for which partial sequences have been defined (SEQ ID NOS. 4–254), these defined sequences may also be used as probes to identify cotranscribed genes. Defined sequences identified by (SEQ ID NOS. 4–254) or portions thereof can be used to prime the synthesis of a cDNA library from total bacterial mRNA. There are many routes to a cDNA library; however regardless of the pathway the first step is the synthesis of a DNA strand complimentary to the mRNA sequence. The reaction requires template RNA, a complementary primer, reverse transcriptase, and deoxyribonucleoside triphosphates, see Maniatis, Id. or S. Berger, et al., *Guide to Molecular Cloning Techniques*, 152:307–389 (1987). This cDNA will contain the transcribed sequence from the mRNA start site to the priming site. This cDNA can be used to detect clones that overlap this region of DNA by Southern Hybridization. From those clones, DNA fragments can be used as probes in Northern Hybridization against total mRNA. Each DNA fragment that hybridizes to the mRNA defined by the original cDNA can be inferred to contain sequences cotranscribed with the original in vivo induced gene sequence defined here. Thus, each coding sequence of the present invention can be used to isolate and identify additional genes that are expressed during infection, each of which may encode products useful for the development of antibiotics and/or vaccines. In the alternative, the defined sequences (SEQ ID NOS. 4–254) may be used to probe DNA libraries to identify and study homologous regions of interest.

EXAMPLE 5

Method of Using the Coding Sequences of the Present Invention to Identify Genes Within the Same Operon As discussed above in Example 4, in vivo induced genes may be identified by the defined regions of the coding sequences of the present invention that are relatively short (70–400 bp). Some bacterial operons are large, greater than 10 kilobases in length. It is reasonable to expect therefore that multiple fusions in the same operon might be recovered by the IVET selection. Three in vivo induced fusions (ndk, SEQ ID NO. 62; orf384, SEQ ID NO. 69; and orf337, SEQ ID NO. 70) are in genes known to be near each other on the *E. coli* chromosome and transcribed in the same direction. Insertion mutations that reduce the expression of the lac gene in the orf337 synthetic operon were isolated. One transposon insertion, which disrupts the coding sequence of ndk, reduces the expression of the downstream orf384 lac fusion, indicating that all three genes, ndk, orf384 and orf337, are transcribed as a unit and may have related functions as they relate to virulence. In this way, fusions to unknown genes that lie close to one another, as determined by mapping, can be analyzed for a common promoter. The existence of such a promoter and the study of its regulation may provide clues to the role of each in vivo induced gene transcribed or cotranscribed with the coding sequences of the present invention during microbial infection of a host.

EXAMPLE 6

Method of Using the Coding Sequences of the Present Invention to Identify Environmental or Host Signals that Coordinate and Regulate Virulence Genes Because the expression of each in vivo induced (ivi) fusion can be easily assayed by measuring the activity of the lac reporter gene, the signals that regulate ivi genes in vivo can be determined. If there are molecules present in host tissues that induce the expression of ivi genes the activity of those molecules can be assayed by their effect on the transcription of the lac gene in the ivi construct. Extracts of host tissues can be used to look for host molecules that induce the expression of ivi lac fusions. Purification of this activity can be further monitored by repeated assays. In this way, host compounds, e.g. cytokines or other molecules which may be used as antibacterial drugs can be identified. Genes have been identified that respond to concentrations of $Mg^{++}$ and/or pH, e.g. SEQ ID NOS. 77 and 84.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

What is claimed is:

1. A polynucleotide sequence selected from the group consisting of SEQ ID NOS: 23, 24, 33, 39, 40, 53, 60, 86, 88, and 104 further comprising a vector sequence.

2. The vector of claim 1, wherein the vector is an expression vector.

3. The vector of claim 1, wherein the vector is a cloning vector.

4. The vector of claim 1, wherein the polynucleotide sequence consists essentially of SEQ ID NO: 23.

5. The vector of claim 1, wherein the polynucleotide sequence consists essentially of SEQ ID NO: 24.

6. The vector of claim 1, wherein the polynucleotide sequence consists essentially of SEQ ID NO: 33.

7. The vector of claim 1, wherein the polynucleotide sequence consists essentially of SEQ ID NO: 39.

8. The vector of claim 1, wherein the polynucleotide sequence consists essentially of SEQ ID NO: 40.

9. The vector of claim 1, wherein the polynucleotide sequence consists essentially of SEQ ID NO: 53.

10. The vector of claim 1, wherein the polynucleotide sequence consists essentially of SEQ ID NO:60.

11. The vector of claim 1, wherein the polynucleotide sequence consists essentially of SEQ ID NO:86.

12. The vector of claim 1, wherein the polynucleotide sequence consists essentially of SEQ ID NO:88.

13. The vector of claim 1, wherein the polynucleotide sequence consists essentially of SEQ ID NO:104.

14. A class of polynucleotide sequences consisting essentially of each and every one of SEQ ID NOS: 4 through 255.

15. A polynucleotide sequence consisting essentially of a nucleic acid sequence corresponding to the group consisting of SEQ ID NOS: 23, 24, 33, 39, 40, 53, 60, 86, 88, and 104.

16. The polynucleotide sequence of claim 15 consisting essentially of a nucleic acid sequence corresponding to SEQ ID NO: 23.

17. The polynucleotide sequence of claim 15 consisting essentially of a nucleic acid sequence corresponding to SEQ. ID NO: 24.

18. The polynucleotide sequence of claim 15 consisting essentially of a nucleic acid sequence corresponding to SEQ ID NO: 33.

19. The polynucleotide sequence of claim 15 consisting essentially of a nucleic acid sequence corresponding to SEQ ID NO: 39.

20. The polynucleotide sequence of claim 15 consisting essentially of a nucleic acid sequence corresponding to SEQ ID NO: 40.

21. The polynucleotide sequence of claim 15 consisting essentially of a nucleic acid sequence corresponding to SEQ ID NO: 53.

22. The polynucleotide sequence of claim 15 consisting essentially of a nucleic acid sequence corresponding to SEQ ID NO: 60.

23. The polynucleotide sequence of claim 15 consisting essentially of a nucleic acid sequence corresponding to SEQ ID NO: 86.

24. The polynucleotide sequence of claim 15 consisting essentially of a nucleic acid sequence corresponding to SEQ ID NO: 88.

25. The polynucleotide sequence of claim 15 consisting essentially of a nucleic acid sequence corresponding to SEQ ID NO: 104.

* * * * *